US009695250B2

(12) United States Patent
Lutterbüse et al.

(10) Patent No.: US 9,695,250 B2
(45) Date of Patent: Jul. 4, 2017

(54) PHARMACEUTICAL COMPOSITIONS WITH RESISTANCE TO SOLUBLE CEA

(71) Applicant: AMGEN RESEARCH (MUNICH) GMBH, Munich (DE)

(72) Inventors: Ralf Lutterbüse, Neuried (DE); Petra Fluhr, Munich (DE); Evelyne Schaller, Sauerlach (DE); Doris Rau, Unterhaching (DE); Susanne Mangold, Cham (CH); Peter Kufer, Moosburg (DE); Alexander Murr, Munich (DE); Tobias Raum, Eurasburg (DE); Monika Wissinger, Gilching (DE)

(73) Assignee: AMGEN RESEARCH (MUNICH) GMBH, Munich (DE)

( * ) Notice: Subject to any disclaimer, the term of this patent is extended or adjusted under 35 U.S.C. 154(b) by 580 days.

(21) Appl. No.: 13/740,358

(22) Filed: Jan. 14, 2013

(65) Prior Publication Data

US 2013/0273050 A1    Oct. 17, 2013

Related U.S. Application Data

(63) Continuation of application No. 12/158,611, filed as application No. PCT/EP2006/012425 on Dec. 21, 2006, now Pat. No. 8,394,926.

(60) Provisional application No. 60/751,963, filed on Dec. 21, 2005, provisional application No. 60/780,861, filed on Mar. 10, 2006.

(30) Foreign Application Priority Data

Dec. 21, 2005  (EP) .................................... 05028064

(51) Int. Cl.
| | |
|---|---|
| *C07K 16/00* | (2006.01) |
| *C07K 16/46* | (2006.01) |
| *A61K 45/06* | (2006.01) |
| *C07K 16/28* | (2006.01) |
| *C07K 16/30* | (2006.01) |
| *A61K 39/395* | (2006.01) |

(52) U.S. Cl.
CPC ........ *C07K 16/46* (2013.01); *A61K 39/39558* (2013.01); *A61K 45/06* (2013.01); *C07K 16/2809* (2013.01); *C07K 16/3007* (2013.01); *C07K 2317/21* (2013.01); *C07K 2317/31* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,394,448 A | 7/1983 | Szoka, Jr. et al. | |
| 5,580,859 A | 12/1996 | Felgner et al. | |
| 5,589,466 A | 12/1996 | Felgner et al. | |
| 6,407,213 B1 | 6/2002 | Carter et al. | |
| 8,394,926 B2 | 3/2013 | Lutterbuse et al. | |
| 8,901,278 B2 * | 12/2014 | Rau .................... | C07K 16/3007 530/350 |
| 2004/0162411 A1 | 8/2004 | Lanzavecchia | |
| 2005/0136050 A1 | 6/2005 | Kufer et al. | |

FOREIGN PATENT DOCUMENTS

| | | |
|---|---|---|
| EP | 0491031 A1 | 6/1992 |
| EP | 0491031 A1 | 6/1992 |
| WO | WO-91/09968 A1 | 7/1991 |
| WO | WO-92/10755 A1 | 6/1992 |
| WO | WO-97/00957 A1 | 1/1997 |
| WO | WO-98/52976 A1 | 11/1998 |
| WO | WO-99/54440 A1 | 10/1999 |
| WO | WO-00/34317 A2 | 6/2000 |
| WO | WO-02/066514 A2 | 8/2002 |
| WO | WO-02/079415 A2 | 10/2002 |
| WO | WO-2005/040220 A1 | 5/2005 |
| WO | WO-2007/071426 | 6/2007 |

OTHER PUBLICATIONS

Blair, S.D., et al., "Comparison of anti-fetal colonic microvillus and anti-CEA antibodies in peroperative radioimmunolocalisation of colorectal cancer", *British J. Cancer*, vol. 61, No. 6, (1990), pp. 891-894.

Blanco, Belén, et al., Induction of Human T Lymphocyte Cytotoxicity and Inhibition of Tumor Growth by Tumor-Specific Diabody-Based Molecules Secreted from Gene-Modified Bystander Cells, *J. Immunology*, vol. 171 (2003), pp. 1070-1077.

Chester, et al., "Production and Tumour-Binding characterization of a chimeric Anti-Cea Fab Expressed in *Escherichia coil*", Int. J. Cancer, vol. 57, 1994, pp. 67-72.

Hollinger, Philipp et. al., "Carcinoembryonic antigen (CEA)—Specific T-Cell Activation in Colon Carcinoma Induced by Anti-CD3Xanti-CEA Bispecific Diabodies and B7Xanti-CEA Bispecific Fusion Proteins", *Cancer Research*, vol. 59, No. 12, 1999, pp. 2909-2916, (XP002426875).

(Continued)

*Primary Examiner* — Brad Duffy
(74) *Attorney, Agent, or Firm* — Marshall, Gerstein & Borun LLP

(57) ABSTRACT

The present disclosure relates to a bispecific single chain antibody which has a first binding domain specifically binding to human CD3, and a second binding domain specifically binding to human CEA, where the second binding domain comprises at least a part of the CDR-H3 or the complete CDR-H3 of murine monoclonal antibody A5B7, a pharmaceutical composition comprising the bispecific single chain antibody, and methods for the treatment of an epithelial tumor in a human with the pharmaceutical compositions containing the bispecific single chain antibody. Furthermore, processes for the production of the pharmaceutical compositions as well as medical/pharmaceutical uses for the specific bispecific single chain antibody molecules bearing specificities for the human CD3 antigen and the human CEA antigen are disclosed.

19 Claims, 27 Drawing Sheets

(56) References Cited

OTHER PUBLICATIONS

Figure 1:
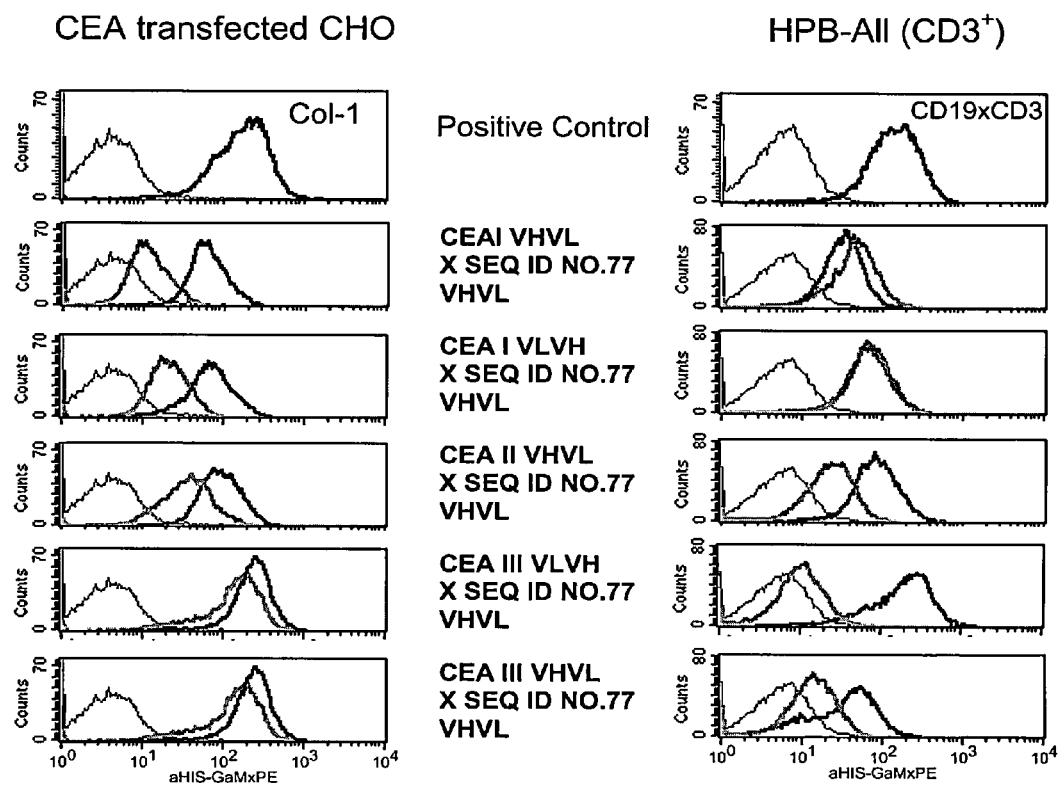

Hombach, A. et al., "A Chimeric Receptor that Selectively Targets Membrane-Bound Carcinoembryonic Antigen (mCEA) in the Presence of Soluble CEA", Gene Therapy, vol. 6, No. 2, (Feb. 1999), pp. 300-304. (XP002426878).
International Search Report for International PCT Application No. PCT/EP2006/012425 mailed Apr. 23, 2007 (4 pgs.).
Kontermann, Roland E. et al., "Recombinant Bispecific Antibodies for Cancer Therapy", ACTA Pharmacologica Sinica, vol. 26, No. 1, (Jan. 2005), pp. 1-9. (XP002426874).
Kuwahara Motohisa et al., "A Mouse/Human-Chimeric Bispecific Antibody Reactive with Human Carcinoembryonic Antigen-Expressing Cells and Human T-Lymphocytes", Anticancer Research, vol. 16, No. 5A, 1996, pp. 2661-2667. (XP009081258).
Lane, D.M., et al., "Radioimmunotherapy of metastatic colorectal tumours with iodine-131-labelled antibody to carcinoembryonic antigen: phase I/II study with comparative biodistribution of intact and F(ab')$_2$ antibodies", British J. Cancer, vol. 70, No. 3 (1994), pp. 521-525.
Murakami Masaaki et al., "Binding Reactivity of Monoclonal Anti-Carcinoembryonic Antigen (CEA) Antibodies with Cell Membrane-bound and with free CEA in solution", Immunologica Investigations, vol. 25, No. 1-2, 1996, pp. 23-35. (XP009081337).
Anderson, Human gene therapy, Nature, 392(6679Suppl):25-30 (1998).
Anderson, Human gene therapy, Science, 256(5058):808-13 (1992).
Arnon et al., "Monoclonal Antibodies for Immunotargeting of Drugs in Cancer Therapy", pp. 243-256 IN: Reisfeld et al. (eds.), Monoclonal Antibodies and Cancer Therapy, Alan R. Liss, Inc. (1985).
Ashkenazi et al., Protection against endotoxic shock by a tumor necrosis factor receptor immunoadhesin, Proc. Natl. Acad. Sci. USA, 88(23):10535-9 (1991).
Beauchemin et al., Redefined nomenclature for members of the carcinoembryonic antigen family, Exp. Cell Res., 252(2):243-9 (1999).
Begent et al., Clinical evidence of efficient tumor targeting based on single-chain Fv antibody selected from a combinatorial library, Nat. Med., 2(9):979-84 (1996).
Behr et al., Radioimmunotherapy of small-volume disease of metastatic colorectal cancer, Cancer, 94(4 Suppl):1373-81 (2002).
Blair et al., Comparison of anti-fetal colonic microvillus and anti-CEA antibodies in peroperative radioimmunolocalisation of colorectal cancer, Br. J. Cancer, 61(6):891-4 (1990).
Blanco et al., Induction of human T lymphocyte cytotoxicity and inhibition of tumor growth by tumor-specific diabody-based molecules secreted from gene-modified bystander cells, J. Immunol., 171(2):1070-7 (2003).
Boehm et al., Crystal structure of the anti-(carcinoembryonic antigen) single-chain Fv antibody MFE-23 and a model for antigen binding based on intermolecular contacts, Biochem. J., 346 Pt. 2:519-28 (2000).
Brutlag et al., Improved sensitivity of biological sequence database searches, Comput. Appl. Biosci., 6(3):237-45 (1990).
Cheson et al., Revised response criteria for malignant lymphoma, J. Clin. Oncol., 25(5):579-86 (2007).
Chester et al., Production and tumour-binding characterization of a chimeric anti-CEA Fab expressed in Escherichia coli, Int. J. Cancer, 57(1):67-72 (1994).
Chester et al., Recombinant anti-carcinoembryonic antigen antibodies for targeting cancer, Cancer Chemother. Pharmacol., 46 Suppl:S8-12 (2000).
Chubet et al., Vectors for expression and secretion of FLAG epitope-tagged proteins in mammalian cells, Biotechniques, 20(1):136-41 (1996).
DeNardo et al., Comparison of 1,4,7,10-tetraazacyclododecane-N,N',N'',N'''-tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts, Clin. Cancer Res., 4(10):2483-90 (1998).
Durbin et al., An epitope on carcinoembryonic antigen defined by the clinically relevant antibody PR1A3, Proc. Natl. Acad. Sci. USA, 91(10):4313-7 (1994).
Fletcher, Carcinoembryonic antigen, Ann. Intern. Med., 104(1):66-73 (1986).
Francis et al., A phase I trial of antibody directed enzyme prodrug therapy (ADEPT) in patients with advanced colorectal carcinoma or other CEA producing tumours, Br. J. Cancer, 87(6):600-7 (2002).
Frangsmyr et al., Cell- and region-specific expression of biliary glycoprotein and its messenger RNA in normal human colonic mucosa, Cancer Res., 55(14):2963-7 (1995).
Frangsmyr et al., Four carcinoembryonic antigen subfamily members, CEA, NCA, BGP and CGM2, selectively expressed in the normal human colonic epithelium, are integral components of the fuzzy coat, Tumour Biol., 20(5):277-92 (1999).
Garnett, Targeted drug conjugates: principles and progress, Adv. Drug Deliv. Rev., 53(2):171-216 (2001).
Giordano et al., Intracoronary gene transfer of fibroblast growth factor-5 increases blood flow and contractile function in an ischemic region of the heart, Nat. Med., 2(5):534-9 (1996).
Gold et al., Specific carcinoembryonic antigens of the human digestive system, J. Exp. Med., 122(3):467-81 (1965).
Greenlee et al., Cancer statistics, 2001, CA Cancer J. Clin., 51(1):15-36 (2001).
Hajjar et al., Phase I radioimmunotherapy trial with iodine-131—labeled humanized MN-14 anti-carcinoembryonic antigen monoclonal antibody in patients with metastatic gastrointestinal and colorectal cancer, Clin. Colorectal Cancer, 2(1):31-42 (2002).
Hammarstrom et al., Is there a role for CEA in innate immunity in the colon?, Trends Microbiol., 9(3):119-25 (2001).
Hammarstrom, The carcinoembryonic antigen (CEA) family: structures, suggested functions and expression in normal and malignant tissues, Semin. Cancer Biol., 9(2):67-81 (1999).
Harwood et al., Mapping epitope characteristics on carcinoembryonic antigen, Br. J. Cancer, 54(1):75-82 (1986).
Hollinger et al., Carcinoembryonic antigen (CEA)-specific T-cell activation in colon carcinoma induced by anti-CD3 × anti-CEA bispecific diabodies and B7 × anti-CEA bispecific fusion proteins, Cancer Res., 59(12):2909-16 (1999).
Hombach et al., A chimeric receptor that selectively targets membrane-bound carcinoembryonic antigen (mCEA) in the presence of soluble CEA, Gene Therapy, 6(2):300-4 (1999).
International Preliminary Report on Patentability, International Application No. PCT/EP2006/012425, dated Jun. 24, 2008.
International Search Report for International PCT Application No. PCT/EP2006/012425. mailed Apr. 23, 2007 (4 pp.).
Kabat et al., Sequences of proteins of immunological interest, 5th ed., Bethesda, MD: National Center for Biotechnology Information, National Library of Medicine (1987).
Kaufmann et al., Selection and coamplification of heterologous genes in mammalian cells, Methods Enzymol., 185:537-66 (1990).
Knappik et al., An improved affinity tag based on the FLAG peptide for the detection and purification of recombinant antibody fragments, Biotechniques, 17(4):754-61 (1994).
Kontermann, Recombinant bispecific antibodies for cancer therapy, Acta Pharmacol. Sin., 26(1):1-9 (2005).
Kufe et al. (eds.), Holland-Frei Cancer Medicine, 6th edition, BC Decker (2003).
Kuwahara et al., A mouse/human-chimeric bispecific antibody reactive with human carcinoembryonic antigen-expressing cells and human T-lymphocytes, Anticancer Res., 16(5A):2661-7 (1996).
Lane et al., Radioimmunotherapy of metastatic colorectal tumours with iodine-131-labelled antibody to carcinoembryonic antigen: phase I/II study with comparative biodistribution of intact and F(ab')2 antibodies, Br. J. Cancer, 70(3):521-5 (1994).
Laver et al., Epitopes on protein antigens: misconceptions and realities, Cell, 61(4):553-6 (1990).
Liersch et al., CEA radioimmunotherapy with 131I-labetuzumab improves survival post salvage resection of colorectal cancer metastases in the liver, J. Clin. Oncol., ASCO Proceedings, 23(16S):3627 (2005).

(56) References Cited

OTHER PUBLICATIONS

Mack et al., A small bispecific antibody construct expressed as a functional single-chain molecule with high tumor cell cytotoxicity, Proc. Natl. Acad. Sci. USA, 92(15):7021-5 (1995).
Mack et al., Biologic properties of a bispecific single-chain antibody directed against 17-1A (EpCAM) and CD3: tumor cell-dependent T cell stimulation and cytotoxic activity, J. Immunol., 158:3965-70 (1997).
Mayer et al., Radioimmunoguided surgery in colorectal cancer using a genetically engineered anti-CEA single-chain Fv antibody, Clin. Cancer Res., 6(5) 1711-9 (2000).
Minton et al., Results of a 400-patient carcinoembryonic antigen second-look colorectal cancer study, Cancer, 55(6):1284-90 (1985).
Muhlhauser et al., VEGF165 expressed by a replication-deficient recombinant adenovirus vector induces angiogenesis in vivo, Circ. Res., 77(6):1077-86 (1995).
Mulcahy et al., The role of carcinoembryonic antigen monitoring in management of colorectal cancer, Curr. Oncol. Rep., 1(2):168-72 (1999).
Murakami et al., Binding Reactivity of Monoclonal Anti-Carcinoembryonic Antigen (CEA) Antibodies with Cell Membrane-Bound CEA and with Free CEA in Solution, Immunologica Investigations, 25(1-2):23-35 (1996).
Neumaier et al., Cloning of the genes for T84.66, an antibody that has a high specificity and affinity for carcinoembryonic antigen, and expression of chimeric human/mouse T84.66 genes in myeloma and Chinese hamster ovary cells, Cancer Res., 50(7):2128-34 (1990).
Oikawa et al., Homotypic and heterotypic Ca(++)—independent cell adhesion activities of biliary glycoprotein, a member of carcinoembryonic antigen family, expressed on CHO cell surface, Biochem. Biophys. Res. Commun., 186(2):881-7 (1992).
Olsen et al., Gene organization of the pregnancy-specific glycoprotein region on human chromosome 19: assembly and analysis of a 700-kb cosmid contig spanning the region, Genomics, 23(3):659-68 (1994).
Onodera et al., Successful peripheral T-lymphocyte-directed gene transfer for a patient with severe combined immune deficiency caused by adenosine deaminase deficiency, Blood, 91(1):30-6 (1998).
Peterson et al., Enzymatic cleavage of peptide-linked radiolabels from immunoconjugates, Bioconjug. Chem., 10(4):553-7 (1999).
Pluckthun, IN: Rosenberg et al. (eds.), The Pharmacology of Monoclonal Antibodies, vol. 113, pp. 269-315, New York: Springer-Verlag (1994).
Primus et al., Immunoperoxidase detection of carcinoembryonic antigen: an overview, Cancer, 42(3 Suppl):1540-5 (1978).
Ries et al., The annual report to the nation on the status of cancer, 1973-1997, with a special section on colorectal cancer, Cancer, 88(10):2398-424 (2000).
Sack et al., Release of carcinoembryonic antigen from human colon cancer cells by phosphatidylinositol-specific phospholipase C, J. Clin. Invest., 82(2):586-93 (1988).
Schaper et al., Molecular mechanisms of coronary collateral vessel growth, Circ. Res., 79(5):911-9 (1996).
Schaper et al., Therapeutic targets in cardiovascular disorders, Curr. Opin. Biotechnol., 7(6):635-40 (1996).
Sela, Antigenicity: some molecular aspects, Science, 166(3911):1365-74 (1969).
Sharkey et al., Evaluation of a complementarity-determining region-grafted (humanized) anti-carcinoembryonic antigen monoclonal antibody in preclinical and clinical studies, Cancer Res., 55(23 Suppl):5935s-5945s (1995).
Shively et al., CEA-related antigens: molecular biology and clinical significance, Crit. Rev. Oncol. Hematol., 2(4):355-99 (1985).
Taylor et al., Inhibition of Macrophage Ia Antigen Expression by Shed Plasma Membrane Vesicles From Metastatic Murine Melanoma Lines, J. Natl. Cancer Inst., 74(4):859-66 (1985).
Thomson et al., The radioimmunoassay of circulating carcinoembryonic antigen of the human digestive system, Proc. Natl. Acad. Sci. USA, 64(1):161-7 (1969).
Verma et al., Gene therapy—promises, problems and prospects, Nature, 389(6648):239-42 (1997).
Verzeletti et al., Herpes simplex virus thymidine kinase gene transfer for controlled graft-versus-host disease and graft-versus-leukemia: clinical follow-up and improved new vectors, Hum. Gene Ther., 9(15):2243-51 (1998).
Wanebo et al., Prospective monitoring trial for carcinoma of colon and rectum after surgical resection, Surg. Gynecol. Obstet., 169(6):479-87 (1989).
Wang et al., Persistent transgene expression in mouse liver following in vivo gene transfer with a delta E1/delta E4 adenovirus vector, Gene Ther., 4(5):393-400 (1997).
Wang et al., Second-generation adenovirus vectors, Nat. Med., 2(6):714-6 (1996).
Yu et al., Phase I trial of iodine 131-labeled COL-1 in patients with gastrointestinal malignancies: influence of serum carcinoembryonic antigen and tumor bulk on pharmacokinetics, J. Clin. Oncol., 14(6):1798-809 (1996).
Zhou et al., Specificity of anti-carcinoembryonic antigen monoclonal antibodies and their effects on CEA-mediated adhesion, Cancer Res., 53(16):3817-22 (1993).

\* cited by examiner

|   | | EC 50 [ng/ml] |
|---|---|---|
| ■ | SEQ ID NO. 77 VHVL x CEAI VHVL | 0.0045 |
| ▲ | SEQ ID NO. 77 VHVL x CEAI VLVH | 0.0035 |
| ◆ | CEAI VLVH x SEQ ID NO. 77 VHVL | 0.0196 |
| ▼ | CEAI VHVL x SEQ ID NO. 77 VHVL | 1.2 |
| ✘ | Negative control | n.a. |

| EC50 [ng/ml] | I –HL | II –HL | III –LH | III –HL |
|---|---|---|---|---|
| CHO-CEA+ | 9.3 | 1.2 | 119 | 139 |

| Sol. CEA [µg/ml] | 0 | 0.1 | 1 |
|---|---|---|---|
| CEA I VHVL x SEQ ID NO.77 VHVL EC50 [ng/ml] | 1.6 | 2.4 | 3.2 |
| CEA I VLVH x SEQ ID NO.77 VHVL EC50 [ng/ml] | 0.034 | 0.024 | 0.058 |

| Sol. CEA [µg/ml] | 0 | 0.004 | 0.02 | 0.1 | 0.5 | 1 |
|---|---|---|---|---|---|---|
| SEQ ID NO.77 VHVLx CEA-I LH EC$_{50}$ [pg/ml] | 3.5 | 2.3 | 0.4 | 3.5 | 1.6 | 5.1 |
| SEQ ID NO.77 VHVL x CEA-I HL EC$_{50}$ [pg/ml] | 4.5 | 6.2 | 7.4 | 8.4 | 9.1 | 11.6 |

| Sol. CEA [µg/ml] | 0 | 0.1 | 1 |
|---|---|---|---|
| CEAII VHVLxSEQ ID NO.77 VHVL EC50 [ng/ml] | 8.2 | 114.6 | 3980 |

CEAII VHVLxSEQ ID NO.77 VHVL

| Sol. CEA [µg/ml] | 0 | 0.02 | 0.1 | 0.5 | 1.0 |
|---|---|---|---|---|---|
| CEAIIVHVLxSEQ ID NO.77VHVL EC50 [ng/ml] | 23 | 14 | 159 | 1415 | 5057 |

| Sol. CEA [µg/ml] | 0 | 0.004 | 0.1 | 0.5 | 1.0 |
|---|---|---|---|---|---|
| CEAIVHVLxSEQ ID NO.77VHVL EC50 [ng/ml] | 3.6 | 3.6 | 65.4 | 6.3 | 5.1 |
| CEAIIVHVLxSEQ ID NO.77VHVL EC50 [ng/ml] | -- | 1.2 | 36.5 | 77.9 | 578 |

CEAII VHVL x SEQ ID NO.77 VHVL

| Sol. CEA [µg/ml] | 0.004 | 0.02 | 0.1 | 0.5 | 1.0 |
|---|---|---|---|---|---|
| CEAIIVHVLxSEQ ID NO.77 VHVL EC50 [ng/ml] | 4.0 | 16 | 60 | 432 | 1983 |

|  | EC 50 [ng/ml] |
|---|---|
| B9 VH - A240 VL x SEQ ID NO.77 VHVL | 0.58 |
| CEA I VH - A240 VL x SEQ ID NO.77 VHVL | 1.61 |
| D8 VH - A240 VL x SEQ ID NO.77 VHVL | 10.0 |
| A5 VH - A240 VL x SEQ ID NO.77 VHVL | 10.5 |

| | EC 50 [pg/ml] |
|---|---|
| SEQ ID NO:77 VHVL x A240 VL - D8 VH | 11.0 |
| SEQ ID NO:77 VHVL x A240 VL - A5 VH | 13.5 |
| SEQ ID NO:77 VHVL x A240 VL - B9 VH | 18.4 |
| SEQ ID NO:77 VHVL x A240 VL - CEA I VH | 29.8 |
| SEQ ID NO:77 VHVL x CEA I VLVH | 40.0 |

| Sol. CEA [µg/ml] | 0 | 0.1 | 1 |
|---|---|---|---|
| B9 VH – A240 VL x SEQ ID NO.77 VHVL EC50 [ng/ml] | 0.58 | 1.04 | 3.65 |
| A5 VH – A240 VL x SEQ ID NO.77 VHVL EC50 [ng/ml] | 10.5 | 10.4 | 14.0 |

| Sol. CEA [µg/ml] | 0 | 0.1 | 1 |
|---|---|---|---|
| D8 VH – A240 VL x SEQ ID NO.77 VHVL EC50 [ng/ml] | 15.1 | 24.1 | 17.5 |
| CEAI VH– A240 VL x SEQ ID NO.77 VHVL EC50 [ng/ml] | 31.6 | 28.8 | 39.0 |

|  | EC 50 [pg/ml] |
|---|---|
| ━■━ A240(VL)-B9(VH) x SEQ ID NO.77 VHVL | 5.3 |
| ····▲···· SEQ ID NO.77 VHVL x A240(VL)-B9(VH) | 22.9 |
| ---□--- SEQ ID NO.77 VHVL x B9(VH) A240(VL) | 74.2 |
| ━◇━ B9(VH) A240(VL) x SEQ ID NO.77 VHVL | 178.2 |
| ---▼--- SEQ ID NO.77 VHVL x CEA I | 538.6 |
| ·····◆ Negative Control | n.a. |

| Sol. CEA [µg/ml] | 0 | 0.1 | 1 |
|---|---|---|---|
| A240 VL – B9 VH x SEQ ID NO.77 VHVL EC50 [pg/ml] | 1.0 | 1.0 | 8.9 |

High Resolution Cation Exchange Chromatography
of A240 VL–B9 VH x SEQ ID NO.77 VHVL

FIGURE 24

Protein stability testing of A240 VL-B9 VHxSEQ ID NO.77 VHVL in human plasma

| | EC 50 [pg/ml] |
|---|---|
| ■ Incubation for 24 h in plasma at 37 °C | 4.0 |
| ▲ Incubation for 24 h in plasma at 4 °C | 16.5 |
| ● Protein dilution immediately before the assay in RPMI | 7.1 |
| ♦ Protein dilution immediately before the assay in plasma | 9.4 |

High Resolution Cation Exchange Chromatography of SEQ ID NO.77 VHVLxE12 VH–A240 VL

Protein stability testing of SEQ ID NO.77 VHVLxE12 VH–A240 VL in human plasma

|  | EC 50 [pg/ml] |
|---|---|
| ■ Incubation for 24 h in plasma at 37 °C | 111.4 |
| ▲ Incubation for 24 h in plasma at 4 °C | 214.0 |
| ● Protein dilution immediately before the assay in RPMI | 159.5 |
| ♦ Protein dilution immediately before the assay in plasma | 59.1 |

| Sol. CEA [µg/ml] | 0 | 0.1 | 1 |
|---|---|---|---|
| SEQ ID NO.77 VHVL x E12 VH - A240 VL EC50 [pg/ml] | 28.2 | 37.6 | 55.3 |

PHARMACEUTICAL COMPOSITIONS WITH RESISTANCE TO SOLUBLE CEA

The present application is a continuation of U.S. application Ser. No. 12/158,611, filed Jun. 20, 2008, now allowed, which is a national stage filing under 35 U.S.C. §371 of PCT Application No.: PCT/EP06/012425, filed on Dec. 21, 2006, which claims benefit of U.S. Application Ser. No. 60/780,861, filed on Mar. 10, 2006; and claims benefit of U.S. Application Ser. No. 60/751,963 filed on Dec. 21, 2005, and which also claims priority to EP 05028064.3 filed on Dec. 21, 2005; and all of the disclosures of which are incorporated herein by reference in their entirety.

More than three decades have passed since Gold and Freedman first described the tumor associated carcinoembryonic antigen (CEA) in human colon cancer tissue extracts (Gold and Freedman; J. Exp. Med. 122 (1965); 467-481).

Meanwhile, 28 other genes/pseudogenes relating to the CEA gene family have been discovered. In an attempt to simplify the nomenclature used for the members of the CEA gene family, the family has recently been renamed the "CEA-related cellular adhesion molecules" (CEACAMs) and the nomenclature for its members has been unified (Beauchemin, Exp. Cell Res. 252 (1999), 243-249). For example, according to this nomenclature, human CEA (CD66e) is termed CEACAM5.

The human CEA gene family is clustered on chromosome 19q13.2 (Olsen et al. Genomics 23 (1994); 659-668). Its 29 genes and pseudogenes can be divided into three subgroups, i.e. the CEA subgroup containing seven expressed genes, the pregnancy-specific-glycoprotein (PSG) subgroup containing eleven expressed genes and the third subgroup which contains only pseudogenes (Hammarström, Sem. Cancer Biol. 9 (1999), 67-81; Beauchemin, Exp. Cell Res. 252 (1999), 243-249). The analysis of the amino acid sequences of CEA and the other family members revealed that they belong to the immunoglobulin (Ig) superfamily (Williams and Barclay, Annul. Rev. Immunol. 6 (1988), 381-405). All members of the CEA subgroup are attached to the cell surface membrane: Biliary glycoprotein (CEACAM1; BGP1; TM-CEA; CD66a), CEA gene family member 1 (CEACAM3; CGM1; CD66d) and CEA gene family member 7 (CEACAM4; CGM7) have hydrophobic transmembrane domains, whereas carcinoembryonic antigen (carcinoembryonic antigen-related cell adhesion molecule 5; CEACAM5; CEA; CD66e), non-specific cross-reacting antigen (CEACAM6; NCA; NCA-50/90; CD66c), CEA gene family member 2 (CEACAM7; CGM2) and CEA gene family member 6 (CEACAM8; CGM6; CD66b) are linked to the plasma membrane by glycosylphosphatidylinositol (GPI) lipid moieties. The CEA proteins are highly glycosylated with a molecular weight of up to approximately 300 kDa, depending on the number of Ig domains.

As regards the biological activity of the CEA proteins, in vitro studies with tumor cell lines suggested that several CEA subfamilies including biliary glycoprotein, CEA and non-specific cross-reacting antigen can act as homophilic and heterotypic cell adhesion molecules when expressed on the tumor cell surface (Oikawa et al., Biochem. Biophys. Res. Commun. 186 (1992), 881-887; Zhou et al., Cancer Res. 53 (1993), 3817-3822). More recently, a possible role of CEA and non-specific cross-reacting antigen in the innate immune defense protecting colon from microbial attack has been discussed (Hammarström and Baranov, Trends Microbiol. 9 (2001), p. 119-125). In particular, it has been proposed that these proteins bind and trap microorganisms preventing them from reaching and invading the epithelial cells of the microvilli.

It was hypothesized that CEA is an oncofetal antigen which is expressed during fetal life, absent in the healthy adult and re-expressed in cancer. However, CEA is also expressed in normal adult tissue. For instance, biliary glycoprotein, CEA, non-specific cross-reacting antigen and CEA gene family member 2 are expressed in normal human colon, particularly in the mature columnar epithelial cells facing the gut lumen and in the highly differentiated cells at the crypt mouth (Frängsmyr et al., Cancer Res. 55 (1995), 2963-2967; Frangsmyr et al., Tumor Biol. 20 (1999), 277-292). More specifically, these proteins are localized to the brush-border glycocalyx of the mature colonocytes lining the free luminal surface. Biliary glycoprotein, CEA and non-specific cross-reacting antigen are also expressed in a number of tumors of epithelial origin (Hammarström, Sem. Cancer Biol. 9 (1999), 67-81; Shively and Beatty CRC Crit. Rev. Oncol. Hematol. 2 (1985), 355-399).

Already in the late 1970s and early 1980s, CEA became a favored target antigen for radioimmunolocalization of colorectal and other epithelial tumors. This is due to the fact that CEA is overexpressed in 95% of gastrointestinal and pancreatic cancers, as well as in most small-cell and non-small-cell lung carcinomas. It is also expressed in breast carcinoma and squamous cell carcinoma of the head and neck (Primus et al., Cancer 42 (1978), 1540-1545). In fact, CEA is one of the most extensively used clinical tumor markers. It is used as a serum tumor marker for colorectal and some other cancers due to its stability, its fairly restricted expression in normal adult tissue and its high expression in tumors of epithelial origin. The bulk of CEA in a healthy individual is produced in colon. There it is released from the apical surface of mature columnar cells into the gut lumen and disappears with the feces. Thus, only very low levels are normally seen in the blood from healthy individuals. For instance, CEA levels in the blood of healthy individuals is less than 2 µg/l. In contrast, CEA levels in serum from patients with colorectal and other carcinomas are increased, ranging up to more than 2000 µg/l (Thomson et al., PNAS 64 (1969), 161-167). In particular, progressive, malignant, or late stage epithelial tumors are frequently accompanied by high serum concentrations of soluble CEA (Fletcher; Ann. Intern. Med. 104 (1986), 66-73). It is known that components from the plasma membrane, including CEA, are continually exfoliated from the surface as plasma membrane-derived vesicles (Taylor and Black, J. Natl. Cancer Inst. 74 (1985), 859-866; Sack et al., J Clin Invest. 82 (1988), 586-93) which through draining lymph and blood vessels can end up in the blood. As the tumor size increases, more CEA will accumulate in the blood. The main use of serum CEA determinations as a tumor marker is in the post-surgical surveillance of colon cancer. Increased CEA levels was the first indicator of recurrent disease in 81% (Minton et al., Cancer 55 (1985), 1284-1290) and 89% (Wanebo et al., Surg. Gynecol. Obstet. 169 (1989), 479-487) of patients, respectively. Serum CEA levels can also be used as a prognostic indicator (Mulcahy and Benson, Curr. Oncol. Rep. 1 (1999), 168-172).

Due to its over-expression in many epithelial cancers CEA is not only used as a tumor marker but also as a target for anti-tumor therapy. For example, gastrointestinal cancers account for a large proportion of human epithelial tumors, with an estimated 21.700 new cases of gastric cancer and 135.400 new cases of colorectal cancer in the United States in the year 2001 (Greenlee; C A Cancer J Clin 51 (2001), 15-36). Colorectal cancer is the third most common malignancy and the third leading cause of death from cancer in both males and females (Ries; Cancer 88 (2000), 2398-2424). In an attempt to find new therapeutics against these tumors, anti-CEA monoclonal antibodies have been explored as possible therapeutics for CEA-positive cancers (Murakami et al., Immunol. Invest. 25 (1996), 23-35).

One example for an approach in which patients with low tumor load (corresponding to low serum CEA levels) have been successfully treated is a study performed by Behr et al. In this approach, a $^{131}$I-labeled variant of labetuzumab (labetuzumab is a humanized form of anti-CEA monoclonal antibody MN-14; Behr et al., Cancer, 94: 1373-1381, (2002), 1559-64) has been analysed in a phase II trial in which 30 CRC patients with small volume metastatic disease chemorefractory to 5-fluorouracil and folinic acid or in an adjuvant setting after liver metastasis have been enrolled. A single injection of $^{131}$I-labeled labetuzumab was given. Of 19 assessable patients, 3 had partial remissions and eight showed minor responses up to 15 months in duration. In the adjuvant setting, 7 of 9 patients were disease free for up to 3 years, whereas the relapse rate in the control group was 67% in the same time period. The serum CEA levels of the patients ranged from 3.9-45 ng/ml (Behr et al., Cancer, 94: 1373-1381, 2002). In another study characterized by patients with low CEA serum levels (<5 ng/ml), CEA radio-immunotherapy with $^{131}$I-labetuzumab (loc. cit.) has been shown to improve survival post salvage resection of colorectal cancer metastases in the liver. 23 patients received a dose of 40-60 mCi/m$^2$ $^{131}$I-labetuzumab. Five-year survival was 51.3% for treated and 7.4% for control groups, respectively (Liersch et al., JCO, 2005, ASCO Proc, Vol 23, No 16S: 3627).

Yet, therapeutic approaches dealing with high serum CEA concentrations frequently resulted in low or no anti-tumor responses. For example, in a clinical study performed to evaluate a humanized anti-CEA monoclonal antibody in clinic, a CDR-grafted version of MN-14 (hMN-14; Sharkey, Cancer Res. 55 (23 Suppl) (1995) 5935s-5945s.) has been labeled with $^{131}$I. 19 patients with advanced CEA-producing tumors received $^{131}$I labeled hMN-14. The biodistribution, tumor targeting, and pharmacokinetic behavior of the hMN-14 was similar to that seen with the murine MN-14. However, patients with elevated CEA (>200 ng/ml) in plasma had more than 30% of the labeled antibody complexed within 1 h after injection. In some of these patients, increased complication resulted in enhanced metabolism of the antibody with more rapid clearance from the blood than that seen in patients with lower plasma CEA (Sharkey, loc. cit.). In another phase I trial carried out by Yu et al., an $^{131}$I-labeled high-affinity murine monoclonal antibody (mAb) against CEA, COL-1 (Muraro, Cancer Res. 45 (1985), 5769-80), has been investigated in patients with gastrointestinal malignancies. In particular, the influence of serum CEA and tumor bulk on pharmacokinetics has been analysed. To this end, 18 patients with advanced gastrointestinal malignancies received 20 mg of COL-1 labeled with $^{131}$I, with doses from 10 mCi/m$^2$ to 75 mCi/m$^2$. Serum CEA level ranged from 6 to 2739 ng/mL (mean+/−SD, 500+/−639). 82% of all tumor-involved organs were positive and 58% of all lesions. However, it has been again observed that elevated serum CEA (>500 ng/mL) and tumor bulk directly correlated with clearance of serum radioactivity. The authors concluded that patients with highly elevated circulating CEA levels and/or increased tumor bulk clear $^{131}$I-labeled COL-1 more rapidly from the circulation (Yu et al., J. Cli. Oncol. 14 (1996), 1798-1809). Similar results have been obtained in a study by Hajjar et al. with iodine-131-labeled humanized MN-14 anti-CEA monoclonal antibody in patients with metastatic gastrointestinal and colorectal cancer. In this phase I trial, 21 patients either after prior external beam radiation or after standard chemotherapy have been treated with antibody. 7 of 21 patients had human anti-human antibodies (HAHAs), but no adverse effects. No antitumor response was observed. Again it has been found that elevated plasma CEA levels increase the clearance of the antibody from the blood and whole body (Hajjar et al., Clin Colorectal Cancer, 2 (2002), 31-42) which at least in part may provide for an explanation of the lacking anti-tumor response observed in this study. The phenomenon of rapid clearance of therapeutic antibody from blood and body may be explained by increased formation of immune complexes which have to be rapidly removed from the body in order to prevent organ damage. No therapeutic effect could be observed in the tumor patients enrolled in these studies, most probably due to the rapid clearance of the monoclonal antibodies.

In order to circumvent problems caused by immune complex formation and rapid clearance of therapeutic monoclonal antibodies which are most likely mediated by the Fc part of the antibodies recognized by Fc receptors of immune cells, antibody derivatives (e.g. scFv constructs) or fragments (e.g. Fab and Fab$_2$ fragments) without Fc part have been produced and analysed in clinic. Most of these studies are directed to tumor imaging and detection/localization (see e.g. Chester et al., Cancer Chemother Pharmacol, 46 (2000) Suppl: S8-12; Mayer et al., Clin Cancer Res, 6: (2000) 1711-1719; Begent et al., Nat Med, 2 (1996): 979-984). Only a few studies investigated the therapeutic efficacy of such antibody derivatives/fragments in clinic. For example, in a clinical approach by Francis et al. (Francis, Br. J. Cancer 87(6) (2002), 600-607) anti-tumor activity of a scFv-carboxypeptidase construct has been investigated. In this phase I trial, the antibody directed enzyme prodrug therapy (AD-EPT) has been used in patients with advanced colorectal carcinoma or other CEA producing tumours. To this end, A5CP, consisting of a F(ab)$_2$ fragment of a mouse monoclonal antibody to CEA (A5B7) linked to the bacterial enzyme carboxypeptidase (CPG2) as the antibody-enzyme targeting agent and ZD2767P, a bis-iodo phenol mustard prodrug have been utilized. As a result, no clinical or radiological responses have been seen in the study. Pre-treatment serum CEA levels ranged up to 1000 ng/ml. These high CEA concentrations in serum of the treated tumor patients may be at least in part responsible for the lacking anti-tumor response observed in this study.

In view of the problems set forth above, the provision of means and methods for efficient therapeutics for progressive, malignant, or late stage epithelial tumors is highly desirable.

Accordingly, one aspect of the invention relates to a pharmaceutical composition, said pharmaceutical composition comprising a bispecific single chain antibody which has
(a) a first binding domain specifically binding to human CD3, and
(b) a second binding domain specifically binding to human CEA, wherein said second binding domain comprises at least the amino acid sequence "DX$_1$X$_2$X$_3$X$_4$FYFDY" (SEQ ID NO. 65), wherein "X$_1$", "X$_2$", "X$_3$" or "X$_4$" represents any amino acid residue, and the amino acid residue "D" corresponds to Kabat position 95 of CDR-H3 of murine monoclonal antibody A5B7 and the amino acid residues "FYFDY" correspond to Kabat positions 100, 100a, 100b, 101, and 102, respectively, of CDR-H3 of murine monoclonal antibody A5B7. In one embodiment, "$X_1$" represents "R" (Arginine), "F" (Phenylalanine), "M" (Methionine), "E" (Glutamic acid), or "T" (Threonine); "$X_2$" represents "G" (Glycine), "Y" (Tyrosine), "A" (Alanine), "D" (Aspartic acid), or "S" (Serine); "$X_3$" represents "L" (Leucine), "F" (Phenylalanine), "M" (Methionine), "E" (Glutamic acid), or "T" (Threonine); and "$X_4$" represents "R" (Arginine), "Y" (Tyrosine), "A" (Alanine), "D" (Aspartic acid), or "S" (Serine).

In an embodiment of the pharmaceutical composition of the invention, said second binding domain specific for human CEA of the bispecific single chain antibody defined herein comprises at least the amino acid sequence "DRGLRFYFDY" (SEQ ID NO. 66) corresponding to Kabat positions 95-102 of the CDR-H3 of murine monoclonal antibody A5B7.

The present invention provides means and methods particularly suited for the treatment of epithelial tumor patients with high soluble CEA concentrations in their plasma. Such high soluble CEA concentrations are found in the serum/plasma of epithelial tumor patients with progressive tumors, recurrent, metastatic, late stage tumors and for patients with high tumor load/burden. It has been found that bispecific single chain antibodies with a CEA binding domain comprising the amino acid sequence "DRGLRFYFDY" (SEQ ID NO. 66) not only bind to CEA-positive target cells, but also to soluble CEA; see Example 3 and FIG. 2 of the present invention; and EP B1 491031. The indicated amino acid sequence "DRGLRFYFDY" corresponds to Kabat positions 95-102 (SEQ ID NO. 66) of the CDR-H3 of murine monoclonal antibody A5B7 (Harwood, Br J. Cancer. 54 (1986), 75-82). Surprisingly, although binding to soluble CEA, said bispecific single chain antibodies kill CEA-bearing tumor cells, even in the presence of high concentrations of soluble CEA (up to 1 µg/ml soluble CEA has been tested). Put in other words, said bispecific constructs are not inhibited by soluble CEA in their cytotoxic activity against CEA-positive tumor cells.

Figure 10:
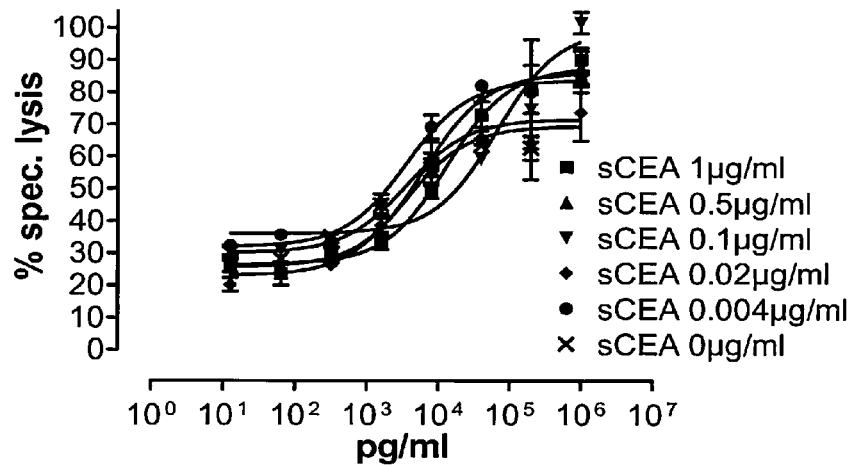
Figure 10:
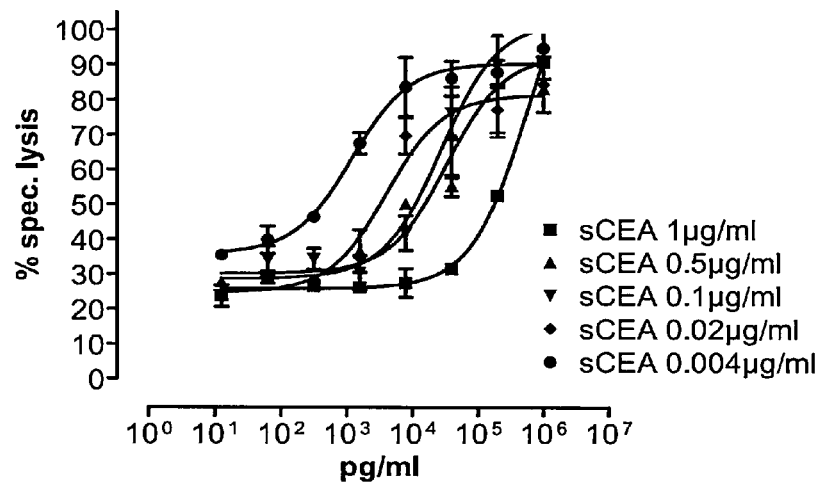

As shown in the following Examples 5 and 8 (in combination with FIGS. 5, 6, 8, 10, 19, 20, 22 and 27), bispecific single chain antibodies with a CEA binding domain comprising the amino acid sequence "DRGLRFYFDY" mediated cytotoxicity to CEA-positive tumor cells, in the presence of even high concentrations of soluble CEA. For instance, FIG. 10 shows a cytotoxicity assay of CEA-reactive bispecific single chain constructs redirected to Kato III cells (CEA-positive human gastric carcinoma cell line) in the presence of increasing amounts of soluble CEA antigen. Stimulated human CD8 positive cytotoxic T cells (CTLs) were used as effector cells. CEAI VHVL×SEQ ID NO.77 VHVL-mediated cytotoxicity is resistant to soluble CEA. In contrast, CEAII VHVL×SEQ ID NO.77 VHVL-mediated cytotoxic activity is inhibited by increasing amounts of soluble CEA. CEAI is a variable region derived from murine mAb A5B7, whereas CEAII VHVL is derived from mAb T84.66.

Importantly, it has been found that the amino acid sequence "DRGLRFYFDY" is sufficient to mediate resistance to soluble CEA when used in a human CEA-binding domain (i.e. a human binding domain specifically binding to human CEA) of anti-CEA×anti-CD3 bispecific single chain antibodies; see e.g. FIGS. 19, 20, 22 and 27. In the following, bispecific single chain antibodies as defined herein are therefore referred to as being resistant to soluble CEA antigen. The term "resistance to soluble CEA antigen", "resistant to soluble CEA" or related terms as used herein refers to the fact that the cytotoxicity against CEA-positive target or tumor cells mediated by said bispecific single chain antibodies is not affected by increasing concentrations of soluble CEA. In particular, the cytotoxic activity is not inhibited by even high concentrations of soluble CEA (up to 1 µg/ml has been tested). As set forth above, CEA levels in the blood of healthy individuals is less than 2 ng/ml. High soluble CEA concentrations in the serum/plasma of tumor patients are characteristic for progressive, recurrent, metastatic, or late stage tumors and for patients with high tumor load. Thus, the present invention provides means and methods particularly suited for the treatment of epithelial tumor patients with such high soluble CEA concentrations in their plasma. The term "high soluble CEA concentrations" as used herein denotes a soluble serum/plasma-CEA concentration higher than 10, 20, 50, 70, 80, 90 or 100 ng/ml. This serum/plasma-CEA concentration may be determined, inter alia, by ELISA. Preferably, said soluble serum/plasma-CEA concentration is higher than 100 ng/ml, as determined e.g. by ELISA.

The generation of said bispecific single chain antibodies with resistance to soluble CEA antigen was no trivial task, as evident from the following Examples. For instance, bispecific single chain antibodies with a CEA binding domain derived from a monoclonal antibody (mAb) known to bind membrane-bound CEA but not soluble CEA, i.e. mAb PR1A3 (Durbin, Proc Natl Acad Sci USA. 91 (1994), 4313-7), could not be produced: When used in the bispecific single chain antibody format, no expression/secretion of the anti-CD3×anti-CEA bispecific single chain construct could be achieved. When a humanized version of PR1A3 (Durbin, loc. cit.) has been utilized for the generation, the bispecific single chain antibody construct was expressed and secreted from the host cell. However, no binding of the anti-CEA binding domain to membrane-bound CEA could be obtained.

Figure 7:
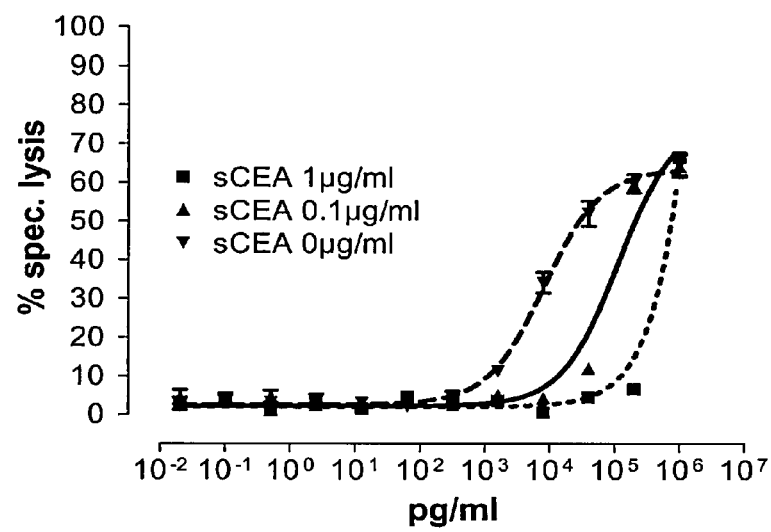

When bispecific single chain antibodies derived from the well-described monoclonal antibodies T84.66 (Neumaier, M. et al., Cancer Res 50 (1990), 2128-34) or MFE-23 (Boehm, M. K. Biochem J 2 (2000), 519-28) have been generated, these bispecific antibodies were highly sensitive to soluble CEA antigen, ie. their cytotoxic activity against CEA-positive target or tumor cells has been blocked in the presence of soluble CEA antigen. Since said constructs have been found to bind to soluble CEA, it was concluded that soluble CEA antigen prevents the antibody from binding to membrane-bound CEA, thereby blocking antibody-mediated cytotoxic activity. For example, FIG. 7 shows a cytotoxicity assay of a CEA-reactive bispecific single chain construct redirected to CHO cells transfected with CEA in the presence of soluble human CEA. Stimulated human CD8 positive cytotoxic T cells (CTLs) were used as effector cells. Cytotoxic activity of CEAII VHVL×SEQ ID NO.77 VHVL is clearly inhibited by increasing amounts of soluble CEA. CEAII VHVL is derived from mAb T84.66; SEQ ID NO.77 is an anti-CD3 VH-VL domain.

Resistance to soluble CEA antigen could be found only for bispecific single chain antibodies, the CEA binding domain of which comprised the amino acid sequence "DRGLRFYFDY" of the CDR-H3 of murine monoclonal antibody A5B7 (Harwood, Br J. Cancer. 54 (1986), 75-82). As for MFE-23- and T84.66-derived bispecific single chain constructs, A5B7-derived bispecific single chain antibodies bind to soluble CEA. In light of the results obtained for MFE-23- and T84.66-derived bispecific single chain constructs, it could not be expected that soluble CEA does not influence cytotoxic activity in A5B7-derived single chain bispecific antibody constructs.

As set forth above, many therapeutic approaches directed against CEA-bearing epithelial tumors in human are seriously hampered by the presence of high levels of soluble CEA antigen in the plasma of patients cancer. For example, increased immune-complex formation and clearance of therapeutic anti-CEA monoclonal antibodies in the presence of high CEA concentrations in plasma has been observed in several clinical studies. In addition, soluble CEA antigen—frequently present in high concentrations in the serum of cancer patients with progressive tumors, recurrent cancer, metastasic tumors, high tumor load/burden, or late-stage tumors—blocks the therapeutics directed against CEA-positive tumor cells, thus preventing tumor cell recognition and destruction. Therefore, the actual amount of the therapeutic which reaches the tumor is reduced, resulting in a decreased, low or even no anti-tumor activity. This limitation so far restricts e.g. antibody-based approaches to those patients with very low amounts of soluble CEA antigen unlikely to prevent therapeutic-tumor cell interaction.

In the present invention, it has been found that it is possible to generate bispecific single chain antibody-therapeutics with specificity for human CD3 and human CEA, wherein the cytotoxic activity directed against tumor cells is resistant to even high concentrations of soluble CEA antigen (up to 1 μg/ml soluble CEA have been tested). This finding is entirely unexpected in view of the fact that the bispecific single chain antibodies of the invention binds to soluble CEA antigen (see Example 3 and FIG. 2 of the present invention; see also EP B1 491031). Nevertheless, the bispecific single chain antibodies as defined herein are entirely resistant to the presence of even high levels of soluble CEA in its cytotoxic activity towards tumor cells. Thus, the present invention provides means and methods particularly suited for the treatment of tumor patients with high soluble CEA concentrations in their plasma, as observed e.g. during tumor progression, for recurrent cancer, for metastasis, for patients with high tumor load/burden, or late-stage tumors.

In accordance with this invention, the term "pharmaceutical composition" relates to a composition for administration to a human patient. Preferably, the pharmaceutical composition comprises suitable formulations of carriers, stabilizers and/or excipients. In a preferred embodiment, the pharmaceutical composition comprises a composition for parenteral, transdermal, intraluminal, intraarterial, intrathecal and/or intranasal administration or by direct injection into tissue. It is in particular envisaged that said composition is administered to a patient via infusion or injection. Administration of the suitable compositions may be effected by different ways, e.g., by intravenous, intraperitoneal, subcutaneous, intramuscular, topical or intradermal administration. The composition of the present invention may further comprise a pharmaceutically acceptable carrier. Examples of suitable pharmaceutical carriers are well known in the art and include phosphate buffered saline solutions, water, various types of wetting agents, sterile solutions, liposomes, etc. Compositions comprising such carriers can be formulated by well known conventional methods. These compositions can be administered to the subject at a suitable dose which can be determined e.g. by dose escalating studies by administration of increasing doses of the bispecific single chain antibody exhibiting resistance to soluble serum CEA antigen described herein. As set forth above, the bispecific single chain antibody described herein with resistance to soluble serum CEA antigen can be advantageously used in the treatment of cancer patients with high CEA serum concentrations, such as progressive tumors, recurrent cancer, metastatic tumors, high tumor load/burden, or late stage tumors.

These compositions can also be administered in combination with other proteinaceous and non-proteinaceous drugs, e.g. in the form of a co-therapy. These drugs may be administered simultaneously with the composition comprising the bispecific single chain antibody as defined herein or separately before or after administration of said bispecific antibody in timely defined intervals and doses. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Preparations for parenteral administration include sterile aqueous or non-aqueous solutions, and suspensions. Examples of non-aqueous solvents are propylene glycol, polyethylene glycol, vegetable oils, and injectable organic esters such as ethyl oleate. Aqueous carriers include water, aqueous solutions, or suspensions, including saline and buffered media. Parenteral vehicles include sodium chloride solution, Ringer's dextrose, dextrose and sodium chloride, or lactated Ringer's. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the composition of the present invention might comprise proteinaceous carriers, like, e.g., serum albumin or immunoglobulin, preferably of human origin. It is envisaged that the co-therapy comprise, in addition to the bispecific single chain antibody as defined herein, further biologically active agents, depending on the intended use of the composition. Such agents might be drugs acting on the gastro-intestinal system, drugs acting as antineoplastic agents, chemotherapeutics, cytostatica, drugs preventing hyperurikemia, drugs inhibiting immunoreactions (e.g. corticosteroids), drugs modulating the inflammatory response, drugs acting on the circulatory system and/or agents such as cytokines known in the art.

Preferably, the bispecific single chain antibody as defined herein is formulated in a buffer, a stabilizer and a surfactant. The buffer may be a phosphate, citrate, succinate or acetate buffer. The stabilizer may be (an) amino acid(s) and/or a sugar. The surfactants may be detergents, PEGs, or the like. More preferably, the bispecific single chain antibody as defined herein is formulated in citrate, lysine, trehalose and Tween 80. As a diluent for the pharmaceutical composition of the invention, isotonic saline and Tween 80 is preferred.

As used herein, a "bispecific single chain antibody" denotes a single polypeptide chain comprising two binding domains. Each "binding domain" as used herein comprises one variable region from an antibody heavy chain ("VH region"), wherein the VH region of the first binding domain specifically binds to said first molecule, i.e. the human CD3 molecule, and the VH region of the second binding domain specifically binds to human CEA, as defined in more detail below. The two binding domains are optionally linked to one another by a short polypeptide spacer generally comprising on the order of 5 amino acids. Each binding domain may additionally comprise one variable region from an antibody light chain ("VL region"), the VH region and VL region within each of the first and second binding domains being linked to one another via a polypeptide linker, for example of the type disclosed and claimed in EP B1 623679, but in any case long enough to allow the VH region and VL region of the first binding domain and the VH region and VL region of the second binding domain to pair with one another such that, together, they are able to specifically bind to the respective first and second molecules. The arrangement of the V regions of the first or second binding domain may be VH-VL or VL-VH. Preferably, the arrangement of the first binding domain specifically binding to human CD3 is VH-VL, as shown in the following Examples. It is envisaged that the first binding domain may be located N-terminally or C-terminally to the second binding domain. Thus, the arrangement of the binding domains of the bispecific single chain antibodies defined herein may be VH$_{CEA}$-VL$_{CEA}$-VH$_{CD3}$-VL$_{CD3}$, VL$_{CEA}$-VH$_{CEA}$-VH$_{CD3}$-VH$_{CD3}$, VH$_{CD3}$-VL$_{CD3}$-VH$_{CEA}$-VL$_{CEA}$ or VH$_{CD3}$-VH$_{CD3}$-VH$_{CEA}$-VH$_{CEA}$. Preferably, said first binding domain specific for CD3 is located C-terminally to the second binding domain. More preferably, the binding domains of the bispecific single chain antibodies defined herein are arranged in the order VH$_{CEA}$-VL$_{CEA}$-VH$_{CD3}$-VL$_{CD3}$ or VL$_{CEA}$-VH$_{CEA}$-VH$_{CD3}$-VL$_{CD3}$. Even more preferred, the arrangement is VL$_{CEA}$-VH$_{CEA}$-VH$_{CD3}$-VL$_{CD3}$. Most preferred is the bispecific single chain antibody construct A240 VL-B9 VH×SEQ ID NO. 77 VHVL as defined in SEQ ID NO. 34. It is envisaged that said first and/or second binding domains of the bispecific single chain antibodies defined herein may be of non-human origin (i.e. derived from non-human sequences). For example, said first and/or second binding domains may be derived from murine monoclonal antibodies. However, bispecific single chain antibodies derived from murine antibodies may be recognised as foreign, when being administered to human patients. Thus, said first and/or second binding domains of the bispecific single chain antibodies defined herein are preferably of human origin (i.e. derived from human sequences). Such human binding domains specifically binding to CEA or CD3 may be identified e.g. by phage display-based techniques. It is also envisaged that e.g. the VH region of the first (or second) binding domain is a human VH region, whereas the corresponding VL region of the first (or second) binding domain may be of non-human origin. Such binding domains may be also referred to as chimeric binding domains. Or one of said binding domains is of non-human origin, whereas the other is of human origin, resulting in a chimeric bispecific single chain antibody. Said first and/or second binding domains may be further modified in order to reduce the immunogenicity of the bispecific single chain antibody described herein, when being administered to human patients. For example, at least one of said first or second binding domains of the bispecific single chain antibodies defined herein may be humanized, CDR-grafted, chimeric and/or deimmunized or human, as set forth in more detail below. It is also envisaged that the polypeptide linker linking the VH and VL region within the first and/or second binding domain is deimmunized. Preferably, the polypeptide linker linking the VH and VL region within the deimmunized first binding domain (specific for CD3) is a deimmunized polypeptide linker having the sequence "GEGTSTGS (G$_2$S)$_2$GGAD" (SEQ ID NO. 141). It is furthermore envisaged, that one or both of said binding domains of the bispecific single chain antibodies defined herein carry so-called "tags" which may be used e.g. for protein expression, purification, detection or enrichment, such as Flag-tags, c-myc-tags, GST-tags or His-tags. For example, for the Flag-tag the most widely used hydrophilic octapeptide now is DYKDDDDK (Chubet and Brizzard, Biotechniques 20 (1996):136-141) though recent studies suggest that a shorter peptide, DYKD, can be recognized with almost the same affinity by the M1 monoclonal antibody (Knappik A, Pluckthun A; Biotechniques 17 (1994):754-761). Flag-tags, c-myc-tags, GST-tags, His-tags or the like may be positioned either at the N-terminus or the C-terminus of the bispecific single chain antibodies such as, for instance, tag-VH$_{CEA}$-VL$_{CEA}$-VH$_{CD3}$-VL$_{CD3}$ or VL$_{CEA}$-VH$_{CEA}$-VH$_{CD3}$-VL$_{CD3}$-tag. The sources for and properties of such tags for expression, detection or purification purposes are well described in the art; see e.g. Lichty, Protein Expr Purif. 41 (2005), 98-105.

As used herein, the term "single-chain Fv" or "scFv" refers to antibody fragments comprising the VH and VL domains of an antibody, wherein these domains are present in a single polypeptide chain. Variable domains can be arranged in the order VH-VL or VL-VH. Generally, the Fv polypeptide further comprises a polypeptide linker between the VH and VL domains which enables the scFv to form the desired structure for antigen binding. For a review of scFv see Pluckthun in The Pharmacology of Monoclonal Antibodies, vol. 113, Rosenburg and Moore eds. Springer-Verlag, New York, pp. 269-315 (1994). In a specific embodiment, the invention relates to anti-CEA scFvs derived from the bispecific single chain antibodies defined herein.

According to the present invention, the term "binding domain" or "variable region" used in the context with Ig-derived antigen-interaction comprises fragments and derivatives of polypeptides which at least comprise one CDR derived from an antibody, antibody fragment or derivative thereof. It is envisaged by the invention, that the second binding domain specifically binding to human CEA of the bispecific single chain antibody defined herein comprises at least one CDR, preferably a CDR-H3, more preferably a part of the CDR-H3 of murine monoclonal antibody A5B7 with the amino acid sequence "FYFDY" (SEQ ID NO. 112) corresponding to Kabat positions 100, 100a, 100b, 101, and 102, respectively, of CDR-H3 of murine monoclonal antibody A5B7; even more preferred with the amino acid sequence "DX$_1$X$_2$X$_3$X$_4$FYFDY" (SEQ ID NO. 65), wherein "X$_1$", "X$_2$", "X$_3$" or "X$_4$" represents any amino acid residue, and the amino acid residue "D" corresponds to Kabat position 95 of CDR-H3 of murine monoclonal antibody A5B7 and the amino acid residues "FYFDY" correspond to Kabat positions 100, 100a, 100b, 101, and 102, respectively, of CDR-H3 of murine monoclonal antibody A5B7. It is envisaged that "X$_1$", "X$_2$", "X$_3$" or "X$_4$" corresponding to Kabat positions 96 ("X$_1$"), 97 ("X$_2$"), 98 ("X$_3$") and 99 ("X$_4$"), respectively, of CDR-H3 of murine monoclonal antibody A5B7, represent amino acid residue "R" (Arginine), "G" (Glycine), "L" (Leucine), "Y" (Tyrosine), "A" (Alanine), "D" (Aspartic acid), "S" (Serine), "W" (Tryptophan), "F" (Phenylalanine) or "T" (Threonine). Herein, it is excluded from the scope of the invention that "X$_1$", "X$_2$", "X$_3$" and "X$_4$" represent the same amino acid, e.g. that "X$_1$", "X$_2$", "X$_3$" and "X$_4$" are all "F" (Phenylalanine). Preferably, "X$_1$" represents "R" (Arginine), "F" (Phenylalanine), "M" (Methionine), "E" (Glutamic acid), or "T" (Threonine); "X$_2$" represents "G" (Glycine), "Y" (Tyrosine), "A" (Alanine), "D" (Aspartic acid), or "S" (Serine); "X$_3$" represents "L" (Leucine), "F" (Phenylalanine), "M" (Methionine), "E" (Glutamic acid), or "T" (Threonine); and "X$_4$" represents "R" (Arginine), "Y" (Tyrosine), "A" (Alanine), "D" (Aspartic acid), or "S" (Serine). Or most preferred the second binding domain specifically binding to human CEA of the bispecific single chain antibody defined herein comprises the complete CDR-H3 of A5B7 with the amino acid sequence "DRGLRFYFDY" (SEQ ID NO. 66) corresponding to Kabat positions 95-102 of the CDR-H3 of A5B7. As shown in the following Examples, the cytotoxic activity against tumor cells of the bispecific single chain antibody defined herein comprising said mAb A5B7-derived CDR-H3 "DRGLRFYFDY" (SEQ ID NO. 66) amino acid sequence in the second binding domain interacting with CEA are resistant to soluble CEA antigen, thereby allowing the treatment of tumor patients with high serum CEA concentrations in their plasma. Determination of CDRs is known to the person skilled in the art; see e.g. http://www.bioinf.org.uk/abs/#cdrid. Numbering of amino acid sequences in antibodies can be carried out e.g. according to the Kabat numbering scheme described in the art; see e.g. Kabat, E. A., T. T. Wu, H. M. Perry, K. S. Gottesman, and C. Foeller. 1991. Sequences of Proteins of Immunological Interest, 5th ed. Bethesda, Md.: National Center for Biotechnology Information, National Library of Medicine.

Most preferably and as documented in the appended examples, the "bispecific single chain antibody" to be employed in the pharmaceutical composition of the invention is a bispecific single chain Fv (scFv) with a deimmunized anti-CD3 binding domain (WO 2005/040220) and a human anti-CEA binding domain comprising at least the amino acid sequence "DRGLRFYFDY" corresponding to Kabat positions 95-102 (SEQ ID NO. 66) of the CDR-H3 of murine monoclonal antibody A5B7. Bispecific single chain molecules are known in the art and are described e.g. in WO 99/54440 or Mack, PNAS, (1995), 92, 7021-7025.

The term "single-chain" as used in accordance with the present invention means that said first and second domain of the bispecific single chain construct are covalently linked, preferably in the form of a co-linear amino acid sequence encodable by a single nucleic acid molecule.

As used herein, "human" refers to the species Homo sapiens. A "human" molecule, e.g. human CEA or human CD3 (CD3 epsilon), is therefore the variant of that molecule as it is naturally expressed in Homo sapiens.

The term "epithelial tumor" as used herein denotes a tumor of epithelial origin which is CEA positive (Cancer Medicine; 6th ed.; Kufe, Donald W.; Pollock, Raphael E.; Weichselbaum, Ralph R.; Bast, Robert C., Jr.; Gansler, Ted S.; Holland, James F.; Frei III, Emil, editors. Hamilton (Canada): BC Decker Inc. 2003; http://www.dkfz.de; http://www.krebsinformationsdienst.de/Krebsarten/index.html). The epithelial tumor to be treated may be a gastrointestinal adenocarcinoma, a breast adenocarcinoma or a lung adenocarcinoma. Said gastrointestinal adenocarcinoma is preferably a colorectal, pancreatic, an oesophageal or a gastric adenocarcinoma. As set forth herein, the pharmaceutical composition of the invention is particularly advantageous for the treatment of patients with progressive tumors, metastasis, recurrent cancer, late stage epithelial tumors, high epithelial tumor load/tumor burden, or tumor patients with a CEA serum concentration higher than 100 ng/ml (as determined e.g. by ELISA), characterized by high levels of soluble CEA antigen in the plasma of the tumor patients. It is also within the scope of the invention that said pharmaceutical composition be used after surgical removal of the primary tumor. For example, disseminated residual tumor cells derived from a CEA producing epithelial tumor also shed CEA into their microenvironments. Thus, in the surrounding of these tumor cells the level of soluble CEA is also high. Accordingly, resistance to soluble CEA of cytotoxic activity of pharmaceutical compositions of the invention is advantageous also for the treatment of minimal residual disease. It is envisaged that said pharmaceutical compositions may be administered in a period in which serum CEA levels decrease (due to the removal of the CEA source, i.e. the primary tumor) in order to kill remaining tumor cells. The pharmaceutical compositions may also be useful after the removal of the primary tumor, in the case that serum CEA levels increase due to the formation of secondary tumors or metastasis. The CEA serum concentration can be determined e.g. by CEA ELISA assays (see e.g. IBL CEA EIA, IBL Hamburg, Germany). As set forth above, in many antibody-based therapeutic approaches, said serum CEA inhibits binding of the antibody to membrane-bound CEA on the tumor cells and blocks the activity of antibody, thereby worsening the success of the anti-tumor therapy.

As used herein, the term "specifically binds" or related expressions such as "specifically binding" or "specific reactivity with/to" etc. refer to the ability of the first and/or second binding domains of the bispecific single chain antibody as defined herein to discriminate between the respective first and/or second molecule to such an extent that, from a pool of a plurality of different molecules as potential binding partners, only said respective first and/or second molecule is/are bound, or is/are significantly bound. Such binding measurements can be routinely performed e.g. on a Biacore apparatus, by ELISA, FACS analysis or the like. More specifically, the first binding domain of the bispecific single chain antibody as defined herein binds to human CD3, preferably human CD3 epsilon. The second binding domain of the bispecific single chain antibodies as defined herein binds to a epithelial tumor antigen, i.e. human CEA (carcinoembryonic antigen, carcinoembryonic antigen-related cell adhesion molecule 5; CEACAM5; CD66e), as set forth below. The term "specifically binding" means in accordance with this invention that the bispecific single chain antibody molecule is capable of specifically interacting with and/or binding to at least two, three, four, five, six, seven, eight or even more amino acids of each of the human target molecule as defined herein. Said term relates to the specificity of the antibody molecule, i.e. to its ability to discriminate between the specific regions of the human target molecule as defined herein. The specific interaction of the antigen-interaction-site with its specific antigen may result in an initiation of a signal, e.g. due to the induction of a change of the conformation of the antigen, an oligomerization of the antigen, etc. Further, said binding may be exemplified by the specificity of a "key-lock-principle". Thus, specific motifs in the amino acid sequence of the antigen-interaction-site and the antigen bind to each other as a result of their primary, secondary or tertiary structure as well as the result of secondary modifications of said structure. The specific interaction of the antigen-interaction-site with its specific antigen may result as well in a binding of said site to the antigen.

The "specific binding" of an antibody is characterized primarily by two parameters: a qualitative parameter (the binding epitope, or where the antibody binds) and a quantitative parameter (the binding affinity, or how strongly it binds where it does). Which epitope is bound by an antibody can advantageously be determined by e.g. known FACS methodology, peptide-spot epitope mapping, mass spectroscopy or peptide ELISA. The strength of antibody binding to a particular epitope may be advantageously be determined by e.g. known Biacore and/or ELISA methodologies. A combination of such techniques allows the calculation of a signal:noise ratio as a representative measure of binding specificity. In such a signal:noise ratio, the signal represents the strength of antibody binding to the epitope of interest, whereas the noise represents the strength of antibody binding to other, non-related epitopes differing from the epitope of interest. Preferably, a signal:noise ratio for an epitope of interest which is about 50-fold higher than for other epitopes different from the epitope of interest may be taken as an indication that the antibody evaluated binds the epitope of interest in a specific manner, i.e. is a "specific binder".

The term "specific binding" or "specific interaction" as used in accordance with the present invention means that the bispecific single chain construct does not or essentially does not cross-react with polypeptides of similar structures. Cross-reactivity of a panel of bispecific single chain construct under investigation may be tested, for example, by assessing binding of said panel of bispecific single chain construct under conventional conditions (see, e.g., Harlow and Lane, Antibodies: A Laboratory Manual, Cold Spring Harbor Laboratory Press, 1988 and Using Antibodies: A Laboratory Manual, Cold Spring Harbor Laboratory Press, 1999) to the polypeptide of interest as well as to a number of more or less (structurally and/or functionally) closely related polypeptides. For example, it is within the scope of the invention that the first binding domain of the bispecific single chain antibody of the invention binds to human CEA (carcinoembryonic antigen; CEACAM5; CEA; CD66e) i.e. both to soluble CEA antigen and to membrane-bound CEA, whereas bispecific antibodies binding to other CEA family members, such as biliary glycoprotein (CEACAM1; BGP1; TM-CEA; CD66a), are excluded from said scope.

Examples for the specific interaction of an antigen-interaction-site with a specific antigen comprise the specificity of a ligand for its receptor. Said definition particularly comprises the interaction of ligands which induce a signal upon binding to its specific receptor. Examples for corresponding ligands comprise cytokines which interact/bind with/to its specific cytokine-receptors. Also particularly comprised by said definition is the binding of an antigen-interaction-site to antigens like antigens of the selectin family, integrins and of the family of growth factors like EGF. Another example for said interaction, which is also particularly comprised by said definition, is the interaction of an antigenic determinant (epitope) with the antigenic binding site of an antibody.

The term "binding to/interacting with" may also relate to a conformational epitope, a structural epitope or a discontinuous epitope consisting of two regions of the human target molecules or parts thereof. In context of this invention, a conformational epitope is defined by two or more discrete amino acid sequences separated in the primary sequence which come together on the surface of the molecule when the polypeptide folds to the native protein (Sela, (1969) Science 166, 1365 and Layer, (1990) Cell 61, 553-6).

The term "discontinuous epitope" means in context of the invention non-linear epitopes that are assembled from residues from distant portions of the polypeptide chain. These residues come together on the surface of the molecule when the polypeptide chain folds into a three-dimensional structure to constitute a conformational/structural epitope.

"CD3" as used herein denotes an antigen that is expressed on T-cells as part of the multimolecular T-cell receptor complex and that consists of at least five different chains, CD3-gamma, -delta, -epsilon, -zeta, and -eta. Clustering of CD3 on T-cells, e.g., by immobilized anti-CD3-antibodies, leads to T-cell activation similar to the engagement of the T-cell receptor but independent from its clone typical specificity. Actually, most anti-CD3-antibodies recognize the CD3 epsilon-chain. The amino acid sequence of human CD3 epsilon is depicted in GenBank accession number NM_000733 and comprises SEQ ID NO. 111.

"CEA" denotes the carcinoembryonic antigen (carcinoembryonic antigen-related cell adhesion molecule 5; CEACAM5; CEA; CD66e), an antigen expressed in a large number of tumors of epithelial origin (Hammarström, Sem. Cancer Biol. 9 (1999), 67-81; Shively and Beatty CRC Crit. Rev. Oncol. Hematol. 2 (1985), 355-399). The amino acid sequence of human CEA is depicted in GenBank accession number NM_004363 and comprises SEQ ID NO. 76.

In the present invention, it has been surprisingly found that it is possible to generate antibody-based therapeutics with specificity for human CD3 and human CEA, wherein the cytotoxic activity directed against tumor cells is resistant to even high concentrations of soluble CEA antigen. This finding is entirely unexpected in view of the fact that the bispecific single chain antibodies of the invention bind to soluble CEA antigen. For example, when bispecific single chain antibody constructs derived from monoclonal antibodies T84.66 or MFE-23 have been generated, these antibodies were highly sensitive to soluble CEA antigen, i.e. their cytotoxic activity has been blocked in the presence of soluble CEA antigen. The inhibition of the cytotoxic activity of said constructs by soluble CEA could also not be overcome by increased amounts of antibody. These constructs have also been found to be capable of binding to soluble CEA. In view of this, it was concluded that soluble CEA antigen prevents the antibody from exerting its cytotoxic activity. In contrast, the bispecific single chain antibodies as defined herein are entirely resistant to the presence of even high levels of soluble CEA in their cytotoxic activity towards tumor cells. Moreover, due to their high cytotoxic activity, said bispecific constructs as defined herein elicit their biological activity at even low concentrations. Hence, low amounts of pharmaceutical compositions comprising the bispecific single chain antibodies as defined herein are sufficient to achieve a therapeutic effect in epithelial tumor patients characterized by high soluble CEA concentrations in their serum/plasma. High soluble CEA concentrations in the serum/plasma of epithelial tumor patients are characteristic for progressive, recurrent, metastatic, or late stage tumors and for patients with high tumor load. Even more surprising, it has been found that the amino acid sequence "DRGLRFYFDY" (SEQ ID NO. 66) corresponding to Kabat positions 95-102 of the CDR-H3 of murine monoclonal antibody A5B7 is sufficient to mediate resistance to soluble CEA antigen when used in a human CEA-binding domain (i.e. human binding domains specifically binding to human CEA) of anti-CEA×anti-CD3 bispecific single chain antibodies. Due to their human origin, said constructs are low or non-immunogenic when being administered to human tumor patients. In summary, the pharmaceutical compositions comprising the bispecific single chain antibodies as defined herein are particularly useful for the treatment of epithelial tumor patients with high soluble CEA concentrations in their plasma, as observed e.g. during tumor progression, for recurrent cancer, for metastasis, for patients with high tumor load/burden, or late-stage tumors.

In another preferred embodiment of the pharmaceutical composition of the invention, said first binding domain specific for CD3 of the bispecific single chain antibodies defined herein is located C-terminally to the second binding domain.

Within the scope of the invention and all embodiments thereof, the order of arrangement of the first and second binding domains on the single polypeptide chain, i.e. within the bispecific single chain antibody defined herein, is relevant. It is envisaged that the arrangement of the binding domains of the bispecific single chain antibodies defined herein may be $VH_{CEA}$-$VL_{CEA}$-$VH_{CD3}$-$VL_{CD3}$, $VL_{CEA}$-$VH_{CEA}$-$VH_{CD3}$-$VL_{CD3}$, $VH_{CD3}$-$VL_{CD3}$-$VH_{CEA}$-$VL_{CEA}$ or $VH_{CD3}$-$VL_{CD3}$-$VL_{CEA}$-$VH_{CEA}$. As shown in the following examples, the advantages as described hereinabove are particularly realizable when the first binding domain (specifically binding to CD3) is located C-terminally to the second binding domain, i.e. closer to the C-terminus of the bispecific single chain antibody than the second binding domain. It is preferred that the first binding domain specifically binding to human CD3 is arranged in the VH-VL orientation. For example, the binding domains of the bispecific single chain antibodies defined herein may be arranged in the order $VH_{CEA}$-$VL_{CEA}$-$VH_{CD3}$-$VL_{CD3}$ or $VL_{CEA}$-$VH_{CEA}$-$VH_{CD3}$-$VL_{CD3}$. As used herein, "N-terminally to" or "C-terminally to" and grammatical variants thereof denote relative location within the primary amino acid sequence rather than placement at the absolute N- or C-terminus of the bispecific single chain antibody. Hence, as a non-limiting example, a first binding domain which is "located C-terminally to the second binding domain" simply denotes that the first binding domain is located to the carboxyl side of the second binding domain within the bispecific single chain antibody, and does not exclude the possibility that an additional sequence, for example a tag as set forth above, or another proteinaceous or non-proteinaceous compound such as a radioisotope, is located at the ultimate C-terminus of the bispecific single chain antibody.

Preferably, said binding domains of the bispecific single chain antibodies defined herein are arranged in the order $VH_{CEA}$-$VL_{CEA}$-$VH_{CD3}$-$VL_{CD3}$ or $VL_{CEA}$-$VH_{CEA}$-$VH_{CD3}$-$VL_{CD3}$. Even more preferred, the arrangement is $VL_{CEA}$-$VH_{CEA}$-$VH_{CD3}$-$VL_{CD3}$. Most preferred is the bispecific single chain antibody construct A240 VL-B9 VH×SEQ ID NO. 77 VHVL as defined in SEQ ID NO. 34.

It is preferred that the second binding domain specifically binding to human CEA of the bispecific single chain antibody defined herein comprises at least one CDR, preferably a CDR-H3, more preferably a part of the CDR-H3 of murine monoclonal antibody A5B7 with the amino acid sequence "FYFDY" (SEQ ID NO. 112) corresponding to Kabat positions 100, 100a, 100b, 101, and 102, respectively, of CDR-H3 of murine monoclonal antibody A5B7; even more preferred with the amino acid sequence "$DX_1X_2X_3X_4FYFDY$" (SEQ ID NO. 65), wherein "$X_1$", "$X_2$", "$X_3$" or "$X_4$" represents any amino acid residue, and the amino acid residue "D" corresponds to Kabat position 95 of CDR-H3 of murine monoclonal antibody A5B7 and the amino acid residues "FYFDY" correspond to Kabat positions 100, 100a, 100b, 101, and 102, respectively, of CDR-H3 of murine monoclonal antibody A5B7. Herein, "$X_1$", "$X_2$", "$X_3$" and "$X_4$" correspond to Kabat positions 96 ("$X_1$"), 97 ("$X_2$"), 98 ("$X_3$") and 99 ("$X_4$"), respectively, of CDR-H3 of murine monoclonal antibody A5B7. It is envisaged that "$X_1$", "$X_2$", "$X_3$" or "$X_4$" represent amino acid residue "R" (Arginine), "G" (Glycine), "L" (Leucine), "Y" (Tyrosine), "A" (Alanine), "D" (Aspartic acid), "S" (Serine), "W" (Tryptophan), "F" (Phenylalanine) or "T" (Threonine). Herein, it is excluded from the scope of the claims of the invention that "$X_1$", "$X_2$", "$X_3$" and "$X_4$" represent the same amino acid, e.g. that "$X_1$", "$X_2$", "$X_3$" and "$X_4$" are all "F" (Phenylalanine). Preferably, "$X_1$" represents "R" (Arginine), "F" (Phenylalanine), "M" (Methionine), "E" (Glutamic acid), or "T" (Threonine); "$X_2$" represents "G" (Glycine), "Y" (Tyrosine), "A" (Alanine), "D" (Aspartic acid), or "S" (Serine); "$X_3$" represents "L" (Leucine), "F" (Phenylalanine), "M" (Methionine), "E" (Glutamic acid), or "T" (Threonine); and "$X_4$" represents "R" (Arginine), "Y" (Tyrosine), "A" (Alanine), "D" (Aspartic acid), or "S" (Serine). Even more preferred, the second binding domain specific for human CEA comprises at least the amino acid sequence "RFYFDY" (SEQ ID NO. 113), "LRFYFDY" (SEQ ID NO. 114), "GLRFYFDY" (SEQ ID NO. 115), or "RGL-RFYFDY" (SEQ ID NO. 116) of CDR-H3 of monoclonal antibody A5B7. Most preferred is the complete CDR-H3 of A5B7 with the amino acid sequence "DRGLRFYFDY" (SEQ ID NO. 66) corresponding to Kabat positions 95 ("D"; Aspartic acid), 96 ("R"; Arginine), 97 ("G"; Glycine), 98 ("L"; Leucine), 99 ("R"; Arginine), 100 ("F"; Phenylalanine), 100a ("Y"; Tyrosine), 100b ("F"; Phenylalanine), 101 ("D"; Aspartic acid), and 102 ("Y"; Tyrosine), respectively. Numbering according to the Kabat system is set forth e.g. in Kabat, E. A., T. T. Wu, H. M. Perry, K. S. Gottesman, and C. Foeller. 1991. Sequences of Proteins of Immunological Interest, 5th ed. Bethesda, Md.: National Center for Biotechnology Information, National Library of Medicine.

As shown in the following Examples, the cytotoxic activity against tumor cells of the bispecific single chain antibody defined herein comprising said mAb A5B7-derived CDR-H3 "DRGLRFYFDY" (SEQ ID NO. 66) amino acid sequence in the second binding domain interacting with CEA are resistant to soluble CEA antigen, thereby allowing the treatment of tumor patients with high serum CEA concentrations in their plasma.

It may be desirable to further modify this A5B7-derived "DRGLRFYFDY" CDR-H3 amino acid sequence e.g. in order to improve affinity for the CEA target antigen (on the epithelial tumor cells) and/or to optimize "fine specificity" of the bispecific single chain antibody as defined herein. To this end, in the amino acid sequence "$DX_1X_2X_3X_4FYFDY$" (SEQ ID NO. 65)", various amino acid residues may be tested at positions "$X_1$", "$X_2$", "$X_3$" and/or "$X_4$" (corresponding to Kabat positions 96 ("$X_1$"), 97 ("$X_2$"), 98 ("$X_3$") and 99 ("$X_4$"), respectively, of CDR-H3 of murine monoclonal antibody A5B7) in order to identify a modified CDR-H3 with improved affinity and/or fine specificity. For instance, "$X_1$", "$X_2$", "$X_3$" or "$X_4$" may represent amino acid residue "R" (Arginine), "G" (Glycine), "L" (Leucine), "Y" (Tyrosine), "A" (Alanine), "D" (Aspartic acid), "S" (Serine), "W" (Tryptophan), "F" (Phenylalanine) or "T" (Threonine). Herein, one, two, three or all four of the indicated "X" positions may be exchanged in comparison to the original "RGLR" amino acid sequence at Kabat positions 96 to 99 in the CDR-H3 "DRGLRFYFDY" (SEQ ID NO. 66) amino acid sequence. However, it is excluded from the scope of the claims of the invention that "$X_1$", "$X_2$", "$X_3$" and "$X_4$" represent the same amino acid, e.g. that "$X_1$", "$X_2$", "$X_3$" and "$X_4$" are all "F" (Phenylalanine). The above-mentioned modification of the A5B7-derived "DRGLRFYFDY" CDR-H3 amino acid sequence can be achieved by methods known in the art, such as PCR using randomized primers, which allows the generation of bispecific single chain antibodies with such modified CDR-H3 regions in the CEA-binding domain. Affinity or fine specificity of these modified bispecific single chain antibodies can be tested by methods described in the art, e.g. by ELISA, Biacore or FACS analysis. The resistance to soluble CEA antigen of a bispecific single chain antibody with such a modified CDR-H3 can be tested in cytotoxicity assays in the presence of increasing amounts of soluble CEA, as described in the following Examples.

More preferably, said second binding domain specific for human CEA of the bispecific single chain antibodies defined herein comprises SEQ ID NO. 65 or 66 and/or a CDR-H1 having the amino acid sequence "SYWMH" (SEQ ID NO. 68) and/or a CDR-H2 having the amino acid sequence "FIRNKANGGTTEYAASVKG" (SEQ ID NO. 67) or "FILNKANGGTTEYAASVKG" (SEQ ID NO. 145). Thus, said second binding domain specific for human CEA of the bispecific single chain antibodies defined herein may comprise one, two or three CDR-H regions as defined above. Alternatively, said second binding domain specific for human CEA of the bispecific single chain antibodies defined herein comprises SEQ ID NO. 65 or 66 and/or a CDR-H1 having the amino acid sequence "TYAMH" (SEQ ID NO. 70) and/or a CDR-H2 having the amino acid sequence "LISNDGSNKYYADSVKG" (SEQ ID NO. 69). Thus, alternatively, said second binding domain specific for human CEA of the bispecific single chain antibodies defined herein may comprise one, two or three CDR-H regions as defined above. Even more preferred, said second binding domain specific for human CEA of the bispecific single chain antibodies defined herein in addition to the one, two or three CDR-H regions as depicted above comprises a CDR-L1 having the amino acid sequence "TLRRGINVGAYSIY" (SEQ ID NO. 73) and/or a CDR-L2 having the amino acid sequence "YKSDSDKQQGS" (SEQ ID NO. 72) and/or a CDR-L3 having the amino acid sequence "MIWHSGASAV" (SEQ ID NO. 71).

The amino acid sequence of the VH region of the second binding domain specific for human CEA of the bispecific single chain antibodies defined herein is preferably SEQ ID NO. 60 comprising "DRGLRFYFDY" (SEQ ID NO. 66) corresponding to Kabat positions 95-102 of the CDR-H3 of murine monoclonal antibody A5B7 and a CDR-H1 having the amino acid sequence "SYWMH" (SEQ ID NO. 68) and a CDR-H2 having the amino acid sequence "FIRNKANGGTTEYAASVKG" (SEQ ID NO. 67).

The amino acid sequence of the VH region of the second binding domain specific for human CEA of the bispecific single chain antibodies defined herein is preferably SEQ ID NO. 146 comprising "DRGLRFYFDY" (SEQ ID NO. 66) corresponding to Kabat positions 95-102 of the CDR-H3 of murine monoclonal antibody A5B7 and a CDR-H1 having the amino acid sequence "SYWMH" (SEQ ID NO. 68) and a CDR-H2 having the amino acid sequence "FILNKANGGTTEYAASVKG" (SEQ ID NO. 145).

The amino acid sequence of the VH region of the second binding domain specific for human CEA of the bispecific single chain antibodies defined herein is preferably SEQ ID NO. 58 or SEQ ID NO. 62 comprising "DRGLRFYFDY" (SEQ ID NO. 66) corresponding to Kabat positions 95-102 of the CDR-H3 of murine monoclonal antibody A5B7 and a CDR-H1 having the amino acid sequence "TYAMH" (SEQ ID NO. 70) and a CDR-H2 having the amino acid sequence "LISNDGSNKYYADSVKG" (SEQ ID NO. 69).

The VL region of the second binding domain specific for human CEA of the bispecific single chain antibodies defined herein is preferably SEQ ID NO. 64 comprising CDR-L1 having the amino acid sequence "TLRRGINVGAYSIY" (SEQ ID NO. 73) and a CDR-L2 having the amino acid sequence "YKSDSDKQQGS" (SEQ ID NO. 72) and a CDR-L3 having the amino acid sequence "MIWHSGASAV" (SEQ ID NO. 71).

As set forth above, the order or arrangement of the variable regions of the second binding domain specifically binding to CEA may be VH-VL or VL-VH. Both arrangements are within the scope of the invention. For a second binding domain comprising the VH of SEQ ID NO. 60 and the VL of SEQ ID NO. 64, the VH-VL arrangement is shown in SEQ ID NO. 52, whereas the VL-VH arrangement is depicted in SEQ ID NO. 122. For a second binding domain comprising the VH of SEQ ID NO. 146 and the VL of SEQ ID NO. 64, the VH-VL arrangement is shown in SEQ ID NO. 147.

For a second binding domain comprising the VH of SEQ ID NO. 58 and the VL of SEQ ID NO. 64, the VH-VL arrangement is shown in SEQ ID NO 50, whereas the VL-VH arrangement is shown in SEQ ID NO. 120. For a second binding domain comprising the VH of SEQ ID NO. 62 and the VL of SEQ ID NO. 64, the VH-VL arrangement is shown in SEQ ID NO. 54, whereas the VL-VH arrangement is depicted in SEQ ID NO. 124. For a second binding domain comprising the VH of SEQ ID NO. 56 and the VL of SEQ ID NO. 64, the VH-VL arrangement is shown in SEQ ID NO. 48, whereas the VL-VH arrangement is depicted in SEQ ID NO. 118.

Even more preferred, the V regions of the second binding domain specific for CEA of the bispecific single chain antibodies defined herein are selected from the group consisting of:

(a) the VH region consists of the amino acid sequence shown in SEQ ID NO. 60 and the VL region consists of the amino acid sequence shown in SEQ ID NO. 64;

(b) the VH region consists of the amino acid sequence shown in SEQ ID NO. 146 and the VL region consists of the amino acid sequence shown in SEQ ID NO. 64;

(c) the VH region consists of the amino acid sequence shown in SEQ ID NO. 58 and the VL region consists of the amino acid sequence shown in SEQ ID NO. 64;

(d) the VH region consists of the amino acid sequence shown in SEQ ID NO. 62 and the VL region consists of the amino acid sequence shown in SEQ ID NO. 64; and (e) the VH region consists of the amino acid sequence shown in SEQ ID NO. 56 and the VL region consists of the amino acid sequence shown in SEQ ID NO. 64.

Most preferred, said bispecific single chain antibody comprises an amino acid sequence selected from the group consisting of:

(a) an amino acid sequence as depicted in any of SEQ ID NOs. 6, 8, 16, 18, 24, 26, 32, 34, 40, 42, 126, 130, 134 or 143;

(b) an amino acid sequence encoded by a nucleic acid sequence as shown in SEQ ID NOs. 5, 7, 15, 17, 23, 25, 31, 33, 39, 41, 125, 129, 133 or 142;

(c) an amino acid sequence encoded by a nucleic acid sequence hybridising under stringent conditions to the complementary nucleic acid sequence of (b);

(d) an amino acid sequence encoded by a nucleic acid sequence which is degenerate as a result of the genetic code to a nucleotide sequence of (b); and (e) an amino acid sequence at least 85% identical, more preferred at least 90% identical, most preferred at least 95% identical to the amino acid sequence of (a) or (b).

In another preferred embodiment of the pharmaceutical composition of the invention, said epithelial tumor to be treated is a gastrointestinal adenocarcinoma, a breast adenocarcinoma or a lung adenocarcinoma. Said gastrointestinal adenocarcinoma is preferably a colorectal, pancreatic, an oesophageal or a gastric adenocarcinoma.

More preferably, said pharmaceutical composition of the invention is for the treatment of progressive tumors, late stage tumors, tumor patients with high tumor load/burden, metastatic tumors, or tumor patients with a CEA serum concentration higher than 100 ng/ml. Said CEA serum concentration may be determined e.g. by ELISA.

In a further preferred embodiment of the pharmaceutical composition of the invention, at least one of said first or second binding domains of the bispecific single chain antibodies defined herein is chimeric, humanized, CDR-grafted, and/or deimmunized or human.

The term "chimeric" as used herein has been defined above. The term "human" binding domain, e.g. a human binding domain specifically binding to human CEA as used herein is to be understood as meaning that the bispecific single chain antibody as defined herein comprises (an) amino acid sequence(s) contained in the human germline antibody repertoire or antibody repertoire having at least the amino acid sequence "FYFDY" corresponding to Kabat positions 100, 100a, 100b, 101, and 102 (SEQ ID NO. 112) of the CDR-H3 of murine monoclonal antibody A5B7 or a A5B7-derived CDR-H3 as defined above. A bispecific single chain antibody as defined herein may also be regarded as human if it consists of (a) sequence(s) that deviate(s) from its (their) closest human germline sequence(s) by no more than would be expected due to the imprint of somatic hypermutation. Additionally, the antibodies of many non-human mammals, for example rodents such as mice and rats, comprise VH CDR amino acid sequences which one may expect to exist in the expressed human antibody repertoire as well. Any such sequence(s) of human or non-human origin which may be expected to exist in the expressed human repertoire would also be considered "human" for the purposes of the present invention.

As used herein, the term "humanized", "humanization" or "human-like" are used interchangeably to refer to a bispecific single chain antibody comprising in at least one of its binding domains at least one complementarity determining region ("CDR") from a non-human antibody or fragment thereof. Humanization approaches are described for example in WO 91/09968 and U.S. Pat. No. 6,407,213. As non-limiting examples, the term encompasses the case in which a variable region of at least one binding domain comprises a single CDR region, for example the third CDR region of the VH, from another non-human animal, for example a rodent, as well as the case in which a or both variable region/s comprise at each of their respective first, second and third CDRs the CDRs from said non-human animal. In the event that all CDRs of a binding domain of the bispecific single chain antibody have been replaced by their corresponding equivalents from, for example, a rodent, one typically speaks of "CDR-grafting", and this term is to be understood as being encompassed by the term "humanized" or grammatically related variants thereof as used herein. The term "humanized" or grammatically related variants thereof also encompasses cases in which, in addition to replacement of one or more CDR regions within a VH and/or VL of the first and/or second binding domain further mutation/s (e.g. substitutions) of at least one single amino acid residue/s within the framework ("FR") regions between the CDRs has/have been effected such that the amino acids at that/those positions correspond/s to the amino acid/s at that/those position/s in the animal from which the CDR regions used for replacement is/are derived. As is known in the art, such individual mutations are often made in the framework regions following CDR-grafting in order to restore the original binding affinity of the non-human antibody used as a CDR-donor for its target molecule. The term "humanized" may further encompass (an) amino acid substitution(s) in the CDR regions from a non-human animal to the amino acid(s) of a corresponding CDR region from a human antibody, in addition to the amino acid substitutions in the framework regions as described above.

As used herein, the term "deimmunized" or "deimmunization" denotes modification of the first and/or second binding domain vis-à-vis an original wild type construct by rendering said wild type construct non-immunogenic or less immunogenic in humans. Deimmunization approaches are shown e.g. in WO 00/34317, WO 98/52976, WO 02/079415 or WO 92/10755. The term "deimmunized" also relates to constructs, which show reduced propensity to generate T cell epitopes. In accordance with this invention, the term "reduced propensity to generate T cell epitopes" relates to the removal of T-cell epitopes leading to specific T-cell activation. Furthermore, "reduced propensity to generate T cell epitopes" means substitution of amino acids contributing to the formation of T cell epitopes, i.e. substitution of amino acids, which are essential for formation of a T cell epitope. In other words, "reduced propensity to generate T cell epitopes" relates to reduced immunogenicity or reduced capacity to induce antigen independent T cell proliferation. The term "T cell epitope" relates to short peptide sequences which can be released during the degradation of peptides, polypeptides or proteins within cells and subsequently be presented by molecules of the major histocompatibility complex (MHC) in order to trigger the activation of T cells; see inter alia WO 02/066514. For peptides presented by MHC class II such activation of T cells can then give rise to an antibody response by direct stimulation of T cells to produce said antibodies. "Reduced propensity to generate T-cell epitopes" and/or "deimmunization" may be measured by techniques known in the art. Preferably, de-immunization of proteins may be tested in vitro by T cell proliferation assay. In this assay PBMCs from donors representing >80% of HLA-DR alleles in the world are screened for proliferation in response to either wild type or de-immunized peptides. Ideally cell proliferation is only detected upon loading of the antigen-presenting cells with wild type peptides. Alternatively, one may test deimmunization by expressing HLA-DR tetramers representing all haplotypes. These tetramers may be tested for peptide binding or loaded with peptides substitute for antigen-presenting cells in proliferation assays. In order to test whether deimmunized peptides are presented on HLA-DR haplotypes, binding of e.g. fluorescence-labeled peptides on PBMCs can be measured. Furthermore, deimmunization can be proven by determining whether antibodies against the deimmunized molecules have been formed after administration in patients. Preferably, antibody derived molecules are deimmunized in the framework regions and most of the CDR regions are not modified in order to generate reduced propensity to induce T cell epitope so that the binding affinity of the CDR regions is not affected. Even elimination of one T cell epitope results in reduced immunogenicity.

In summary, the above approaches help to reduce the immunogenicity of the therapeutic bispecific single chain antibodies as defined herein when being administered to epithelial tumor patients. For example, the first binding domain specifically binding to CD3 as shown in SEQ ID NO. 77 is deimmunized; see also WO2005/040220. Preferably, the arrangement of the V regions in this CD3-binding domain is VH-VL.

In another aspect, the invention relates to a bispecific single chain antibody comprising an amino acid sequence selected from the group consisting of:
   (a) an amino acid sequence as depicted in any of SEQ ID NOs. 6, 8, 16, 18, 24, 26, 32, 34, 40, 42, 126, 130, 134 or 143;
   (b) an amino acid sequence encoded by a nucleic acid sequence as shown in SEQ ID NOs. 5, 7, 15, 17, 23, 25, 31, 33, 39, 41, 125, 129, 133 or 142;
   (c) an amino acid sequence encoded by a nucleic acid sequence hybridising under stringent conditions to the complementary nucleic acid sequence of (b);
   (d) an amino acid sequence encoded by a nucleic acid sequence which is degenerate as a result of the genetic code to a nucleotide sequence of (b); and (e) an amino acid sequence at least 85% identical, more preferred at least 90% identical, most preferred at least 95% identical to the amino acid sequence of (a) or (b).

In one embodiment, the invention relates to a composition comprising a bispecific single chain antibodies as defined above. Preferably, said bispecific single chain antibodies as defined above are used as pharmaceutical compositions for the treatment of an epithelial tumor or epithelial tumors in a human. Said epithelial tumor(s) is (are) CEA-positive. The cytotoxic activity against CEA-positive epithelial tumor cells of these pharmaceutical compositions is resistant to even high concentrations of soluble CEA antigen in the plasma of tumor patients. Moreover, said bispecific single chain antibodies as defined above or anti-CEA scFvs derived thereof may be used as diagnostic compositions for the detection of an epithelial tumor or epithelial tumors in a human as set forth in more detail below.

The term "hybridizing under stringent conditions" as used herein refers to nucleic acid sequences capable of hybridizing, under stringent hybridization conditions, to sequences depicted in SEQ ID NOs. 5, 7, 15, 17, 23, 25, 31, 33, 39, 41, 125, 129, 133 or 142, or the complement thereof, and which encode a bispecific single chain antibody having cytotoxic activity against CEA-positive tumor cells. "Stringent hybridization conditions" refers to an overnight incubation at 42° C. in a solution comprising 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

Whether any particular nucleic acid molecule or polypeptide is at least 80%, 85%, 90%, 95%, 96%, 97%, 98% or 99% identical to a nucleotide or amino acid sequence defined herein can be determined conventionally using known computer programs. A preferred method for determining the best overall match between a query sequence (a sequence defined herein) and a subject sequence, also referred to as a global sequence alignment, can be determined using the FASTDB computer program based on the algorithm of Brutlag et al. (Comp. App. Biosci. 6:237-245 (1990)). In a sequence alignment the query and subject sequences are both DNA sequences. An RNA sequence can be compared by converting U's to T's.

The invention also provides for a pharmaceutical composition comprising a nucleic acid sequence encoding a bispecific single chain antibody as defined herein. Said nucleic acid can be utilized e.g. for gene therapy approaches in order to treat an epithelial tumor in a human, as set forth in more detail below.

The invention further relates to a pharmaceutical composition comprising a vector which comprises a nucleic acid sequence as defined above. Preferably, said vector further comprises a regulatory sequence which is operably linked to said nucleic acid sequence defined above. More preferably, said vector is an expression vector. Furthermore, the vector of the present invention may also be a gene transfer or gene targeting vector. Gene therapy, which is based on introducing therapeutic genes or nucleic acids into cells by ex-vivo or in-vivo techniques is one of the most important applications of gene transfer. Suitable vectors, methods or gene-delivering systems for in-vitro or in-vivo gene therapy are described in the literature and are known to the person skilled in the art; see, e.g., Giordano, Nature Medicine 2 (1996), 534-539; Schaper, Circ. Res. 79 (1996), 911-919; Anderson, Science 256 (1992), 808-813, Isner, Lancet 348 (1996), 370-374; Muhlhauser, Circ. Res. 77 (1995), 1077-1086; Onodua, Blood 91 (1998), 30-36; Verzeletti, Hum. Gene Ther. 9 (1998), 2243-2251; Verma, Nature 389 (1997), 239-242; Anderson, Nature 392 (Supp. 1998), 25-30; Wang, Gene Therapy 4 (1997), 393-400; Wang, Nature Medicine 2 (1996), 714-716; WO 94/29469; WO 97/00957; U.S. Pat. No. 5,580,859; U.S. Pat. No. 5,589,466; U.S. Pat. No. 4,394,448 or Schaper, Current Opinion in Biotechnology 7 (1996), 635-640, and references cited therein. The nucleic acid molecules and vectors as defined herein may be designed for direct introduction or for introduction via liposomes, viral vectors (e.g. adenoviral, retroviral), electroporation, or other delivery systems into the cell. Additionally, a baculoviral system can be used as eukaryotic expression system for the nucleic acid molecules as defined herein. The introduction and gene therapeutic approach should, preferably, lead to the expression of a functional bispecific single chain antibody construct as defined herein, whereby said expressed bispecific single chain antibody construct is particularly useful in the treatment, amelioration and/or prevention of an epithelial tumor in a human.

In a further aspect, the invention relates to a pharmaceutical composition comprising a host transformed or transfected with a vector or a nucleic acid as defined above.

A further aspect of the invention relates to a pharmaceutical composition as defined hereinabove, further comprising a proteinaceous compound capable of providing an activation signal for immune effector cells.

Preferably, the pharmaceutical composition further comprises suitable formulations of carriers, stabilizers and/or excipients.

In another aspect, the invention relates to a process for the production of a pharmaceutical composition as defined above, said process comprising culturing a host as defined above under conditions allowing the expression of the bispecific single chain antibody as defined hereinabove and recovering the produced bispecific single chain antibody from the culture.

A further aspect of the invention relates to a use of a bispecific single chain antibody as defined hereinabove or as produced by the process as defined hereinabove, a nucleic acid molecule as defined hereinabove, a vector as defined hereinabove or a host as defined hereinabove for the preparation of a pharmaceutical composition for the prevention, treatment or amelioration of an epithelial tumor in a human. Another aspect of the invention relates to a method for the prevention, treatment or amelioration of an epithelial tumor in a human, said method comprising the step of administration of an effective amount of a pharmaceutical composition of the invention or as produced according by the process set forth above. The person skilled in the art, in particular the attending physician can evaluate the successful treatment of the patient in need of administration of the bispecific molecule/bispecific single chain antibody of the invention. Accordingly, the administration scheme as well as the dosage and the administration time may be assessed by said person skilled in the art: A corresponding "amelioration" and/or "treatment" to be assessed is defined below.

As used herein, an "effective amount" or "therapeutically effective amount" of a pharmaceutical composition of the invention in the context of epithelial tumors refers to that amount of the therapeutic agent sufficient to destroy, modify, control or remove primary, regional or metastatic tumor tissue. A therapeutically effective amount may refer to the amount of therapeutic agent sufficient to delay or minimize the spread of the epithelial tumor(s). A therapeutically effective amount may also refer to the amount of the therapeutic agent or pharmaceutical agent that provides a therapeutic benefit in the treatment or management of the epithelial tumor(s). Further, a therapeutically effective amount with respect to a therapeutic agent or pharmaceutical agent of the invention means that amount of therapeutic agent or pharmaceutical agent alone, or in combination with other therapies, that provides a therapeutic benefit in the treatment or management of an epithelial tumor. Used in connection with an amount of the bispecific single chain antibody defined herein, the term can encompass an amount that improves overall therapy, reduces or avoids unwanted effects, or enhances the therapeutic efficacy of or synergies (as defined herein) with another therapeutic agent. Preferably, a therapeutically effective amount of a therapeutic improves overall therapy, reduces or avoids unwanted effects, or enhances the therapeutic efficacy of or synergies with another therapeutic agent in the treatment of (an) epithelial tumor(s). For example, a bispecific single chain antibody as defined herein may cause a shrinkage of the diameter of an epithelial tumor of 20% if administered to a patient as a mono-therapy. In contrast, a second therapeutic e.g. an anti-cancer agent as defined below, may cause a tumor shrinkage of 10%. However, if both the bispecific single chain antibody as defined herein and said second therapeutic are administered in combination in form of a co-therapy, a tumor shrinkage of 50% may be observed. Such an effect is understood as a synergestic effect as used herein.

As referred to herein, the term "therapy" refers to any administration scheme, method and/or agent that can be used in the prevention, treatment or amelioration of an epithelial tumor. The term "prevention, treatment or amelioration of an epithelial tumor" is set forth in more detail below. The terms "therapies" and "therapy" may refer to a biological therapy, supportive therapy, chemotherapy, radiation therapy and/or other therapies useful in treatment, prevention, or amelioration of an epithelial tumor, or one or more symptoms thereof.

As used herein, the terms "treat", "treatment" and "treating" in the context of administering a therapy or therapies to a patient refer to the reduction or amelioration of the progression, severity, and/or duration of an epithelial tumor. Said epithelial tumor(s) may be associated with aberrant expression e.g., overexpression or activity of CEA, and/or the amelioration of one or more symptoms thereof resulting from the administration of one or more therapies (including the administration of one or more pharmaceutical or therapeutic agents).

The most preferred mode of administration is an intravenous administration over a given time/time period. While the bispecific single chain antibody as defined herein may be administered per alone, preferred is administration in a pharmaceutically acceptable carrier. Examples of suitable pharmaceutical carriers are well known in the art and include phosphate buffered saline solutions, water, liposomes, various types of wetting agents, sterile solutions, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depends upon many factors, including the patient's size, body surface area, age, the particular compound to be administered, sex, time and route of administration, general health, and other drugs being administered concurrently. Preparations for parenteral administration include sterile aqueous or non-aqueous solutions, and suspensions. Examples of non-aqueous solvents are propylene glycol, polyethylene glycol, and injectable organic esters such as ethyl oleate. Aqueous carriers include water, aqueous solutions, or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishes, electrolyte replenishers (such as those based on Ringer's dextrose), and the like. Preservatives and other additives may also be present such as, for example, antimicrobials, anti-oxidants, chelating agents, and inert gases and the like. In addition, the composition might comprise proteinaceous carriers, like, e.g., serum albumine or immunoglobuline, preferably of human origin. It is envisaged that the co-therapy might comprise, in addition to the proteinaceous bispecific single chain antibody further biologically active agents, depending on the intended use of the pharmaceutical composition. Such agents might be agents acting on the gastro-intestinal system, agents acting as cytostatica, agents preventing hyperurikemia, agents inhibiting immune reactions (e.g. corticosteroids, FK506), drugs acting on the circulatory system and/or agents such as T-cell co-stimulatory molecules or cytokines known in the art. Preferably, the bispecific single chain antibody as defined herein is formulated in a buffer, a stabilizer and a surfactant. The buffer may be a phosphate, citrate, succinate or acetate buffer. The stabilizer may be (an) amino acid(s) and/or a sugar. The surfactants may be detergents, PEGs, or the like. More preferably, the bispecific single chain antibody as defined herein is formulated in citrate, lysine, trehalose and Tween 80. As a diluent for said pharmaceutical composition, isotonic saline and Tween 80 is preferred.

The term "amelioration" as used herein refers to an improvement or a moderation in the severity of a disease, i.e. an epithelial tumor. For example, such an amelioration may be the achievement of a stable disease—or even more preferred—a shrinkage of the epithelial tumor(s), i.e. a minimal, partial response or complete response, due to the administration of the pharmaceutical compositions of the invention. "Stable disease" refers to a disease state in which no or no significant tumor progression/growth can be observed or detected by clinical and/or histological diagnostic methods. For example, a shrinkage of the tumor greater than 50% shrinkage of the sum of cross-sectional areas of index lesions may be considered as a "partial response". A "complete response" denotes a state in which no lesion(s) can be detected any more after treatment. A response with a tumor shrinkage between stable disease and partial response may be considered as a minimal response. For instance, a 20%, 25% or 30% shrinkage of the sum of cross-sectional areas of index lesions may be referred to as a minimal response.

The term "amelioration" as used herein encompasses also a reduction of the number of epithelial tumors. It furthermore denotes the prevention/slowdown of tumor progression. Moreover, an improvement of the overall survival of treated tumor patients in comparison to non-treated tumor patients may be considered as an "amelioration" as used herein. This applies mutatis mutandis to an improvement of the progression-free survival or the relapse-free survival of treated tumor patients as compared to non-treated tumor patients. In addition, the term "amelioration" can also refer to a reduction of the intensity of the symptoms of an epithelial tumor, resulting e.g. in an improvement of the quality of life of the treated tumor patients.

The term "prevention of an epithelial tumor" as used herein is to be understood as follows: After surgical removal of the primary epithelial tumor(s) from a human patient and/or after chemotherapeutic or radiological treatment of the primary epithelial tumor(s), it may be the case that not all tumor cells could be eliminated from the body. However, these remaining tumor cells may give rise to recurrent cancer, i.e. local recurrence and/or metastases in the patient. Metastasis is a frequent complication of cancer, yet the process through which cancer cells disseminate from the primary tumor(s) to form distant colonies is poorly understood. Metastatic cancers are almost without exception uncurable raising the necessity for new therapeutic modalities. The pharmaceutical composition of the invention can be used to kill these disseminated tumor cells in order to prevent the formation of secondary tumors (originating from the tumor cells remaining in the body after primary therapy). In this way, the pharmaceutical composition helps to prevent the formation of local recurrence and/or metastases in tumor patients.

The success of the anti-tumor therapy may be monitored by established standard methods for the respective disease entities, e.g. by computer-aided tomography, X-ray, nuclear magnetic resonance tomography (e.g. for National Cancer Institute-criteria based response assessment [Cheson (1999), J. Clin. Oncol.; 17(4):1244]), positron-emission tomography scanning, endoscopy, Fluorescence Activated Cell Sorting, aspiration of bone marrow, pleural or peritoneal fluid, tissue/histologies, and various epithelial tumor specific clinical chemistry parameters (e.g. soluble CEA concentration in serum) and other established standard methods may be used. In addition, assays determining T cell activation may be used; see e.g. WO99/054440. Statistics for the determination of overall survival, progression-free survival or relapse-free survival of treated tumor patients in comparison to non-treated tumor patients may also be used.

Preferably, said epithelial tumor is a gastrointestinal adenocarcinoma, a breast adenocarcinoma or a lung adenocarcinoma. Said gastrointestinal adenocarcinoma is more preferably a colorectal, pancreatic, an oesophageal or a gastric adenocarcinoma.

Even more preferred, said pharmaceutical composition of the invention is for the treatment of progressive tumors, late stage tumors, tumor patients with high tumor load/burden, metastatic tumors, or tumor patients with a CEA serum concentration higher than 100 ng/ml (as determined e.g. by ELISA).

In another preferred embodiment of the uses or methods of the invention, said pharmaceutical composition as defined hereinabove is suitable to be administered in combination with an additional drug, i.e. as part of a co-therapy.

In certain embodiments, the bispecific single chain antibody or pharmaceutical composition as defined herein is administered in combination with one or more other therapies. In certain embodiments, the bispecific single chain antibody or pharmaceutical composition as defined herein is administered to a patient concurrently with one or more other therapies. Preferably, such therapies are useful for the treatment of epithelial tumors. The term "concurrently" is not limited to the administration of pharmaceutical compositions or therapeutic agents at exactly the same time, but rather it is meant that the bispecific single chain antibody or pharmaceutical composition as defined herein and the other agent(s) are administered to a patient in a sequence and within a time interval such that the bispecific single chain antibody or pharmaceutical composition as defined herein can act together with the other agent to provide an increased benefit than if they were administered otherwise. For example, each therapeutic agent may be administered at the same time or sequentially in any order at different points in time; however, if not administered at the same time, they should be administered sufficiently close in time so as to provide the desired therapeutic effect.

Each therapeutic agent can be administered separately, in any appropriate form and by any suitable route. In other embodiments, the bispecific single chain antibody or pharmaceutical composition as defined herein are administered before, concurrently or after surgery. Preferably the surgery completely removes localized epithelial tumors or reduces the size of large epithelial tumors. Surgery can also be done as a preventive measure or to relieve pain.

The dosage amounts and frequencies of administration provided herein are encompassed by the term "therapeutically effective" as defined above. The dosage and frequency further will typically vary according to factors specific for each patient depending on the specific therapeutic or prophylactic agents administered, the severity and type of epithelial tumor, the route of administration, as well as age, body weight, response, and the past medical history of the patient. Suitable regimens can be selected by one skilled in the art by considering such factors and by following, for example, dosages reported in the literature and recommended in the Physicians' Desk Reference (59th ed., 2005).

In some embodiments, therapy by administration of the bispecific single chain antibody or pharmaceutical composition as defined herein is combined with the administration of one or more therapies such as chemotherapies, radiation therapies, hormonal therapies, and/or biological therapies/immunotherapies. Therapeutic agents include, but are not limited to, proteinaceous molecules, including, but not limited to, peptides, polypeptides, proteins, including post-translationally modified proteins, antibodies etc.; or small molecules (less than 1000 daltons), inorganic or organic compounds; or nucleic acid molecules including double-stranded or single-stranded DNA, or double-stranded or single-stranded RNA, as well as triple helix nucleic acid molecules. Therapeutic agents can be derived from any known organism (including, but not limited to, animals, plants, bacteria, fungi, and protista, or viruses) or from a library of synthetic molecules.

In a specific embodiment, the methods and uses of the invention encompass administration of the bispecific single chain antibody or pharmaceutical composition as defined herein in combination with the administration of one or more therapeutic agents that are inhibitors of kinases such as Gefitinib (Iressa), Erlotinib (Tarceva), anti-EGFR-antibodies (e.g. Cetuximab; Erbitux), or anti-Her2/neu-antibodies (e.g. Trastuzumab; Herceptin) described in the art; see e.g., Hardie and Hanks (1995) The Protein Kinase Facts Book, I and II, Academic Press, San Diego, Calif.

In another specific embodiment, the methods and uses of the invention encompass administration of the bispecific single chain antibody or pharmaceutical composition as defined herein in combination with the administration of one or more therapeutic agents that are angiogenesis inhibitors such as anti-VEGF-antibodies (e.g. Bevacizumab; Avastin), small molecular compounds (e.g. Vatalanib or Sorafenib) or COX-inhibitors described in the art.

In another specific embodiment, the methods and uses of the invention encompass administration of the bispecific single chain antibody or pharmaceutical composition as defined herein in combination with the administration of one or more therapeutic agents that are anti-cancer agents such as 5-Fluorouracil, Leucovorin, Capecitabine, Oxaliplatin, Irinotecan, Gemcitabine, Doxorubicin, Epirubicin, Etoposide, Cisplatin, Carboplatin, Taxanes (e.g. Docetaxel, Paclitaxel) described in the art.

Preferably, a co-therapy of a patient with an epithelial tumor using a bispecific single chain antibody or pharmaceutical composition as defined herein in combination with (a) further therapeutic agent(s) results in an synergistic effect. As used herein, the term "synergistic" refers to a combination of therapies (e.g., a combination of a bispecific single chain antibody as defined herein and (a) further therapeutic agent(s) as set forth above) which is more effective than the additive effects of any two or more single therapies (e.g., one or more therapeutic agents). For example, a bispecific single chain antibody as defined herein may cause a shrinkage of the diameter of an epithelial tumor of 20% if administered to a patient as a mono-therapy. In contrast, a second therapeutic e.g. an anti-cancer agent as defined below, may cause a tumor shrinkage of 10%. However, if both the bispecific single chain antibody as defined herein and said second therapeutic are administered in combination in form of a co-therapy, a tumor shrinkage of 50% may be observed.

A synergistic effect of a combination of therapies (e.g., a combination of a bispecific single chain antibody as defined herein and (a) further therapeutic agent(s) as set forth above) permits the use of lower dosages of one or more of therapies (e.g., one or more therapeutic agents) and/or less frequent administration of said therapies to a patient with a disease, e.g. an epithelial tumor. The ability to utilize lower dosages of therapies (e.g., therapeutic agents) and/or to administer said therapies less frequently reduces the toxicity associated with the administration of said therapies to a subject without reducing the efficacy of said therapies in the prevention or treatment of a disease, e.g. an epithelial tumor. In addition, a synergistic effect can result in improved efficacy of therapies (e.g., therapeutic agents) in the prevention, management, treatment and/or amelioration of an epithelial tumor (which may be associated with aberrant expression (e.g., overexpression) or activity of CEA). Finally, synergistic effect of a combination of therapies (e.g., therapeutic agents) may avoid or reduce adverse or unwanted side effects associated with the use of any single therapy.

In said co-therapy, an active agent may be optionally included in the same pharmaceutical composition as the bispecific single chain antibody defined herein, or may be included in a separate pharmaceutical composition. In this latter case, said separate pharmaceutical composition is suitable for administration prior to, simultaneously as or following administration of said pharmaceutical composition comprising the bispecific single chain antibody as defined herein. The additional drug or pharmaceutical composition may be a non-proteinaceous compound or a proteinaceous compound. In the case that the additional drug is a proteinaceous compound, it is advantageous that the proteinaceous compound be capable of providing an activation signal for immune effector cells.

Preferably, said proteinaceous compound or non-proteinaceous compound may be administered simultaneously or non-simultaneously with a bispecific single chain antibody as defined hereinabove, a nucleic acid molecule as defined hereinabove, a vector as defined as defined hereinabove, or a host as defined as defined hereinabove. Preferably, said subject to be treated is a human.

In a further embodiment, a single chain bispecific antibody or anti-CEA scFvs as defined herein may be conjugated to a diagnostic or detectable agent. Such diagnosis and detection can be accomplished by coupling the antibody or scFv to detectable substances for example to various enzymes, such as horseradish peroxidase, alkaline phosphatase, beta-galactosidase, or acetylcholinesterase; prosthetic groups, such as streptavidin/biotin and avidin/biotin; fluorescent materials, such as, umbelliferone, fluorescein, fluorescein isothiocyanate, rhodamine, dichlorotriazinylamine fluorescein, dansyl chloride or phycoerythrin; luminescent materials, such as, luminol; bioluminescent materials, such as, luciferase, luciferin, and aequorin; radioactive materials and isotopes, such as cobalt (57Co), indium (115In, 113In, 112In, 111In), iodine (131I, 125I, 123I, 121I), or yttrium (90Y), positron emitting metals using various positron emission tomographies, and nonradioactive paramagnetic metal ions.

Techniques for conjugating moieties to antibodies are well known. Moieties can be conjugated to antibodies by any method known in the art, including, but not limited to aldehyde/Schiff linkage, sulphydryl linkage, acid-labile linkage, cis-aconityl linkage, hydrazone linkage, enzymatically degradable linkage; see generally Garnett, 2002, Adv. Drug Deliv. Rev. 53:171-216. Additional techniques for conjugating moieties to antibodies are well known, see, e.g., Arnon et al., Monoclonal Antibodies For Immunotargeting Of Drugs In Cancer Therapy. In Monoclonal Antibodies And Cancer Therapy, Reisfeld et al. (eds.), pp. 243-56 (Alan R. Liss, Inc. 1985). Methods for fusing or conjugating antibodies to polypeptide moieties are known in the art; see, e.g.; Ashkenazi et al., 1991, PNAS 88: 10535-10539. The fusion of an antibody to a moiety does not necessarily need to be direct, but may occur through linker sequences. Such linker molecules are commonly known in the art and described in Denardo et al., 1998, Clin Cancer Res. 4:2483-90; Peterson et al., 1999, Bioconjug. Chem. 10:553.

In a further aspect, the invention relates to a kit comprising a bispecific single chain antibody as defined hereinabove, a nucleic acid molecule as defined hereinabove, a vector as defined hereinabove, or a host as defined hereinabove.

These and other embodiments are disclosed and encompassed by the description and Examples of the present invention. Recombinant techniques and methods in immunology are described e.g. in Sambrook et al. Molecular Cloning: A Laboratory Manual; Cold Spring Harbor Laboratory Press, 3$^{rd}$ edition 2001; Lefkovits; Immunology Methods Manual; The Comprehensive Sourcebook of Techniques; Academic Press, 1997; Golemis; Protein-Protein Interactions: A Molecular Cloning Manual; Cold Spring Laboratory Press, 2002. Further literature concerning any one of the antibodies, methods, uses and compounds to be employed in accordance with the present invention may be retrieved from public libraries and databases, using for example electronic devices. For example, the public database "Medline", available on the Internet, may be utilized, for example under http://www.ncbi.nlm.nih.qov/PubMed/medline.html. Further databases and addresses, such as http://www.ncbi.nim.nih.qov/, http://www.infobioaen.fr/, http://www.fmi.ch/bioloqv/researchtools.html, http://www-.tiqr.or Q/. are known to the person skilled in the art and can also be obtained using, e.g., http://www.lvcos.com. For tumor-related topics see e.g. http://www.nih.qov or http://www.dkfz.de.

The Figures show:

FIG. 1: FACS binding analysis of various human CEA-reactive bispecific single chain constructs to CHO cells transfected with human CEA and CD3 positive HPB-All cells, respectively. As a positive control for binding to CEA, monoclonal antibody Col-1 has been used. For control of binding to human CD3, a CD19×CD3 bispecific single chain construct as described in WO 99/054440 was used. In this positive control, the thick line represents cells incubated with 10 µg/ml purified CD19×CD3 bispecific single chain antibody that was subsequently incubated with the anti-His antibody and the detection antibody. The thin histogram line reflects the negative control: cells incubated with the anti-His antibody and the detection antibody. Binding activity for human (membrane-bound) CEA and human CD3 were detectable for CEAI VHVL×SEQ ID NO.77 VHVL, CEAI VLVH×SEQ ID NO.77 VHVL, CEAII VHVL×SEQ ID NO.77 VHVL, CEAIII VLVH×SEQ ID NO.77 VHVL and CEAIII VHVL×SEQ ID NO.77 VHVL. In the respective histograms corresponding to the bispecific single chain antibodies as described in the invention, the thin line represents the negative control, the bright thick line represents cells incubated with culture supernatant, whereas the dark thick (most right) line represents cells incubated with 10 µg/ml purified bispecific single chain antibody.

Figure 2:
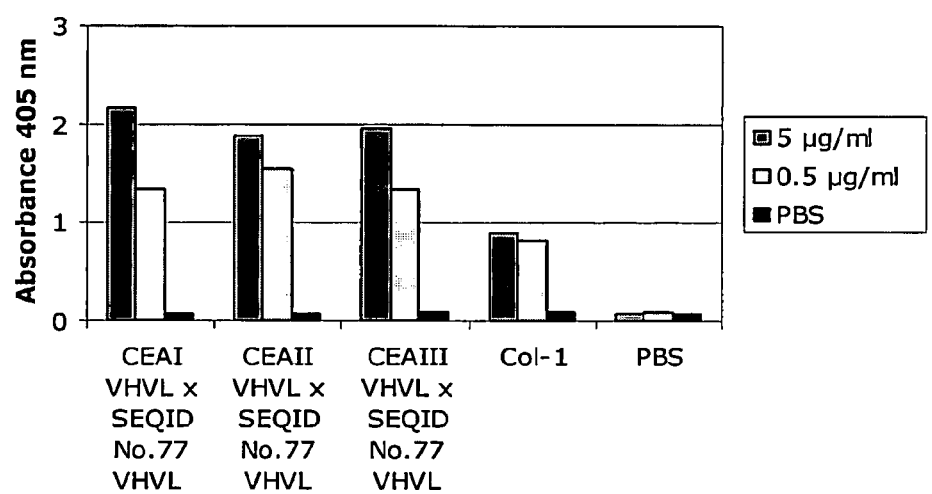

FIG. 2: Binding signals of bispecific single chain anti-CEA/anti-CD3 antibodies CEAI VHVL×SEQ ID NO. 77 VHVL, CEAII VHVL×SEQ ID NO. 77 VHVL and CEAIII VHVL×SEQ ID NO. 77 VHVL and anti-CEA antibody Col-1 to soluble CEA detected by direct ELISA. CEAI VHVL×SEQ ID NO. 77 VHVL (anti-CEA binding domain derived from mAb A5B7), CEAII VHVL×SEQ ID NO.77 VHVL (anti-CEA binding domain derived from mAb T84.66), and CEAIII VHVL×SEQ ID NO.77 VHVL (anti-CEA binding domain derived from mAb MFE-23) bispecific single chain antibodies and the mouse monoclonal antibody Col-1 specifically bound to immobilized soluble human CEA. No binding signal was observed in the absence of the soluble CEA antigen (PBS control).

Figure 3:
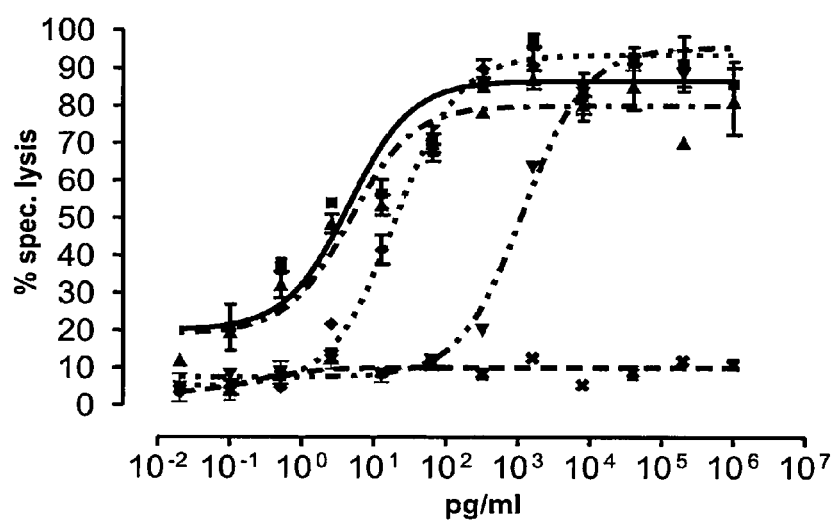

FIG. 3: The indicated CEA-reactive bispecific single chain constructs redirected T cells to lyse CHO cells transfected with CEA, in the absence of soluble CEA. Stimulated human CD8 positive CTLs were used as effector cells. To demonstrate the specificity of the redirected lysis, a non-CEA reactive bispecific single chain construct was included as negative control. Cytotoxic activity against human CEA-transfected target cells (CHO-CEA$^+$ cells) for various domain arrangements, i.e. for SEQ ID NO.77 VHVL×CEAI VHVL and SEQ ID NO.77 VHVL×CEAI VLVH (both constructs with anti-CD3 binding domain N-terminally), as well as for CEAI VLVH×SEQ ID NO.77 VHVL and CEAI VHVL×SEQ ID NO.77 VHVL (anti-CD3 binding domain C-terminally) could be shown. Non-transfected CHO cells (lacking human CEA) were used as a negative control.

Figure 4:
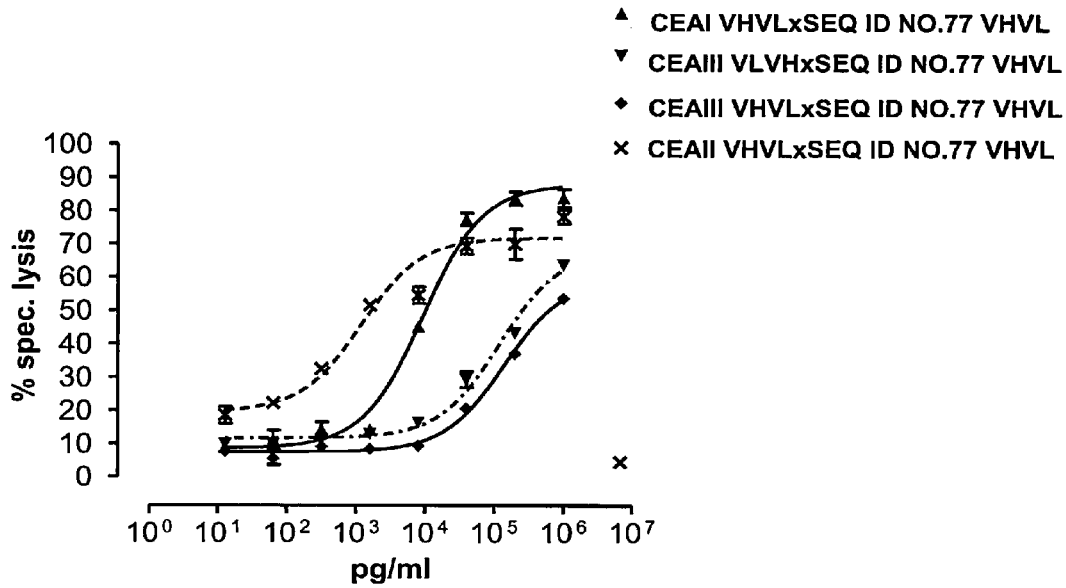
Figure 4:
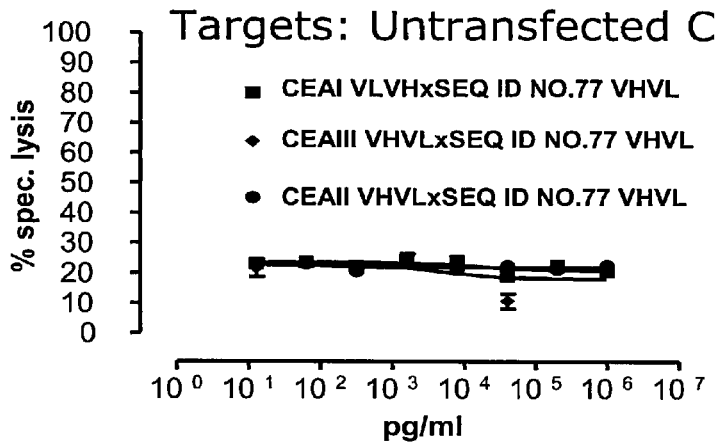

FIG. 4: The indicated CEA-reactive bispecific single chain constructs redirected T cells to lyse CHO cells transfected with CEA, in the absence of soluble CEA. To demonstrate the specificity of the redirected lysis, non-transfected CHO cells were included as negative control. Stimulated human CD8 positive CTLs were used as effector cells. CEA I-HL (CEAI VHVL×SEQ ID NO.77 VHVL), CEA III-LH (CEAIII VLVH×SEQ ID NO.77 VHVL), CEA III-HL (CEAIII VHVL×SEQ ID NO.77 VHVL), and CEA II HL (CEAII VHVL×SEQ ID NO.77 VHVL) showed cytotoxic activity against human CEA-transfected CHO cells. Non-transfected CHO cells (lacking human CEA) were used as a negative control for CEA I-LH (CEAI VLVH×SEQ ID NO.77 VHVL), CEA III-HL (CEAIII VHVL×SEQ ID NO.77 VHVL) and CEA II HL (CEAII VHVL×SEQ ID NO.77 VHVL). CEAI denotes a variable region derived from murine mAb A5B7, CEAII is a variable region derived from murine mAb T84.66 and CEAIII refers to a variable region from murine mAb MFE-23.

Figure 5:
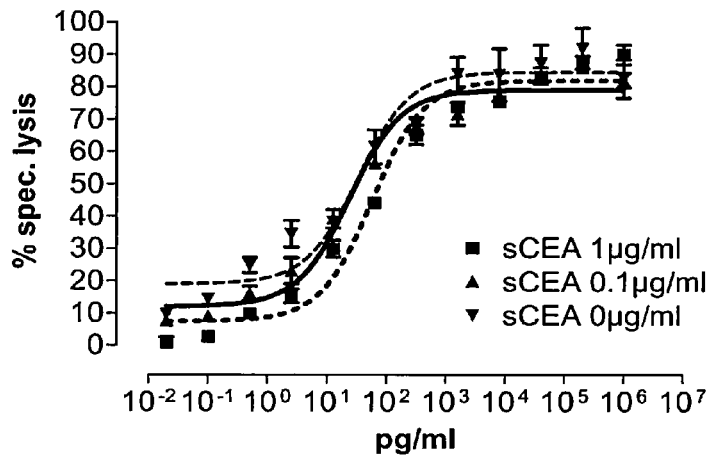
Figure 5:
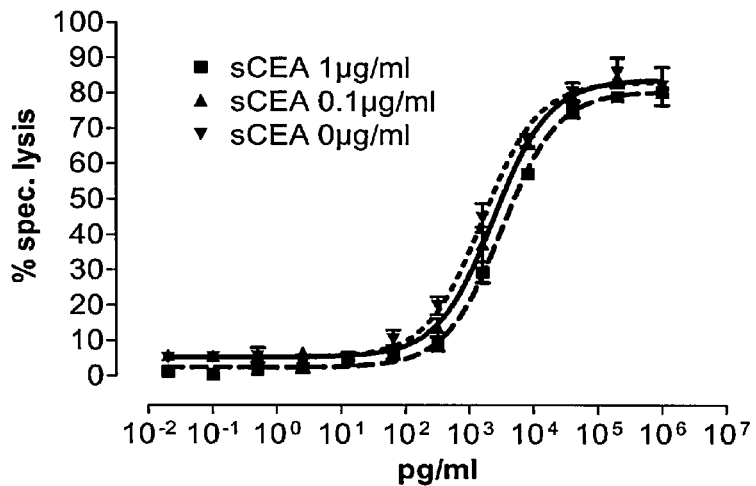

FIG. 5: The indicated CEA-reactive bispecific single chain constructs redirected T cells to lyse CHO cells transfected with CEA in the presence of soluble human CEA. Stimulated human CD8 positive CTLs were used as effector cells. The cytotoxic activity mediated by CEAI VLVH×SEQ ID NO.77 VHVL and CEAI VHVL×SEQ ID NO.77 VHVL is not inhibited by increasing amounts of soluble human CEA, up to 1 µg/ml. CEAI is a variable region derived from murine mAb A5B7.

Figure 6:
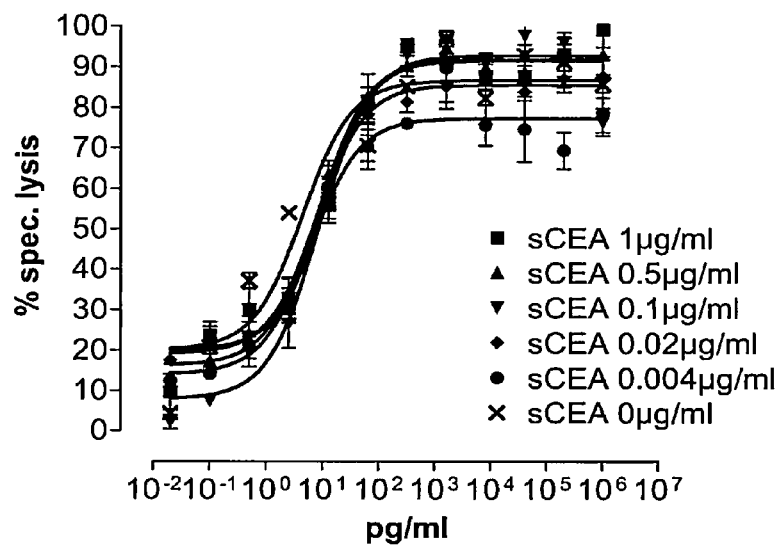
Figure 6:
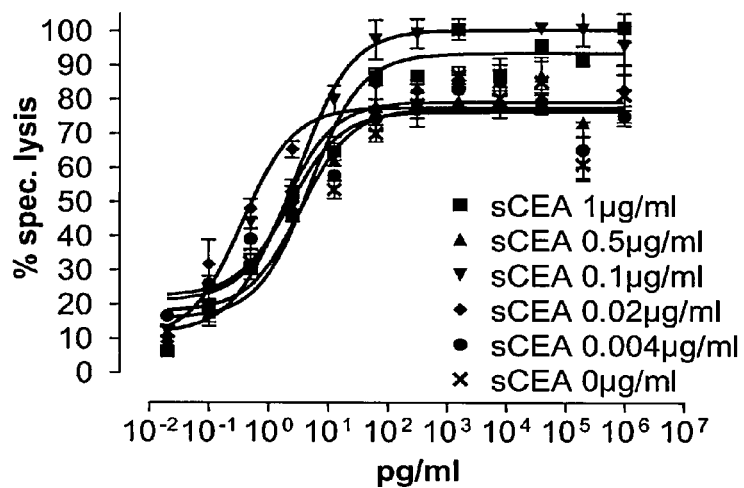

FIG. 6: The indicated CEA-reactive bispecific single chain constructs redirected T cells to lyse CHO cells transfected with CEA in the presence of soluble human CEA. Stimulated human CD8 positive CTLs were used as effector cells. The cytotoxic activity mediated by SEQ ID NO.77 VHVL×CEAI VHVL and SEQ ID NO.77 VHVL×CEAI VLVH is not inhibited by increasing amounts of soluble human CEA, up to 1 µg/ml. CEAI is a variable region derived from murine mAb A5B7.

FIG. 7: The indicated CEA-reactive bispecific single chain construct redirected T cells to lyse CHO cells transfected with CEA in the presence of soluble human CEA. Stimulated human CD8 positive CTLs were used as effector cells. Cytotoxic activity of CEAII VHVL×SEQ ID NO.77 VHVL is inhibited by increasing amounts of soluble CEA. CEAII VHVL is derived from mAb T84.66.

Figure 8:
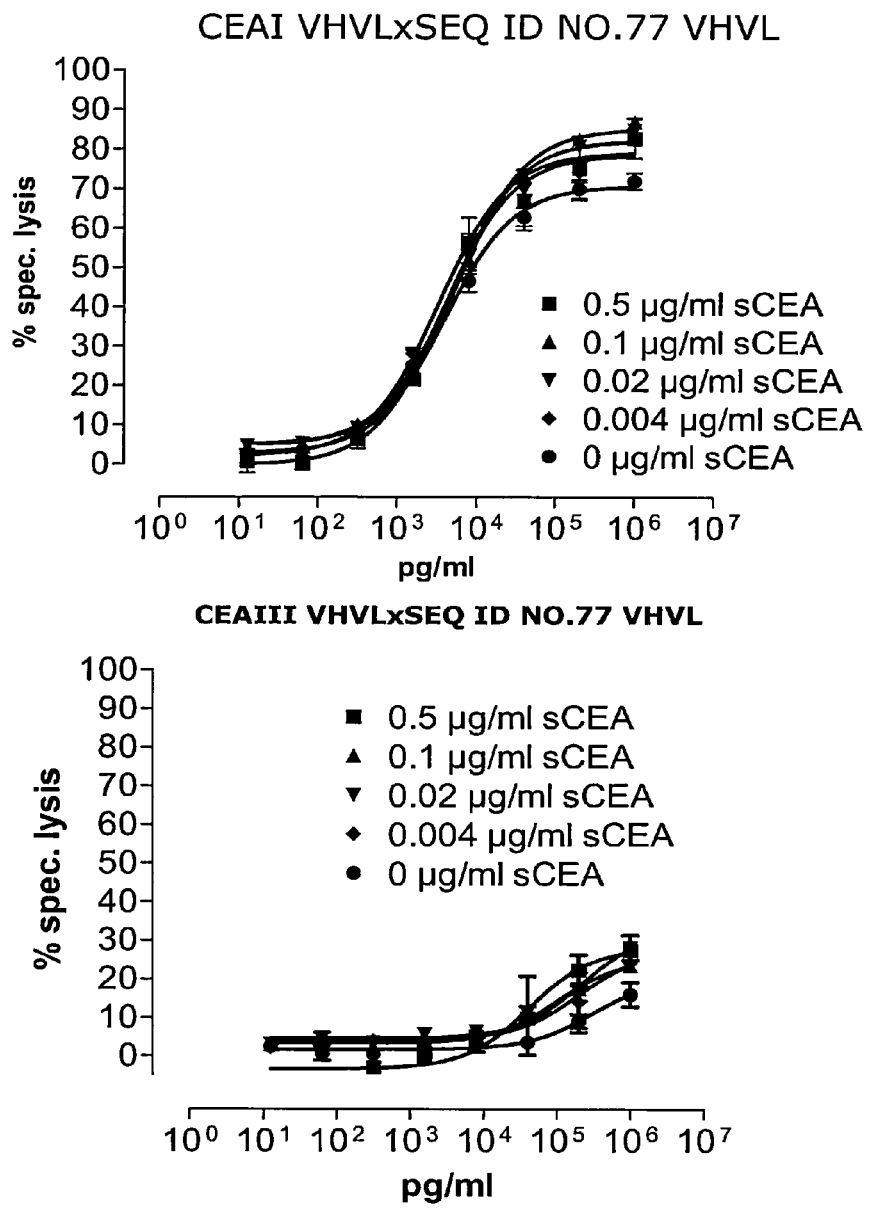

FIG. 8: The indicated CEA-reactive bispecific single chain constructs redirected T cells to lyse CHO cells transfected with CEA in the presence of soluble human CEA. Stimulated human CD8 positive CTLs were used as effector cells. Whereas CEAI VHVL×SEQ ID NO.77 VHVL-mediated cytotoxicity is resistant to inhibition by soluble CEA antigen, CEAIII VHVL×SEQ ID NO.77 VHVL-mediated cytotoxic activity is inhibited by even low amounts of soluble CEA. CEAIII VHVL is derived from mAb MFE-23, whereas CEAI is a variable region derived from murine mAb A5B7.

Figure 9:
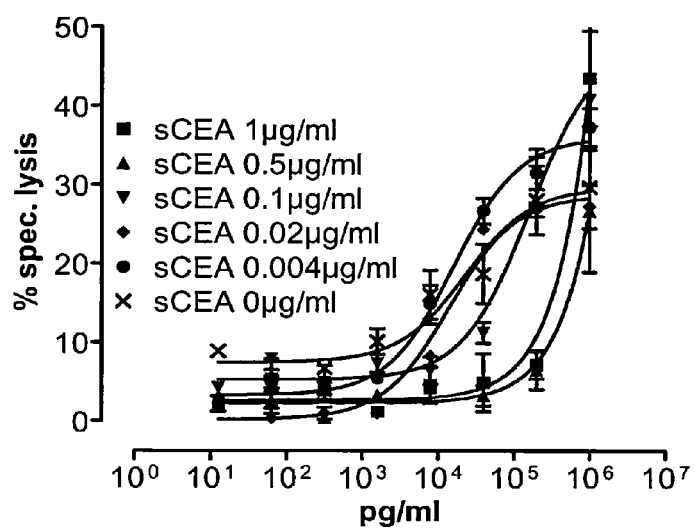

FIG. 9: The indicated CEA-reactive bispecific single chain constructs redirected T cells to lyse Kato III cells in the presence of increasing amounts of soluble CEA antigen. Native human PBMCs were used as effector cells. CEAII VHVL×SEQ ID NO. 77-mediated cytotoxic activity is not resistant to soluble CEA. CEAII VHVL is derived from mAb T84.66.

FIG. 10: The indicated CEA-reactive bispecific single chain constructs redirected T cells to lyse Kato III cells in the presence of increasing amounts of soluble CEA antigen. Stimulated human CD8 positive CTLs were used as effector cells. CEAI VHVL×SEQ ID NO.77 VHVL-mediated cytotoxicity is resistant to soluble CEA. In contrast, CEAII VHVL×SEQ ID NO.77 VHVL-mediated cytotoxic activity is inhibited by increasing amounts of soluble CEA. CEAII VHVL is derived from mAb T84.66, whereas CEAI is a variable region derived from murine mAb A5B7.

Figure 11:
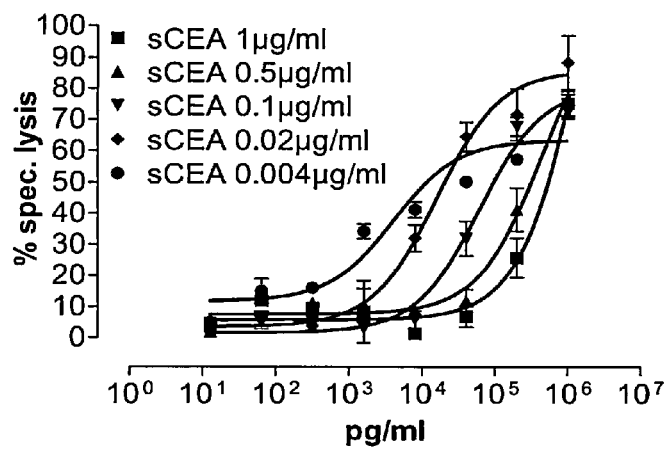

FIG. 11: The indicated CEA-reactive bispecific single chain constructs redirected T cells to lyse CHO cells transfected with CEA in the presence of increasing amounts of soluble CEA antigen. Stimulated human CD8 positive CTLs were used as effector cells. CEAII VHVL×SEQ ID NO.77 VHVL-mediated cytotoxic activity is inhibited by increasing amounts of soluble CEA. CEAII VHVL is derived from mAb T84.66.

Figure 12:
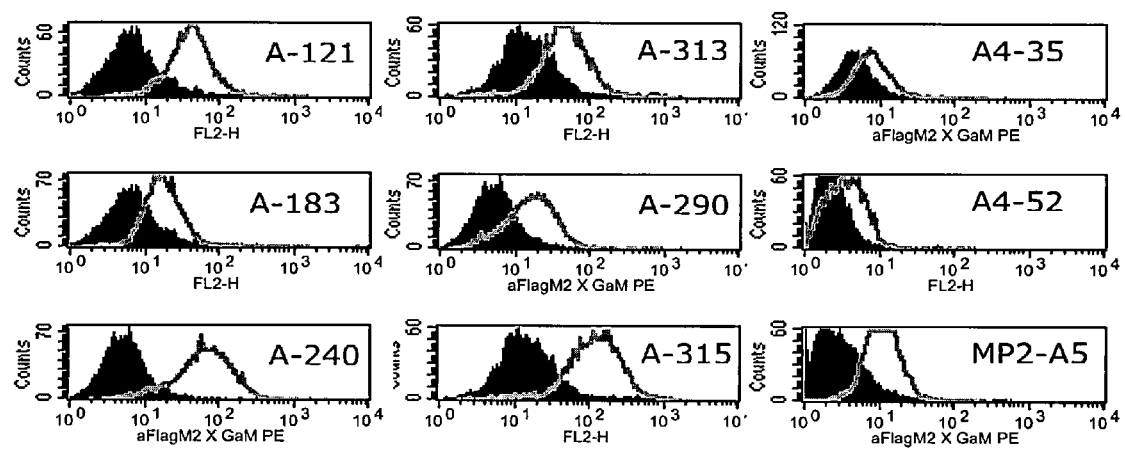

FIG. 12: Flow cytometric analysis of periplasmic preparations containing Flag-tagged scFv protein fragments from selected clones. Periplasmic preparations of soluble scFv protein fragments were added to 100,000 to 200,000 CEA-transfected CHO cells. For detection a monoclonal anti-Flag antibody was used followed by a PE-labeled polyclonal anti-mouse antibody. ScFvs binding to cells was measured by an increase in fluorescence intensity as compared to cells that were incubated with PBS alone. Fluorescence intensity is blotted on the X-axis, the number of events is blotted on the Y-axis. The negative control (PBS and detection reagents) is shown as filled curve, the respective scFvs are shown as grey lines. Shifting to the right indicates positive binding to the cells. All of the scFvs, i.e. A-121, A-183, A-240, A-313, A-290, A-315, A4-35, A4-52 and MP2-A5, bind to membrane-bound CEA on CHO cells. Each of the scFv consists of the murine A5B7 VH region and a human VL region, as described in Example 6.

Figure 13:
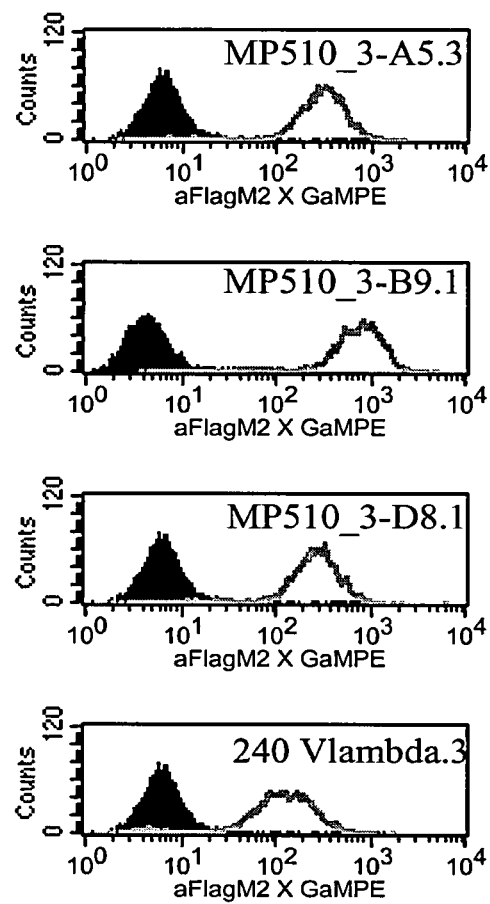

FIG. 13: Flow cytometric analysis of periplasmic preparations containing Flag-tagged scFv protein fragments from selected. Periplasmic preparations of soluble scFv protein fragments were added to 100,000 to 200,000 CEA-transfected CHO cells. Detection was performed by a monoclonal anti-Flag antibody followed by a PE-labeled polyclonal anti-mouse antibody. ScFvs binding to cells was measured by an increase in fluorescence intensity as compared to cells that were incubated with PBS alone. Fluorescence intensity is blotted on the X-axis, the number of events is blotted on the Y-axis. The negative control (PBS and detection reagents) is shown as filled curve, the respective scFvs are shown as grey lines. Shifting to the right indicates positive binding to the cells. The fully human scFv constructs MP510_3-A5.3, MP510_3-B9.1, and MP510_3-D8.1 bind to membrane-bound CEA on CHO cells. Each of these scFvs consists of a human VH region and the human VL region A240, as described in Example 7. 240 Vlambda.3 is a scFv consisting of the murine A5B7 VH region and the human VL A-240 region. This construct shows also CEA-binding activity.

Figure 14:
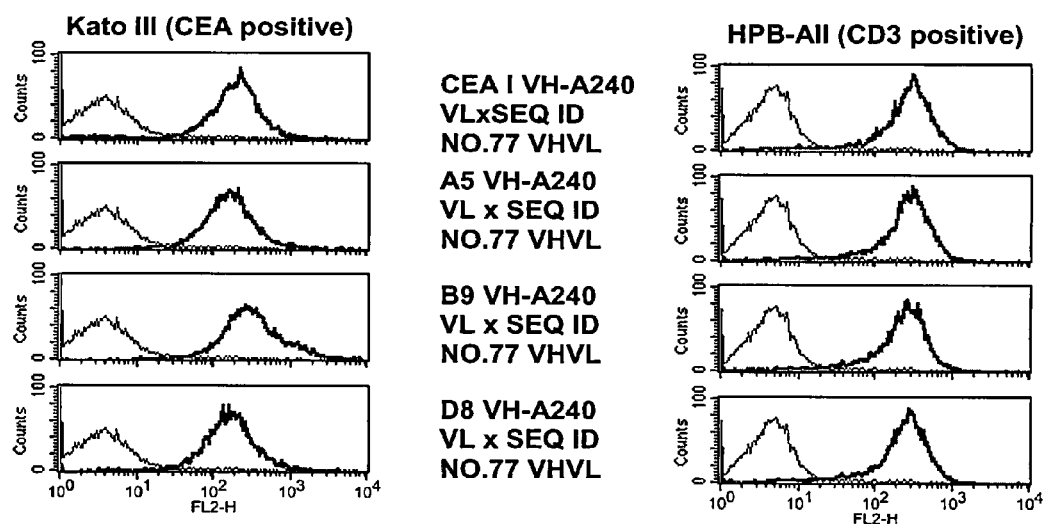

FIG. 14: FACS binding analysis of various human CEA-reactive bispecific single chain constructs to Kato III cells and HPB-All cells, respectively. The thick line represents cells incubated with cell culture supernatant of transfected CHO cells incubated with the anti-His antibody and the detection antibody. The thin histogram line reflects the negative control: cells incubated with the anti-His antibody and the detection antibody. The human bispecific single chain antibody constructs A5 VH-A240 VL×SEQ ID NO.77 VHVL, B9 VH-A240 VL×SEQ ID NO.77 VHVL, and D8 VH-A240 VL×SEQ ID NO.77 VHVL bind to human CEA on Kato cells and to human CD3 on HPB-All cells. CEAI VH-A240 VL×SEQ ID NO.77 VHVL with the VH region of the CEA binding domain derived from mAb A5B7 shows the same binding activity.

Figure 15:
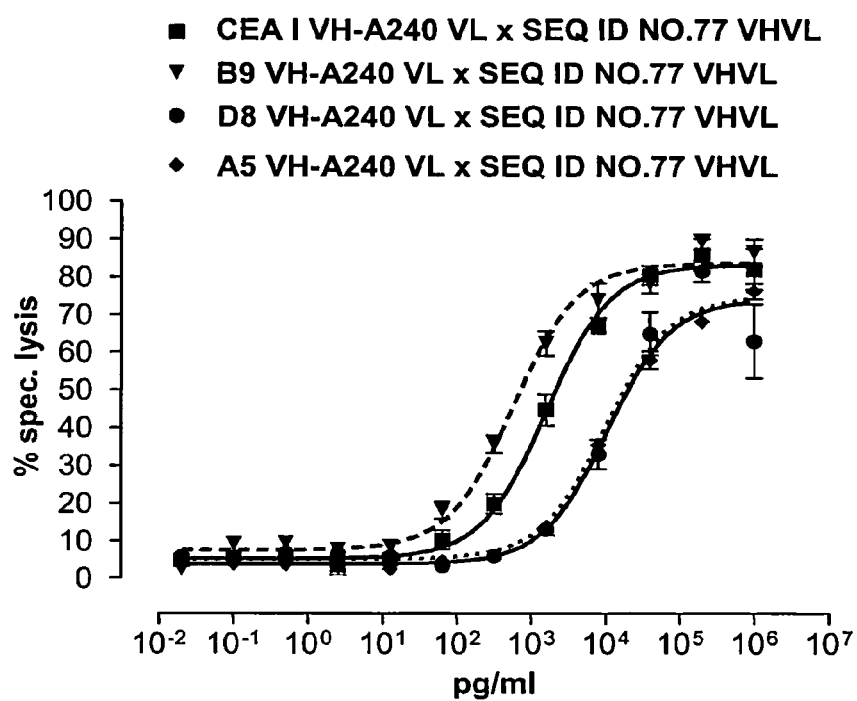

FIG. 15: Cytotoxicity assay of the indicated CEA-reactive bispecific single chain constructs redirected to CHO cells transfected with CEA, in the absence of soluble CEA. Stimulated human CD8 positive CTLs were used as effector cells. Cytotoxic activity could be detected for A5 VH-A240 VL×SEQ ID NO.77 VHVL, B9 VH-A240 VL×SEQ ID NO.77 VHVL, D8 VH-A240 VL×SEQ ID NO.77 VHVL and CEAI VH-A240 VL×SEQ ID N0.77 VHVL. CEAI VH is a VH region derived from mAb A5B7.

Figure 16:
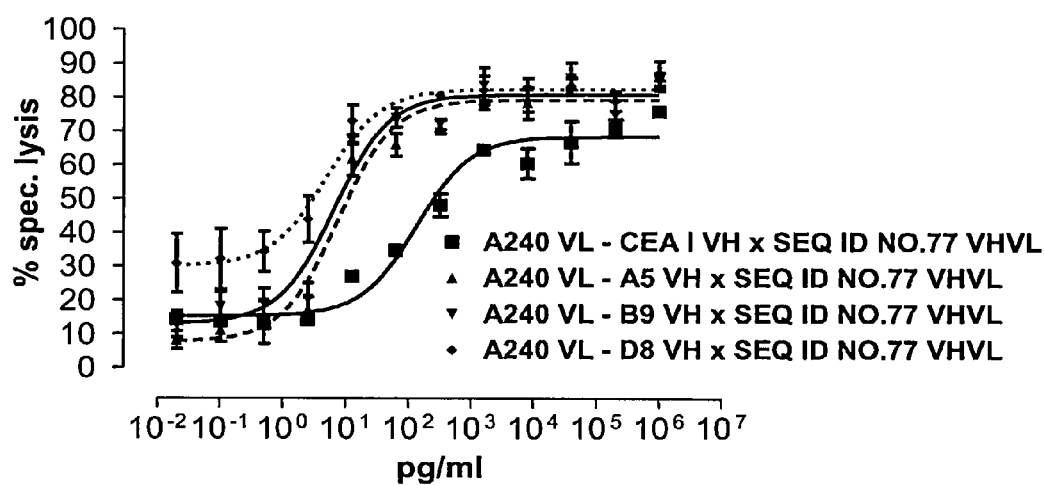

FIG. 16: Cytotoxicity assay of the indicated CEA-reactive bispecific single chain constructs redirected to CHO cells transfected with CEA, in the absence of soluble CEA. Stimulated human CD8 positive CTLs were used as effector cells. This Figure demonstrates cytotoxic activity for A240 VL-A5 VH×SEQ ID NO.77 VHVL, A240 VL-B9 VH×SEQ ID NO.77 VHVL, A240 VL-D8 VH×SEQ ID NO.77 VHVL, and A240 VL-CEAI VH×SEQ ID NO.77 VHVL.

Figure 17:
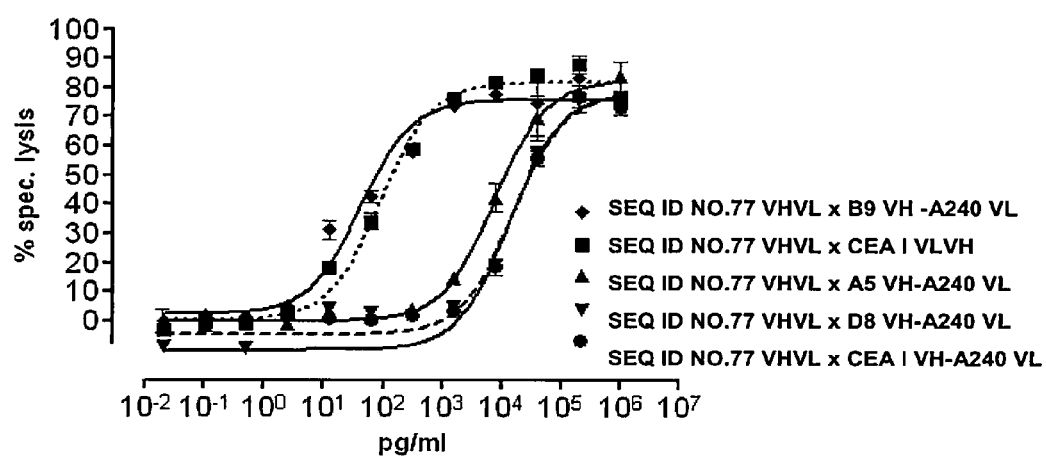

FIG. 17: Cytotoxicity assay of the indicated CEA-reactive bispecific single chain constructs redirected to CHO cells transfected with CEA, in the absence of soluble CEA. Stimulated human CD8 positive CTLs were used as effector cells. Cytotoxicity against CEA+ target cells is shown for SEQ ID NO.77 VHVL×A5 VH-A240 VL, SEQ ID NO.77 VHVL×B9 VH-A240 VL, SEQ ID NO.77 VHVL×D8 VH-A240 VL, SEQ ID NO.77 VHVL×CEAI VH-A240 VL and SEQ ID NO.77 VHVL×CEAI VLVH.

Figure 18:
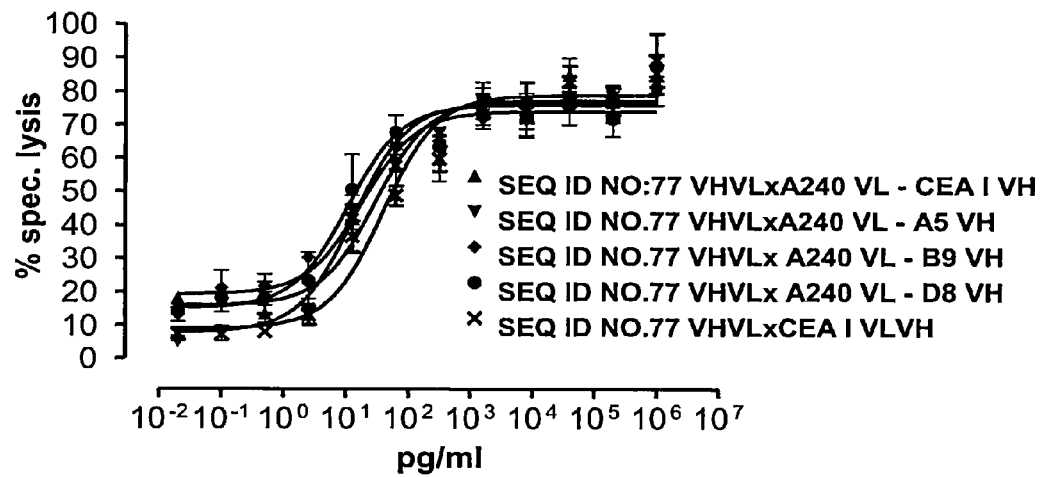

FIG. 18: Cytotoxicity assay of the indicated CEA-reactive bispecific single chain constructs redirected to CHO cells transfected with CEA, in the absence of soluble CEA. Stimulated human CD8 positive CTLs were used as effector cells. Cytotoxic activity is shown for SEQ ID NO.77 VHVL×A240 VL-A5 VH, SEQ ID NO.77 VHVL×A240 VL-B9 VH, SEQ ID NO.77 VHVL×A240 VL-D8 VH, and SEQ ID NO.77 VHVL×A240VL-CEAI VH and SEQ ID NO.77 VHVL×CEAI VLVH.

Figure 19:
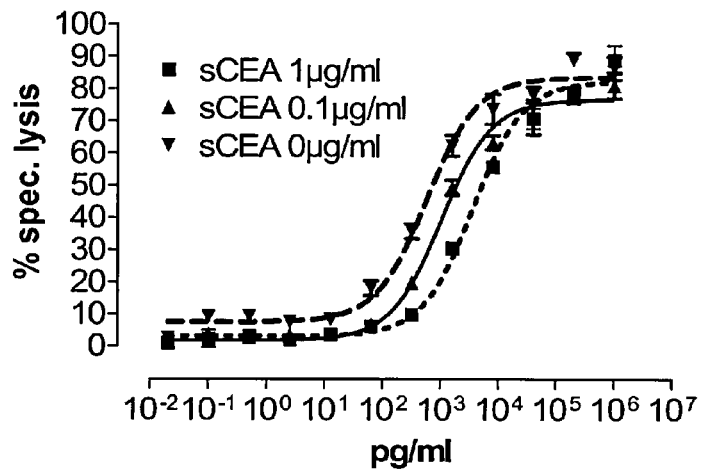
Figure 19:
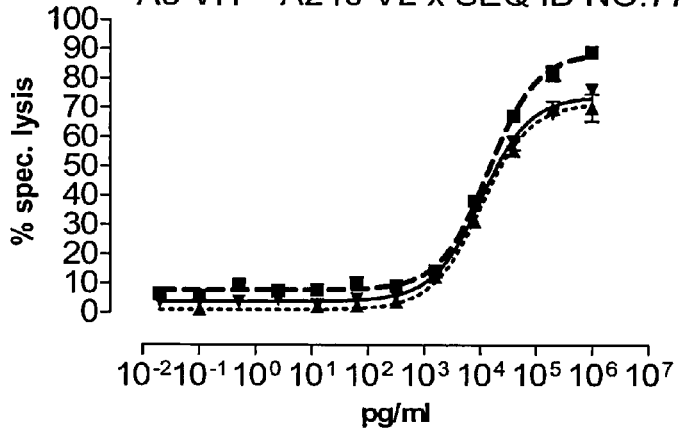

FIG. 19: Cytotoxicity assay of the indicated CEA-reactive bispecific single chain constructs redirected to CHO cells transfected with CEA in the presence of increasing amounts of soluble CEA antigen. Stimulated human CD8 positive CTLs were used as effector cells. The Figure demonstrates the resistance of cytotoxic activity of human bispecific single chain antibody constructs to soluble CEA antigen, as exemplified for A5 VH-A240 VL×SEQ ID NO.77 VHVL and B9 VH-A240 VL×SEQ ID NO.77 VHVL.

Figure 20:
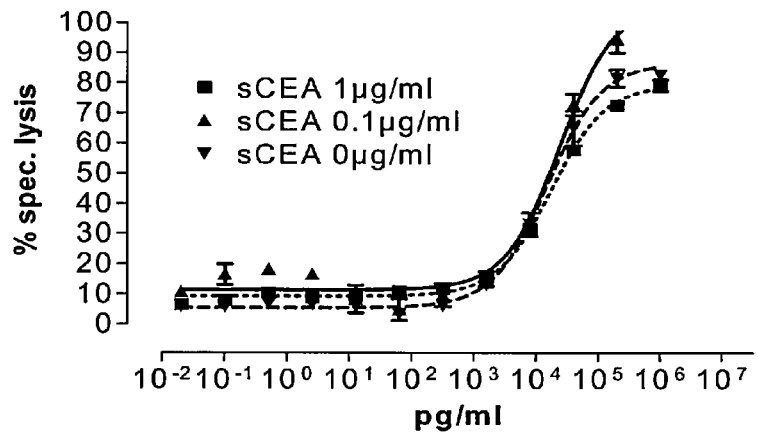
Figure 20:
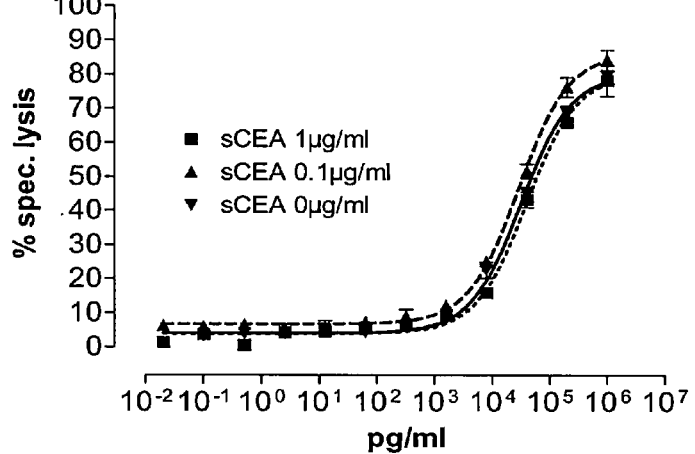

FIG. 20: Cytotoxicity assay of the indicated CEA-reactive bispecific single chain constructs redirected to CHO cells transfected with CEA in the presence of increasing amounts of soluble CEA antigen. Stimulated human CD8 positive CTLs were used as effector cells. Human bispecific single chain antibody constructs D8 VH-A240 VL×SEQ ID NO.77 VHVL and CEAI VH-A240 VL×SEQ ID NO.77 VHVL also show resistance to soluble CEA antigen.

Figure 21:
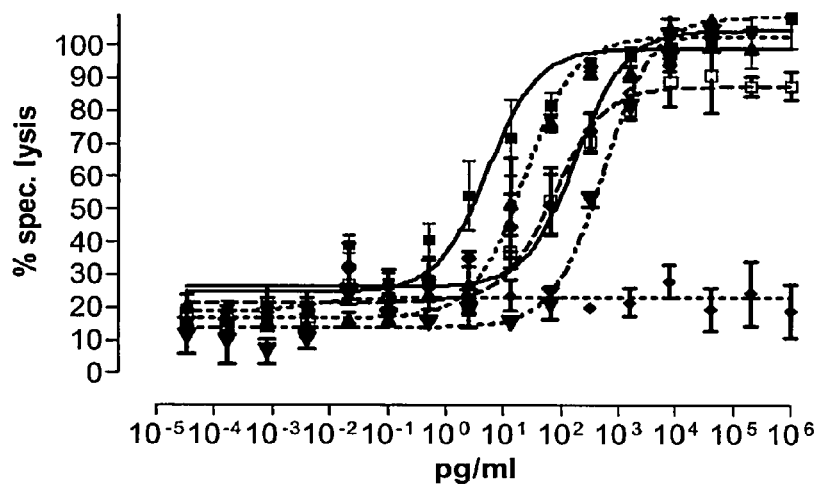

FIG. 21: The indicated CEA-reactive bispecific single chain constructs redirected T cells to lyse CHO cells transfected with CEA, in the absence of soluble CEA. To demonstrate the specificity of the redirected lysis, non-transfected CHO cells were included as negative control. Stimulated human CD8 positive CTLs were used as effector cells. A240 VL-B9 VH×SEQ ID NO.77 VHVL, SEQ ID NO.77 VHVL×A240 VL-B9 VH, SEQ ID NO.77 VHVL× B9 VH-A240 VL, B9 VH-A240 VL×SEQ ID NO.77 VHVL, and SEQ ID NO.77 VHVL×CEA I VHVL revealed cytotoxic activity against human CEA-transfected CHO cells.

Figure 22:
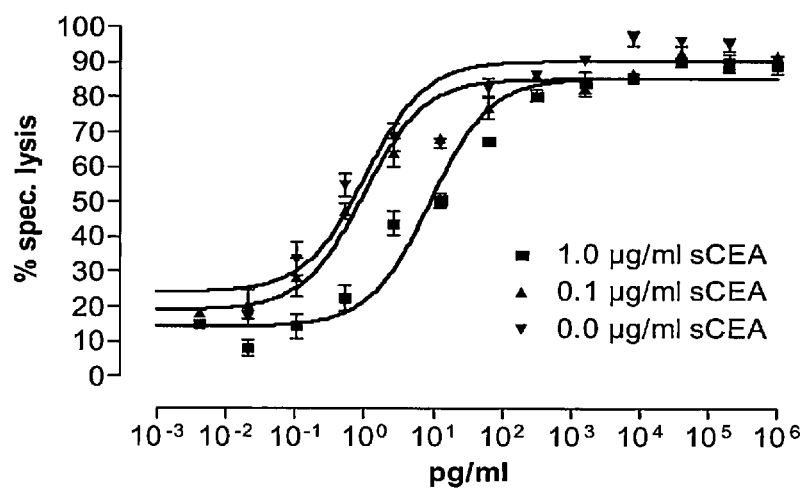

FIG. 22: The indicated CEA-reactive bispecific single chain construct redirected T cells to lyse CHO-CEA+ cells in the presence of increasing amounts of soluble CEA antigen. Stimulated human CD8+ T cells were used as effector cells. A240 VL-B9 VH×SEQ ID NO.77 VHVL-mediated cytotoxic activity is resistant to soluble CEA.

Figure 23:
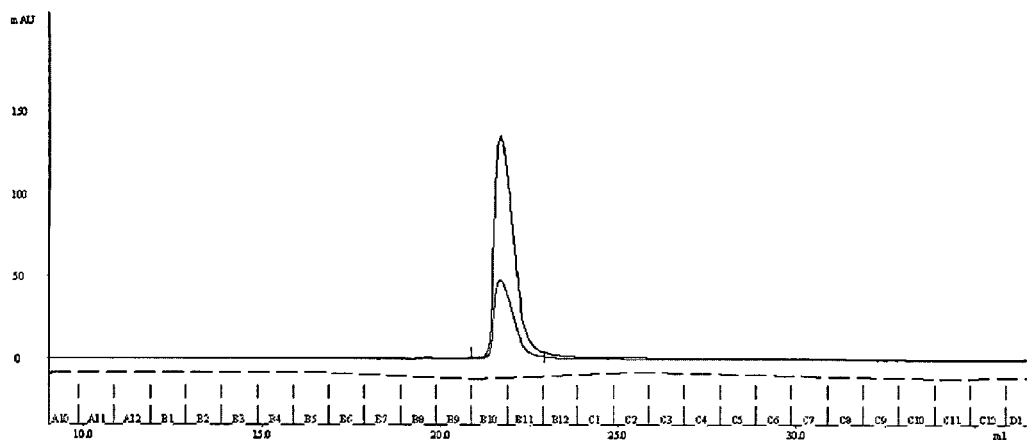

FIG. 23: High resolution cation exchange chromatogram of the bispecific single chain construct A240 VL-B9 VH×SEQ ID NO.77 VHVL, the blue line (upper curve) shows the overall charge isoforms of the protein. One single peak was detected showing high homogeneity of the construct.

FIG. 24: Protein stability assay based on the assessment of cytotoxicity after incubation in human plasma for 24 h. The CEA-reactive bispecific single chain construct redirected to CHO cells transfected with CEA, in the absence of soluble CEA. Stimulated human CD8 positive CTLs were used as effector cells. The Figure demonstrates the plasma stability of the bispecific single chain construct A240 VL-B9 VH×SEQ ID NO.77 VHVL in human plasma. Cytotoxic activity of the construct is not influenced by plasma proteins under physiological conditions.

Figure 25:
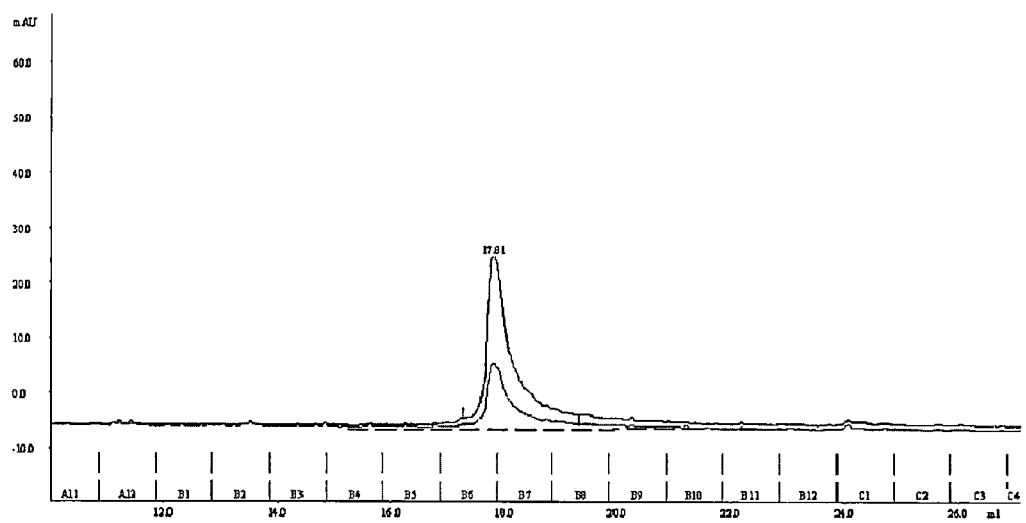

FIG. 25: High resolution cation exchange chromatogram of the bispecific single chain construct SEQ ID NO.77 VHVL×E12 VH-A240 VL, the blue line (upper curve) shows the overall charge isoforms of the protein. The Figure demonstrates the homogeneity of the bispecific single chain construct SEQ ID NO.77 VHVL×E12 VH-A240 VL.

Figure 26:
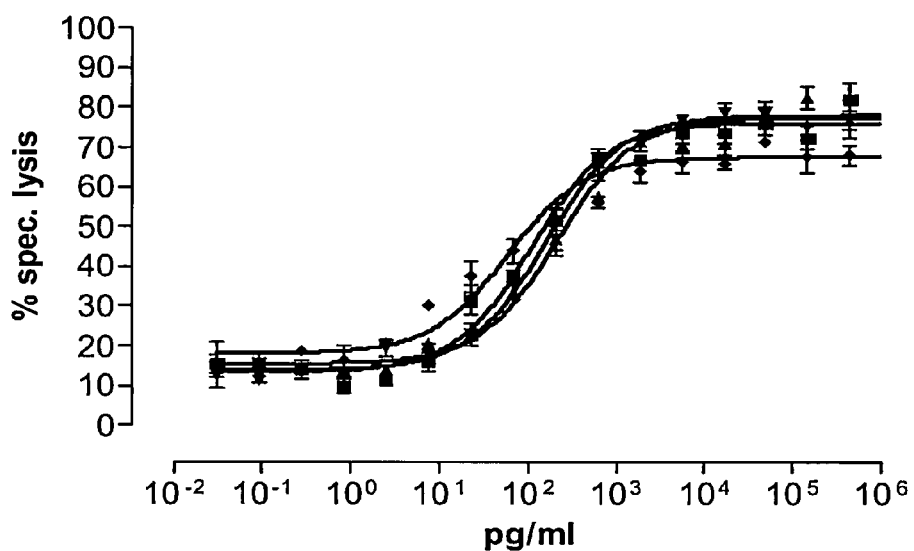

FIG. 26: Protein stability assay based on the assessment of cytotoxicity after incubation in human plasma for 24 h. The CEA-reactive bispecific single chain construct redirected to CHO cells transfected with CEA, in the absence of soluble CEA. Stimulated human CD8 positive CTLs were used as effector cells. This Figure demonstrates the plasma stability of the bispecific single chain construct SEQ ID NO.77 VHVL×E12 VH-A240 VL in human plasma. Cytotoxic activity of the construct is not influenced by plasma proteins under physiological conditions.

Figure 27:
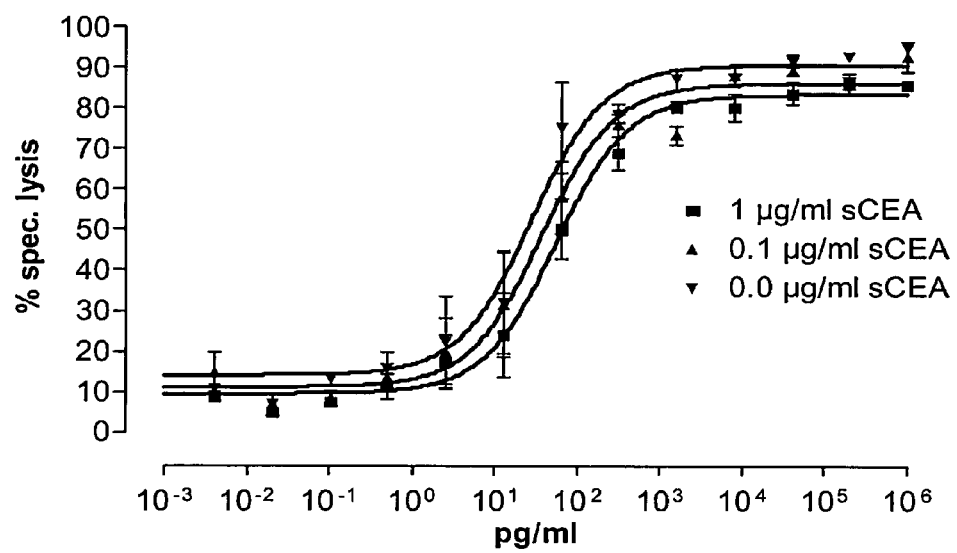

FIG. 27: The indicated CEA-reactive bispecific single chain construct redirected T cells to lyse CHO-CEA+ cells in the presence of increasing amounts of soluble CEA antigen. Stimulated human CD8+ T cells were used as effector cells. The bispecific single chain construct SEQ ID NO.77 VHVL×E12 VH-A240 VL mediated cytotoxic activity that is resistant to soluble CEA.

The following Examples illustrate the invention:

EXAMPLE 1

Generation of CHO Cells Transfected with Human CEA (Carcinoembryonic Antigen-Related Cell Adhesion Molecule 5; CEACAM5)

CEA-positive Kato III cells (human gastric carcinoma cell line; ATCC HTB-103) were used to obtain the total RNA that was isolated according to the instructions of the kit manual (Qiagen, RNeasy Mini Kit). The obtained RNA was used for cDNA synthesis by random-primed reverse transcription. For cloning of the full length sequence of the CEA antigen, the following oligonucleotides were used: 5' CEACAM5 EcoRI GAATTCGCCACCATGGAGTCTCCCTCGGCCCC (SEQ ID NO. 74) and 3'CEACAM5 Sal I GTCGACCTATATCAGAGCAACCCC (SEQ ID NO. 75). A PCR (denaturation at 93° C. for 5 min, annealing at 58° C. for 1 min, elongation at 72° C. for 1 min for the first cycle; denaturation at 93° C. for 1 min, annealing at 58° C. for 1 min, elongation at 72° C. for 1 min for 30 cycles; terminal extension at 72° C. for 5 min) was used to amplify the coding sequence. The PCR product was subsequently digested with EcoRI and SalI, ligated into the appropriately digested expression vector pEF-DHFR, and transformed into E. coli. The isolated plasmid DNA was sequenced and compared with the established nucleotide sequence of CEACAM5 (NM_004363 at the National Center for biotechnology information, http://www.ncbi.nlm.nih.gov/) The aforementioned procedures were carried out according to standard protocols (Sambrook, Molecular Cloning; A Laboratory Manual, Cold Spring Harbour Laboratory Press, Cold Spring Harbour, N.Y. (1989; 2001). The clone with the verified nucleotide sequence was transfected into DHFR deficient CHO cells for eukaryotic expression of the construct. Eukaryotic protein expression in DHFR deficient CHO cells was performed as described in Kaufmann (Kaufmann R. J., Methods Enzymol. 185 (1990), 537-566). Gene amplification of the construct was induced by increasing concentrations of MTX to a final concentration of up to 20 nM MTX. The transfected cells were then tested for expression of CEA antigen using an FACS assay. For that purpose, $2.5 \times 10^5$ transfected cells were incubated with 5 μg/ml of the murine monoclonal antibody COL-1 (No. MS-613-P1ABX, Neomakers; Fremont, Calif., USA). The binding of the antibody was detected with a R-Phycoerythrin-conjugated affinity purified F(ab')2 fragment, goat anti-mouse IgG, Fc-gamma fragment specific antibody, diluted 1:100 in 50 μl PBS with 2% FCS (obtained from Dianova, Hamburg, Germany). Cells were analyzed by flow cytometry on a FACS-Calibur (Becton Dickinson, Heidelberg). FACS staining and measuring of the fluorescence intensity were performed as described in Current Protocols in Immunology (Coligan, Kruisbeek, Margulies, Shevach and Strober, Wiley-Interscience, 2002). As a result, the transfectants demonstrated a clearly positive staining for the human CEA antigen.

EXAMPLE 2

Generation of CEA×CD3 Bispecific Single Chain Antibodies

Generally, bispecific single chain antibody molecules, each comprising a domain with binding specificity for the human CEA antigen as well as a deimmunized domain with binding specificity for the human CD3 antigen depicted in SEQ ID NO.77 were designed as set out in Table 1. The arrangement of the V regions in this CD3 binding domain is always VH-VL. This de-immunised anti-CD3 binding domain used in the bispecific single chain antibodies as defined herein has been described previously, e.g. in WO2005/040220.

1. Formats of Bispecific Single Chain Antibody Molecules Comprising Anti-CEA and Anti-CD3 Specificities (Table 1)

| SEQ ID NO. (amino acid sequence) | Formats of protein constructs (N terminus→ C terminus) |
|---|---|
| 2 | SEQ ID NO. 77 VHVL x CEA I VLVH |
| 4 | SEQ ID NO. 77 VHVL x CEA I VHVL |
| 6 | CEA I VLVH x SEQ ID NO. 77 VHVL |
| 8 | CEA I VHVL x SEQ ID NO. 77 VHVL |
| 10 | CEA II VHVL x SEQ ID NO. 77 VHVL |
| 12 | CEA III VLVH x SEQ ID NO. 77 VHVL |
| 14 | CEA III VHVL x SEQ ID NO. 77 VHVL |
| 16 | CEA I VH-A240VL x SEQ ID NO. 77 VHVL |
| 18 | A240VL - CEA I VH x SEQ ID NO. 77 VHVL |
| 20 | SEQ ID NO. 77 VHVL x CEA I VH - A240 VL |
| 22 | SEQ ID NO. 77 VHVL x A240 VL - CEA I VH |
| 24 | A5 VH - A240 VL x SEQ ID NO. 77 VHVL |
| 26 | A240 VL - A5 VH x SEQ ID NO. 77 VHVL |
| 28 | SEQ ID NO. 77 VHVL x A240 VL - A5 VH |
| 30 | SEQ ID NO. 77 VHVL x A5 VH - A240 VL |
| 32 | B9 VH - A240 VL x SEQ ID NO. 77 VHVL |
| 34 | A240 VL - B9 VH x SEQ ID NO. 77 VHVL |
| 36 | SEQ ID NO. 77 VHVL x B9 VH - A240 VL |

-continued

| SEQ ID NO. (amino acid sequence) | Formats of protein constructs (N terminus→ C terminus) |
|---|---|
| 38 | SEQ ID NO. 77 VHVL x A240 VL - B9 VH |
| 40 | D8 VH - A240 VL x SEQ ID NO. 77 VHVL |
| 42 | A240 VL - D8 VH x SEQ ID NO. 77 VHVL |
| 44 | SEQ ID NO. 77 VHVL x D8 VH - A240 VL |
| 46 | SEQ ID NO. 77 VHVL x A240 VL - D8 VH |
| 126 | A5 VH-A240 VL# x SEQ ID NO. 77 VHVL |
| 128 | SEQ ID NO. 77 VHVLxA5 VH-A240VL# |
| 130 | B9 VH-A240 VL# x SEQ ID NO. 77 VHVL |
| 132 | SEQ ID NO. 77 VHVLxB9 VH-A240VL# |
| 134 | D8 VH-A240 VL# x SEQ ID NO. 77 VHVL |
| 136 | SEQ ID NO. 77 VHVLxD8 VH-A240VL# |
| 143 | SEQ ID NO. 77 VHVLxE12 VH-A240VLI |

The aforementioned constructs containing the variable light-chain (VL) and variable heavy-chain (VH) regions specific for the human CEA antigen derived from monoclonal antibodies, hybridomas or obtained by phage display guided selection (PDGS) were obtained by gene synthesis and subsequent cloning into an expression vector comprising the CD3-specific VH and VL combinations. The generation of said bispecific single chain constructs can also be carried out according to recombinant techniques described e.g. in Sambrook (loc.cit.). A detailed instruction therefor is provided for e.g. in WO 99/054440.

The anti-CD3 binding domain corresponds to a de-immunized domain with binding specificity for the human CD3 antigen. The arrangement of the V regions of the deimmunized anti-CD3 binding domain in the bispecific single chain constructs described herein is always VH-VL. The corresponding amino acid sequence of said VH-VL domain is depicted in SEQ ID NO. 77. CEAI, CEAII and CEAIII specific for the human carcinoembryonic antigen contain the variable light-chain (VL) and variable heavy-chain (VH) regions derived from mAbs A5B7 (Chester, K. A. et al., Int J Cancer 57 (1994), 67-72), T84.66 (Neumaier, M. et al., Cancer Res 50 (1990), 2128-34) and MFE-23 (Boehm, M. K. Biochem J 2 (2000), 519-28), respectively. A5, B9, D8, and E12 are human VH regions specific for human CEA, whereas A240 is a human VL region with the same specificity. The generation of the human A5, B9, D8, E12 and A240 V regions is described in detail in Examples 6 and 7.

The corresponding nucleotide and amino acid sequences of all bispecific single chain antibodies described herein are shown in the sequence listing.

In the following the generation of the CEA I VLVH×SEQ ID NO.77 VHVL (SEQ ID NO.6) construct is described in more detail. The generation of the other constructs mentioned above can be performed accordingly with the necessary implementation of modifications to the methods being well in the scope of the person skilled in the art.

To generate bispecific single chain antibody molecules comprising the aforementioned CEAI specificity and the deimmunized anti-CD3 (SEQ ID NO.77) specificity firstly the variable regions of CEAI obtained by gene synthesis according to standard protocols had to be modified by PCR to obtain the corresponding single chain Fv antibody fragment. To this end a two-step fusion PCR was used to amplify the sequence coding for the variable regions. A set of appropriate primers was designed to perform the PCR-based cloning steps, finally resulting in a single chain antibody connecting the two variable domains with a 15 amino acid linker ($[Gly_4Ser]_3$) in the order VL-Linker-VH.

In short the following primer combinations were used:

| PCR step | Used primers | | PCR step | Used primers | Resulting scFv |
|---|---|---|---|---|---|
| 1 | 5'CEAI LH + 3'CEAI VL Linker | -> | Fusion | 5'CEAI LH + | CEAI LH |
| 2 | 5'CEAI VH Linker + 3'CEAI LH | -> | PCR | 3'CEAI LH | |

The nucleotide sequences of the oligonucleotide primers are given below:

5'CEAI LH:
(SEQ ID NO: 137)
5' AGGTGTACACTCCGACATTGAGCTCACCCAG 3'

3'CEAI VL Linker:
(SEQ ID NO: 138)
5' GGAGCCGCCGCCGCCAGAACCACCACCACCTTTGATCTCGAGCTTG G 3'

5'CEAI VH Linker:
(SEQ ID NO: 139)
5' GGCGGCGGCGGCTCCGGTGGTGGTGGTTCTCAGGTCCAACTGCAGGA G 3'

3'CEAI LH:
(SEQ ID NO: 140)
5' AATCCGGAGGAGACGGTGACCG 3'

To generate the single chain antibody, two PCRs with the respective primer combinations described above as PCR step 1 and 2 were performed. During this PCR overlapping complementary sequences were introduced into the PCR-products (stemming from the respective linker primers) that combined to form the coding sequence of the 15 amino acid linker during the subsequent fusion PCR. Subsequently the amplified VH and VL domains were joined in this fusion PCR in which only the outer primers and both PCR-products were required. The resulting scFv antibody is flanked at the 5' end with the restriction enzyme recognition site for BsrGI and at the 3' end with the restriction enzyme recognition site for BspEI. Addition of the BsrGI site was performed as to allow for the in frame fusion with the coding sequence of a murine immunoglobulin leader peptide as described in WO2005/040220. The BspEI site was created as to allow for the in frame fusion with the sequence coding for the CD3 specific single chain antibody to generate the bispecific single chain antibody. To accomplish the fusion of the single chain Fv antibodies and to allow for eukaryotic expression the coding sequence of the CEA specific single chain Fv antibody was cloned via BsrGI and BspEI into the pEFD-HFR expression vector (pEFDHFR was described in Mack et al. Proc. Natl. Acad. Sci. USA 92 (1995) 7021-7025) containing the deimmunized anti-CD3 single chain Fv antibody as described in WO2005/040220; in the present invention referred to as SEQ ID NO.77. Single clones of the construct were isolated and sequenced with primers complementary to flanking regions in the expression vector according to standard protocols (Sambrock, Molecular Cloning; A Laboratory Manual, 2nd edition, Cold Spring Harbour laboratory Press, Cold Spring Harbour, N.Y. (1989)). For further experiments a clone of the construct with a verified nucleotide sequence was selected.

2. Expression and Purification of the CEA×CD3 Bispecific Single Chain Antibodies The bispecific single chain antibodies were expressed in chinese hamster ovary (CHO) cells. Eukaryotic protein expression in DHFR deficient CHO cells was performed as described in Kaufmann (loc. cit.). Gene amplification of the constructs were induced by increasing concentrations of MTX to a final concentration of up to 20 nM MTX. After two passages of stationary culture the cells were grown in roller bottles with CHO modified DMEM medium (HiQ®, HiClone) for 7 days before harvest. The cells were removed by centrifugation and the supernatant containing the expressed protein was stored at −20° C.

Äkta® FPLC System (Pharmacia) and Unicorn® Software were used for chromatography. All chemicals were of research grade and purchased from Sigma (Deisenhofen) or Merck (Darmstadt). Immobilized metal affinity chromatography ("IMAC") was performed using a Fractogel® column (Merck) which was loaded with $ZnCl_2$ according to the protocol provided by the manufacturer. The column was equilibrated with buffer A2 (20 mM sodium phosphate buffer pH 7.5, 0.4 M NaCl) and the cell culture supernatant (500 ml) was applied to the column (10 ml) at a flow rate of 3 ml/min. The column was washed with buffer A2 to remove unbound sample. Bound protein was eluted using a 2 step gradient of buffer B2 (20 mM sodium phosphate buffer pH 7.5, 0.4 M NaCl, 0.5 M Imidazol) according to the following:

Step 1: 20% buffer B2 in 6 column volumes;
Step 2: 100% buffer B2 in 6 column volumes.

Eluted protein fractions from step 2 were pooled for further purification. Gel filtration chromatography was performed on a Sephadex S200 HiPrep column (Pharmacia) equilibrated with PBS (Gibco). Eluted protein samples (flow rate 1 ml/min) were subjected to standard SDS-PAGE and Western Blot for detection. Prior to purification, the column was calibrated for molecular weight determination (molecular weight marker kit, Sigma MW GF-200). Protein concentrations were determined using protein assay dye (MicroBCA, Pierce) and IgG (Biorad) as standard protein.

The CEA×CD3 bispecific single chain antibodies were isolated in a two step purification process of IMAC and gel filtration. The main product had a molecular weight of ca. 52 kDa under native conditions as determined by gel filtration in PBS. This molecular weight corresponds to the bispecific single chain antibody. All constructs were purified according to this method.

Purified bispecific single chain antibody protein was analyzed in SDS PAGE under reducing conditions performed with pre-cast 4-12% Bis Tris gels (Invitrogen). Sample preparation and application were performed according to the protocol provided by the manufacturer. The molecular weight was determined with MultiMark protein standard (Invitrogen). The gel was stained with colloidal Coomassie (Invitrogen protocol). The purity of the isolated protein was >95% as determined by SDS-PAGE.

Western Blot was performed using an Optitran® BA-S83 membrane and the Invitrogen Blot Module according to the protocol provided by the manufacturer. The antibodies used were directed against the His Tag (Penta His, Qiagen) and Goat-anti-mouse Ig labeled with alkaline phosphatase (AP) (Sigma), and BCIP/NBT (Sigma) as substrate. The bispecific single chain antibody could be specifically detected by Western Blot. A single band was detected at 52 kD corresponding to the purified bispecific single chain antibody molecule.

3. Flow Cytometric Binding Analysis of the CEA×CD3 Bispecific Single Chain Antibodies In order to test the functionality of the constructs with regard to binding capability to membrane-bound human CEA and human CD3, FACS analysis was performed. For this purpose, human CEA-transfected CHO cells and CD3 positive human T cell leukemia cell line HPB-All (DSMZ, Braunschweig, ACC483) were used. 200,000 CEA positive CHO cells or 200,000 HPB-All cells were incubated for 30 min on ice with 50 µl of the pure cell supernatant of CHO cell cultures each expressing bispecific antibodies with different arrangements of VH and VL regions of CEA and CD3 (as described above). The cells were washed twice in PBS and binding of the construct was detected with an unlabeled murine Penta His antibody (diluted 1:20 in 50 µl PBS with 2% FCS; Qiagen), which specifically binds to cell-bound construct via the construct's C-terminal histidine tag. A washing step followed to remove unbound murine Penta His antibody. Bound anti-His antibodies were detected with an Fc gamma-specific antibody (Dianova) conjugated to phycoerythrin, diluted 1:100 in 50 µl PBS with 2% FCS. As a positive control for binding to human CEA, monoclonal antibody Col-1 (see Example 3) has been used. For control of binding to human CD3, a CD19×CD3 bispecific single chain construct as described in WO 99/054440 has been utilized. As a negative control fresh culture medium was used in place of culture supernatant.

Cells were analyzed by flow cytometry (FACS-Calibur; Becton Dickinson, Heidelberg). FACS staining and measuring of the fluorescence intensity were performed as described in Current Protocols in Immunology (Coligan, Kruisbeek, Margulies, Shevach and Strober, Wiley-Interscience, 2002).

As shown in FIG. 1, several domain arrangements of the bispecific single chain antibodies, i.e. CEAI VHVL×SEQ ID NO.77 VHVL (SEQ ID NO. 8), CEAI VLVH×SEQ ID NO.77 VHVL (SEQ ID NO. 6), CEAII VHVL×SEQ ID NO.77 VHVL (SEQ ID NO. 10), CEAIII VLVH×SEQ ID NO.77 VHVL (SEQ ID NO. 12) and CEAIII VHVL×SEQ ID NO.77 VHVL (SEQ ID NO. 14), bound to human membrane-bound CEA and human CD3. As a negative control, culture medium and 1. and 2. detection antibodies have been used.

EXAMPLE 3

Binding of CEA×CD3 Bispecific Single Chain Antibodies to Soluble Human CEA

In order to determine the specificity against soluble human CEA, various CEA×CD3 bispecific single chain antibodies were tested in ELISA.

To this end, soluble human CEA antigen was first biotinylated. Biotinylation was accomplished in PBS containing 5% DMSO (Sigma) with a fifteen-fold molar excess of EZ-Link Sulfo NHS-LC-LC-Biotin (Pierce) for 1 hour at room temperature in a sample mixer (Dynal). For the separation of free Biotin and biotinylated CEA antigen, the assay was excessively dialyzed against PBS according to standard protocols. The retained bioactivity of the biotin-labeled CEA was confirmed in ELISA binding experiments.

The direct ELISA to determine the specificity of CEA×CD3 bispecific single chain antibody against soluble human CEA was carried out according to standard procedures. Briefly, 50 µl/well PBS or soluble biotinylated human CEA (Abcam; 5 µg/ml in 1×PBS) were immobilized on a 96-well streptavidin-coated ELISA plate (Nunc) by incubating at 4° C. for about 16 hours. After washing with 200 µl water per well 200 µl of blocking solution (PBS/3% BSA) was added. After blocking for 1 h at room temperature the blocking solution was removed. All subsequent washing (200 µl/well of 1×PBS/0.05% (v/v) Tween20) and incubation steps were performed at room temperature. After washing once, the CEAI VHVL×SEQ ID NO.77 VHVL (SEQ ID NO. 8; anti-CEA part derived from mAb A5B7), CEAII VHVL×SEQ ID NO.77 VHVL (SEQ ID NO. 10; anti-CEA part derived from mAb T84.66), and CEAIII VHVL×SEQ ID NO.77 VHVL (SEQ ID NO. 14; anti-CEA part derived from mAb MFE-23) bispecific single chain antibodies, and mouse monoclonal antibody CEA/CD66 Ab-3 (Col-1; Dunn) were incubated in different concentrations (0.5 µg/ml and 5 µg/ml in 1×PBS; 50 µl/well) for 1 hour. 1×PBS (50 µl/well) was added as a control for unspecific binding. 3 washing steps were followed by adding 50 µl/well Penta-His IgG (Qiagen; 2 µg/ml in 1×PBS) for detection of the His-tagged bispecific single chain antibodies. Subsequently, the wells were washed 3 times and incubated with 50 µl of a horseradish peroxidase-labelled goat anti-mouse Fc gamma-specific antibody (Jackson ImmuneResearch; 1:1000 in 1×PBS) for 1 hour. After washing 3 times the ELISA was developed by adding ABTS substrate solution (Roche) and the absorbance was measured at a wavelength of 405 nm.

FIG. 2 shows the absorbance of the different bispecific single chain antibodies detected in the ELISA. The CEAI VHVL×SEQ ID NO.77 VHVL (SEQ ID NO. 8; anti-CEA part derived from mAb A5B7), CEAII VHVL×SEQ ID NO.77 VHVL (SEQ ID NO. 10; anti-CEA part derived from mAb T84.66), and CEAIII VHVL×SEQ ID NO.77 VHVL (SEQ ID NO. 14; anti-CEA part derived from mAb MFE-23) bispecific single chain antibodies and the mouse monoclonal antibody Col-1 specifically bound to soluble human CEA. No binding signal was observed in the absence of the CEA antigen (PBS control). In summary, the anti-CEA binding domains derived from mAbs A5B7, T84.66 and MFE-23 bind to both soluble and membrane-bound CEA.

EXAMPLE 4

Bioactivity of CEA×CD3 Bispecific Single Chain Antibodies

Bioactivity of the generated CEA×CD3 bispecific single chain antibodies was analyzed by in vitro chromium release cytotoxicity assays using the human gastric carcinoma cell line Kato III or the human CEA-transfected CHO cells as target cells and stimulated human CD8 positive T cells or native PBMC as effector cells, respectively.

The generation of the stimulated CD8+ T cells was performed as follows:
A petri dish (145 mm diameter, greiner bio-one) was pre-coated with an anti-CD3 antibody (OKT3 Janssen-Cilag GmbH, Orthoclone 1 mg/ml; final concentration 1 µg/ml) and an anti-CD28 antibody (BD, 1 mg/ml; final concentration 1 µg/ml) for 1 hour at 37° C. After the incubation period, the unbound protein was removed by one washing step with PBS. The fresh PBMC's were isolated from peripheral blood (30-50 ml) by Ficoll gradient centrifugation according to standard protocols. 3-5×10$^7$ PBMCs were added to the precoated petri dish in 150 ml of RPMI 1640/10% FCS/IL-2 20 U/ml (Proleukin, Chiron) and stimulated for 2 days. At the third day the cells were collected, washed once with RPMI 1640 and transferred to a large T-flask. IL-2 was added to a final concentration of 20 U/ml and cultivated again for one day. The CD8+ CTLs were isolated with help of the CD8 negative isolation kit (Dynal Biotech) by following the instructions of the manual. The native PBMC's were used directly after the Ficoll gradient centrifugation without the stimulation procedure. Target cells were washed twice with PBS and labeled with 11.1 MBq $^{51}$Cr in a final volume of 100 µl RPMI with 50% FCS for 45 minutes at 37° C. Subsequently, the labeled target cells were washed 3 times with 5 ml RPMI and then used in the cytotoxicity assay. The assay was performed in a 96 round bottom plate in a total volume of 250 µl supplemented RPMI (as above) with an E:T ratio of 10:1 corresponding to 5000 target cells and 50000 effector cells per well. For the evaluation of the constructs a starting concentration of 1 µg/ml of the bispecific single chain molecules in the assay volume and 12 threefold dilutions thereof were applied. The assay time was 18 hours and cytotoxicity was measured as relative values of released chromium in the supernatant related to the difference of maximum lysis (addition of Triton-X) and spontaneous lysis (without effector cells). All measurements were done in triplicates. Measurement of chromium activity in the supernatants was performed with a Wizard 3 gammacounter (Perkin Elmer Life Sciences GmbH, Köln, Germany). Analysis of the experimental data was performed with Prism 4 for Windows (version 4.02, GraphPad Software Inc., San Diego, Calif., USA). Sigmoidal dose response curves typically had $R^2$ values >0.90 as determined by the software. $EC_{50}$ values calculated by the analysis program were used for comparison of bioactivity.

FIG. 3 shows cytotoxic activity against human CEA-transfected target cells (CHO-CEA$^+$ cells) for various domain arrangements, i.e. for SEQ ID NO.77 VHVL×CEAI VHVL (SEQ ID NO. 4) and SEQ ID NO.77 VHVL×CEAI VLVH (SEQ ID NO. 2) (both constructs with anti-CD3 part N-terminally), as well as for CEAI VLVH×SEQ ID NO.77 VHVL (SEQ ID NO. 6) and CEAI VHVL×SEQ ID NO.77 VHVL (SEQ ID NO. 8) (anti-CD3 C-terminally). Non-transfected CHO cells (lacking human CEA) were used as a negative control.

In FIG. 4, CEAI VHVL×SEQ ID NO.77 VHVL (SEQ ID NO. 8), CEAIII VLVH×SEQ ID NO.77 VHVL (SEQ ID NO. 12), CEAIII VHVL×SEQ ID NO.77 VHVL (SEQ ID NO. 14), and CEAII VHVL×SEQ ID NO.77 VHVL (SEQ ID NO. 10) exhibited cytotoxic activity against human CEA-transfected CHO cells. Non-transfected CHO cells (lacking human CEA) were used as a negative control. As set forth above, CEAI denotes a variable region derived from murine mAb A5B7, CEAII is a variable region derived from murine mAb T84.66 and CEAIII refers to a variable region from murine mAb MFE-23.

In summary, all tested constructs showed cytotoxic activity against (human) CEA expressing Kato III and human CEA-transfected CHO cells, in the absence of soluble human CEA.

EXAMPLE 5

Bioactivity of CEA×CD3 Bispecific Single Chain Antibodies Specific in the Presence of Soluble CEA Antigen The competition assays are performed as described in Example 4, with the following exception: The bioactivity of the CEA×CD3 bispecific single chain antibodies is tested in the presence of various concentrations of soluble human CEA antigen. The soluble human CEA antigen (AbCAM Ltd. Cambridge UK) used was isolated from a metastatic colonic carcinoma from the liver of a single patient. Experimentally, the competition assay was carried out by pre-incubation of a given amount of the bispecific single chain antibody with increasing amounts of soluble human CEA antigen (either 0 µg/ml; 0.1 µg/ml; 1 µg/ml, or 0 µg/ml; 0.004 µg/ml; 0.02 µg/m; 0.1 µg/ml; 0.5 µg/ml; 1 µg/ml) for 30 minutes at 37° C. prior to the addition of the cells. The remainder of the assay was carried out as described in Example 4. The results of these competition experiments are shown in FIGS. 5 to 11.

Cytotoxic activity of bispecific single chain antibodies CEAII VHVL×SEQ ID NO.77 VHVL (SEQ ID NO. 10; see FIGS. 7 and 9 to 11) with the anti-CEA part derived from mAb T84.66, and CEAIII VLVH×SEQ ID NO.77 VHVL (SEQ ID NO. 12; see FIG. 8) with the anti-CEA region derived from mAb MFE-23, against human CEA-positive target cells was drastically inhibited by increasing amounts of soluble human CEA antigen. As set forth above, said constructs bind to both membrane-bound and soluble human CEA antigen; see e.g. Examples 2 and 3 and FIGS. 1 and 2. Thus, most probably, soluble human CEA prevents the anti-CEA part of said bispecific single chain antibodies from binding to membrane-bound human CEA on the target cells, for instance CHO-CEA+ or Kato III tumor cells, thereby inhibiting the cytotoxic activity mediated by said antibody constructs.

In contrast, it has been surprisingly found that bispecific single chain antibodies with an anti-CEA part derived from mAb A5B7 are resistant to soluble human CEA: For instance, the cytotoxic activity mediated by CEAI VLVH× SEQ ID NO.77 VHVL (SEQ ID NO. 6; see FIG. 5), CEAI VHVL×SEQ ID NO.77 VHVL (SEQ ID NO. 8; see FIGS. 5, 8 and 10), SEQ ID NO.77 VHVL×CEAI VHVL (SEQ ID NO. 4; see FIG. 6) and SEQ ID NO.77 VHVL×CEAI VLVH (SEQ ID NO. 2; see FIG. 6) is not inhibited by increasing amounts of soluble human CEA, not even by high concentrations (1 µg/ml). This could not be expected in view of the fact that the anti-CEA part of said bispecific single chain antibodies binds to soluble human CEA (FIG. 2). Rather, inhibition of cytotoxic activity against CEA-positive target cells by increasing amounts of soluble human CEA could have been expected, as it was the case for T84.66- and MFE-23-derived constructs; see above.

Thus, the present invention provides for pharmaceutical compositions with cytotoxic anti-tumor activity in the presence of even high levels of soluble CEA antigen. Therefore, these pharmaceutical compositions are particularly suitable for the treatment of tumor patients with high soluble CEA antigen concentrations in their plasma, such as patients with progressive epithelial tumors, metastatic epithelial tumors, high tumor load/burden, late stage epithelial tumors or tumor patients with a CEA serum concentration higher than 100 ng/ml, as determined by ELISA.

EXAMPLE 6

Selection of Human VL Regions

In order to provide for pharmaceutical compositions with reduced immunogenicity when being administered to cancer patients, human bispecific single chain antibodies with resistance to soluble CEA antigen have been generated. In a first step, human VL regions with resistance to soluble CEA have been isolated. Thus, the aim of this experiment is the selection of human VL regions which can pair with the maternal, murine VH of monoclonal antibody (mAb) A5B7.

1. Biotinylation of Soluble Human CEA Antigen

For phage library selection, soluble CEA antigen was biotinylated. Biotinylation was accomplished in PBS containing 5% DMSO (Sigma) with a fifteenfold molar excess of EZ-Link Sulfo NHS-LC-LC-Biotin (Pierce) for 1 hour at room temperature in a sample mixer (Dynal). For the separation of free Biotin and biotinylated CEA antigen, the assay was excessively dialized against PBS according to standard protocols. The retained bioactivity of the biotin-labeled CEA was confirmed in ELISA binding experiments.

2. Isolation of RNA from Human B-Cells 100 mL blood were taken from five healthy human donors. Peripheral blood mononuclear cells (PBMCs) were isolated by a ficoll-gradient according to standard methods. Total RNA was isolated from the isolated cells using the RNeasy® Midi Kit (QIAGEN) following the manufacturer's instructions. cDNA was synthesized according to standard methods (Sambrook, Cold Spring Harbor Laboratory Press 1989, 2001).

3. PCR-Amplification of Variable Light Chain Regions (VL-Regions)

For the isolation of light chain V-region DNA, RT-PCR was carried out using V-kappa- (5'-huVK1-SacI-2001 (5'-GAGCCGCACG AGCCCGAGCT CCAGATGACC CAGTCTCC-3') (SEQ ID NO. 78), 5'-huVK2/4-SacI-2001 (5'-GAGCCGCACG AGCCCGAGCT CGTGATGACY CAGTCTCC-3') (SEQ ID NO. 79), 5'-huVK3-SacI-2001 (5'-GAGCCGCACG AGCCCGAGCT CGTGWTGACR CAGTCTCC-3') (SEQ ID NO. 80), 5'-huVK5-SacI-2001 (5'-GAGCCGCACG AGCCCGAGCT CACACTCACG CAGTCTCC-3') (SEQ ID NO. 81), 5'-huVK6-SacI-2001 (5'-GAGCCGCACG AGCCCGAGCT CGTGCTGACT CAGTCTCC-3') (SEQ ID NO. 82), 3'-hu-Vk-J1-SpeI-BsiWI (5'-GACGACACTA GTTGCAGCCA CCG-TACGTTT GATTTCCACC TTGGTCC-3') (SEQ ID NO. 83), 3'-hu-Vk-J2/4-SpeI-BsiWI (5'-GACGACACTA GTT-GCAGCCA CCGTACGTTT GATCTCCASC TTGGTCC-3') (SEQ ID NO. 84), 3'-hu-Vk-J3-SpeI-BsiWI (5'-GACGA-CACTA GTTGCAGCCA CCGTACGTTT GATATCCACT TTGGTCC-3') (SEQ ID NO. 85), 3'-hu-Vk-J5-SpeI-BsiWI (5'-GACGACACTA GTTGCAGCCA CCGTACGTTT AATCTCCAGT CGTGTCC-3') (SEQ ID NO. 86)) and V lambda (5"-huVL1a-SacI-2001 (GAG CCG CAC GAG CCC GAG CTC GTG TTG ACG CAG CCG CCC TC) (SEQ ID NO. 87), 5"-huVL1b-SacI-2001 (GAG CCG CAC GAG CCC GAG CTC GTG CTG ACT CAG CCA CCC TC) (SEQ ID NO. 88), 5"-huVL2-SacI-2001 (GAG CCG CAG GAG CCC GAG CTC GCC CTG ACT CAG CCT SCC TCC GT) (SEQ ID NO. 89), 5"-huVL4-SacI-2001 (ACC TGC GAG CTC GTG CTG ACT CAR YCM YCC TCT GC) (SEQ ID NO. 90), 5"-huVL5-SacI-2001 (ACC TGC GAG CTC GTG CTG ACT CAG CCR SCT TCC) (SEQ ID NO. 91), 5"-huVL6-SacI-2001 (ACC TGC GAG CTC ATG CTG ACT CAG CCC CAC TC) (SEQ ID NO. 92), 5'-huVL3/9-SacI-2001 (GAG CCG CAC GAG CCC GAG CTC GWG CTG ACT CAG CCA CCY TC) (SEQ ID NO. 93), 5"-huVL7/8-SacI-2001 (GAG CCG CAC GAG CCC GAG CTC GTG GTG ACY CAG GAG CCM TC) (SEQ ID NO. 94), 3'-hu-Vlam-BlnI-SpeI-2001 (CGT GGG ACT AGT CTT GGG CTG ACC TAG GAC GGT) (SEQ ID NO. 95), 3"-hu-Vlam2-BlnI-SpeI-2002: CGT GGG ACT AGT CTT GGG CTG ACC GAG GAC GGT) (SEQ ID NO. 96) primer sets. RNA from human B-cells was transcribed into cDNA (as described above) and used as template DNA in PCR reactions. Per PCR reaction, one 5'-primer was combined with one 3'-primer. The number of different PCR reactions was determined by the number of possible combinations of 5'- and 3'-primers. The following PCR-program was used for amplification: Denaturation at 94° C. for 15 seconds, primer annealing at 52° C. for 50 seconds and primer extension at 72° C. for 90 seconds were performed over 40 cycles, followed by final extension at 72° C. for 10 minutes. Light chain DNA V-fragments were then isolated according to standard protocols.

4. Library Construction—Cloning of the Human VL Pool

A phage display library was generally constructed based on standard procedures, as for example disclosed in "Phage Display: A Laboratory Manual"; Ed. Barbas, Burton, Scott & Silverman; Cold Spring Harbor Laboratory Press, 2001.

The primers chosen for PCR amplification gave rise to 5'-SacI and 3'-SpeI recognition sites for the light chain V-fragments. Four ligation reactions were set up, each consisting of 400 ng of light chain fragments (SacI-SpeI digested, 2×kappa and 2×lambda) and 1400 ng of the phagemid pComb3H5BHis (SacI-SpeI digested; large fragment; this vector is described in the thesis dissertation of Dr. Ralf Lutterbüse. The four resulting antibody V-light chain pools were then each transformed into 300 µL of electrocompetent *Escherichia coli* XL1 Blue by electroporation (2.5 kV, 0.2 cm gap cuvette, 25 mF, 200 Ohm, Biorad gene-pulser) resulting in library sizes of
kappa1: 2×10$^8$
kappa2: 6×10$^7$
lambda1: 9×10$^7$
lambda2: 6×10$^7$
independent clones.

Kappa (light chain) DNA-fragments from the different PCR amplifications were weighted for each ligation as follows: Each 5'-primer defines a specific group. Within these groups the 3'-primers define the subgroups. The kappa subgroups were weighted 1:2:1:1 corresponding to the primers 3'-hu-Vk-J1-SpeI-BsiWI:3'-hu-Vk-J2/4-SpeI-BsiWI:3'-hu-Vk-J3-SpeI-BsiWI:3'-hu-Vk-J5-SpeI-BsiWI. The groups were weighted according to their germline distribution 1:1:1:0.2:0.2 corresponding to the primers 5'-huVK1-Sac-2001:5'-huVK3-Sac-2001:5'-huVK2/4-Sac-2001:5'-huVK5-Sac-2001:5'-huVK6-Sac-2001.

Lambda (light chain) DNA-fragments from the different PCR amplifications were weighted for each ligation as follows: Each 5'-primer defines a specific group. Within these groups the 3'-primers define the subgroups. The lambda subgroups were weighted 3:1 corresponding to the primers 3'-hu-Vlam-BlnI-SpeI-2001: 3'-hu-Vlam2-BlnI-SpeI-2002.

The groups were weighted according to their germline distribution 1:1:2:2:2:3 corresponding to the primers 5'-huVL1a-SacI-2001:5'-huVL1b-SacI-2001:5'-huVL2-SacI-2001:5'-huVL4-SacI-2001+5'-huVL5-SacI-2001:5'-huVL6-SacI-2001+5'-huVL7/8-SacI-2001:5'-huVL3/9-SacI-2001.

After electroporation each reaction was incubated in SOC broth (Fluke) for phenotype expression. The two kappa cultures were combined as well as the two lambda cultures. The resulting kappa culture and the resulting lambda culture were then each incubated in 500 mL of SB selection medium containing 50 µg/mL carbenicillin and 2% w/v glucose overnight. The next day, cells were harvested by centrifugation and plasmid preparation was carried out using a commercially available plasmid preparation kit (Qiagen).

5. Construction of the Antibody Library—Human VL—Maternal VH

PCR was performed to amplify the maternal VH of mAb A5B7 from a vector containing said maternal VH. For amplification a PCR protocol according to standard procedures was followed using the 5'-primer 5'-AVH-XhoI (5'-GTC ACA CTC GAG TCA GGA GGA GGC TTG GTA C-3') (SEQ ID NO. 97) and the 3'-primer 3'-AVH-BstEII (5'-GTC ACA GGT GAC CGT GGT CCC TTG GCC CCA G-3' (SEQ ID NO. 98). After purification of the approximately 350 bp amplification product from an analytical agarose gel, the DNA fragment was cut with the restriction enzymes BstEII and XhoI. The phagemid pComb3H5BHis (this vector is described in the thesis dissertation of Dr. Ralf Lutterbüse) was digested accordingly and the large fragment was ligated with the above mentioned fragment. After transformation into *E. coli* XL1 blue, a single clone was cultivated in 100 mL SB medium (containing 50 µg/mL carbenicilline) and the plasmid was prepared according to standard protocols. The successful cloning was confirmed by sequencing the insert (Sequiserve, Munich). This vector pComb3H5BHis/maternalVH of mAb A5B7 was restricted with the restriction enzymes SacI and SpeI. The large vector fragment was isolated. Plasmid-DNA containing the Vkappa—and the Vlambda library was restricted with the restriction enzymes SacI and SpeI. The small Vkappa—and the respective Vlambda fragment (each approximately 350 bp) were isolated according to standard protocols. 1200 ng of the vector fragment were ligated with a mix of each 200 ng of both the Vkappa and the Vlambda fragments. The ligation reaction was transformed into 300 µL of electrocompetent *E. coli* XL1 Blue by electroporation (2.5 kV, 0.2 cm gap cuvette, 25 mF, 200 Ohm) resulting in a total scFv library size of 1.2×10$^8$ independent clones.

After phenotype expression and slow adaptation to carbenicillin, the antibody library was transferred into SB-Carbenicillin (50 µg/mL) selection medium. The antibody library was then infected with an infectious dose of 1×10$^{12}$ particles of helper phage VCSM13 resulting in the production and secretion of filamentous M13 phage, wherein each phage particle contained single stranded pComb3H5BHis-DNA encoding a half-human scFv-fragment and displayed the corresponding scFv-protein as a translational fusion to phage coat protein III.

6. Phage Display Selection of a Human VL

The phage particles carrying the scFv-repertoire were harvested from the culture supernatant by PEG8000/NaCl precipitation and centrifugation. Then approximately 1×10$^{11}$ to 1×10$^{12}$ scFv phage particles were resuspended in 0.5 mL of TBS/1% BSA and incubated with biotinylated soluble CEA, that was immobilized in Streptavidine coated wells of an ELISA plate (Nunc) for 1 h. A 10 µg antigen/ml PBS solution (50 μl) was incubated for over night at 4° C. in the streptavidine coated wells, washed once with water, followed by blocking for 1 hour at 37° C. with 200 μl of 3% BSA in TBS, that was removed after incubation.

scFv phage that did not specifically bind to the target antigen were eliminated by washing steps with TBS/0.05% Tween. This washing procedure was repeated up to 10 times in further rounds.

After washing, binding entities were eluted by using HCl-glycine, pH 2.2. Following neutralization with 2 M Tris, pH 12, the eluate was used for infection of a fresh uninfected *E. coli* XL1 Blue culture.

To elute remaining high binding entities 50 μL of a fresh *E. coli* XL1 blue culture (OD600≥0.5) were added to the wells and incubated for 15 minutes. Both cultures were then mixed and cells successfully transduced with a phagemid copy, encoding a human scFv-fragment, were again selected for carbenicillin resistance and subsequently infected with VCMS13 helper phage to start the second round of antibody display and in vitro selection.

Plasmid DNA corresponding to 4 rounds of panning was isolated from *E. coli* cultures. For the production of soluble scFv-protein, VH-VL-DNA fragments were excised from the plasmids (XhoI-SpeI), and cloned via the same restriction sites in the plasmid pComb3H5BFlag/His, in which the expression construct (e.g. scFv) includes a Flag-tag (TGDYKDDDDK) (SEQ ID NO. 99) between the scFv and the His6-tag and the additional phage proteins are deleted.

After ligation each pool (different rounds of panning) of plasmid DNA was transformed into 100 μL heat shock competent *E. coli* TG1 and plated onto carbenicillin LB-agar. Single colonies were picked and inoculated into 120 μL of LB carb (50 μg/mL) 1% glucose in 96-well plates (Greiner). The wells were sealed with a semipermeable membrane (Greiner) and the plates were incubated overnight at 37° C. in a shaking incubator (master plate). Then 10 μL of the master plate cultures were transferred into a second 96 well plate (working plate) containing 90 μL LB Garb (50 μg/mL) 0.1% glucose per well. After incubation for 4 h in a 37° C. shaking incubator, scFv production was induced by adding 20 μL LB carb 6 mM IPTG to each well. After another incubation step overnight at 30° C. with shaking, cells were lysed in a 1 h incubation at room temperature with 40 μL lysis buffer (400 mM boric acid, 320 mM NaCl, 4 mM EDTA pH 8, 2.5 mg/mL lysozyme). Residual cells and cell debris were separated by centrifugation for 12 minutes at 1,900×g (Hettich).

The supernatants containing scFv molecules were then tested for binding in flow cytometric binding assays. CHO cells transfected with human CEA were used as CEA-positive cell line. Cell binding assays were carried out by initially incubating between 100,000 and 200,000 cells with periplasmic preparation containing human scFv or relevant controls. After incubation the cells were washed in PBS/1% FCS (fetal calf serum) and further incubated with 5-10 μg/ml of anti-FLAG M2 antibody (Sigma). After the cells had again been washed, they were incubated with polyclonal, PE-labeled anti-mouse antibodies (Dianova) and subsequently analyzed by flow cytometry. Approximately 600 clones were tested for binding signals on CEA-positive CHO cells. 27 positive clones were obtained. After sequencing of the respective scFv DNA, a total of 9 different sequences were obtained.

FIG. 12 depicts binding of the nine different half-human scFv (i.e. murine A5B7 VH-human VL) constructs to various cell lines as measured by flow cytometric analysis. The Figure contains multiple diagrams, one for each construct tested. In any given diagram, the black distribution shows fluorescence intensity for cells incubated only with PBS alone in the absence of any construct but with all appropriate detection agents as used for detection of scFvs. In this way, any fluorescence shift observed can be definitely attributed to scFv construct rather than detection agents or buffer. Shifts in fluorescence which are indicative of construct binding to the respective cell line are depicted by a gray line in each diagram. Generally, a shift of higher magnitude away from, i.e. further to the (black) control indicates stronger binding, whereas a shift of lower magnitude away from, i.e. closer to the (black) control indicates weaker binding.

It can be seen from FIG. 12 that the constructs A-121, A-183, A-240, A-313, A-290, A-315, A4-35, A4-52, MP2-A5 show clearly discernable shifts in fluorescence intensity as compared to the respective control, indicative of binding of the scFvs to membrane-bound CEA on the CHO target cells. In the following, the human VL region of scFv A-240 (SEQ ID NO. 48) has been selected and used for the isolation of a human VH region. Said human VL region is depicted in SEQ ID NOs. 63 (nucleotide sequence) and 64 (amino acid sequence).

EXAMPLE 7

Construction of the Antibody Libraries and Phage Display Selection of Human VH Regions Resistant to Soluble CEA Antigen The aim of the following experiments is the selection of a set of human VH regions resistant to soluble CEA antigen that pair with the human VL region of scFv A-240, selected as described in Example 6. Said human VL region is depicted in SEQ ID NOs. 63 (nucleotide sequence) and 64 (amino acid sequence).

1. Isolation Of RNA from Peripheric Blood Mononuclear Cells (PBMCs)

100 mL blood were taken from five healthy human donors. Peripheral blood mononuclear cells (PBMCs) were isolated by a ficoll-gradient according to standard methods. Total RNA was isolated from PBMCs using the RNeasy® Midi Kit (QIAGEN) following the manufacturer's instructions. cDNA was synthesized according to standard methods (Sambrook, Cold Spring Harbor Laboratory Press 1989, 2001).

2. PCR-Amplification of Variable Heavy Chain Regions (VH-Regions)

The VH library was constructed and named Lib 134-VH. This VH-library consists of the human repertoire of FR1-CDR1-FR2-CDR2-FR3 from the PCR amplified VH-regions of the above described PBMC pool, linked operatively to the VH CDR3 of the maternal antibody followed by a human FR4 germline sequence.

For the isolation of human template VH-regions, RT-PCR was carried out using a 5'-VH-specific primer set (5'-huVH1, 3,5-XhoI-2001 (5'-AGG TGC AGC TGC TCG AGT CTG G-3') (SEQ ID NO. 100), 5'-huVH4-XhoI-2001 (5'-CAG GTG CAG CTG CTC GAG TCG GG-3') (SEQ ID NO. 101), 5'-huVH4B-XhoI-2001 (5'-CAG GTG CAG CTA CTC GAG TGG GG-3') (SEQ ID NO. 102)) and a set of two 3'-VH-specific primers (3'-hu-VH-BstEII-2001 (5'-CTG AGG AGA CGG TGA CC-3') (SEQ ID NO. 103), 3'-hu-VH-J3-BstEII-2001 (5'-CTG AAG AGA CGG TGA CC-3') (SEQ ID NO. 104)). Per PCR reaction, one 5'-primer was combined with one 3'-primer; the number of different PCR reactions was determined by the number of possible combinations of 5'- and 3'-primers. The PBMC cDNA of five donors was used as a source of VH-genes. The following PCR-program was used for amplification: Denaturation at 94° C. for 15 seconds, primer annealing at 52° C. for 50 seconds and primer extension at 72° C. for 60 seconds was performed over 40 cycles, followed by final extension at 72° C. for 10 minutes. The amplification products with a size of approximately 350 bp were isolated according to standard methods.

For the isolation of Lib 134-VH-regions, RT-PCR was carried out in two steps. First, the human heavy chain VH-segments (FR1-CDR1-FR2-CDR2-FR3) were PCR-amplified from the isolated template VH fragments using the same 5'-VH-specific primer set as described above (5'-huVH1,3,5-XhoI-2001, 5'-huVH4-XhoI-2001, 5'-huVH4B-XhoI-2001; SEQ ID NOs. 100-102) and a 3'-specific primer set (3'-A134-VH1A (5'-GTA GTC AAA GTA GAA CCG TAG CCC CCT ATC TCT YGC ACA GTA ATA CAC GGC-3') (SEQ ID NO. 105), 3'-A134-VH1B (5'-GTA GTC AAA GTA GAA CCG TAG CCC CCT ATC TCT YGC ACA GTA ATA CAY RGC-3') (SEQ ID NO. 106), 3'-A134-VH3A (5'-GTA GTC AAA GTA GAA CCG TAG CCC CCT ATC TCT TGY ACA GTA ATA CAC RGC-3') (SEQ ID NO. 107), wherein the indicated "T" may also be replaced by "A", "C" or "G", 3'-A134-VH3B (5'-GTA GTC AAA GTA GAA CCG TAG CCC CCT ATC TCT TGC ACA GTA ATA CAA RGC-3') (SEQ ID NO. 108), wherein the indicated "T" may also be replaced by "A", "C" or "G", 3'-A134-VH4 (5'-GTA GTC AAA GTA GAA CCG TAG CCC CCT ATC TCT SGC ACA GTA ATA CAC RGC-3') (SEQ ID NO. 109)) for the human VH subfamilies 1, 3 and 4 matching in the very terminal region of FR3.

The following primer combinations were used:
a) 5'-huVH1,3,5-XhoI-2001×3'-A134-VH1A
b) 5'-huVH1,3,5-XhoI-2001×3'-A134-VH1B
c) 5'-huVH1,3,5-XhoI-2001×3'-A134-VH3A
d) 5'-huVH1,3,5-XhoI-2001×3'-A134-VH3B
e) 5'-huVH4-XhoI-2001×3'-A134-VH4
f) 5'-huVH4B-XhoI-2001×3'-A134-VH4

Per PCR reaction, one 5'-primer was combined with the 3'-primer; the number of different PCR reactions was determined by the number of possible combinations of 5'- and the 3'-primer. The following PCR-program was used for amplification: Denaturation at 94° C. for 15 seconds, primer annealing at 52° C. for 50 seconds and primer extension at 72° C. for 90 seconds was performed over 40 cycles, followed by final extension at 72° C. for 10 minutes. Through this PCR step and the respective 3'-primer sequence, the human VH segments are prolonged for a part of the maternal VH CDR3, which then in turn is the priming site for the second step PCR 3'-primer. These VH-(FR1-CDR1-FR2-CDR2-FR3) DNA-fragments were then used as templates in a second PCR reaction using again the respective 5'VH-specific primer and a universal 3' primer matching to the universal 3'-terminus of the amplified DNA-fragments (3'A134-JH6-BstEII, 5'-CGA GAC GGT GAC CGT GGT CCC TTG GCC CCA GTA GTC AAA GTA GAA CCG TAG CC-3') (SEQ ID NO. 110).

The following PCR-program was used for amplification:
Denaturation at 94° C. for 15 seconds, primer annealing at 52° C. for 50 seconds and primer extension at 72° C. for 60 seconds were performed over 40 cycles, followed by final extension at 72° C. for 10 minutes. The DNA V-fragments were isolated according to standard protocols.

3. Library Construction—Cloning of the Human VH Pool

In a second round of the foregoing method, the human VL of scFv A-240 identified in the first, previous selection (see Example 6) was chosen, and subsequently combined with the library of human VH fragments with the aim of generating a human scFv. A phage display library was generally constructed based on standard procedures, as for example disclosed in "Phage Display: A Laboratory Manual"; Ed. Barbas, Burton, Scott & Silverman; Cold Spring Harbor Laboratory Press, 2001. Heavy chain DNA-fragments from the different PCR amplifications were weighted for each ligation as follows:
a:b:c:d:e:f=3:1:3:1:1:1, wherein a-f have the following meanings:
a) 5'-huVH1,3,5-XhoI-2001×3'-A134-VH1A
b) 5'-huVH1,3,5-XhoI-2001×3'-A134-VH1B
c) 5'-huVH1,3,5-XhoI-2001×3'-A134-VH3A
d) 5'-huVH1,3,5-XhoI-2001×3'-A134-VH3B
e) 5'-huVH4-XhoI-2001×3'-A134-VH4
f) 5'-huVH4B-XhoI-2001×3'-A134-VH4

One ligation reaction was set up consisting of 400 ng of human Lib 134-VH fragment pool (XhoI-BstEII digested) and 1200 ng of the plasmid pComb3H5BHis/A-240 VL (the DNA encoding the VL region of scFv A-240 was cloned via the restriction sites SacI and SpeI into pComb3H5BHis according to standard procedures). The resulting antibody human VH pool was then transformed into 300 µL of electrocompetent *Escherichia coli* XL1 Blue by electroporation (2.5 kV, 0.2 cm gap cuvette, 25 mF, 200 Ohm, Biorad gene-pulser) resulting in a library size of $0.8 \times 10^8$ independent clones in total.

After electroporation the assay was incubated in SOC broth (Fluka) for phenotype expression. The cultures were then each incubated in 500 mL of SB selection medium containing 50 µg/mL carbenicillin and 2% v/v glucose overnight. The next day, cells of the cultures were harvested by centrifugation and plasmid preparation was carried out using a commercially available plasmid preparation kit (Qiagen) to preserve the DNA library.

1.5 µg of this plasmid pool encoding the respective scFv pool were then electroporated into *E. coli* XL1 blue (2.5 kV, 0.2 cm gap cuvette, 25 mF, 200 Ohm, Biorad gene-pulser) resulting in a library size of $2.4 \times 10^9$ independent clones in total. After phenotype expression and slow adaptation to carbenicillin the antibody library was transferred into SB-Carbenicillin (50 µg/mL) selection medium. The antibody library was then infected with an infectious dose of $1 \times 10^{12}$ particles of helper phage VCSM13 resulting in the production and secretion of filamentous M13 phage, wherein each phage particle contained single stranded pComb3H5BHis-DNA encoding a human scFv-fragment and displayed the corresponding scFv-protein as a translational fusion to phage coat protein III.

4. Phage Display Selection of a Human VH

The phage particles carrying the human scFv-repertoire were harvested from the culture supernatant by PEG8000/NaCl precipitation and centrifugation. Then approximately $1 \times 10^{11}$ to $1 \times 10^{12}$ scFv phage particles were resuspended in 0.5 mL of TBS/1% BSA and incubated with biotinylated soluble CEA, that was immobilized in Streptavidine coated wells of an ELISA plate (Nunc) for 1 h. A 10 µg antigen/ml PBS solution (50 µl) was incubated for over night at 4° C. in the streptavidine coated wells, washed once with water, followed by blocking for 1 hour at 37° C. with 200 µl of 3% BSA in TBS, that was removed after incubation.

scFv phage that did not specifically bind to the target antigen were eliminated by washing steps with TBS/0.05% Tween. This washing procedure was repeated up to 10 times in further rounds.

After washing, binding entities were eluted by using HCl-glycine, pH 2.2. Following neutralization with 2 M Tris, pH 12, the eluate was used for infection of a fresh uninfected E. coli XL1 Blue culture.

To elute remaining high binding entities 50 μL of a fresh E. coli XL1 blue culture (OD600≥0.5) were added to the wells and incubated for 15 minutes. Both cultures were then mixed and cells successfully transduced with a phagemid copy, encoding a human scFv-fragment, were again selected for carbenicillin resistance and subsequently infected with VCMS13 helper phage to start the second round of antibody display and in vitro selection.

Plasmid DNA corresponding to 4 rounds of panning was isolated from E. coli cultures. For the production of soluble scFv-protein, VH-VL-DNA fragments were excised from the plasmids (XhoI-SpeI), and cloned via the same restriction sites in the plasmid pComb3H5BFlag/His, in which the expression construct (e.g. scFv) includes a Flag-tag (TGDYKDDDDK; SEQ ID NO. 99) between the scFv and the His6-tag and the additional phage proteins are deleted.

After ligation each pool (different rounds of panning) of plasmid DNA was transformed into 100 μL heat shock competent E. coli TG1 and plated onto carbenicillin LB-agar. Single colonies were picked and inoculated into 120 μL of LB carb (50 μg/mL) 1% glucose in 96-well plates (Greiner). The wells were sealed with a semipermeable membrane (Greiner) and the plates were incubated overnight at 37° C. in a shaking incubator (master plate). Then 10 μL of the master plate cultures were transferred into a second 96 well plate (working plate) containing 90 μL LB carb (50 μg/mL) 0.1% glucose per well. After incubation for 4 h in a 37° C. shaking incubator, scFv production was induced by adding 20 μL LB Garb 6 mM IPTG to each well. After another incubation step overnight at 30° C. with shaking, cells were lysed in a 1 h incubation at room temperature with 40 μL lysis buffer (400 mM boric acid, 320 mM NaCl, 4 mM EDTA pH 8, 2.5 mg/mL lysozyme). Residual cells and cell debris were separated by centrifugation for 12 minutes at 1,900×g (Hettich).

The supernatants containing scFv molecules were then tested for binding in flow cytometric binding assays.

CHO cells transfected with human CEA were used as CEA-positive cell line. Cell binding assays were carried out by initially incubating between 100,000 and 200,000 cells with periplasmic preparation containing human scFv or relevant controls. After incubation the cells were washed in PBS/1% FCS (fetal calf serum) and further incubated with 5-10 μg/ml of anti-FLAG M2 antibody. After the cells had again been washed, they were incubated with polyclonal, PE-labeled anti-mouse antibodies (Dianova) and subsequently analyzed by flow cytometry. 46 clones were tested for binding signals on CEA-positive CHO cells. All of them showed positive signals. After sequencing of the respective scFv DNA a total of 9 different sequences were obtained, eight of which displayed a high degree of homology. The human constructs MP510_3-A5.3 (MP510-A5; SEQ ID NO. 50), MP510_3-B9.1 (MP511-B9; SEQ ID NO. 52), MP510_3-D8.1 (MP511-D8; SEQ ID NO. 54) have been selected for further characterization. The corresponding amino acid sequences are shown in the sequence listing.

Periplasmic extracts of said human constructs MP510-A5, MP511-B9, MP511-D8 as well as the half human construct A-240 Vlambda.3 (murine VH A5B7/human VL A240; SEQ ID NO. 48) were further analyzed in flow cytometric experiments with CEA-positive and -negative cell lines. It can be seen from FIG. 13, that the human constructs MP510-A5 (SEQ ID NO. 50), MP511-B9 (SEQ ID NO. 52), MP511-D8 (SEQ ID NO. 54) show clearly discernable shifts in fluorescence intensity as compared to the respective half-human control A-240 Vlambda.3 (murine VH A5B7/human VL A240; SEQ ID NO. 48). Thus, the human scFv constructs show stronger binding activity to membrane-bound human CEA than the half human construct A-240 Vlambda.3. In addition, all of the human constructs showed distinct binding to CEA-positive human KATO III cells (human gastric cancer cell line), whereas none of them showed binding to CEA-negative, untransfected CHO cells as well as to CEA-negative human NALM 6 cells (human B cell line) (data not shown).

EXAMPLE 8

Generation and Cytotoxic Activity of Human CEA×CD3 Bispecific Single Chain Antibodies 1. Arrangements In the next step, various domain arrangements of human bispecific single chain antibody molecules have been generated. These molecules comprise the human anti-CEA binding domain (the generation of which has been described in Example 7, supra) and the de-immunized binding domain with specificity for the human CD3 antigen shown in SEQ ID NO.77 VHVL were designed as set out in Table 1; see also Example 2, supra. All bispecific single chain antibody constructs with the human anti-CEA binding domains described herein (apparently) bind to soluble human CEA antigen since they have been isolated after four rounds of phage display selection on soluble CEA antigen immobilized on ELISA plates.

In particular, the following arrangements have been generated:
(a) human anti-CEA part located N-terminally:
(i) VH-VL orientation of anti-CEA:
A5 VH-A240 VL×SEQ ID NO.77 VHVL (SEQ ID NO. 24),
A5 VH-A240 VL#×SEQ ID NO.77 VHVL (SEQ ID NO. 126),
B9 VH-A240 VL×SEQ ID NO.77 VHVL (SEQ ID NO. 32),
B9 VH-A240 VL#×SEQ ID NO.77 VHVL (SEQ ID NO. 130),
D8 VH-A240 VL×SEQ ID NO.77 VHVL (SEQ ID NO. 40)
D8 VH-A240 VL#×SEQ ID NO.77 VHVL (SEQ ID NO. 134), and
CEAI VH-A240 VL×SEQ ID NO.77 VHVL (SEQ ID NO. 16).
(ii) VL-VH Orientation of Anti-CEA:
A240 VL-A5 VH×SEQ ID NO.77 VHVL (SEQ ID NO. 26),
A240 VL-B9 VH×SEQ ID NO.77 VHVL (SEQ ID NO. 34),
A240 VL-D8 VH×SEQ ID NO.77 VHVL (SEQ ID NO. 42),
and A240 VL-CEAI VH×SEQ ID NO.77 VHVL (SEQ ID NO. 18).
(b) Human Anti-CEA Part Located C-Terminally:
(i) VH-VL Orientation of Anti-CEA:
SEQ ID NO.77 VHVL×A5 VH-A240VL (SEQ ID NO. 30),
SEQ ID NO.77 VHVL×A5 VH-A240VL# (SEQ ID NO. 128),
SEQ ID NO.77 VHVL×B9 VH-A240VL (SEQ ID NO. 36),
SEQ ID NO.77 VHVL×E12 VH-A240VL (SEQ ID NO. 143),
SEQ ID NO.77 VHVL×B9 VH-A240VL# (SEQ ID NO. 132), SEQ ID NO.77 VHVL×D8 VH-A240VL (SEQ ID NO. 44),
SEQ ID NO.77 VHVL×D8 VH-A240VL# (SEQ ID NO. 136),
and SEQ ID NO.77 VHVL×CEAI VH-A240VL (SEQ ID NO. 20).

(ii) VL-VH Orientation of Anti-CEA:
SEQ ID NO.77 VHVL×A240VL-A5 VH (SEQ ID NO. 28),
SEQ ID NO.77 VHVL×A240VL-B9VH (SEQ ID NO. 38),
SEQ ID NO.77 VHVL×A240VL-D8VH (SEQ ID NO. 46), and
SEQ ID NO.77 VHVL×A240VL-CEAI VH (SEQ ID NO. 22).

CEAI VH (SEQ ID NO. 56) denotes a VH region derived from murine mAb A5B7, whereas CEAI VHVL or CEAI VLVH refer to a VH-VL domain and a VL-VH domain, respectively, derived from mAb A5B7. A240 corresponds to a human VL region (see SEQ ID NO. 64 and Example 7). Accordingly, e.g. CEAI VH-A240 VL×SEQ ID NO.77 VHVL (SEQ ID NO.16) corresponds to a bispecific construct with a half-human CEA-binding domain having a murine VH region from mAb7 and a human VL region A240. For the cloning of the human antibody library, the nucleotide sequences encoding the original N-termini of the A240 VL region had to be converted to restriction sites. In A5 VH-A240 VL#×SEQ ID NO.77 VHVL (SEQ ID NO. 126), SEQ ID NO.77 VHVL×A5 VH-A240VL# (SEQ ID NO. 128), B9 VH-A240 VL#×SEQ ID NO.77 VHVL (SEQ ID NO. 130), SEQ ID NO.77 VHVL×B9 VH-A240VL# (SEQ ID NO. 132), D8 VH-A240 VL#×SEQ ID NO.77 VHVL (SEQ ID NO. 134), and SEQ ID NO.77 VHVL×D8 VH-A240VL# (SEQ ID NO. 136), the original N-termini have been reintroduced. The bispecific single chain antibody construct SEQ ID NO.77 VHVL×E12 VH-A240VL (SEQ ID NO. 143) differs from the SEQ ID NO.77 VHVL×B9 VH-A240VL (SEQ ID NO. 36) construct in only one amino acid residue: The CDR-H2 sequence in the E12 VH reads "FILNKANGGTTEYAASVKG" (SEQ ID NO. 145), whereas in the B9 VH it reads "FIRNKANGGTTEYAASVKG" (SEQ ID NO. 67). The human E12 VH region has been isolated as set forth in Example 7.

2. Expression, Purification and Flow Cytometry Analysis

Expression, purification and flow cytometry analysis of these human CEA×CD3 bispecific single chain antibodies has been carried out by methods described in Example 2, supra.

3. Binding Activity

As exemplified in FIG. 14, human bispecific single chain antibody constructs A5 VH-A240 VL×SEQ ID NO.77 VHVL (SEQ ID NO. 24), B9 VH-A240 VL×SEQ ID NO.77 VHVL (SEQ ID NO. 32), D8 VH-A240 VL×SEQ ID NO.77 VHVL (SEQ ID NO. 40) and CEAI VH-A240 VL×SEQ ID NO.77 VHVL (SEQ ID NO. 16) bind to CEA-positive human Kato III cells and to CD3-positive HPB-ALL cells.

4. Cytotoxic Activity in the Absence of Soluble CEA Antigen

Cytotoxic activity against CHO-CEA+ target cells has been demonstrated for the following domain arrangements of the human bispecific single chain antibodies:

For constructs with the anti-CEA part located N-terminally and a VH-VL orientation of the anti-CEA part, FIG. 15 shows cytotoxic activity for A5 VH-A240 VL×SEQ ID NO.77 VHVL (SEQ ID NO. 24), B9 VH-A240 VL×SEQ ID NO.77 VHVL (SEQ ID NO. 32), D8 VH-A240 VL×SEQ ID NO.77 VHVL (SEQ ID NO. 40) and CEAI VH-A240 VL×SEQ ID NO.77 VHVL (SEQ ID NO. 16). FIG. 16 demonstrates cytotoxic activity for the VL-VH orientation of the anti-CEA domain (located N-terminally) for A240 VL-A5 VH×SEQ ID NO.77 VHVL (SEQ ID NO. 26), A240 VL-B9 VH×SEQ ID NO.77 VHVL (SEQ ID NO. 34), A240 VL-D8 VH×SEQ ID NO.77 VHVL (SEQ ID NO. 42), and A240 VL-CEAI VH×SEQ ID NO.77 VHVL (SEQ ID NO. 18).

For constructs with the anti-CEA part located C-terminally and a VH-VL orientation of the anti-CEA part, FIG. 17 exhibits cytotoxicity against CEA+ target cells for SEQ ID NO.77 VHVL×A5 VH-A240VL (SEQ ID NO. 30), SEQ ID NO.77 VHVL×B9 VH-A240VL (SEQ ID NO. 36), SEQ ID NO.77 VHVL×D8 VH-A240VL (SEQ ID NO. 44), and SEQ ID NO.77 VHVL×CEAI VH-A240VL (SEQ ID NO. 20). SEQ ID NO.77 VHVL×CEAI LH was used as a positive control. FIG. 18 shows cytotoxic activity of constructs with VL-VH orientation of the anti-CEA domain (located C-terminally) for SEQ ID NO.77 VHVL×A240VL-A5 VH (SEQ ID NO. 28), SEQ ID NO.77 VHVL×A240VL-B9VH (SEQ ID NO. 38), SEQ ID NO.77 VHVL×A240VL-D8VH (SEQ ID NO. 46), and SEQ ID NO.77 VHVL×A240VL-CEAIVH (SEQ ID NO. 22). SEQ ID NO.77 VHVL×CEAI LH (SEQ ID NO. 2) was used as a positive control.

FIG. 21 shows cytotoxic activity of bispecific single chain antibody constructs comprising the human B9 VH region and the human A240 VL region in different arrangements: A240 VL-B9 VH×SEQ ID NO.77 VHVL (SEQ ID NO. 34), SEQ ID NO.77 VHVL×A240 VL-B9 VH (SEQ ID NO. 38), SEQ ID NO.77 VHVL×B9 VH-A240 VL (SEQ ID NO. 36), and B9 VH-A240 VL×SEQ ID NO.77 VHVL (SEQ ID NO. 32) revealed cytotoxic activity against human CEA-transfected CHO cells.

5. Resistance of Human CEA×CD3 Bispecific Single Chain Antibodies to Soluble CEA Antigen Competition assays in the presence of soluble human CEA antigen for the human bispecific single chain antibodies have been performed as set out in Example 5, supra. FIGS. 19 and 20 demonstrate the resistance to soluble CEA antigen of cytotoxic activity also for human constructs, as exemplified for constructs A5 VH-A240 VL×SEQ ID NO.77 VHVL (SEQ ID NO. 24), B9 VH-A240 VL×SEQ ID NO.77 VHVL (SEQ ID NO. 32), D8 VH-A240 VL×SEQ ID NO.77 VHVL (SEQ ID NO. 40) and CEAI VH-A240 VL×SEQ ID NO.77 VHVL (SEQ ID NO. 16); for resistance to soluble CEA of murine-derived bispecific single chain antibodies see Example 5. Moreover, FIG. 22 shows that CEA-reactive bispecific single chain construct A240 VL-B9 VH×SEQ ID NO.77 VHVL (SEQ ID NO. 34) redirected T cells to lyse CHO-CEA+ cells in the presence of increasing amounts of soluble CEA antigen. This experiment demonstrates that also A240 VL-B9 VH×SEQ ID NO.77 VHVL-mediated cytotoxic activity is resistant to soluble CEA. Finally, as can be derived from FIG. 27, bispecific single chain construct SEQ ID NO.77 VHVL×E12 VH-A240 VL (SEQ ID NO. 143)-mediated cytotoxic activity is resistant to soluble CEA.

Thus, the present invention provides for pharmaceutical compositions with cytotoxic anti-tumor activity in the presence of even high levels of soluble CEA antigen. As set forth above, high serum CEA concentrations in patients with epithelial tumors reduce the success of anti-CEA antibody-based therapeutics. Therefore, the pharmaceutical compositions of the invention are particularly suitable for the treatment of patients with progressive epithelial tumors (e.g. secondary, metastatic tumors after surgical removal of the primary tumor(s)), malignant epithelial tumors, high (epithelial) tumor load and late stage epithelial tumors characterized by high soluble CEA antigen concentrations in the serum/plasma of said patients. Further, pharmaceutical compositions of the invention are also expected to be administered at low dosages.

In addition, said pharmaceutical compositions are unlikely to be immunogenic when administered to the patients due to the human origin of the anti-CEA part and the de-immunised anti-CD3 part of the bispecific single chain antibodies in the pharmaceutical compositions of the invention. Moreover, the pharmaceutical compositions of the invention are expected to provide for high tumor penetration due to the low molecular weight and small size of the bispecific single chain constructs. Additionally, for the tumor treatment low amounts of bispecific single chain antibodies will be used because of the high cytotoxic activity of said molecules. Because low amounts are expected to be administered to the patients, the adverse effects for the patients are also expected to be reduced. Finally, bispecific single chain antibodies without resistance to soluble CEA would be highly sensitive to even low concentrations of soluble CEA antigen in the plasma of tumor patients since they would be administered in low concentrations, as set forth above. This problem is also circumvented by the pharmaceutical compositions of the invention.

EXAMPLE 9

Protein Homogeneity Assessment of Purified Monomer of A240 VL-B9 VH×SEQ ID NO.77 VHVL (SEQ ID NO. 34) by High Resolution Cation Exchange Chromatography To further characterize the homogeneity of the purified A240 VL-B9 VH×SEQ ID NO.77 VHVL (SEQ ID NO. 34) construct, the isolated monomer fraction was subjected to a High Resolution Cation Exchange Chromatography. The chromatography was performed on a MiniS column (Mini S PE 4.6/50 CatX 0.8 ml; GE Healthcare 17-5005-01), equilibrated with 20 mM MES buffer pH 5.5. The sample was diluted 1:3 with the same buffer before loading to the column. Bound protein was eluted with a gradient of equilibration buffer containing 1M NaCl: 0-30% in 60 column volumes. Remaining protein was eluted in 3 column volumes of 1M NaCl. The resulting chromatogram is shown in FIG. 23 and exhibits a homogenous protein fraction with a single main peak.

EXAMPLE 10

Plasma Stability of A240 VL-B9 VH×SEQ ID NO.77 VHVL (SEQ ID NO. 34)

The plasma stability of the A240 VL-B9 VH×SEQ ID NO.77 VHVL (SEQ ID NO. 34) construct was tested under different incubation conditions followed by a standard 51-chromium release based cytotoxicity assay as described in Example 4.

A human plasma pool with the blood of five healthy donors was generated by collecting blood in EDTA-coated syringes. The cellular components were removed by centrifugation and the upper plasma phase was collected and subsequently pooled. The A240 VL-B9 VH×SEQ ID NO.77 VHVL (SEQ ID NO. 34) construct was either incubated at 37° C. or 4° C. in the presence or absence of plasma. As controls, the construct was diluted immediately prior to the cytotoxicity assay in plasma or RPMI 1640 medium, respectively. CHO-CEA+ served as target cells; stimulated CD8+ T cells were used as effector cells. The effector:target (E:T) ratio was 10:1. The assay duration was 18 hours.

As shown in FIG. 24, the CEA-reactive bispecific single chain construct A240 VL-B9 VH×SEQ ID NO.77 VHVL (SEQ ID NO. 34) proved to be very stable; no loss of cytotoxic activity could be detected after incubation in human plasma for 24 hours at 37° C.

EXAMPLE 11

Protein Homogeneity Assessment of Purified Monomer of SEQ ID NO.77 VHVL×E12 VH-A240 VL (SEQ ID NO. 143) by High Resolution Cation Exchange Chromatography The experiment was conducted in analogy with Example 9, except that SEQ ID NO.77 VHVL×E12 VH-A240 VL (SEQ ID NO. 143) was analyzed. The resulting chromatogram is shown in FIG. 25 and exhibits a homogenous protein fraction with a single main peak.

EXAMPLE 12

Plasma Stability of SEQ ID NO.77 VHVL×E12 VH-A240 VL (SEQ ID NO. 143)

The experiment was conducted in analogy with Example 10, except that SEQ ID NO.77 VHVL×E12 VH-A240 VL (SEQ ID NO. 143) was analyzed. As displayed in FIG. 26, the CEA-reactive bispecific single chain construct SEQ ID NO.77 VHVL×E12 VH-A240 VL (SEQ ID NO. 143) proved to be very stable; no loss of cytotoxic activity could be detected after incubation in human plasma for 24 hours at 37° C.

The invention claimed is:

1. A bispecific single chain antibody which comprises:
    (a) a first binding domain specifically binding to human CD3, and
    (b) a second binding domain specifically binding to human CEA,
wherein said second binding domain comprises a variable light chain ($V_L$) region and a variable heavy chain ($V_H$) region,
wherein said $V_L$ region comprises:
a CDR-L1 having the amino acid sequence "TLRRGINV-GAYSIY" (SEQ ID NO. 73);
a CDR-L2 having the amino acid sequence "YKSDSD-KQQGS" (SEQ ID NO. 72); and
a CDR-L3 having the amino acid sequence "MIWHS-GASAV" (SEQ ID NO. 71); and
wherein said $V_L$ region comprises:
a CDR-HI having the amino acid sequence "TYAMH" (SEQ ID NO. 70);
a CDR-H2 having the amino acid sequence "LISNDG-SNKYYADSVKG" (SEQ ID NO. 69); and
a CDR-H3 having the amino acid sequence "DRGL-RFYFDY" (SEQ ID NO. 66).

2. The bispecific single chain antibody of claim 1, wherein said first binding domain specific for CD3 is located C-terminally to said second binding domain.

3. The bispecific single chain antibody of claim 1, wherein said binding domains are arranged in the order $VH_{CEA}$-$VL_{CEA}$-$VH_{CD3}$-$VL_{CD3}$ or $VL_{CEA}$-$VH_{CEA}$-$VH_{CD3}$-$VL_{CD3}$.

4. The bispecific single chain antibody of claim 1, wherein the amino acid sequence of the VH region of the second binding domain specific for human CEA is SEQ ID NO: 58 or 62.

5. The bispecific single chain antibody of claim 1, wherein the amino acid sequence of the VL region of the second binding domain specific for human CEA is SEQ ID NO: 64.

6. The bispecific single chain antibody of claim 1, wherein the V regions of the second binding domain specific for CEA comprise
    the VH region consisting of the amino acid sequence shown in SEQ ID NO: 58 and the VL region consisting of the amino acid sequence shown in SEQ ID NO: 64; or
    the VH region consisting of the amino acid sequence shown in SEQ ID NO: 62 and the VL region consisting of the amino acid sequence shown in SEQ ID NO: 64.

7. The bispecific single chain antibody of claim 1, wherein said bispecific single chain antibody comprises:
    (a) an amino acid sequence set forth in SEQ ID NO: 24, 26, 40, 42, 44, 46, 126, 128, 134, or 136; or (b) an amino acid sequence encoded by a nucleotide sequence as shown in SEQ ID NO: 23, 25, 27, 29, 39, 41, 43, 45, 125, 127, 133, or 135.

8. The bispecific single chain antibody of claim 1, wherein at least one of said first or second binding domains is chimeric, humanized, CDR-grafted, and/or deimmunized or human.

9. The bispecific single chain antibody according to claim 1, in a composition comprising a proteinaceous compound capable of providing an activation signal for immune effector cells.

10. A method for treating an epithelial tumor that expresses CEA in a subject in the need thereof, said method comprising the step of administering an effective amount of the bispecific single chain antibody of claim 1.

11. The method of claim 10, wherein said epithelial tumor is a gastrointestinal adenocarcinoma, a breast adenocarcinoma or a lung adenocarcinoma.

12. The method according to claim 11, wherein said gastrointestinal adenocarcinoma is a colorectal adenocarcinoma, a pancreatic adenocarcinoma, an oesophageal adenocarcinoma, or a gastric adenocarcinoma.

13. The method according to claim 10, wherein the subject in need thereof suffers from a progressive tumor, a late stage tumor, a high tumor load/burden, a metastatic tumor, or a CEA serum concentration higher than 100 ng/ml.

14. The method of claim 10, wherein said bispecific single chain antibody is administered in combination with an additional drug.

15. The method of claim 14, wherein said additional drug is a non-proteinaceous compound.

16. The bispecific single chain antibody of claim 1, wherein said bispecific single chain antibody comprises a His-tag.

17. A composition comprising the bispecific single chain antibody of claim 1.

18. The method of claim 15, wherein the non-proteinaceous compound is administered non-simultaneously with the bispecific single chain antibody.

19. The method of claim 15, wherein the non-proteinaceous compound is administered simultaneously with the bispecific single chain antibody.

* * * * *

SEQUENCE LISTING

```
<160> NUMBER OF SEQ ID NOS: 147

<210> SEQ ID NO 1
<211> LENGTH: 1476
<212> TYPE: DNA
<213> ORGANISM: artificial sequence
<220> FEATURE:
<223> OTHER INFORMATION: SEQ ID NO: 77 VHVL x CEA I VLVH ; Bispecific
      single chain antibody

<400> SEQUENCE: 1
gacgtccaac tggtgcagtc aggggctgaa gtgaaaaaac ctggggcctc agtgaaggtg        60
tcctgcaagg cttctggcta cacctttact aggtacacga tgcactgggt aaggcaggca       120
cctggacagg gtctggaatg gattggatac attaatccta gccgtggtta tactaattac       180
gcagacagcg tcaagggccg cttcacaatc actacagaca aatccaccag cacagcctac       240
```

```
atggaactga gcagcctgcg ttctgaggac actgcaacct attactgtgc aagatattat    300
gatgatcatt actgccttga ctactggggc caaggcacca cggtcaccgt ctcctcaggc    360
gaaggtacta gtactggttc tggtggaagt ggaggttcag gtggagcaga cgacattgta    420
ctgacccagt ctccagcaac tctgtctctg tctccagggg agcgtgccac cctgagctgc    480
agagccagtc aaagtgtaag ttacatgaac tggtaccagc agaagccggg caaggcaccc    540
aaaagatgga tttatgacac atccaaagtg gcttctggag tccctgctcg cttcagtggc    600
agtgggtctg ggaccgacta ctctctcaca atcaacagct ggaggctga agatgctgcc    660 acttattact gccaacagtg gagtagtaac ccgctcacgt tcggtggcgg gaccaaggtg    720
gagatcaaat ccggaggtgg tggatccgac attgagctca cccagtctcc agcaatcctg    780
tctgcatctc caggggagaa ggtcacaatg acttgcaggg ccagctcaag tgtaacttac    840
attcactggt accagcagaa gccaggatcc tcccccaaat cctggattta tgccacatcc    900
aacctggctt ctggagtccc tgctcgcttc agtggcagtg ggtctgggac ctcttactct    960
ctcacaatca gcagagtgga ggctgaagat gctgccactt attactgcca acattggagt   1020
agtaaaccac cgacgttcgg tggagggacc aagctcgaga tcaaaggtgg tggtggttct   1080
ggcggcggcg gctccggtgg tggtggttct caggtccaac tgcaggagtc aggaggaggc   1140
ttggtacagc ctggggggtt ctctgagactc tcctgtgcaa cttctgggtt caccttcact   1200
gattactaca tgaactgggt ccgccagcct ccaggaaagg cacttgagtg gttgggtttt   1260
attggaaaca agctaatgg ttacacaaca gagtacagtg catctgtgaa gggtcggttc   1320
accatctcca gagataaatc ccaaagcatc ctctatcttc aaatgaacac cctgagagct   1380
gaggacagtg ccacttatta ctgtaccaga gatagggggc tacggttcta ctttgactac   1440
tggggccaag ggaccacggt caccgtctcc tcctag                              1476
```

<210> SEQ ID NO 2
<211> LENGTH: 491
<212> TYPE: PRT
<213> ORGANISM: artificial sequence
<220> FEATURE:
<223> OTHER INFORMATION: SEQ ID NO: 77 VHVL x CEA I VLVH ; Bispecific
      single chain antibody

<400> SEQUENCE: 2

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

-continued

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Ser Gly Gly Gly Ser Asp Ile Glu Leu Thr Gln Ser
                245                 250                 255

Pro Ala Ile Leu Ser Ala Ser Pro Gly Glu Lys Val Thr Met Thr Cys
                260                 265                 270

Arg Ala Ser Ser Ser Val Thr Tyr Ile His Trp Tyr Gln Gln Lys Pro
            275                 280                 285

Gly Ser Ser Pro Lys Ser Trp Ile Tyr Ala Thr Ser Asn Leu Ala Ser
        290                 295                 300

Gly Val Pro Ala Arg Phe Ser Gly Ser Gly Ser Gly Thr Ser Tyr Ser
305                 310                 315                 320

Leu Thr Ile Ser Arg Val Glu Ala Glu Asp Ala Ala Thr Tyr Tyr Cys
                325                 330                 335

Gln His Trp Ser Ser Lys Pro Pro Thr Phe Gly Gly Gly Thr Lys Leu
            340                 345                 350

Glu Ile Lys Gly Gly Gly Gly Ser Gly Gly Gly Ser Gly Gly Gly
        355                 360                 365

Gly Ser Gln Val Gln Leu Gln Glu Ser Gly Gly Leu Val Gln Pro
370                 375                 380

Gly Gly Ser Leu Arg Leu Ser Cys Ala Thr Ser Gly Phe Thr Phe Thr
385                 390                 395                 400

Asp Tyr Tyr Met Asn Trp Val Arg Gln Pro Pro Gly Lys Ala Leu Glu
                405                 410                 415

Trp Leu Gly Phe Ile Gly Asn Lys Ala Asn Gly Tyr Thr Thr Glu Tyr
            420                 425                 430

Ser Ala Ser Val Lys Gly Arg Phe Thr Ile Ser Arg Asp Lys Ser Gln
        435                 440                 445

Ser Ile Leu Tyr Leu Gln Met Asn Thr Leu Arg Ala Glu Asp Ser Ala
    450                 455                 460

Thr Tyr Tyr Cys Thr Arg Asp Arg Gly Leu Arg Phe Tyr Phe Asp Tyr
465                 470                 475                 480

Trp Gly Gln Gly Thr Thr Val Thr Val Ser Ser
                485                 490

<210> SEQ ID NO 3
<211> LENGTH: 1476
<212> TYPE: DNA
<213> ORGANISM: artificial sequence
<220> FEATURE:
<223> OTHER INFORMATION: SEQ ID NO: 77 VHVL x CEA I VHVL ; Bispecific
      single chain antibody

<400> SEQUENCE: 3
gacgtccaac tggtgcagtc agggctgaa gtgaaaaaac ctggggcctc agtgaaggtg     60

```
tcctgcaagg cttctggcta ccctttact aggtacacga tgcactgggt aaggcaggca      120
cctggacagg tctggaatg gattggatac attaatccta gccgtggtta tactaattac      180
gcagacagcg tcaagggccg cttcacaatc actacagaca atccaccag cacagcctac      240 atggaactga gcagcctgcg ttctgaggac actgcaacct attactgtgc aagatattat      300
gatgatcatt actgccttga ctactggggc caaggcacca cggtcaccgt ctcctcaggc      360
gaaggtacta gtactggttc tggtggaagt ggaggttcag gtggagcaga cgacattgta      420
ctgacccagt ctccagcaac tctgtctctg tctccagggg agcgtgccac cctgagctgc      480
agagccagtc aaagtgtaag ttacatgaac tggtaccagc agaagccggg caaggcaccc      540
aaaagatgga tttatgacac atccaaagtg gcttctggag tccctgctcg cttcagtggc      600
agtgggtctg ggaccgacta ctctctcaca atcaacagct ggaggctga agatgctgcc      660 acttattact gccaacagtg gagtagtaac ccgctcacgt tcggtggcgg gaccaaggtg      720
gagatcaaat ccggaggtgg tggatcccag gtccaactgc aggagtcagg aggaggcttg      780
gtacagcctg ggggttctct gagactctcc tgtgcaactt ctgggttcac cttcactgat      840
tactacatga actgggtccg ccagcctcca ggaaaggcac ttgagtggtt gggttttatt      900
ggaaacaaag ctaatggtta cacaacagag tacagtgcat ctgtgaaggg tcggttcacc      960
atctccagag ataaatccca aagcatcctc tatcttcaaa tgaacaccct gagagctgag     1020
gacagtgcca cttattactg taccagagat aggggctac ggttctactt tgactactgg     1080
ggccaaggga ccacggtcac cgtctcctcc ggtggtggtg gttctggcgg cggcggctcc     1140
ggtggtggtg gttctgacat tgagctcacc cagtctccag caatcctgtc tgcatctcca     1200
ggggagaagg tcacaatgac ttgcagggcc agctcaagtg taacttacat tcactggtac     1260
cagcagaagc aggatcctc ccccaaatcc tggatttatg ccacatccaa cctggcttct     1320
ggagtccctg ctcgcttcag tggcagtggg tctgggacct cttactctct cacaatcagc     1380
agagtggagg ctgaagatgc tgccacttat tactgccaac attggagtag taaaccaccg     1440
acgttcggtg gagggaccaa gctcgagatc aaatag                                1476
```

<210> SEQ ID NO 4
<211> LENGTH: 491
<212> TYPE: PRT
<213> ORGANISM: artificial sequence
<220> FEATURE:
<223> OTHER INFORMATION: SEQ ID NO: 77 VHVL x CEA I VHVL ; Bispecific single chain antibody

<400> SEQUENCE: 4

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
        50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly

```
                100              105              110
Thr Thr Val Thr Val Ser Ser Gly Glu Gly Thr Ser Thr Gly Ser Gly
            115              120              125
Gly Ser Gly Gly Ser Gly Gly Ala Asp Asp Ile Val Leu Thr Gln Ser
        130              135              140
Pro Ala Thr Leu Ser Leu Ser Pro Gly Glu Arg Ala Thr Leu Ser Cys
145              150              155              160
Arg Ala Ser Gln Ser Val Ser Tyr Met Asn Trp Tyr Gln Gln Lys Pro
                165              170              175
Gly Lys Ala Pro Lys Arg Trp Ile Tyr Asp Thr Ser Lys Val Ala Ser
            180              185              190
Gly Val Pro Ala Arg Phe Ser Gly Ser Gly Ser Gly Thr Asp Tyr Ser
        195              200              205
Leu Thr Ile Asn Ser Leu Glu Ala Glu Asp Ala Ala Thr Tyr Tyr Cys
    210              215              220
Gln Gln Trp Ser Ser Asn Pro Leu Thr Phe Gly Gly Gly Thr Lys Val
225              230              235              240
Glu Ile Lys Ser Gly Gly Gly Gly Ser Gln Val Gln Leu Gln Glu Ser
                245              250              255
Gly Gly Gly Leu Val Gln Pro Gly Gly Ser Leu Arg Leu Ser Cys Ala
            260              265              270
Thr Ser Gly Phe Thr Phe Thr Asp Tyr Tyr Met Asn Trp Val Arg Gln
        275              280              285
Pro Pro Gly Lys Ala Leu Glu Trp Leu Gly Phe Ile Gly Asn Lys Ala
    290              295              300
Asn Gly Tyr Thr Thr Glu Tyr Ser Ala Ser Val Lys Gly Arg Phe Thr
305              310              315              320
Ile Ser Arg Asp Lys Ser Gln Ser Ile Leu Tyr Leu Gln Met Asn Thr
                325              330              335
Leu Arg Ala Glu Asp Ser Ala Thr Tyr Tyr Cys Thr Arg Asp Arg Gly
            340              345              350
Leu Arg Phe Tyr Phe Asp Tyr Trp Gly Gln Gly Thr Thr Val Thr Val
        355              360              365
Ser Ser Gly Gly Gly Ser Gly Gly Gly Ser Gly Gly Gly Gly Ser Asp
    370              375              380
Ser Asp Ile Glu Leu Thr Gln Ser Pro Ala Ile Leu Ser Ala Ser Pro
385              390              395              400
Gly Glu Lys Val Thr Met Thr Cys Arg Ala Ser Ser Ser Val Thr Tyr
                405              410              415
Ile His Trp Tyr Gln Gln Lys Pro Gly Ser Ser Pro Lys Ser Trp Ile
            420              425              430
Tyr Ala Thr Ser Asn Leu Ala Ser Gly Val Pro Ala Arg Phe Ser Gly
        435              440              445
Ser Gly Ser Gly Thr Ser Tyr Ser Leu Thr Ile Ser Arg Val Glu Ala
    450              455              460
Glu Asp Ala Ala Thr Tyr Tyr Cys Gln His Trp Ser Ser Lys Pro Pro
465              470              475              480
Thr Phe Gly Gly Gly Thr Lys Leu Glu Ile Lys
                485              490

<210> SEQ ID NO 5
<211> LENGTH: 1473
<212> TYPE: DNA
<213> ORGANISM: artificial sequence
```

-continued

```
<220> FEATURE:
<223> OTHER INFORMATION: CEA I VLVH x SEQ ID NO: 77 VHVL ; Bispecific
      single-chain antibody

<400> SEQUENCE: 5
gacattgagc tcacccagtc tccagcaatc ctgtctgcat ctccagggga gaaggtcaca      60
atgacttgca gggccagctc aagtgtaact tacattcact ggtaccagca gaagccagga     120
tcctccccca atcctggat ttatgccaca tccaacctgg cttctggagt ccctgctcgc      180
ttcagtggca gtgggtctgg gacctcttac tctctcacaa tcagcagagt ggaggctgaa     240
gatgctgcca cttattactg ccaacattgg agtagtaaac caccgacgtt cggtggaggg     300
accaagctcg agatcaaagg tggtggtggt tctggcggcg gcggctccgg tggtggtggt     360
tctcaggtcc aactgcagga gtcaggagga ggcttggtac agcctggggg ttctctgaga     420
ctctcctgtg caacttctgg gttcaccttc actgattact acatgaactg ggtccgccag     480
cctccaggaa aggcacttga gtggttgggt tttattggaa acaaagctaa tggttacaca     540
acagagtaca gtgcatctgt gaaggtcgg ttcaccatct ccagagataa atcccaaagc      600
atcctctatc ttcaaatgaa caccctgaga gctgaggaca gtgccactta ttactgtacc     660
agagatgggg ggctacggtt ctactttgac tactggggcc aagggaccac ggtcaccgtc     720
tcctccggag gtggtggatc cgacgtccaa ctggtgcagt caggggctga agtgaaaaaa     780
cctggggcct cagtgaaggt gtcctgcaag gcttctggct acacctttac taggtacacg     840
atgcactggg taaggcaggc acctggacag ggtctggaat ggattggata cattaatcct     900
agccgtggtt atactaatta cgcagacagc gtcaagggcc gcttcacaat cactacagac     960
aaatccacca gcacagccta catggaactg agcagcctgc gttctgagga cactgcaacc    1020
tattactgtg caagatatta tgatgatcat tactgccttg actactgggg ccaaggcacc    1080
acggtcaccg tctcctcagg cgaaggtact agtactggtt ctggtggaag tggaggttca    1140
ggtggagcag acgacattgt actgacccag tctccagcaa ctctgtctct gtctccaggg    1200
gagcgtgcca ccctgagctg cagagccagt caaagtgtaa gttacatgaa ctggtaccag    1260
cagaagccgg gcaaggcacc caaaagatgg atttatgaca catccaaagt ggcttctgga    1320
gtccctgctc gcttcagtgg cagtgggtct gggaccgact actctctcac aatcaacagc    1380
ttggaggctg aagatgctgc cacttattac tgccaacagt ggagtagtaa cccgctcacg    1440
ttcggtggcg ggaccaaggt ggagatcaaa tag                                 1473

<210> SEQ ID NO 6
<211> LENGTH: 490
<212> TYPE: PRT
<213> ORGANISM: artificial sequence
<220> FEATURE:
<223> OTHER INFORMATION: CEA I VLVH x SEQ ID NO: 77 VHVL ; Bispecific
      single chain antibody

<400> SEQUENCE: 6

Asp Ile Glu Leu Thr Gln Ser Pro Ala Ile Leu Ser Ala Ser Pro Gly
1               5                   10                  15

Glu Lys Val Thr Met Thr Cys Arg Ala Ser Ser Ser Val Thr Tyr Ile
            20                  25                  30

His Trp Tyr Gln Gln Lys Pro Gly Ser Ser Pro Lys Ser Trp Ile Tyr
        35                  40                  45

Ala Thr Ser Asn Leu Ala Ser Gly Val Pro Ala Arg Phe Ser Gly Ser
    50                  55                  60
```

```
Gly Ser Gly Thr Ser Tyr Ser Leu Thr Ile Ser Arg Val Glu Ala Glu
 65                  70                  75                  80

Asp Ala Ala Thr Tyr Tyr Cys Gln His Trp Ser Ser Lys Pro Pro Thr
                 85                  90                  95

Phe Gly Gly Gly Thr Lys Leu Glu Ile Lys Gly Gly Gly Gly Ser Gly
            100                 105                 110

Gly Gly Gly Ser Gly Gly Gly Ser Gln Val Gln Leu Gln Glu Ser
            115                 120                 125

Gly Gly Gly Leu Val Gln Pro Gly Gly Ser Leu Arg Leu Ser Cys Ala
        130                 135                 140

Thr Ser Gly Phe Thr Phe Thr Asp Tyr Tyr Met Asn Trp Val Arg Gln
145                 150                 155                 160

Pro Pro Gly Lys Ala Leu Glu Trp Leu Gly Phe Ile Gly Asn Lys Ala
                165                 170                 175

Asn Gly Tyr Thr Thr Glu Tyr Ser Ala Ser Val Lys Gly Arg Phe Thr
            180                 185                 190

Ile Ser Arg Asp Lys Ser Gln Ser Ile Leu Tyr Leu Gln Met Asn Thr
        195                 200                 205

Leu Arg Ala Glu Asp Ser Ala Thr Tyr Tyr Cys Thr Arg Asp Arg Gly
210                 215                 220

Leu Arg Phe Tyr Phe Asp Tyr Trp Gly Gln Gly Thr Val Thr Val
225                 230                 235                 240

Ser Ser Gly Gly Gly Gly Ser Asp Val Gln Leu Val Gln Ser Gly Ala
                245                 250                 255

Glu Val Lys Lys Pro Gly Ala Ser Val Lys Val Ser Cys Lys Ala Ser
            260                 265                 270

Gly Tyr Thr Phe Thr Arg Tyr Thr Met His Trp Val Arg Gln Ala Pro
        275                 280                 285

Gly Gln Gly Leu Glu Trp Ile Gly Tyr Ile Asn Pro Ser Arg Gly Tyr
        290                 295                 300

Thr Asn Tyr Ala Asp Ser Val Lys Gly Arg Phe Thr Ile Thr Thr Asp
305                 310                 315                 320

Lys Ser Thr Ser Thr Ala Tyr Met Glu Leu Ser Ser Leu Arg Ser Glu
                325                 330                 335

Asp Thr Ala Thr Tyr Tyr Cys Ala Arg Tyr Tyr Asp Asp His Tyr Cys
            340                 345                 350

Leu Asp Tyr Trp Gly Gln Gly Thr Val Thr Val Ser Ser Gly Glu
        355                 360                 365

Gly Thr Ser Thr Gly Ser Gly Ser Gly Ser Gly Gly Ala Asp
        370                 375                 380

Asp Ile Val Leu Thr Gln Ser Pro Ala Thr Leu Ser Leu Ser Pro Gly
385                 390                 395                 400

Glu Arg Ala Thr Leu Ser Cys Arg Ala Ser Gln Ser Val Ser Tyr Met
                405                 410                 415

Asn Trp Tyr Gln Gln Lys Pro Gly Lys Ala Pro Lys Arg Trp Ile Tyr
            420                 425                 430

Asp Thr Ser Lys Val Ala Ser Gly Val Pro Ala Arg Phe Ser Gly Ser
        435                 440                 445

Gly Ser Gly Thr Asp Tyr Ser Leu Thr Ile Asn Ser Leu Glu Ala Glu
        450                 455                 460

Asp Ala Ala Thr Tyr Tyr Cys Gln Gln Trp Ser Ser Asn Pro Leu Thr
465                 470                 475                 480

Phe Gly Gly Gly Thr Lys Val Glu Ile Lys
```

<210> SEQ ID NO 7
<211> LENGTH: 1476
<212> TYPE: DNA
<213> ORGANISM: artificial sequence
<220> FEATURE:
<223> OTHER INFORMATION: CEA I VHVL x SEQ ID NO: 77 VHVL ; Bispecific single chain antibody

<400> SEQUENCE: 7

```
caggtccaac tgcaggagtc aggaggaggc ttggtacagc ctgggggttc tctgagactc      60
tcctgtgcaa cttctgggtt caccttcact gattactaca tgaactgggt ccgccagcct     120
ccaggaaagg cacttgagtg gttgggtttt attggaaaca agctaatgg ttacacaaca      180
gagtacagtg catctgtgaa gggtcggttc accatctcca gagataaatc caaagcatc     240
ctctatcttc aaatgaacac cctgagagct gaggacagtg ccacttatta ctgtaccaga     300
gatagggggc tacggttcta ctttgactac tggggccaag gaccacggt caccgtctcc      360
tccggtggtg gtggttctgg cggcggcggc tccggtggtg gtggttctga cattgagctc     420
acccagtctc cagcaatcct gtctgcatct ccaggggaga aggtcacaat gacttgcagg     480
gccagctcaa gtgtaactta cattcactgg taccagcaga gccaggatc ctcccccaaa      540
tcctggattt atgccacatc caacctggct tctggagtcc ctgctcgctt cagtggcagt     600
gggtctggga cctcttactc tctcacaatc agcagagtgg aggctgaaga tgctgccact     660
tattactgcc aacattggag tagtaaacca ccgacgttcg gtggagggac caagctcgag     720
atcaaatccg gaggtggtgg atccgacgtc caactggtgc agtcagggg ctgaagtgaaa     780
aaacctgggg cctcagtgaa ggtgtcctgc aaggcttctg gctacacctt tactaggtac     840
acgatgcact gggtaaggca ggcacctgga cagggtctgg aatggattgg atacattaat     900
cctagccgtg gttatactaa ttacgcagac agcgtcaagg gccgcttcac aatcactaca     960
gacaaatcca ccagcacagc ctacatggaa ctgagcagcc tgcgttctga ggacactgca    1020
acctattact gtgcaagata ttatgatgat cattactgcc ttgactactg gggccaaggc    1080
accacggtca ccgtctcctc aggcgaaggt actagtactg ttctggtgg aagtggaggt    1140
tcaggtggag cagacgacat tgtactgacc cagtctccag caactctgtc tctgtctcca    1200
ggggagcgtg ccaccctgag ctgcagagcc agtcaaagtg taagttacat gaactggtac    1260
cagcagaagc cgggcaaggc acccaaaaga tggatttatg acacatccaa agtggcttct    1320
ggagtccctg ctcgcttcag tggcagtggg tctgggaccg actactctct cacaatcaac    1380
agcttggagg ctgaagatgc tgccacttat tactgccaac agtggagtag taacccgctc    1440
acgttcggtg cgggaccaa ggtggagatc aaatag                              1476
```

<210> SEQ ID NO 8
<211> LENGTH: 491
<212> TYPE: PRT
<213> ORGANISM: artificial sequence
<220> FEATURE:
<223> OTHER INFORMATION: CEA I VHVL x SEQ ID NO: 77 VHVL ; Bispecific single chain antibody

<400> SEQUENCE: 8

```
Gln Val Gln Leu Gln Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30
```

```
Tyr Met Asn Trp Val Arg Gln Pro Pro Gly Lys Ala Leu Glu Trp Leu
         35                  40                  45
Gly Phe Ile Gly Asn Lys Ala Asn Gly Tyr Thr Thr Glu Tyr Ser Ala
 50                  55                  60
Ser Val Lys Gly Arg Phe Thr Ile Ser Arg Asp Lys Ser Gln Ser Ile
 65                  70                  75                  80
Leu Tyr Leu Gln Met Asn Thr Leu Arg Ala Glu Asp Ser Ala Thr Tyr
                 85                  90                  95
Tyr Cys Thr Arg Asp Arg Gly Leu Arg Phe Tyr Phe Asp Tyr Trp Gly
            100                 105                 110
Gln Gly Thr Thr Val Thr Val Ser Ser Gly Gly Gly Ser Gly Gly
            115                 120                 125
Gly Gly Ser Gly Gly Gly Ser Asp Ile Glu Leu Thr Gln Ser Pro
130                 135                 140
Ala Ile Leu Ser Ala Ser Pro Gly Glu Lys Val Thr Met Thr Cys Arg
145                 150                 155                 160
Ala Ser Ser Ser Val Thr Tyr Ile His Trp Tyr Gln Gln Lys Pro Gly
                165                 170                 175
Ser Ser Pro Lys Ser Trp Ile Tyr Ala Thr Ser Asn Leu Ala Ser Gly
            180                 185                 190
Val Pro Ala Arg Phe Ser Gly Ser Gly Ser Gly Thr Ser Tyr Ser Leu
            195                 200                 205
Thr Ile Ser Arg Val Glu Ala Glu Asp Ala Ala Thr Tyr Tyr Cys Gln
210                 215                 220
His Trp Ser Ser Lys Pro Pro Thr Phe Gly Gly Gly Thr Lys Leu Glu
225                 230                 235                 240
Ile Lys Ser Gly Gly Gly Gly Ser Asp Val Gln Leu Val Gln Ser Gly
                245                 250                 255
Ala Glu Val Lys Lys Pro Gly Ala Ser Val Lys Val Ser Cys Lys Ala
            260                 265                 270
Ser Gly Tyr Thr Phe Thr Arg Tyr Thr Met His Trp Val Arg Gln Ala
            275                 280                 285
Pro Gly Gln Gly Leu Glu Trp Ile Gly Tyr Ile Asn Pro Ser Arg Gly
            290                 295                 300
Tyr Thr Asn Tyr Ala Asp Ser Val Lys Gly Arg Phe Thr Ile Thr Thr
305                 310                 315                 320
Asp Lys Ser Thr Ser Thr Ala Tyr Met Glu Leu Ser Ser Leu Arg Ser
                325                 330                 335
Glu Asp Thr Ala Thr Tyr Tyr Cys Ala Arg Tyr Tyr Asp Asp His Tyr
            340                 345                 350
Cys Leu Asp Tyr Trp Gly Gln Gly Thr Thr Val Thr Val Ser Ser Gly
            355                 360                 365
Glu Gly Thr Ser Thr Gly Ser Gly Gly Ser Gly Gly Ser Gly Gly Ala
            370                 375                 380
Asp Asp Ile Val Leu Thr Gln Ser Pro Ala Thr Leu Ser Leu Ser Pro
385                 390                 395                 400
Gly Glu Arg Ala Thr Leu Ser Cys Arg Ala Ser Gln Ser Val Ser Tyr
                405                 410                 415
Met Asn Trp Tyr Gln Gln Lys Pro Gly Lys Ala Pro Lys Arg Trp Ile
            420                 425                 430
Tyr Asp Thr Ser Lys Val Ala Ser Gly Val Pro Ala Arg Phe Ser Gly
            435                 440                 445
```

Ser Gly Ser Gly Thr Asp Tyr Ser Leu Thr Ile Asn Ser Leu Glu Ala
    450                 455                 460

Glu Asp Ala Ala Thr Tyr Tyr Cys Gln Gln Trp Ser Ser Asn Pro Leu
465                 470                 475                 480

Thr Phe Gly Gly Gly Thr Lys Val Glu Ile Lys
                485                 490

<210> SEQ ID NO 9
<211> LENGTH: 1491
<212> TYPE: DNA
<213> ORGANISM: artificial sequence
<220> FEATURE:
<223> OTHER INFORMATION: CEA II VHVL x SEQ ID NO: 77 VHVL ; Bispecific
      single chain antibody

<400> SEQUENCE: 9

```
gaggttcagc tgcagcagtc tggggcagag cttgtggagc caggggcctc agtcaagttg      60
tcctgcacag cttctggctt caacattaaa gacacctata tgcactgggt gaagcagagg     120
cctgaacagg gcctggaatg gattggaagg attgatcctg cgaatggtaa tagtaaatat     180
gtcccgaagt tccagggcaa ggccactata acagcagaca catcctccaa cacagcctac     240
ctgcagctca ccagcctgac atctgaggac actgccgtct attattgtgc tccgtttggt     300
tactacgtgt ctgactatgc tatggcctac tggggtcaag gaacctcagt caccgtctcc     360
tccggtggtg gtggttctgg cggcggcggc tccggtggtg gtggttctga cattgtgctg     420
acccaatctc cagcttcttt ggctgtgtct cttgggcaga gggccaccat gtcctgcaga     480
gccggtgaaa gtgttgatat ttttggcgtt gggttttgc actggtacca gcagaaacca     540
ggacagccac ccaaactcct catctatcgt gcatccaacc tagaatctgg gatccctgtc     600
aggttcagtg gcactgggtc taggacagac ttcaccctca tcattgatcc tgtggaggct     660
gatgatgttg ccacctatta ctgtcagcaa actaatgagg atccgtacac gttcggaggg     720
gggaccaagc tcgagataaa atccggaggt ggtggatccg acgtccaact ggtgcagtca     780
ggggctgaag tgaaaaaacc tggggcctca gtgaaggtgt cctgcaaggc ttctggctac     840
accttttacta ggtacacgat gcactgggta aggcaggcac ctggacaggg tctggaatgg     900
attggataca ttaatcctag ccgtggttat actaattacg cagacagcgt caagggccgc     960
ttcacaatca ctacagacaa atccaccagc acagcctaca tggaactgag cagcctgcgt    1020
tctgaggaca ctgcaaccta ttactgtgca agatattatg atgatcatta ctgccttgac    1080
tactggggcc aaggcaccac ggtcaccgtc tcctcaggcg aagtactag tactggttct    1140
ggtggaagtg gaggttcagg tggagcagac gacattgtac tgacccagtc tccagcaact    1200
ctgtctctgt ctccagggga gcgtgccacc ctgagctgca gagccagtca agtgtaagt    1260
tacatgaact ggtaccagca gaagccgggc aaggcaccca aaagatggat ttatgacaca    1320
tccaaagtgg cttctggagt ccctgctcgc ttcagtggca gtgggtctgg gaccgactac    1380
tctctcacaa tcaacagctt ggaggctgaa gatgctgcca ttattactg ccaacagtgg    1440
agtagtaacc cgctcacgtt cggtggcggg accaaggtgg agatcaaata g             1491
```

<210> SEQ ID NO 10
<211> LENGTH: 496
<212> TYPE: PRT
<213> ORGANISM: artificial sequence
<220> FEATURE:
<223> OTHER INFORMATION: CEA II VHVL x SEQ ID NO: 77 VHVL ; Bispecific
      single chain antibody

<400> SEQUENCE: 10

```
Glu Val Gln Leu Gln Gln Ser Gly Ala Glu Leu Val Glu Pro Gly Ala
1               5                   10                  15

Ser Val Lys Leu Ser Cys Thr Ala Ser Gly Phe Asn Ile Lys Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Ser Lys Tyr Val Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Thr Ser Leu Thr Ser Glu Asp Thr Ala Val Tyr Tyr Cys
                85                  90                  95

Ala Pro Phe Gly Tyr Tyr Val Ser Asp Tyr Ala Met Ala Tyr Trp Gly
            100                 105                 110

Gln Gly Thr Ser Val Thr Val Ser Ser Gly Gly Gly Ser Gly Gly
        115                 120                 125

Gly Gly Ser Gly Gly Gly Ser Asp Ile Val Leu Thr Gln Ser Pro
    130                 135                 140

Ala Ser Leu Ala Val Ser Leu Gly Gln Arg Ala Thr Met Ser Cys Arg
145                 150                 155                 160

Ala Gly Glu Ser Val Asp Ile Phe Gly Val Gly Phe Leu His Trp Tyr
                165                 170                 175

Gln Gln Lys Pro Gly Gln Pro Pro Lys Leu Leu Ile Tyr Arg Ala Ser
            180                 185                 190

Asn Leu Glu Ser Gly Ile Pro Val Arg Phe Ser Gly Thr Gly Ser Arg
        195                 200                 205

Thr Asp Phe Thr Leu Ile Ile Asp Pro Val Glu Ala Asp Asp Val Ala
    210                 215                 220

Thr Tyr Tyr Cys Gln Gln Thr Asn Glu Asp Pro Tyr Thr Phe Gly Gly
225                 230                 235                 240

Gly Thr Lys Leu Glu Ile Lys Ser Gly Gly Gly Ser Asp Val Gln
                245                 250                 255

Leu Val Gln Ser Gly Ala Glu Val Lys Lys Pro Gly Ala Ser Val Lys
            260                 265                 270

Val Ser Cys Lys Ala Ser Gly Tyr Thr Phe Thr Arg Tyr Thr Met His
        275                 280                 285

Trp Val Arg Gln Ala Pro Gly Gln Gly Leu Glu Trp Ile Gly Tyr Ile
    290                 295                 300

Asn Pro Ser Arg Gly Tyr Thr Asn Tyr Ala Asp Ser Val Lys Gly Arg
305                 310                 315                 320

Phe Thr Ile Thr Thr Asp Lys Ser Thr Ser Thr Ala Tyr Met Glu Leu
                325                 330                 335

Ser Ser Leu Arg Ser Glu Asp Thr Ala Thr Tyr Tyr Cys Ala Arg Tyr
            340                 345                 350

Tyr Asp Asp His Tyr Cys Leu Asp Tyr Trp Gly Gln Gly Thr Thr Val
        355                 360                 365

Thr Val Ser Ser Gly Glu Gly Thr Ser Thr Gly Ser Gly Gly Ser Gly
    370                 375                 380

Gly Ser Gly Gly Ala Asp Asp Ile Val Leu Thr Gln Ser Pro Ala Thr
385                 390                 395                 400

Leu Ser Leu Ser Pro Gly Glu Arg Ala Thr Leu Ser Cys Arg Ala Ser
                405                 410                 415
```

| Gln | Ser | Val | Ser | Tyr | Met | Asn | Trp | Tyr | Gln | Gln | Lys | Pro | Gly | Lys | Ala |
|---|---|---|---|---|---|---|---|---|---|---|---|---|---|---|---|
| | | | 420 | | | | 425 | | | | 430 | | | | |

| Pro | Lys | Arg | Trp | Ile | Tyr | Asp | Thr | Ser | Lys | Val | Ala | Ser | Gly | Val | Pro |
|---|---|---|---|---|---|---|---|---|---|---|---|---|---|---|---|
| | | 435 | | | | 440 | | | | 445 | | | | | |

| Ala | Arg | Phe | Ser | Gly | Ser | Gly | Ser | Gly | Thr | Asp | Tyr | Ser | Leu | Thr | Ile |
|---|---|---|---|---|---|---|---|---|---|---|---|---|---|---|---|
| 450 | | | | | 455 | | | | | 460 | | | | | |

| Asn | Ser | Leu | Glu | Ala | Glu | Asp | Ala | Ala | Thr | Tyr | Tyr | Cys | Gln | Gln | Trp |
|---|---|---|---|---|---|---|---|---|---|---|---|---|---|---|---|
| 465 | | | | 470 | | | | | 475 | | | | | | 480 |

| Ser | Ser | Asn | Pro | Leu | Thr | Phe | Gly | Gly | Gly | Thr | Lys | Val | Glu | Ile | Lys |
|---|---|---|---|---|---|---|---|---|---|---|---|---|---|---|---|
| | | | | 485 | | | | | 490 | | | | | 495 | |

<210> SEQ ID NO 11
<211> LENGTH: 1470
<212> TYPE: DNA
<213> ORGANISM: artificial sequence
<220> FEATURE:
<223> OTHER INFORMATION: CEA III VLVH x SEQ ID NO: 77 VHVL ; Bispecific
      single chain antibody

<400> SEQUENCE: 11

```
gagaacgttc tcacccagtc tccagcaatc atgtctgcat ctccagggga gaaggtcacc      60
atcacctgca gtgccagctc aagcgtcagc tacatgcact ggttccagca gaagccaggc     120
acctccccca aactctggat ttattctaca tccaacctgg cttctggagt ccctgctcgc     180
ttctctggca gtgggtctgg gacctcttac tctctcacaa tcagcagaat ggaggctgaa     240
gatgctgcca cttattactg ccagcagaga agtagttacc cactcacgtt cggtgctggg     300
accaagctcg agctgaaagg tggtggtggt tctggcggcg gcggctccgg tggtggtggt     360
tctcaggtta gctgcagca gtctggggca gagcttgtga gatcagggac atcagtcaag     420
ttgtcctgca cagcttctgg cttcaacatt aaagactcct atatgcactg gctgaggcag     480
gggcctgaac agggcctgga gtggattgga tggattgatc ctgagaatgg tgatactgaa     540
tatgccccga gttccaggg caaggccact ttcactactg acacatcctc caacacagcc     600
tacctgcagc tcagcagcct gacatctgag gacactgccg tctattactg taacgagggc     660
acacctacag ggccttacta ctttgactac tggggccaag gcaccactgt cacagtctcc     720
tccggaggtg gtggatccga cgtccaactg gtgcagtcag gggctgaagt gaaaaaacct     780
ggggcctcag tgaaggtgtc ctgcaaggct tctggctaca cctttactag gtacacgatg     840
cactgggtaa ggcaggcacc tggacagggt ctggaatgga ttggatacat taatcctagc     900
cgtggttata ctaattacgc agacagcgtc aagggccgct tcacaatcac tacagacaaa     960
tccaccagca cagcctacat ggaactgagc agcctgcgtt ctgaggacac tgcaacctat    1020
tactgtgcaa gatattatga tgatcattac tgccttgact actggggcca aggcaccacg    1080
gtcaccgtct cctcaggcga aggtactagt actggttctg gtggaagtgg aggttcaggt    1140
ggagcagacg acattgtact gacccagtct ccagcaactc tgtctctgtc tccagggag    1200
cgtgccaccc tgagctgcag agccagtcaa agtgtaagtt acatgaactg gtaccagcag    1260
aagccgggca aggcacccaa agatggatt tatgacacat ccaaagtggc ttctggagtc    1320
cctgctcgct tcagtggcag tgggtctggg accgactact ctctcacaat caacagcttg    1380
gaggctgaag atgctgccac ttattactgc caacagtgga gtagtaaccc gctcacgttc    1440
ggtggcggga ccaaggtgga gatcaaatag                                     1470
```

<210> SEQ ID NO 12

```
<211> LENGTH: 489
<212> TYPE: PRT
<213> ORGANISM: artificial sequence
<220> FEATURE:
<223> OTHER INFORMATION: CEA III VLVH x SEQ ID NO: 77 VHVL ; Bispecific
      single chain antibody

<400> SEQUENCE: 12

Glu Asn Val Leu Thr Gln Ser Pro Ala Ile Met Ser Ala Ser Pro Gly
1               5                   10                  15

Glu Lys Val Thr Ile Thr Cys Ser Ala Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Leu Thr
                85                  90                  95

Phe Gly Ala Gly Thr Lys Leu Glu Leu Lys Gly Gly Gly Gly Ser Gly
            100                 105                 110

Gly Gly Gly Ser Gly Gly Gly Ser Gln Val Lys Leu Gln Gln Ser
        115                 120                 125

Gly Ala Glu Leu Val Arg Ser Gly Thr Ser Val Lys Leu Ser Cys Thr
    130                 135                 140

Ala Ser Gly Phe Asn Ile Lys Asp Ser Tyr Met His Trp Leu Arg Gln
145                 150                 155                 160

Gly Pro Glu Gln Gly Leu Glu Trp Ile Gly Trp Ile Asp Pro Glu Asn
                165                 170                 175

Gly Asp Thr Glu Tyr Ala Pro Lys Phe Gln Gly Lys Ala Thr Phe Thr
            180                 185                 190

Thr Asp Thr Ser Ser Asn Thr Ala Tyr Leu Gln Leu Ser Ser Leu Thr
        195                 200                 205

Ser Glu Asp Thr Ala Val Tyr Tyr Cys Asn Glu Gly Thr Pro Thr Gly
    210                 215                 220

Pro Tyr Tyr Phe Asp Tyr Trp Gly Gln Gly Thr Thr Val Thr Val Ser
225                 230                 235                 240

Ser Gly Gly Gly Gly Ser Asp Val Gln Leu Val Gln Ser Gly Ala Glu
                245                 250                 255

Val Lys Lys Pro Gly Ala Ser Val Lys Val Ser Cys Lys Ala Ser Gly
            260                 265                 270

Tyr Thr Phe Thr Arg Tyr Thr Met His Trp Val Arg Gln Ala Pro Gly
        275                 280                 285

Gln Gly Leu Glu Trp Ile Gly Tyr Ile Asn Pro Ser Arg Gly Tyr Thr
    290                 295                 300

Asn Tyr Ala Asp Ser Val Lys Gly Arg Phe Thr Ile Thr Thr Asp Lys
305                 310                 315                 320

Ser Thr Ser Thr Ala Tyr Met Glu Leu Ser Ser Leu Arg Ser Glu Asp
                325                 330                 335

Thr Ala Thr Tyr Tyr Cys Ala Arg Tyr Tyr Asp His Tyr Cys Leu
            340                 345                 350

Asp Tyr Trp Gly Gln Gly Thr Thr Val Thr Val Ser Ser Gly Glu Gly
        355                 360                 365

Thr Ser Thr Gly Ser Gly Gly Ser Gly Gly Ser Gly Gly Ala Asp Asp
```

```
                 370                 375                 380
Ile Val Leu Thr Gln Ser Pro Ala Thr Leu Ser Leu Ser Pro Gly Glu
385                 390                 395                 400

Arg Ala Thr Leu Ser Cys Arg Ala Ser Gln Ser Val Ser Tyr Met Asn
            405                 410                 415

Trp Tyr Gln Gln Lys Pro Gly Lys Ala Pro Lys Arg Trp Ile Tyr Asp
                420                 425                 430

Thr Ser Lys Val Ala Ser Gly Val Pro Ala Arg Phe Ser Gly Ser Gly
            435                 440                 445

Ser Gly Thr Asp Tyr Ser Leu Thr Ile Asn Ser Leu Glu Ala Glu Asp
        450                 455                 460

Ala Ala Thr Tyr Tyr Cys Gln Gln Trp Ser Ser Asn Pro Leu Thr Phe
465                 470                 475                 480

Gly Gly Gly Thr Lys Val Glu Ile Lys
            485
```

<210> SEQ ID NO 13
<211> LENGTH: 1473
<212> TYPE: DNA
<213> ORGANISM: artificial sequence
<220> FEATURE:
<223> OTHER INFORMATION: CEA III VHVL x SEQ ID NO: 77 VHVL ; Bispecific
      single chain antibody

<400> SEQUENCE: 13

```
caggttaagc tgcagcagtc tggggcagag cttgtgagat cagggacatc agtcaagttg      60
tcctgcacag cttctggctt caacattaaa gactcctata tgcactggct gaggcagggg     120
cctgaacagg gcctggagtg gattggatgg attgatcctg agaatggtga tactgaatat     180
gccccgaagt tccagggcaa ggccactttc actactgaca catcctccaa cacagcctac     240
ctgcagctca gcagcctgac atctgaggac actgccgtct attactgtaa cgagggcaca     300
cctacagggc cttactactt tgactactgg ggccaaggca ccactgtcac agtctcctcc     360
ggtggtggtg gttctggcgg cggcggctcc ggtggtggtg gttctgagaa cgttctcacc     420
cagtctccag caatcatgtc tgcatctcca ggggagaagg tcaccatcac ctgcagtgcc     480
agctcaagcg tcagctacat gcactggttc cagcagaagc caggcacctc ccccaaactc     540
tggatttatt ctacatccaa cctggcttct ggagtccctg ctcgcttctc tggcagtggg     600
tctgggacct cttactctct cacaatcagc agaatggagg ctgaagatgc tgccacttat     660
tactgccagc agagaagtag ttacccactc acgttcggtg ctgggaccaa gctcgagctg     720
aaatccggag gtggtggatc cgacgtccaa ctggtgcagt cagggctga agtgaaaaaa     780
cctgggcct cagtgaaggt gtcctgcaag gcttctggct acacctttac taggtacacg     840
atgcactggg taaggcaggc acctggacag ggtctggaat ggattggata cattaatcct     900
agccgtggtt atactaatta cgcagacagc gtcaagggcc gcttcacaat cactacagac     960
aaatccacca gcacagccta catggaactg agcagcctgc gttctgagga cactgcaacc    1020
tattactgtg caagatatta tgatgatcat actgccttg actactgggg ccaaggcacc    1080
acggtcaccg tctcctcagg cgaaggtact agtactggtt ctggtggaag tggaggttca    1140
ggtggagcag acgacattgt actgacccag tctccagcaa ctctgtctct gtctccaggg    1200
gagcgtgcca ccctgagctg cagagccagt caaagtgtaa gttacatgaa ctggtaccag    1260
cagaagccgg gcaaggcacc caaaagatgg atttatgaca catccaaagt ggcttctgga    1320
gtccctgctc gcttcagtgg cagtgggtct ggaccgact actctctcac aatcaacagc    1380
```

```
ttggaggctg aagatgctgc cacttattac tgccaacagt ggagtagtaa cccgctcacg    1440
ttcggtggcg ggaccaaggt ggagatcaaa tag                                 1473
```

<210> SEQ ID NO 14
<211> LENGTH: 490
<212> TYPE: PRT
<213> ORGANISM: artificial sequence
<220> FEATURE:
<223> OTHER INFORMATION: CEA III VHVL x SEQ ID NO: 77 VHVL ; Bispecific single chain antibody

<400> SEQUENCE: 14

```
Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
            20                  25                  30

Tyr Met His Trp Leu Arg Gln Gly Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

Gly Thr Thr Val Thr Val Ser Gly Gly Gly Gly Ser Gly Gly Gly
        115                 120                 125

Gly Ser Gly Gly Gly Gly Ser Glu Asn Val Leu Thr Gln Ser Pro Ala
    130                 135                 140

Ile Met Ser Ala Ser Pro Gly Glu Lys Val Thr Ile Thr Cys Ser Ala
145                 150                 155                 160

Ser Ser Ser Val Ser Tyr Met His Trp Phe Gln Gln Lys Pro Gly Thr
                165                 170                 175

Ser Pro Lys Leu Trp Ile Tyr Ser Thr Ser Asn Leu Ala Ser Gly Val
            180                 185                 190

Pro Ala Arg Phe Ser Gly Ser Gly Ser Gly Thr Ser Tyr Ser Leu Thr
        195                 200                 205

Ile Ser Arg Met Glu Ala Glu Asp Ala Ala Thr Tyr Tyr Cys Gln Gln
    210                 215                 220

Arg Ser Ser Tyr Pro Leu Thr Phe Gly Ala Gly Thr Lys Leu Glu Leu
225                 230                 235                 240

Lys Ser Gly Gly Gly Gly Ser Asp Val Gln Leu Val Gln Ser Gly Ala
                245                 250                 255

Glu Val Lys Lys Pro Gly Ala Ser Val Lys Val Ser Cys Lys Ala Ser
            260                 265                 270

Gly Tyr Thr Phe Thr Arg Tyr Thr Met His Trp Val Arg Gln Ala Pro
        275                 280                 285

Gly Gln Gly Leu Glu Trp Ile Gly Tyr Ile Asn Pro Ser Arg Gly Tyr
    290                 295                 300

Thr Asn Tyr Ala Asp Ser Val Lys Gly Arg Phe Thr Ile Thr Thr Asp
305                 310                 315                 320

Lys Ser Thr Ser Thr Ala Tyr Met Glu Leu Ser Ser Leu Arg Ser Glu
                325                 330                 335
```

```
Asp Thr Ala Thr Tyr Tyr Cys Ala Arg Tyr Tyr Asp Asp His Tyr Cys
            340                 345                 350

Leu Asp Tyr Trp Gly Gln Gly Thr Thr Val Thr Val Ser Ser Gly Glu
        355                 360                 365

Gly Thr Ser Thr Gly Ser Gly Gly Ser Gly Gly Ser Gly Gly Ala Asp
        370                 375                 380

Asp Ile Val Leu Thr Gln Ser Pro Ala Thr Leu Ser Leu Ser Pro Gly
385                 390                 395                 400

Glu Arg Ala Thr Leu Ser Cys Arg Ala Ser Gln Ser Val Ser Tyr Met
                405                 410                 415

Asn Trp Tyr Gln Gln Lys Pro Gly Lys Ala Pro Lys Arg Trp Ile Tyr
                420                 425                 430

Asp Thr Ser Lys Val Ala Ser Gly Val Pro Ala Arg Phe Ser Gly Ser
            435                 440                 445

Gly Ser Gly Thr Asp Tyr Ser Leu Thr Ile Asn Ser Leu Glu Ala Glu
        450                 455                 460

Asp Ala Ala Thr Tyr Tyr Cys Gln Gln Trp Ser Ser Asn Pro Leu Thr
465                 470                 475                 480

Phe Gly Gly Gly Thr Lys Val Glu Ile Lys
                485                 490
```

<210> SEQ ID NO 15
<211> LENGTH: 1506
<212> TYPE: DNA
<213> ORGANISM: artificial sequence
<220> FEATURE:
<223> OTHER INFORMATION: CEA I VH-A240VL x SEQ ID NO: 77 VHVL ;
      Bispecific single chain antibody

<400> SEQUENCE: 15

```
gaggtgcagc tggtcgagtc aggaggaggc ttggtacagc ctgggggttc tctgagactc    60
tcctgtgcaa cttctggggtt cacccttcact gattactaca tgaactgggt ccgccagcct   120
ccaggaaagg cacttgagtg gttgggtttt attggaaaca agctaatgg ttacacaaca    180 gagtacagtg catctgtgaa gggtcggttc accatctcca gagataaatc caaagcatc    240 ctctatcttc aaatgaacac cctgagagct gaggacagtg ccacttatta ctgtaccaga   300
gatagggggc tacggttcta ctttgactac tggggccaag gaccacggt caccgtctcc    360 tcaggtggtg gtggttctgg cggcggcggc tccgtggtg gtggttctca ggccgtgctg   420
actcagccgg cttccctctc tgcatctcct ggagcatcag ccagtctcac ctgcaccttg   480 cgcagggca tcaatgttgg tgcctacagt atatactggt accagcagaa gccagggagt   540
cctccccagt atctcctgag gtacaaatca gactcagata agcagcaggg ctctggagtc   600
tccagccgct tctctgcatc caaagatgct tcggccaatg cagggatttt actcatctct   660
gggctccagt ctgaggatga ggctgactat tactgtatga tttggcacag cggcgcttct   720
gcggtgttcg gcggagggac caagttgacc gtcctatccg aggtggtgg atccgacgtc   780 caactggtgc agtcagggc tgaagtgaaa aaacctgggg cctcagtgaa ggtgtcctgc   840
aaggcttctg gctacacctt tactaggtac acgatgcact gggtaaggca ggcacctgga   900
cagggtctgg aatggattgg atacattaat cctagccgtg gttatactaa ttacgcagac   960
agcgtcaagg gccgcttcac aatcactaca gacaaatcca ccagcacagc ctacatggaa  1020
ctgagcagcc tgcgttctga ggacactgca acctattact gtgcaagata ttatgatgat  1080
cattactgcc ttgactactg gggccaaggc accacggtca ccgtctcctc aggcgaaggt  1140
```

```
actagtactg gttctggtgg aagtggaggt tcaggtggag cagacgacat tgtactgacc   1200
cagtctccag caactctgtc tctgtctcca ggggagcgtg ccaccctgag ctgcagagcc   1260
agtcaaagtg taagttacat gaactggtac cagcagaagc cgggcaaggc acccaaaaga   1320
tggatttatg acacatccaa agtggcttct ggagtccctg ctcgcttcag tggcagtggg   1380
tctgggaccg actactctct cacaatcaac agcttggagg ctgaagatgc tgccacttat   1440
tactgccaac agtggagtag taacccgctc acgttcggtg cgggaccaa ggtggagatc    1500 aaatag                                                              1506
```

<210> SEQ ID NO 16
<211> LENGTH: 501
<212> TYPE: PRT
<213> ORGANISM: artificial sequence
<220> FEATURE:
<223> OTHER INFORMATION: CEA I VH-A240VL x SEQ ID NO: 77 VHVL ;
    Bispecific single chain antibody

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Gln Ala Val Leu Thr Gln Pro Ala
    130                 135                 140

Ser Leu Ser Ala Ser Pro Gly Ala Ser Ala Ser Leu Thr Cys Thr Leu
145                 150                 155                 160

Arg Arg Gly Ile Asn Val Gly Ala Tyr Ser Ile Tyr Trp Tyr Gln Gln
                165                 170                 175

Lys Pro Gly Ser Pro Pro Gln Tyr Leu Leu Arg Tyr Lys Ser Asp Ser
            180                 185                 190

Asp Lys Gln Gln Gly Ser Gly Val Ser Ser Arg Phe Ser Ala Ser Lys
        195                 200                 205

Asp Ala Ser Ala Asn Ala Gly Ile Leu Leu Ile Ser Gly Leu Gln Ser
    210                 215                 220

Glu Asp Glu Ala Asp Tyr Tyr Cys Met Ile Trp His Ser Gly Ala Ser
225                 230                 235                 240

Ala Val Phe Gly Gly Gly Thr Lys Leu Thr Val Leu Ser Gly Gly Gly
                245                 250                 255

Gly Ser Asp Val Gln Leu Val Gln Ser Gly Ala Glu Val Lys Lys Pro
            260                 265                 270

Gly Ala Ser Val Lys Val Ser Cys Lys Ala Ser Gly Tyr Thr Phe Thr
        275                 280                 285
```

```
Arg Tyr Thr Met His Trp Val Arg Gln Ala Pro Gly Gln Gly Leu Glu
        290                 295                 300

Trp Ile Gly Tyr Ile Asn Pro Ser Arg Gly Tyr Thr Asn Tyr Ala Asp
305                 310                 315                 320

Ser Val Lys Gly Arg Phe Thr Ile Thr Thr Asp Lys Ser Thr Ser Thr
                325                 330                 335

Ala Tyr Met Glu Leu Ser Ser Leu Arg Ser Glu Asp Thr Ala Thr Tyr
            340                 345                 350

Tyr Cys Ala Arg Tyr Tyr Asp Asp His Tyr Cys Leu Asp Tyr Trp Gly
        355                 360                 365

Gln Gly Thr Thr Val Thr Val Ser Ser Gly Glu Gly Thr Ser Thr Gly
    370                 375                 380

Ser Gly Gly Ser Gly Gly Ser Gly Gly Ala Asp Asp Ile Val Leu Thr
385                 390                 395                 400

Gln Ser Pro Ala Thr Leu Ser Leu Ser Pro Gly Glu Arg Ala Thr Leu
                405                 410                 415

Ser Cys Arg Ala Ser Gln Ser Val Ser Tyr Met Asn Trp Tyr Gln Gln
            420                 425                 430

Lys Pro Gly Lys Ala Pro Lys Arg Trp Ile Tyr Asp Thr Ser Lys Val
        435                 440                 445

Ala Ser Gly Val Pro Ala Arg Phe Ser Gly Ser Gly Ser Gly Thr Asp
    450                 455                 460

Tyr Ser Leu Thr Ile Asn Ser Leu Glu Ala Glu Asp Ala Ala Thr Tyr
465                 470                 475                 480

Tyr Cys Gln Gln Trp Ser Ser Asn Pro Leu Thr Phe Gly Gly Gly Thr
                485                 490                 495

Lys Val Glu Ile Lys
            500

<210> SEQ ID NO 17
<211> LENGTH: 1503
<212> TYPE: DNA
<213> ORGANISM: artificial sequence
<220> FEATURE:
<223> OTHER INFORMATION: A240VL - CEA I VH x SEQ ID NO: 77 VHVL ;
      Bispecific single chain antibody

<400> SEQUENCE: 17
caggccgtgc tgactcagcc ggcttccctc tctgcatctc ctggagcatc agccagtctc    60
acctgcacct tgcgcagggg catcaatgtt ggtgcctaca gtatatactg gtaccagcag   120
aagccaggga gtcctcccca gtatctcctg aggtacaaat cagactcaga taagcagcag   180
ggctctggag tctccagccg cttctctgca tccaaagatg cttcggccaa tgcaggcatt   240
ttactcatct ctgggctcca gtctgaggat gaggctgact attactgtat gatttggcac   300
agcggcgctt ctgcggtgtt cggcggaggg accaagttga ccgtcctagg tggtggtggt   360
tctggcggcg cggctccggt ggtggtggt tctgaggtgc agctggtcga gtcaggagga   420
ggcttggtac agcctggggg ttctctgaga ctctcctgtg caacttctgg gttcaccttc   480
actgattact acatgaactg ggtccgccag cctccaggaa aggcacttga gtggttgggt   540
tttattggaa acaaagctaa tggttacaca acagagtaca gtgcatctgt gaagggtcgg   600
ttcaccatct ccagagataa atcccaaagc atcctctatc ttcaaatgaa caccctgaga   660
gctgaggaca gtgccactta ttactgtacc agagataggg ggctacggtt ctactttgac   720
tactggggcc aagggaccac ggtcaccgtc tcctccggag gtggtggatc cgacgtccaa   780
```

```
ctggtgcagt cagggggctga agtgaaaaaa cctggggcct cagtgaaggt gtcctgcaag    840
gcttctggct acacctttac taggtacacg atgcactggg taaggcaggc acctggacag    900
ggtctggaat ggattggata cattaatcct agccgtggtt atactaatta cgcagacagc    960
gtcaagggcc gcttcacaat cactacagac aaatccacca gcacagccta catggaactg   1020
agcagcctgc gttctgagga cactgcaacc tattactgtg caagatatta tgatgatcat   1080
tactgccttg actactgggg ccaaggcacc acggtcaccg tctcctcagg cgaaggtact   1140
agtactggtt ctggtggaag tggaggttca ggtggagcag acgacattgt actgacccag   1200
tctccagcaa ctctgtctct gtctccaggg gagcgtgcca ccctgagctg cagagccagt   1260
caaagtgtaa gttacatgaa ctggtaccag cagaagccgg gcaaggcacc caaaagatgg   1320
atttatgaca catccaaagt ggcttctgga gtccctgctc gcttcagtgg cagtgggtct   1380
gggaccgact actctctcac aatcaacagc ttggaggctg aagatgctgc cacttattac   1440
tgccaacagt ggagtagtaa cccgctcacg ttcggtggcg ggaccaaggt ggagatcaaa   1500
tag                                                                  1503

<210> SEQ ID NO 18
<211> LENGTH: 500
<212> TYPE: PRT
<213> ORGANISM: artificial sequence
<220> FEATURE:
<223> OTHER INFORMATION: A240VL - CEA I VH x SEQ ID NO: 77 VHVL ;
      Bispecific single chain antibody

<400> SEQUENCE: 18

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Lys Pro Gly Ser Pro Pro Gln Tyr
        35                  40                  45

Leu Leu Arg Tyr Lys Ser Asp Ser Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Thr Ser Gly Phe Thr Phe
145                 150                 155                 160

Thr Asp Tyr Tyr Met Asn Trp Val Arg Gln Pro Pro Gly Lys Ala Leu
                165                 170                 175

Glu Trp Leu Gly Phe Ile Gly Asn Lys Ala Asn Gly Tyr Thr Thr Glu
            180                 185                 190

Tyr Ser Ala Ser Val Lys Gly Arg Phe Thr Ile Ser Arg Asp Lys Ser
        195                 200                 205

Gln Ser Ile Leu Tyr Leu Gln Met Asn Thr Leu Arg Ala Glu Asp Ser
    210                 215                 220
```

```
Ala Thr Tyr Tyr Cys Thr Arg Asp Arg Gly Leu Arg Phe Tyr Phe Asp
225                 230                 235                 240

Tyr Trp Gly Gln Gly Thr Thr Val Thr Val Ser Ser Gly Gly Gly Gly
            245                 250                 255

Ser Asp Val Gln Leu Val Gln Ser Gly Ala Glu Val Lys Lys Pro Gly
        260                 265                 270

Ala Ser Val Lys Val Ser Cys Lys Ala Ser Gly Tyr Thr Phe Thr Arg
    275                 280                 285

Tyr Thr Met His Trp Val Arg Gln Ala Pro Gly Gln Gly Leu Glu Trp
290                 295                 300

Ile Gly Tyr Ile Asn Pro Ser Arg Gly Tyr Thr Asn Tyr Ala Asp Ser
305                 310                 315                 320

Val Lys Gly Arg Phe Thr Ile Thr Thr Asp Lys Ser Thr Ser Thr Ala
            325                 330                 335

Tyr Met Glu Leu Ser Ser Leu Arg Ser Glu Asp Thr Ala Thr Tyr Tyr
        340                 345                 350

Cys Ala Arg Tyr Tyr Asp Asp His Tyr Cys Leu Asp Tyr Trp Gly Gln
    355                 360                 365

Gly Thr Thr Val Thr Val Ser Ser Gly Glu Gly Thr Ser Thr Gly Ser
370                 375                 380

Gly Gly Ser Gly Gly Ser Gly Gly Ala Asp Asp Ile Val Leu Thr Gln
385                 390                 395                 400

Ser Pro Ala Thr Leu Ser Leu Ser Pro Gly Glu Arg Ala Thr Leu Ser
            405                 410                 415

Cys Arg Ala Ser Gln Ser Val Ser Tyr Met Asn Trp Tyr Gln Gln Lys
        420                 425                 430

Pro Gly Lys Ala Pro Lys Arg Trp Ile Tyr Asp Thr Ser Lys Val Ala
    435                 440                 445

Ser Gly Val Pro Ala Arg Phe Ser Gly Ser Gly Ser Gly Thr Asp Tyr
450                 455                 460

Ser Leu Thr Ile Asn Ser Leu Glu Ala Glu Asp Ala Ala Thr Tyr Tyr
465                 470                 475                 480

Cys Gln Gln Trp Ser Ser Asn Pro Leu Thr Phe Gly Gly Gly Thr Lys
            485                 490                 495

Val Glu Ile Lys
            500

<210> SEQ ID NO 19
<211> LENGTH: 1506
<212> TYPE: DNA
<213> ORGANISM: artificial sequence
<220> FEATURE:
<223> OTHER INFORMATION: SEQ ID NO: 77 VHVL x CEA I VH - A240 VL ;
      Bispecific single chain antibody

<400> SEQUENCE: 19
gacgtccaac tggtgcagtc aggggctgaa gtgaaaaaac ctggggcctc agtgaaggtg      60
tcctgcaagg cttctggcta cacctttact aggtacacga tgcactgggt aaggcaggca     120
cctggacagg gtctgaatg gattggatac attaatccta gccgtggtta tactaattac     180
gcagacagcg tcaagggccg cttcacaatc actacagaca atccaccag cacagcctac     240 atggaactga gcagcctgcg ttctgaggac actgcaacct attactgtgc aagatattat     300
gatgatcatt actgcttga ctactggggc caaggcacca cggtcaccgt ctcctcaggc     360
gaaggtacta gtactggttc tggtggaagt ggaggttcag gtggagcaga cgacattgta     420
```

```
ctgacccagt ctccagcaac tctgtctctg tctccagggg agcgtgccac cctgagctgc      480
agagccagtc aaagtgtaag ttacatgaac tggtaccagc agaagccggg caaggcaccc      540
aaaagatgga tttatgacac atccaaagtg gcttctggag tccctgctcg cttcagtggc      600
agtgggtctg ggaccgacta ctctctcaca atcaacagct ggaggctga agatgctgcc       660 acttattact gccaacagtg gagtagtaac ccgctcacgt tcggtggcgg gaccaaggtg      720
gagatcaaat ccggaggtgg tggatccgag gtgcagctgg tcgagtcagg aggaggcttg      780
gtacagcctg ggggttctct gagactctcc tgtgcaactt ctgggttcac cttcactgat      840
tactacatga actgggtccg ccagcctcca ggaaaggcac ttgagtggtt gggttttatt       900
ggaaacaaag ctaatggtta cacaacagag tacagtgcat ctgtgaaggg tcggttcacc      960
atctccagag ataaatccca aagcatcctc tatcttcaaa tgaacaccct gagagctgag     1020
gacagtgcca cttattactg taccagagat agggggctac ggttctactt tgactactgg    1080
ggccaaggga ccacggtcac cgtctcctca ggtggtggtg ttctggcgg cggcggctcc      1140 ggtggtggtg ttctgagct cgtgctgact cagccggctt ccctctctgc atctcctgga      1200
gcatcagcca gtctcacctg cacccttgcgc aggggcatca atgttggtgc ctacagtata    1260
tactggtacc agcagaagcc agggagtcct ccccagtatc tcctgaggta caaatcagac     1320
tcagataagc agcagggctc tggagtctcc agccgcttct ctgcatccaa agatgcttcg    1380
gccaatgcag ggattttact catctctggg ctccagtctg aggatgaggc tgactattac     1440
tgtatgattt ggcacagcgg cgcttctgcg gtgttcggcg agggaccaa gttgaccgtc      1500 ctatag                                                                1506
```

<210> SEQ ID NO 20
<211> LENGTH: 501
<212> TYPE: PRT
<213> ORGANISM: artificial sequence
<220> FEATURE:
<223> OTHER INFORMATION: SEQ ID NO: 77 VHVL x CEA I VH - A240 VL ;
      Bispecific single chain antibody

<400> SEQUENCE: 20

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

```
Arg Ala Ser Gln Ser Val Ser Tyr Met Asn Trp Tyr Gln Gln Lys Pro
            165                 170                 175
Gly Lys Ala Pro Lys Arg Trp Ile Tyr Asp Thr Ser Lys Val Ala Ser
        180                 185                 190
Gly Val Pro Ala Arg Phe Ser Gly Ser Gly Ser Gly Thr Asp Tyr Ser
    195                 200                 205
Leu Thr Ile Asn Ser Leu Glu Ala Glu Asp Ala Ala Thr Tyr Tyr Cys
210                 215                 220
Gln Gln Trp Ser Ser Asn Pro Leu Thr Phe Gly Gly Gly Thr Lys Val
225                 230                 235                 240
Glu Ile Lys Ser Gly Gly Gly Ser Glu Val Gln Leu Val Glu Ser
            245                 250                 255
Gly Gly Gly Leu Val Gln Pro Gly Gly Ser Leu Arg Leu Ser Cys Ala
        260                 265                 270
Thr Ser Gly Phe Thr Phe Thr Asp Tyr Tyr Met Asn Trp Val Arg Gln
    275                 280                 285
Pro Pro Gly Lys Ala Leu Glu Trp Leu Gly Phe Ile Gly Asn Lys Ala
290                 295                 300
Asn Gly Tyr Thr Thr Glu Tyr Ser Ala Ser Val Lys Gly Arg Phe Thr
305                 310                 315                 320
Ile Ser Arg Asp Lys Ser Gln Ser Ile Leu Tyr Leu Gln Met Asn Thr
            325                 330                 335
Leu Arg Ala Glu Asp Ser Ala Thr Tyr Tyr Cys Thr Arg Asp Arg Gly
        340                 345                 350
Leu Arg Phe Tyr Phe Asp Tyr Trp Gly Gln Gly Thr Thr Val Thr Val
    355                 360                 365
Ser Ser Gly Gly Gly Gly Ser Gly Gly Gly Gly Ser Gly Gly Gly Gly
370                 375                 380
Ser Glu Leu Val Leu Thr Gln Pro Ala Ser Leu Ser Ala Ser Pro Gly
385                 390                 395                 400
Ala Ser Ala Ser Leu Thr Cys Thr Leu Arg Arg Gly Ile Asn Val Gly
            405                 410                 415
Ala Tyr Ser Ile Tyr Trp Tyr Gln Gln Lys Pro Gly Ser Pro Pro Gln
        420                 425                 430
Tyr Leu Leu Arg Tyr Lys Ser Asp Ser Asp Lys Gln Gln Gly Ser Gly
    435                 440                 445
Val Ser Ser Arg Phe Ser Ala Ser Lys Asp Ala Ser Ala Asn Ala Gly
450                 455                 460
Ile Leu Leu Ile Ser Gly Leu Gln Ser Glu Asp Glu Ala Asp Tyr Tyr
465                 470                 475                 480
Cys Met Ile Trp His Ser Gly Ala Ser Ala Val Phe Gly Gly Gly Thr
            485                 490                 495
Lys Leu Thr Val Leu
        500

<210> SEQ ID NO 21
<211> LENGTH: 1506
<212> TYPE: DNA
<213> ORGANISM: artificial sequence
<220> FEATURE:
<223> OTHER INFORMATION: SEQ ID NO: 77 VHVL x A240 VL - CEA I VH ;
      Bispecific single chain antibody

<400> SEQUENCE: 21
gacgtccaac tggtgcagtc aggggctgaa gtgaaaaaac ctggggcctc agtgaaggtg      60
```

```
tcctgcaagg cttctggcta cacctttact aggtacacga tgcactgggt aaggcaggca    120
cctggacagg gtctggaatg gattggatac attaatccta gccgtggtta tactaattac    180
gcagacagcg tcaagggccg cttcacaatc actacagaca atccaccag cacagcctac      240 atggaactga gcagcctgcg ttctgaggac actgcaacct attactgtgc aagatattat    300
gatgatcatt actgccttga ctactggggc caaggcacca cggtcaccgt ctcctcaggc    360
gaaggtacta gtactggttc tggtggaagt ggaggttcag gtggagcaga cgacattgta    420
ctgacccagt ctccagcaac tctgtctctg tctccagggg agcgtgccac cctgagctgc    480
agagccagtc aaagtgtaag ttacatgaac tggtaccagc agaagccggg caaggcaccc    540
aaaagatgga tttatgacac atccaaagtg gcttctggag tccctgctcg cttcagtggc    600
agtgggtctg ggaccgacta ctctctcaca atcaacagct ggaggctga agatgctgcc      660 acttattact gccaacagtg gagtagtaac ccgctcacgt tcggtggcgg gaccaaggtg    720
gagatcaaat ccggaggtgg tggatcccag gccgtgctga ctcagccggc ttccctctct    780
gcatctcctg gagcatcagc cagtctcacc tgcaccttgc gcaggggcat caatgttggt    840
gcctacagta tactggtacc agcagaag ccagggagtc ctccccagta tctcctgagg       900
tacaaatcag actcagataa gcagcagggc tctggagtct ccagccgctt ctctgcatcc    960
aaagatgctt cggccaatgc agggatttta ctcatctctg gctccagtc tgaggatgag      1020 gctgactatt actgtatgat ttggcacagc ggcgcttctg cggtgttcgg cggagggacc    1080
aagttgaccg tcctaggtgg tggtggttct ggcggcggcg gctccggtgg tggtggttct    1140
gaggtgcagc tggtcgagtc aggaggaggc ttggtacagc ctggggggttc tctgagactc    1200 tcctgtgcaa cttctgggtt caccttcact gattactaca tgaactgggt ccgccagcct    1260
ccaggaaagg cacttgagtg gttgggttt attggaaaca agctaatgg ttacacaaca       1320 gagtacagtg catctgtgaa gggtcggttc accatctcca gagataaatc ccaaagcatc    1380
ctctatcttc aaatgaacac cctgagagct gaggacagtg ccacttatta ctgtaccaga    1440 gataggggc tacggttcta ctttgactac tggggccaag ggaccacggt caccgtctcc      1500
tcctag                                                                                                                              1506
```

<210> SEQ ID NO 22
<211> LENGTH: 501
<212> TYPE: PRT
<213> ORGANISM: artificial sequence
<220> FEATURE:
<223> OTHER INFORMATION: SEQ ID NO: 77 VHVL x A240 VL - CEA I VH ;
      Bispecific single chain antibody

<400> SEQUENCE: 22

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

```
Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
            115                 120                 125

Gly Ser Gly Gly Ser Gly Gly Ala Asp Asp Ile Val Leu Thr Gln Ser
            130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
            195                 200                 205

Leu Thr Ile Asn Ser Leu Glu Ala Glu Asp Ala Ala Thr Tyr Tyr Cys
            210                 215                 220

Gln Gln Trp Ser Ser Asn Pro Leu Thr Phe Gly Gly Gly Thr Lys Val
225                 230                 235                 240

Glu Ile Lys Ser Gly Gly Gly Ser Gln Ala Val Leu Thr Gln Pro
            245                 250                 255

Ala Ser Leu Ser Ala Ser Pro Gly Ala Ser Ala Ser Leu Thr Cys Thr
            260                 265                 270

Leu Arg Arg Gly Ile Asn Val Gly Ala Tyr Ser Ile Tyr Trp Tyr Gln
            275                 280                 285

Gln Lys Pro Gly Ser Pro Pro Gln Tyr Leu Leu Arg Tyr Lys Ser Asp
            290                 295                 300

Ser Asp Lys Gln Gln Gly Ser Gly Val Ser Ser Arg Phe Ser Ala Ser
305                 310                 315                 320

Lys Asp Ala Ser Ala Asn Ala Gly Ile Leu Leu Ile Ser Gly Leu Gln
                325                 330                 335

Ser Glu Asp Glu Ala Asp Tyr Tyr Cys Met Ile Trp His Ser Gly Ala
            340                 345                 350

Ser Ala Val Phe Gly Gly Gly Thr Lys Leu Thr Val Leu Gly Gly Gly
            355                 360                 365

Gly Ser Gly Gly Gly Ser Gly Gly Gly Ser Glu Val Gln Leu
            370                 375                 380

Val Glu Ser Gly Gly Gly Leu Val Gln Pro Gly Gly Ser Leu Arg Leu
385                 390                 395                 400

Ser Cys Ala Thr Ser Gly Phe Thr Phe Thr Asp Tyr Tyr Met Asn Trp
            405                 410                 415

Val Arg Gln Pro Pro Gly Lys Ala Leu Glu Trp Leu Gly Phe Ile Gly
            420                 425                 430

Asn Lys Ala Asn Gly Tyr Thr Thr Glu Tyr Ser Ala Ser Val Lys Gly
            435                 440                 445

Arg Phe Thr Ile Ser Arg Asp Lys Ser Gln Ser Ile Leu Tyr Leu Gln
            450                 455                 460

Met Asn Thr Leu Arg Ala Glu Asp Ser Ala Thr Tyr Tyr Cys Thr Arg
465                 470                 475                 480

Asp Arg Gly Leu Arg Phe Tyr Phe Asp Tyr Trp Gly Gln Gly Thr Thr
                485                 490                 495

Val Thr Val Ser Ser
            500
```

<210> SEQ ID NO 23
<211> LENGTH: 1500
<212> TYPE: DNA
<213> ORGANISM: artificial sequence
<220> FEATURE:
<223> OTHER INFORMATION: A5 VH - A240 VL x SEQ ID NO: 77 VHVL ;
      Bispecific single chain antibody

<400> SEQUENCE: 23

```
gaggtgcagc tggtcgagtc tgggggaggc gtggtccagc ctggggaggtc cctgagactc    60
tcctgtgcag cctctggatt caccctcagt acctatgcca tgcactgggt ccgccaggct   120
ccaggcaagg gactggagtg ggtggcactt atatcaaatg atggaagcaa taaatactat   180
gcagactccg tgaagggccg attcaccatc tccagagaca attccaagaa cacgctgtat   240
ctgcaaatga acagcctgag agctgaggac acggccgtgt attactgtgc gagagatagg   300
gggctacggt tctactttga ctactggggc caagggacca cggtcaccgt ctcctcaggt   360
ggtggtggtt ctggcggcgg cggctccggt ggtggtggtt ctgagctcgt gctgactcag   420
ccggcttccc tctctgcatc tcctggagca tcagccagtc tcacctgcac cttgcgcagg   480
ggcatcaatg ttggtgccta cagtatatac tggtaccagc agaagccagg gagtcctccc   540
cagtatctcc tgaggtacaa atcagactca gataagcagc agggctctgg agtctccagc   600
cgcttctctg catccaaaga tgcttcggcc aatgcaggga ttttactcat ctctgggctc   660
cagtctgagg atgaggctga ctattactgt atgatttggc acagcggcgc ttctgcggtg   720
ttcggcggag ggaccaagtt gaccgtccta tccggaggtg gtggatccga cgtccaactg   780
gtgcagtcag ggctgaagt gaaaaaacct ggggcctcag tgaaggtgtc ctgcaaggct   840
tctggctaca cctttactag gtacacgatg cactgggtaa ggcaggcacc tggacagggt   900
ctggaatgga ttggatacat taatcctagc cgtggttata ctaattacgc agacagcgtc   960
aagggccgct tcacaatcac tacagacaaa tccaccagca cagcctacat ggaactgagc  1020
agcctgcgtt ctgaggacac tgcaacctat tactgtgcaa gatattatga tgatcattac  1080
tgccttgact actggggcca aggcaccacg gtcaccgtct cctcaggcga aggtactagt  1140
actggttctg gtgaagtgg aggttcaggt ggagcagacg acattgtact gacccagtct  1200
ccagcaactc tgtctctgtc tccaggggag cgtgccaccc tgagctgcag agccagtcaa  1260
agtgtaagtt acatgaactg gtaccagcag aagccgggca aggcacccaa agatgggatt  1320
tatgacacat ccaaagtggc ttctggagtc cctgctcgct tcagtggcag tgggtctggg  1380
accgactact ctctcacaat caacagcttg gaggctgaag atgctgccac ttattactgc  1440
caacagtgga gtagtaaccc gctcacgttc ggtggcggga ccaaggtgga gatcaaatag  1500
```

<210> SEQ ID NO 24
<211> LENGTH: 499
<212> TYPE: PRT
<213> ORGANISM: artificial sequence
<220> FEATURE:
<223> OTHER INFORMATION: A5 VH - A240 VL x SEQ ID NO: 77 VHVL ;
      Bispecific single chain antibody

<400> SEQUENCE: 24

Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

```
Ala Leu Ile Ser Asn Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Arg Phe Tyr Phe Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Glu Leu Val Leu Thr Gln Pro Ala Ser Leu
    130                 135                 140

Ser Ala Ser Pro Gly Ala Ser Ala Ser Leu Thr Cys Thr Leu Arg Arg
145                 150                 155                 160

Gly Ile Asn Val Gly Ala Tyr Ser Ile Tyr Trp Tyr Gln Gln Lys Pro
                165                 170                 175

Gly Ser Pro Pro Gln Tyr Leu Leu Arg Tyr Lys Ser Asp Ser Asp Lys
            180                 185                 190

Gln Gln Gly Ser Gly Val Ser Ser Arg Phe Ser Ala Ser Lys Asp Ala
        195                 200                 205

Ser Ala Asn Ala Gly Ile Leu Leu Ile Ser Gly Leu Gln Ser Glu Asp
    210                 215                 220

Glu Ala Asp Tyr Tyr Cys Met Ile Trp His Ser Gly Ala Ser Ala Val
225                 230                 235                 240

Phe Gly Gly Gly Thr Lys Leu Thr Val Leu Ser Gly Gly Gly Gly Ser
                245                 250                 255

Asp Val Gln Leu Val Gln Ser Gly Ala Glu Val Lys Lys Pro Gly Ala
            260                 265                 270

Ser Val Lys Val Ser Cys Lys Ala Ser Gly Tyr Thr Phe Thr Arg Tyr
        275                 280                 285

Thr Met His Trp Val Arg Gln Ala Pro Gly Gln Gly Leu Glu Trp Ile
    290                 295                 300

Gly Tyr Ile Asn Pro Ser Arg Gly Tyr Thr Asn Tyr Ala Asp Ser Val
305                 310                 315                 320

Lys Gly Arg Phe Thr Ile Thr Thr Asp Lys Ser Thr Ser Thr Ala Tyr
                325                 330                 335

Met Glu Leu Ser Ser Leu Arg Ser Glu Asp Thr Ala Thr Tyr Tyr Cys
            340                 345                 350

Ala Arg Tyr Tyr Asp Asp His Tyr Cys Leu Asp Tyr Trp Gly Gln Gly
        355                 360                 365

Thr Thr Val Thr Val Ser Ser Gly Glu Gly Thr Ser Thr Gly Ser Gly
    370                 375                 380

Gly Ser Gly Gly Ser Gly Gly Ala Asp Asp Ile Val Leu Thr Gln Ser
385                 390                 395                 400

Pro Ala Thr Leu Ser Leu Ser Pro Gly Glu Arg Ala Thr Leu Ser Cys
                405                 410                 415

Arg Ala Ser Gln Ser Val Ser Tyr Met Asn Trp Tyr Gln Gln Lys Pro
            420                 425                 430

Gly Lys Ala Pro Lys Arg Trp Ile Tyr Asp Thr Ser Lys Val Ala Ser
        435                 440                 445

Gly Val Pro Ala Arg Phe Ser Gly Ser Gly Ser Gly Thr Asp Tyr Ser
    450                 455                 460
```

Leu Thr Ile Asn Ser Leu Glu Ala Glu Asp Ala Ala Thr Tyr Tyr Cys
465                 470                 475                 480

Gln Gln Trp Ser Ser Asn Pro Leu Thr Phe Gly Gly Gly Thr Lys Val
                485                 490                 495

Glu Ile Lys

<210> SEQ ID NO 25
<211> LENGTH: 1497
<212> TYPE: DNA
<213> ORGANISM: artificial sequence
<220> FEATURE:
<223> OTHER INFORMATION: A240 VL - A5 VH x SEQ ID NO: 77 VHVL ;
      Bispecific single chain antibody

<400> SEQUENCE: 25

| | | | | |
|---|---|---|---|---|
| caggccgtgc | tgactcagcc | ggcttccctc | tctgcatctc | ctggagcatc | agccagtctc | 60 |
| acctgcacct | tgcgcagggg | catcaatgtt | ggtgcctaca | gtatatactg | gtaccagcag | 120 |
| aagccaggga | gtcctcccca | gtatctcctg | aggtacaaat | cagactcaga | taagcagcag | 180 |
| ggctctggag | tctccagccg | cttctctgca | tccaaagatg | cttcggccaa | tgcagggatt | 240 |
| ttactcatct | ctgggctcca | gtctgaggat | gaggctgact | attactgtat | gatttggcac | 300 |
| agcggcgctt | ctgcggtgtt | cggcggaggg | accaagttga | ccgtcctagg | tggtggtggt | 360 |
| tctggcggcg | gcggctccgg | tggtggtggt | tctgaggtgc | agctggtcga | gtctggggga | 420 |
| ggcgtggtcc | agcctgggag | gtccctgaga | ctctcctgtg | cagcctctgg | attcaccctc | 480 |
| agtacctatg | ccatgcactg | ggtccgccag | gctccaggca | aggggctgga | gtgggtggca | 540 |
| cttatatcaa | atgatggaag | caataaatac | tatgcagact | ccgtgaaggg | ccgattcacc | 600 |
| atctccagag | acaattccaa | gaacacgctg | tatctgcaaa | tgaacagcct | gagagctgag | 660 |
| gacacggccg | tgtattactg | tgcgagagat | aggggggctac | ggttctactt | tgactactgg | 720 |
| ggccaaggga | ccacggtcac | cgtctcctcc | ggaggtggtg | gatccgacgt | ccaactggtg | 780 |
| cagtcagggg | ctgaagtgaa | aaaacctggg | gcctcagtga | aggtgtcctg | caaggcttct | 840 |
| ggctacacct | ttactaggta | cacgatgcac | tgggtaaggc | aggcacctgg | acagggtctg | 900 |
| gaatggattg | gatacattaa | tcctagccgt | ggttatacta | attacgcaga | cagcgtcaag | 960 |
| ggccgcttca | caatcactac | agacaaatcc | accagcacag | cctacatgga | actgagcagc | 1020 |
| ctgcgttctg | aggacactgc | aacctattac | tgtgcaagat | attatgatga | tcattactgc | 1080 |
| cttgactact | ggggccaagg | caccacggtc | accgtctcct | caggcgaagg | tactagtact | 1140 |
| ggttctggtg | aagtggagg | ttcaggtgga | gcagacgaca | ttgtactgac | ccagtctcca | 1200 |
| gcaactctgt | ctctgtctcc | aggggagcgt | gccacccctga | gctgcagagc | cagtcaaagt | 1260 |
| gtaagttaca | tgaactggta | ccagcagaag | ccgggcaagg | cacccaaaag | atggatttat | 1320 |
| gacacatcca | agtggcttc | tggagtccct | gctcgcttca | gtggcagtgg | gtctgggacc | 1380 |
| gactactctc | tcacaatcaa | cagcttggag | gctgaagatg | ctgccactta | ttactgccaa | 1440 |
| cagtggagta | gtaacccgct | cacgttcggt | ggcgggacca | aggtggagat | caaatag | 1497 |

<210> SEQ ID NO 26
<211> LENGTH: 498
<212> TYPE: PRT
<213> ORGANISM: artificial sequence
<220> FEATURE:
<223> OTHER INFORMATION: A240 VL - A5 VH x SEQ ID NO: 77 VHVL ;
      Bispecific single chain antibody

<400> SEQUENCE: 26

```
Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
            35                  40                  45

Leu Leu Arg Tyr Lys Ser Asp Ser Asp Lys Gln Gln Gly Ser Gly Val
50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Gly Gly Gly Ser Gly Gly Gly Ser Gly Gly Gly
            115                 120                 125

Gly Gly Ser Glu Val Gln Leu Val Glu Ser Gly Gly Gly Val Val Gln
130                 135                 140

Pro Gly Arg Ser Leu Arg Leu Ser Cys Ala Ala Ser Gly Phe Thr Leu
145                 150                 155                 160

Ser Thr Tyr Ala Met His Trp Val Arg Gln Ala Pro Gly Lys Gly Leu
            165                 170                 175

Glu Trp Val Ala Leu Ile Ser Asn Asp Gly Ser Asn Lys Tyr Tyr Ala
            180                 185                 190

Asp Ser Val Lys Gly Arg Phe Thr Ile Ser Arg Asp Asn Ser Lys Asn
            195                 200                 205

Thr Leu Tyr Leu Gln Met Asn Ser Leu Arg Ala Glu Asp Thr Ala Val
            210                 215                 220

Tyr Tyr Cys Ala Arg Asp Arg Gly Leu Arg Phe Tyr Phe Asp Tyr Trp
225                 230                 235                 240

Gly Gln Gly Thr Thr Val Thr Val Ser Ser Gly Gly Gly Gly Ser Asp
            245                 250                 255

Val Gln Leu Val Gln Ser Gly Ala Glu Val Lys Lys Pro Gly Ala Ser
            260                 265                 270

Val Lys Val Ser Cys Lys Ala Ser Gly Tyr Thr Phe Thr Arg Tyr Thr
            275                 280                 285

Met His Trp Val Arg Gln Ala Pro Gly Gln Gly Leu Glu Trp Ile Gly
            290                 295                 300

Tyr Ile Asn Pro Ser Arg Gly Tyr Thr Asn Tyr Ala Asp Ser Val Lys
305                 310                 315                 320

Gly Arg Phe Thr Ile Thr Thr Asp Lys Ser Thr Ser Thr Ala Tyr Met
            325                 330                 335

Glu Leu Ser Ser Leu Arg Ser Glu Asp Thr Ala Thr Tyr Tyr Cys Ala
            340                 345                 350

Arg Tyr Tyr Asp Asp His Tyr Cys Leu Asp Tyr Trp Gly Gln Gly Thr
            355                 360                 365

Thr Val Thr Val Ser Ser Gly Glu Gly Thr Ser Thr Gly Ser Gly Gly
            370                 375                 380

Ser Gly Gly Ser Gly Gly Ala Asp Asp Ile Val Leu Thr Gln Ser Pro
385                 390                 395                 400

Ala Thr Leu Ser Leu Ser Pro Gly Glu Arg Ala Thr Leu Ser Cys Arg
            405                 410                 415
```

| | | | | | | | | | | | |
|---|---|---|---|---|---|---|---|---|---|---|---|
|Ala|Ser|Gln|Ser|Val|Ser|Tyr|Met|Asn|Trp|Tyr|Gln Gln Lys Pro Gly|
| | | |420| | | |425| | | |430|

Lys Ala Pro Lys Arg Trp Ile Tyr Asp Thr Ser Lys Val Ala Ser Gly
         435                  440               445

Val Pro Ala Arg Phe Ser Gly Ser Gly Ser Gly Thr Asp Tyr Ser Leu
   450                       455                  460

Thr Ile Asn Ser Leu Glu Ala Glu Asp Ala Ala Thr Tyr Tyr Cys Gln
465                   470                  475                  480

Gln Trp Ser Ser Asn Pro Leu Thr Phe Gly Gly Gly Thr Lys Val Glu
                  485                  490               495

Ile Lys

<210> SEQ ID NO 27
<211> LENGTH: 1500
<212> TYPE: DNA
<213> ORGANISM: artificial sequence
<220> FEATURE:
<223> OTHER INFORMATION: SEQ ID NO: 77 VHVL x A240 VL - A5 VH ;
     Bispecific single chain antibody

<400> SEQUENCE: 27

```
gacgtccaac tggtgcagtc aggggctgaa gtgaaaaaac tggggcctc agtgaaggtg      60 tcctgcaagg cttctggcta cacctttact aggtacacga tgcactgggt aaggcaggca     120
cctggacagg tctggaatg gattggatac attaatccta gccgtggtta tactaattac     180
gcagacagcg tcaagggccg cttcacaatc actacagaca atccaccag cacagcctac     240 atggaactga gcagcctgcg ttctgaggac actgcaacct attactgtgc aagatattat     300
gatgatcatt actgccttga ctactggggc caaggcacca cggtcaccgt ctcctcaggc     360
gaaggtacta gtactggttc tggtggaagt ggaggttcag gtggagcaga cgacattgta     420
ctgacccagt ctccagcaac tctgtctctg tctccagggg agcgtgccac cctgagctgc     480
agagccagtc aaagtgtaag ttacatgaac tggtaccagc agaagccggg caaggcaccc     540
aaaagatgga tttatgacac atccaaagtg gcttctggag tccctgctcg cttcagtggc     600
agtgggtctg ggaccgacta ctctctcaca atcaacagct ggaggctga agatgctgcc     660 acttattact gccaacagtg gagtagtaac ccgctcacgt tcggtggcgg gaccaaggtg     720
gagatcaaat ccggaggtgg tggatcccag gccgtgctga ctcagccggc ttccctctct     780
gcatctcctg gagcatcagc cagtctcacc tgcaccttgc gcaggggcat caatgttggt     840
gcctacagta tactggta ccagcagaag ccagggagtc ctccccagta tctcctgagg     900
tacaaatcag actcagataa gcagcagggc tctggagtct ccagccgctt ctctgcatcc     960
aaagatgctt cggccaatgc agggatttta ctcatctctg gctccagtc tgaggatgag    1020 gctgactatt actgtatgat tggcacagc ggcgcttctg cggtgttcgg cggagggacc    1080
aagttgaccg tcctaggtgg tggtggttct ggcggcggcg gctccggtgg tggtggttct    1140
gaggtgcagc tggtcgagtc tgggggaggc gtggtccagc ctgggaggtc cctgagactc    1200
tcctgtgcag cctctggatt caccctcagt acctatgcca tgcactgggt ccgccaggct    1260
ccaggcaagg gctggagtg gtggcactt atatcaaatg atggaagcaa taaatactat    1320
gcagactccg tgaagggccg attcaccatc tccagagaca attccaagaa cacgctgtat    1380
ctgcaaatga acagcctgag agctgaggac acggccgtgt attactgtgc gagagatagg    1440
gggctacggt tctactttga ctactggggc caagggacca cggtcaccgt ctcctcctag    1500
```

```
<210> SEQ ID NO 28
<211> LENGTH: 499
<212> TYPE: PRT
<213> ORGANISM: artificial sequence
<220> FEATURE:
<223> OTHER INFORMATION: SEQ ID NO: 77 VHVL x A240 VL - A5 VH ;
      Bispecific single chain antibody

<400> SEQUENCE: 28

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Ser Gly Gly Gly Ser Gln Ala Val Leu Thr Gln Pro
                245                 250                 255

Ala Ser Leu Ser Ala Ser Pro Gly Ala Ser Ala Ser Leu Thr Cys Thr
            260                 265                 270

Leu Arg Arg Gly Ile Asn Val Gly Ala Tyr Ser Ile Tyr Trp Tyr Gln
        275                 280                 285

Gln Lys Pro Gly Ser Pro Pro Gln Tyr Leu Leu Arg Tyr Lys Ser Asp
    290                 295                 300

Ser Asp Lys Gln Gln Gly Ser Gly Val Ser Ser Arg Phe Ser Ala Ser
305                 310                 315                 320

Lys Asp Ala Ser Ala Asn Ala Gly Ile Leu Leu Ile Ser Gly Leu Gln
                325                 330                 335

Ser Glu Asp Glu Ala Asp Tyr Tyr Cys Met Ile Trp His Ser Gly Ala
            340                 345                 350

Ser Ala Val Phe Gly Gly Gly Thr Lys Leu Thr Val Leu Gly Gly Gly
        355                 360                 365
```

Gly Ser Gly Gly Gly Gly Ser Gly Gly Gly Ser Glu Val Gln Leu
370                 375                 380

Val Glu Ser Gly Gly Gly Val Val Gln Pro Gly Arg Ser Leu Arg Leu
385                 390                 395                 400

Ser Cys Ala Ala Ser Gly Phe Thr Leu Ser Thr Tyr Ala Met His Trp
                405                 410                 415

Val Arg Gln Ala Pro Gly Lys Gly Leu Glu Trp Val Ala Leu Ile Ser
                420                 425                 430

Asn Asp Gly Ser Asn Lys Tyr Tyr Ala Asp Ser Val Lys Gly Arg Phe
                435                 440                 445

Thr Ile Ser Arg Asp Asn Ser Lys Asn Thr Leu Tyr Leu Gln Met Asn
    450                 455                 460

Ser Leu Arg Ala Glu Asp Thr Ala Val Tyr Tyr Cys Ala Arg Asp Arg
465                 470                 475                 480

Gly Leu Arg Phe Tyr Phe Asp Tyr Trp Gly Gln Gly Thr Thr Val Thr
                485                 490                 495

Val Ser Ser

<210> SEQ ID NO 29
<211> LENGTH: 1500
<212> TYPE: DNA
<213> ORGANISM: artificial sequence
<220> FEATURE:
<223> OTHER INFORMATION: SEQ ID NO: 77 VHVL x A5 VH - A240 VL ;
      Bispecific single chain antibody

<400> SEQUENCE: 29

```
gacgtccaac tggtgcagtc aggggctgaa gtgaaaaaac tggggcctc  agtgaaggtg      60 tcctgcaagg cttctggcta cacctttact aggtacacga tgcactgggt aaggcaggca    120
cctggacagg gtctggaatg gattggatac attaatccta gccgtggtta tactaattac    180
gcagacagcg tcaagggccg cttcacaatc actacagaca atccaccag cacagcctac    240 atggaactga gcagcctgcg ttctgaggac actgcaacct attactgtgc aagatattat    300
gatgatcatt actgccttga ctactgggc caaggcacca cggtcaccgt ctcctcaggc    360
gaaggtacta gtactggttc tggtggaagt ggaggttcag gtggagcaga cgacattgta    420
ctgacccagt ctccagcaac tctgtctctg tctccagggg agcgtgccac cctgagctgc    480
agagccagtc aaagtgtaag ttacatgaac tggtaccagc agaagccggg caaggcaccc    540
aaaagatgga tttatgacac atccaaagtg gcttctggag tccctgctcg cttcagtggc    600
agtgggtctg ggaccgacta ctctctcaca atcaacagct ggaggctga agatgctgcc    660 acttattact gccaacagtg gagtagtaac ccgctcacgt tcggtggcgg gaccaaggtg    720
gagatcaaat ccggaggtgg tggatccgag gtgcagctgg tcgagtctgg ggaggcgtg    780 gtccagcctg ggaggtccct gagactctcc tgtgcagcct ctggattcac cctcagtacc    840
tatgccatgc actgggtccg ccaggctcca ggcaaggggc tggagtgggt ggcacttata    900
tcaaatgatg gaagcaataa atactatgca gactccgtga agggccgatt caccatctcc    960
agagacaatt ccaagaacac gctgtatctg caaatgaaca gcctgagagc tgaggacacg   1020
gccgtgtatt actgtgcgag agataggggg ctacggttct actttgacta ctggggccaa   1080
gggaccacgg tcaccgtctc ctcaggtggt ggtggttctg gcggcggcgg ctccggtggt   1140
ggtggttctg agctcgtgct gactcagccg gcttccctct ctgcatctcc tggagcatca   1200
gccagtctca cctgcacctt gcgcagggc atcaatgttg tgcctacag tatatactgg   1260
```

```
taccagcaga agccaggag tcctccccag tatctcctga ggtacaaatc agactcagat   1320
aagcagcagg gctctggagt ctccagccgc ttctctgcat ccaaagatgc ttcggccaat   1380
gcagggattt tactcatctc tgggctccag tctgaggatg aggctgacta ttactgtatg   1440
atttggcaca cggcgcttc tgcggtgttc ggcggaggga ccaagttgac cgtcctatag   1500
```

<210> SEQ ID NO 30
<211> LENGTH: 499
<212> TYPE: PRT
<213> ORGANISM: artificial sequence
<220> FEATURE:
<223> OTHER INFORMATION: SEQ ID NO: 77 VHVL x A5 VH - A240 VL ;
      Bispecific single chain antibody

<400> SEQUENCE: 30

```
Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Ser Gly Gly Gly Gly Ser Glu Val Gln Leu Val Glu Ser
                245                 250                 255

Gly Gly Gly Val Val Gln Pro Gly Arg Ser Leu Arg Leu Ser Cys Ala
            260                 265                 270

Ala Ser Gly Phe Thr Leu Ser Thr Tyr Ala Met His Trp Val Arg Gln
        275                 280                 285

Ala Pro Gly Lys Gly Leu Glu Trp Val Ala Leu Ile Ser Asn Asp Gly
    290                 295                 300

Ser Asn Lys Tyr Tyr Ala Asp Ser Val Lys Gly Arg Phe Thr Ile Ser
305                 310                 315                 320
```

```
Arg Asp Asn Ser Lys Asn Thr Leu Tyr Leu Gln Met Asn Ser Leu Arg
            325                 330                 335

Ala Glu Asp Thr Ala Val Tyr Tyr Cys Ala Arg Asp Arg Gly Leu Arg
        340                 345                 350

Phe Tyr Phe Asp Tyr Trp Gly Gln Gly Thr Thr Val Thr Val Ser Ser
    355                 360                 365

Gly Gly Gly Gly Ser Gly Gly Gly Ser Gly Gly Gly Gly Ser Glu
370                 375                 380

Leu Val Leu Thr Gln Pro Ala Ser Leu Ser Ala Ser Pro Gly Ala Ser
385                 390                 395                 400

Ala Ser Leu Thr Cys Thr Leu Arg Arg Gly Ile Asn Val Gly Ala Tyr
                405                 410                 415

Ser Ile Tyr Trp Tyr Gln Gln Lys Pro Gly Ser Pro Pro Gln Tyr Leu
            420                 425                 430

Leu Arg Tyr Lys Ser Asp Ser Asp Lys Gln Gln Gly Ser Gly Val Ser
        435                 440                 445

Ser Arg Phe Ser Ala Ser Lys Asp Ala Ser Ala Asn Ala Gly Ile Leu
    450                 455                 460

Leu Ile Ser Gly Leu Gln Ser Glu Asp Glu Ala Asp Tyr Tyr Cys Met
465                 470                 475                 480

Ile Trp His Ser Gly Ala Ser Ala Val Phe Gly Gly Gly Thr Lys Leu
                485                 490                 495

Thr Val Leu

<210> SEQ ID NO 31
<211> LENGTH: 1506
<212> TYPE: DNA
<213> ORGANISM: artificial sequence
<220> FEATURE:
<223> OTHER INFORMATION: B9 VH - A240 VL x SEQ ID NO: 77 VHVL ;
      Bispecific single chain antibody

<400> SEQUENCE: 31
gaggtgcagc tggtcgagtc tgggggaggc ttggtccagc ctggagggtc cctgagactc      60
tcctgtgcag cgtctggatt caccgtcagt agctactgga tgcactgggt ccgccaagct     120
ccagggaagg gctggaatg gtaggtttc attagaaaca agctaatgg tgggacaaca        180
gaatacgccg cgtctgtgaa aggcagattc accatctcaa gagatgattc aagaacacg     240
ctgtatcttc aaatgaacag cctgagagcc gaggacacgg ccgtgtatta ctgtgcaaga     300
gatagggggc tacggttcta ctttgactac tgggccaag ggaccacggt caccgtctcc      360
tcaggtggtg gtggttctgg cggcggcggc tccggtggtg gtggttctga gctcgtgctg     420
actcagccgg cttccctctc tgcatctcct ggagcatcag ccagtctcac ctgcaccttg     480
cgcaggggca tcaatgttgg tgcctacagt atatactggt accagcagaa gccagggagt     540
cctcccccagt atctcctgag gtacaaatca gactcagata agcagcaggg ctctggagtc   600
tccagccgct tctctgcatc caaagatgct tcggccaatg caggattt actcatctct       660
gggctccagt ctgaggatga ggctgactat tactgtatga tttggcacag cggcgcttct     720
gcggtgttcg gcggagggac caagttgacc gtcctatccg gaggtggtgg atccgacgtc    780
caactggtgc agtcagggggc tgaagtgaaa aaacctgggg cctcagtgaa ggtgtcctgc    840
aaggcttctg gctacacctt tactaggtac acgatgcact gggtaaggca ggcacctgga     900
cagggtctgg aatggattgg atacattaat cctagccgtg gttatactaa ttacgcagac    960
agcgtcaagg gccgcttcac aatcactaca gacaaatcca ccagcacagc ctacatggaa   1020
```

```
ctgagcagcc tgcgttctga ggacactgca acctattact gtgcaagata ttatgatgat    1080
cattactgcc ttgactactg gggccaaggc accacggtca ccgtctcctc aggcgaaggt    1140
actagtactg gttctggtgg aagtggaggt tcaggtggag cagacgacat tgtactgacc    1200
cagtctccag caactctgtc tctgtctcca ggggagcgtg ccaccctgag ctgcagagcc    1260
agtcaaagtg taagttacat gaactggtac cagcagaagc cgggcaaggc acccaaaaga    1320
tggatttatg acacatccaa agtggcttct ggagtccctg ctcgcttcag tggcagtggg    1380
tctgggaccg actactctct cacaatcaac agcttggagg ctgaagatgc tgccacttat    1440
tactgccaac agtggagtag taacccgctc acgttcggtg cgggaccaa ggtggagatc    1500 aaatag                                                               1506
```

<210> SEQ ID NO 32
<211> LENGTH: 501
<212> TYPE: PRT
<213> ORGANISM: artificial sequence
<220> FEATURE:
<223> OTHER INFORMATION: B9 VH - A240 VL x SEQ ID NO: 77 VHVL ;
      Bispecific single chain antibody

<400> SEQUENCE: 32

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Glu Leu Val Leu Thr Gln Pro Ala
    130                 135                 140

Ser Leu Ser Ala Ser Pro Gly Ala Ser Ala Ser Leu Thr Cys Thr Leu
145                 150                 155                 160

Arg Arg Gly Ile Asn Val Gly Ala Tyr Ser Ile Tyr Trp Tyr Gln Gln
                165                 170                 175

Lys Pro Gly Ser Pro Pro Gln Tyr Leu Leu Arg Tyr Lys Ser Asp Ser
            180                 185                 190

Asp Lys Gln Gln Gly Ser Gly Val Ser Ser Arg Phe Ser Ala Ser Lys
        195                 200                 205

Asp Ala Ser Ala Asn Ala Gly Ile Leu Leu Ile Ser Gly Leu Gln Ser
    210                 215                 220

Glu Asp Glu Ala Asp Tyr Tyr Cys Met Ile Trp His Ser Gly Ala Ser
225                 230                 235                 240

Ala Val Phe Gly Gly Gly Thr Lys Leu Thr Val Leu Ser Gly Gly Gly
                245                 250                 255

Gly Ser Asp Val Gln Leu Val Gln Ser Gly Ala Glu Val Lys Lys Pro
```

```
                260             265             270
Gly Ala Ser Val Lys Val Ser Cys Lys Ala Ser Gly Tyr Thr Phe Thr
            275             280             285

Arg Tyr Thr Met His Trp Val Arg Gln Ala Pro Gly Gln Gly Leu Glu
            290             295             300

Trp Ile Gly Tyr Ile Asn Pro Ser Arg Gly Tyr Thr Asn Tyr Ala Asp
305             310             315             320

Ser Val Lys Gly Arg Phe Thr Ile Thr Thr Asp Lys Ser Thr Ser Thr
            325             330             335

Ala Tyr Met Glu Leu Ser Ser Leu Arg Ser Glu Asp Thr Ala Thr Tyr
            340             345             350

Tyr Cys Ala Arg Tyr Tyr Asp Asp His Tyr Cys Leu Asp Tyr Trp Gly
            355             360             365

Gln Gly Thr Thr Val Thr Val Ser Ser Gly Glu Gly Thr Ser Thr Gly
            370             375             380

Ser Gly Gly Ser Gly Gly Ser Gly Gly Ala Asp Asp Ile Val Leu Thr
385             390             395             400

Gln Ser Pro Ala Thr Leu Ser Leu Ser Pro Gly Glu Arg Ala Thr Leu
            405             410             415

Ser Cys Arg Ala Ser Gln Ser Val Ser Tyr Met Asn Trp Tyr Gln Gln
            420             425             430

Lys Pro Gly Lys Ala Pro Lys Arg Trp Ile Tyr Asp Thr Ser Lys Val
            435             440             445

Ala Ser Gly Val Pro Ala Arg Phe Ser Gly Ser Gly Ser Gly Thr Asp
450             455             460

Tyr Ser Leu Thr Ile Asn Ser Leu Glu Ala Glu Asp Ala Ala Thr Tyr
465             470             475             480

Tyr Cys Gln Gln Trp Ser Ser Asn Pro Leu Thr Phe Gly Gly Gly Thr
            485             490             495

Lys Val Glu Ile Lys
            500

<210> SEQ ID NO 33
<211> LENGTH: 1503
<212> TYPE: DNA
<213> ORGANISM: artificial sequence
<220> FEATURE:
<223> OTHER INFORMATION: A240 VL - B9 VH x SEQ ID NO: 77 VHVL ;
      Bispecific single chain antibody

<400> SEQUENCE: 33
caggccgtgc tgactcagcc ggcttccctc tctgcatctc ctggagcatc agccagtctc      60
acctgcacct tgcgcagggg catcaatgtt ggtgcctaca gtatatactg gtaccagcag     120
aagccaggga gtcctcccca gtatctcctg aggtacaaat cagactcaga taagcagcag     180
ggctctggag tctccagccg cttctctgca tccaaagatg cttcggccaa tgcaggatt      240 ttactcatct ctgggctcca gtctgaggat gaggctgact attactgtat gatttggcac     300
agcggcgctt ctgcggtgtt cggcggaggg accaagttga ccgtcctagg tggtggtggt     360
tctggcggcg cggctccgg tggtggtggt tctgaggtgc agctggtcga gtctggggga     420
ggcttggtcc agcctgggag gtccctgaga ctctcctgtg cagcgtctgg attcaccgtc     480
agtagctact ggatgcactg ggtccgccaa gctccaggga aggggctgga atgggtaggt     540
ttcattagaa acaaagctaa tggtgggaca acagaatacg ccgcgtctgt gaaaggcaga     600
ttcaccatct caagagatga ttccaagaac acgctgtatc ttcaaatgaa cagcctgaga     660
```

```
gccgaggaca cggccgtgta ttactgtgca agagataggg ggctacggtt ctactttgac    720
tactggggcc aagggaccac ggtcaccgtc tcctccggag gtggtggatc cgacgtccaa    780
ctggtgcagt caggggctga agtgaaaaaa cctggggcct cagtgaaggt gtcctgcaag    840
gcttctggct acacctttac taggtacacg atgcactggg taaggcaggc acctggacag    900
ggtctggaat ggattggata cattaatcct agccgtggtt atactaatta cgcagacagc    960
gtcaagggcc gcttcacaat cactacagac aaatccacca gcacagccta catggaactg   1020
agcagcctgc gttctgagga cactgcaacc tattactgtg caagatatta tgatgatcat   1080
tactgccttg actactgggg ccaaggcacc acggtcaccg tctcctcagg cgaaggtact   1140
agtactggtt ctggtggaag tggaggttca ggtggagcag acgacattgt actgacccag   1200
tctccagcaa ctctgtctct gtctccaggg gagcgtgcca ccctgagctg cagagccagt   1260
caaagtgtaa gttacatgaa ctggtaccag cagaagccgg gcaaggcacc caaaagatgg   1320
atttatgaca catccaaagt ggcttctgga gtccctgctc gcttcagtgg cagtgggtct   1380
gggaccgact actctctcac aatcaacagc ttggaggctg aagatgctgc cacttattac   1440
tgccaacagt ggagtagtaa cccgctcacg ttcggtggcg ggaccaaggt ggagatcaaa   1500
tag                                                                 1503
```

<210> SEQ ID NO 34
<211> LENGTH: 500
<212> TYPE: PRT
<213> ORGANISM: artificial sequence
<220> FEATURE:
<223> OTHER INFORMATION: A240 VL - B9 VH x SEQ ID NO: 77 VHVL ;
      Bispecific single chain antibody

<400> SEQUENCE: 34

```
Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Arg Ser Leu Arg Leu Ser Cys Ala Ala Ser Gly Phe Thr Val
145                 150                 155                 160

Ser Ser Tyr Trp Met His Trp Val Arg Gln Ala Pro Gly Lys Gly Leu
                165                 170                 175

Glu Trp Val Gly Phe Ile Arg Asn Lys Ala Asn Gly Gly Thr Thr Glu
            180                 185                 190

Tyr Ala Ala Ser Val Lys Gly Arg Phe Thr Ile Ser Arg Asp Asp Ser
```

```
                  195                 200                 205
Lys Asn Thr Leu Tyr Leu Gln Met Asn Ser Leu Arg Ala Glu Asp Thr
                210                 215                 220

Ala Val Tyr Tyr Cys Ala Arg Asp Arg Gly Leu Arg Phe Tyr Phe Asp
225                 230                 235                 240

Tyr Trp Gly Gln Gly Thr Thr Val Thr Val Ser Ser Gly Gly Gly Gly
                245                 250                 255

Ser Asp Val Gln Leu Val Gln Ser Gly Ala Glu Val Lys Lys Pro Gly
                260                 265                 270

Ala Ser Val Lys Val Ser Cys Lys Ala Ser Gly Tyr Thr Phe Thr Arg
                275                 280                 285

Tyr Thr Met His Trp Val Arg Gln Ala Pro Gly Gln Gly Leu Glu Trp
                290                 295                 300

Ile Gly Tyr Ile Asn Pro Ser Arg Gly Tyr Thr Asn Tyr Ala Asp Ser
305                 310                 315                 320

Val Lys Gly Arg Phe Thr Ile Thr Thr Asp Lys Ser Thr Ser Thr Ala
                325                 330                 335

Tyr Met Glu Leu Ser Ser Leu Arg Ser Glu Asp Thr Ala Thr Tyr Tyr
                340                 345                 350

Cys Ala Arg Tyr Tyr Asp Asp His Tyr Cys Leu Asp Tyr Trp Gly Gln
                355                 360                 365

Gly Thr Thr Val Thr Val Ser Ser Gly Glu Gly Thr Ser Thr Gly Ser
370                 375                 380

Gly Gly Ser Gly Gly Ser Gly Gly Ala Asp Asp Ile Val Leu Thr Gln
385                 390                 395                 400

Ser Pro Ala Thr Leu Ser Leu Ser Pro Gly Glu Arg Ala Thr Leu Ser
                405                 410                 415

Cys Arg Ala Ser Gln Ser Val Ser Tyr Met Asn Trp Tyr Gln Gln Lys
                420                 425                 430

Pro Gly Lys Ala Pro Lys Arg Trp Ile Tyr Asp Thr Ser Lys Val Ala
                435                 440                 445

Ser Gly Val Pro Ala Arg Phe Ser Gly Ser Gly Ser Gly Thr Asp Tyr
                450                 455                 460

Ser Leu Thr Ile Asn Ser Leu Glu Ala Glu Asp Ala Ala Thr Tyr Tyr
465                 470                 475                 480

Cys Gln Gln Trp Ser Ser Asn Pro Leu Thr Phe Gly Gly Gly Thr Lys
                485                 490                 495

Val Glu Ile Lys
                500

<210> SEQ ID NO 35
<211> LENGTH: 1506
<212> TYPE: DNA
<213> ORGANISM: artificial sequence
<220> FEATURE:
<223> OTHER INFORMATION: SEQ ID NO: 77 VHVL x B9 VH-A240 VL ; Bispecific
      single chain antibody

<400> SEQUENCE: 35
gacgtccaac tggtgcagtc aggggctgaa gtgaaaaaac ctggggcctc agtgaaggtg      60
tcctgcaagg cttctggcta cacctttact aggtacacga tgcactgggt aaggcaggca     120
cctggacagg gtctggaatg gattggatac attaatccta gccgtggtta tactaattac     180
gcagacagcg tcaagggccg cttcacaatc actacagaca aatccaccag cacagcctac     240
atggaactga gcagcctgcg ttctgaggac actgcaacct attactgtgc aagatattat     300
```

```
gatgatcatt actgccttga ctactggggc caaggcacca cggtcaccgt ctcctcaggc    360
gaaggtacta gtactggttc tggtggaagt ggaggttcag gtggagcaga cgacattgta    420
ctgacccagt ctccagcaac tctgtctctg tctccagggg agcgtgccac cctgagctgc    480
agagccagtc aaagtgtaag ttacatgaac tggtaccagc agaagccggg caaggcaccc    540
aaaagatgga tttatgacac atccaaagtg gcttctggag tccctgctcg cttcagtggc    600
agtgggtctg ggaccgacta ctctctcaca atcaacagct ggaggctga agatgctgcc    660 acttattact gccaacagtg gagtagtaac ccgctcacgt tcggtggcgg gaccaaggtg    720
gagatcaaat ccgaggtgg tggatccgag gtgcagctgg tcgagtctgg gggaggcttg    780
gtccagcctg gagggtccct gagactctcc tgtgcagcgt ctggattcac cgtcagtagc    840
tactggatgc actgggtccg ccaagctcca gggaaggggc tggaatgggt aggtttcatt    900
agaaacaaag ctaatggtgg gacaacagaa tacgccgcgt ctgtgaaagg cagattcacc    960
atctcaagag atgattccaa aaacacgctg tatcttcaaa tgaacagcct gagagccgag   1020
gacacggccg tgtattactg tgcaagagat aggggggctac ggttctactt tgactactgg   1080
ggccaaggga ccacggtcac cgtctcctca ggtggtggtg gttctggcgg cggcggctcc   1140
ggtggtggtg gttctgagct cgtgctgact cagccggctt ccctctctgc atctcctgga   1200
gcatcagcca gtctcacctg caccttgcgc agggggcatca atgttggtgc ctacagtata   1260
tactggtacc agcagaagcc agggagtcct ccccagtatc tcctgaggta caaatcagac   1320
tcagataagc agcagggctc tggagtctcc agccgcttct ctgcatccaa agatgcttcg   1380
gccaatgcag ggattttact catctctggg ctccagtctg aggatgaggc tgactattac   1440
tgtatgattt ggcacagcgg cgcttctgcg gtgttcggcg gagggaccaa gttgaccgtc   1500
ctatag                                                              1506
```

<210> SEQ ID NO 36
<211> LENGTH: 501
<212> TYPE: PRT
<213> ORGANISM: artificial sequence
<220> FEATURE:
<223> OTHER INFORMATION: SEQ ID NO: 77 VHVL x B9 VH - A240 VL ; Bispecific single chain antibody

<400> SEQUENCE: 36

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser

```
            130             135             140
Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
                195                 200                 205

Leu Thr Ile Asn Ser Leu Glu Ala Glu Asp Ala Ala Thr Tyr Tyr Cys
210                 215                 220

Gln Gln Trp Ser Ser Asn Pro Leu Thr Phe Gly Gly Gly Thr Lys Val
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Arg Ser Leu Arg Leu Ser Cys Ala
            260                 265                 270

Ala Ser Gly Phe Thr Val Ser Ser Tyr Trp Met His Trp Val Arg Gln
            275                 280                 285

Ala Pro Gly Lys Gly Leu Glu Trp Val Gly Phe Ile Arg Asn Lys Ala
            290                 295                 300

Asn Gly Gly Thr Thr Glu Tyr Ala Ala Ser Val Lys Gly Arg Phe Thr
305                 310                 315                 320

Ile Ser Arg Asp Asp Ser Lys Asn Thr Leu Tyr Leu Gln Met Asn Ser
                325                 330                 335

Leu Arg Ala Glu Asp Thr Ala Val Tyr Tyr Cys Ala Arg Asp Arg Gly
            340                 345                 350

Leu Arg Phe Tyr Phe Asp Tyr Trp Gly Gln Gly Thr Thr Val Thr Val
            355                 360                 365

Ser Ser Gly Gly Gly Gly Ser Gly Gly Gly Ser Gly Gly Gly Gly
            370                 375                 380

Ser Glu Leu Val Leu Thr Gln Pro Ala Ser Leu Ser Ala Ser Pro Gly
385                 390                 395                 400

Ala Ser Ala Ser Leu Thr Cys Thr Leu Arg Arg Gly Ile Asn Val Gly
                405                 410                 415

Ala Tyr Ser Ile Tyr Trp Tyr Gln Gln Lys Pro Gly Ser Pro Pro Gln
            420                 425                 430

Tyr Leu Leu Arg Tyr Lys Ser Asp Ser Asp Lys Gln Gln Gly Ser Gly
            435                 440                 445

Val Ser Ser Arg Phe Ser Ala Ser Lys Asp Ala Ser Ala Asn Ala Gly
450                 455                 460

Ile Leu Leu Ile Ser Gly Leu Gln Ser Glu Asp Glu Ala Asp Tyr Tyr
465                 470                 475                 480

Cys Met Ile Trp His Ser Gly Ala Ser Ala Val Phe Gly Gly Gly Thr
                485                 490                 495

Lys Leu Thr Val Leu
            500

<210> SEQ ID NO 37
<211> LENGTH: 1506
<212> TYPE: DNA
<213> ORGANISM: artificial sequence
<220> FEATURE:
<223> OTHER INFORMATION: SEQ ID NO: 77 VHVL x A240 VL - B9 VH ;
      Bispecific single chain antibody
```

<400> SEQUENCE: 37

```
gacgtccaac tggtgcagtc aggggctgaa gtgaaaaaac ctggggcctc agtgaaggtg      60
tcctgcaagg cttctggcta cacctttact aggtacacga tgcactgggt aaggcaggca     120
cctggacagg gtctggaatg gattggatac attaatccta gccgtggtta tactaattac     180
gcagacagcg tcaagggccg cttcacaatc actacagaca atccaccag cacagcctac      240
atggaactga gcagcctgcg ttctgaggac actgcaacct attactgtgc aagatattat     300
gatgatcatt actgccttga ctactggggc caaggcacca cggtcaccgt ctcctcaggc     360
gaaggtacta gtactggttc tggtggaagt ggaggttcag gtggagcaga cgacattgta     420
ctgacccagt ctccagcaac tctgtctctg tctccagggg agcgtgccac cctgagctgc     480
agagccagtc aaagtgtaag ttacatgaac tggtaccagc agaagccggg caaggcaccc     540
aaaagatgga tttatgacac atccaaagtg gcttctggag tccctgctcg cttcagtggc     600
agtgggtctg ggaccgacta ctctctcaca atcaacagct ggaggctga agatgctgcc      660
acttattact gccaacagtg gagtagtaac ccgctcacgt tcggtggcgg gaccaaggtg     720
gagatcaaat ccggaggtgg tggatcccag gccgtgctga ctcagccggc ttccctctct     780
gcatctcctg gagcatcagc cagtctcacc tgcaccttgc gcaggggcat caatgttggt     840
gcctacagta tactggta ccagcagaag ccagggagtc ctccccagta tctcctgagg       900
tacaaatcag actcagataa gcagcagggc tctggagtct ccagccgctt ctctgcatcc     960
aaagatgctt cggccaatgc agggatttta ctcatctctg gctccagtc tgaggatgag     1020
gctgactatt actgtatgat tggcacagc ggcgcttctg cggtgttcgg cggagggacc     1080
aagttgaccg tcctaggtgg tggtggttct ggcggcggcg gctccggtgg tggtggttct     1140
gaggtgcagc tggtcgagtc tgggggaggc ttggtccagc ctgggaggtc cctgagactc     1200
tcctgtgcag cgtctggatt caccgtcagt agctactgga tgcactgggt ccgccaagct     1260
ccagggaagg gctggaatg gtaggtttc attagaaaca agctaatgg tgggacaaca       1320
gaatacgccg cgtctgtgaa aggcagattc accatctcaa gagatgattc caagaacacg     1380
ctgtatcttc aaatgaacag cctgagagcc gaggacacgg ccgtgtatta ctgtgcaaga    1440
gatagggggc tacggttcta ctttgactac tggggccaag gaccacggt caccgtctcc     1500
tcctag                                                                1506
```

<210> SEQ ID NO 38
<211> LENGTH: 501
<212> TYPE: PRT
<213> ORGANISM: artificial sequence
<220> FEATURE:
<223> OTHER INFORMATION: SEQ ID NO: 77 VHVL x A240 VL - B9 VH ;
      Bispecific single chain antibody

<400> SEQUENCE: 38

```
Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
```

```
                65                  70                  75                  80
        Met Glu Leu Ser Ser Leu Arg Ser Glu Asp Thr Ala Thr Tyr Tyr Cys
                            85                  90                  95

Ala Arg Tyr Tyr Asp Asp His Tyr Cys Leu Asp Tyr Trp Gly Gln Gly
                        100                 105                 110

Thr Thr Val Thr Val Ser Ser Gly Glu Gly Thr Ser Thr Gly Ser Gly
                    115                 120                 125

Gly Ser Gly Gly Ser Gly Gly Ala Asp Asp Ile Val Leu Thr Gln Ser
                130                 135                 140

Pro Ala Thr Leu Ser Leu Ser Pro Gly Glu Arg Ala Thr Leu Ser Cys
        145                 150                 155                 160

Arg Ala Ser Gln Ser Val Ser Tyr Met Asn Trp Tyr Gln Gln Lys Pro
                        165                 170                 175

Gly Lys Ala Pro Lys Arg Trp Ile Tyr Asp Thr Ser Lys Val Ala Ser
                    180                 185                 190

Gly Val Pro Ala Arg Phe Ser Gly Ser Gly Ser Gly Thr Asp Tyr Ser
                195                 200                 205

Leu Thr Ile Asn Ser Leu Glu Ala Glu Asp Ala Ala Thr Tyr Tyr Cys
            210                 215                 220

Gln Gln Trp Ser Ser Asn Pro Leu Thr Phe Gly Gly Gly Thr Lys Val
        225                 230                 235                 240

Glu Ile Lys Ser Gly Gly Gly Gly Ser Gln Ala Val Leu Thr Gln Pro
                        245                 250                 255

Ala Ser Leu Ser Ala Ser Pro Gly Ala Ser Ala Ser Leu Thr Cys Thr
                    260                 265                 270

Leu Arg Arg Gly Ile Asn Val Gly Ala Tyr Ser Ile Tyr Trp Tyr Gln
                275                 280                 285

Gln Lys Pro Gly Ser Pro Pro Gln Tyr Leu Leu Arg Tyr Lys Ser Asp
            290                 295                 300

Ser Asp Lys Gln Gln Gly Ser Gly Val Ser Ser Arg Phe Ser Ala Ser
        305                 310                 315                 320

Lys Asp Ala Ser Ala Asn Ala Gly Ile Leu Leu Ile Ser Gly Leu Gln
                        325                 330                 335

Ser Glu Asp Glu Ala Asp Tyr Tyr Cys Met Ile Trp His Ser Gly Ala
                    340                 345                 350

Ser Ala Val Phe Gly Gly Gly Thr Lys Leu Thr Val Leu Gly Gly Gly
                355                 360                 365

Gly Ser Gly Gly Gly Gly Ser Gly Gly Gly Gly Ser Glu Val Gln Leu
            370                 375                 380

Val Glu Ser Gly Gly Gly Leu Val Gln Pro Gly Arg Ser Leu Arg Leu
        385                 390                 395                 400

Ser Cys Ala Ala Ser Gly Phe Thr Val Ser Ser Tyr Trp Met His Trp
                        405                 410                 415

Val Arg Gln Ala Pro Gly Lys Gly Leu Glu Trp Val Gly Phe Ile Arg
                    420                 425                 430

Asn Lys Ala Asn Gly Gly Thr Thr Glu Tyr Ala Ala Ser Val Lys Gly
                435                 440                 445

Arg Phe Thr Ile Ser Arg Asp Asp Ser Lys Asn Thr Leu Tyr Leu Gln
            450                 455                 460

Met Asn Ser Leu Arg Ala Glu Asp Thr Ala Val Tyr Tyr Cys Ala Arg
        465                 470                 475                 480

Asp Arg Gly Leu Arg Phe Tyr Phe Asp Tyr Trp Gly Gln Gly Thr Thr
                        485                 490                 495
```

Val Thr Val Ser Ser
            500

<210> SEQ ID NO 39
<211> LENGTH: 1500
<212> TYPE: DNA
<213> ORGANISM: artificial sequence
<220> FEATURE:
<223> OTHER INFORMATION: D8 VH - A240 VL x SEQ ID NO: 77 VHVL ;
      Bispecific single chain antibody

<400> SEQUENCE: 39

| | | | | |
|---|---|---|---|---|
| gaggtgcagc | tggtcgagtc | tgggggaggc | gtggtccagc | ctgggaggtc cctgagactc | 60 |
| tcctgtgcag | cctctggatt | caccctcagt | acctatgcca | tgcactgggt ccgccaggct | 120 |
| ccaggcaagg | ggctggagtg | ggtggcactt | atatcaaatg | atggaagcaa taaatactat | 180 |
| gcagactccg | tgaagggccg | attcaccatc | tccagagaca | attccaagaa cacgctgtat | 240 |
| ctgcaaatga | acagcctgag | agctgaggac | acggctgtgt | attactgtac tagagatagg | 300 |
| gggctacggt | tctactttga | ctactgggc | caagggacca | cggtcaccgt ctcctcaggt | 360 |
| ggtggtggtt | ctggcggcgg | cggctccggt | ggtggtggtt | ctgagctcgt gctgactcag | 420 |
| ccggcttccc | tctctgcatc | tcctggagca | tcagccagtc | tcacctgcac cttgcgcagg | 480 |
| ggcatcaatg | ttggtgccta | cagtatatac | tggtaccagc | agaagccagg gagtcctccc | 540 |
| cagtatctcc | tgaggtacaa | atcagactca | gataagcagc | agggctctgg agtctccagc | 600 |
| cgcttctctg | catccaaaga | tgcttcggcc | aatgcaggga | ttttactcat ctctgggctc | 660 |
| cagtctgagg | atgaggctga | ctattactgt | atgatttggc | acagcggcgc ttctgcggtg | 720 |
| ttcggcggag | ggaccaagtt | gaccgtccta | tccggaggtg | gtggatccga cgtccaactg | 780 |
| gtgcagtcag | gggctgaagt | gaaaaaacct | ggggcctcag | tgaaggtgtc ctgcaaggct | 840 |
| tctggctaca | cctttactag | gtacacgatg | cactgggtaa | ggcaggcacc tggacagggt | 900 |
| ctggaatgga | ttggatacat | taatcctagc | cgtggttata | ctaattacgc agacagcgtc | 960 |
| aagggccgct | tcacaatcac | tacagacaaa | tccaccagca | cagcctacat ggaactgagc | 1020 |
| agcctgcgtt | ctgaggacac | tgcaacctat | tactgtgcaa | gatattatga tgatcattac | 1080 |
| tgccttgact | actggggcca | aggcaccacg | gtcaccgtct | cctcaggcga aggtactagt | 1140 |
| actggttctg | gtggaagtgg | aggttcaggt | ggagcagacg | acattgtact gacccagtct | 1200 |
| ccagcaactc | tgtctctgtc | tccaggggag | cgtgccaccc | tgagctgcag agccagtcaa | 1260 |
| agtgtaagtt | acatgaactg | gtaccagcag | aagccgggca | aggcacccaa agatggatt | 1320 |
| tatgacacat | ccaaagtggc | ttctggagtc | cctgctcgct | tcagtggcag tgggtctggg | 1380 |
| accgactact | ctctcacaat | caacagcttg | gaggctgaag | atgctgccac ttattactgc | 1440 |
| caacagtgga | gtagtaaccc | gctcacgttc | ggtggcggga | ccaaggtgga gatcaaatag | 1500 |

<210> SEQ ID NO 40
<211> LENGTH: 499
<212> TYPE: PRT
<213> ORGANISM: artificial sequence
<220> FEATURE:
<223> OTHER INFORMATION: D8 VH - A240 VL x SEQ ID NO: 77 VHVL ;
      Bispecific single chain antibody

<400> SEQUENCE: 40

Glu Val Gln Leu Val Glu Ser Gly Gly Gly Val Val Gln Pro Gly Arg
1               5                   10                  15

```
Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Arg Gly Leu Arg Phe Tyr Phe Asp Tyr Trp Gly Gln Gly
            100                 105                 110

Thr Thr Val Thr Val Ser Ser Gly Gly Gly Ser Gly Gly Gly Gly
            115                 120                 125

Ser Gly Gly Gly Ser Glu Leu Val Leu Thr Gln Pro Ala Ser Leu
    130                 135                 140

Ser Ala Ser Pro Gly Ala Ser Ala Ser Leu Thr Cys Thr Leu Arg Arg
145                 150                 155                 160

Gly Ile Asn Val Gly Ala Tyr Ser Ile Tyr Trp Tyr Gln Gln Lys Pro
                165                 170                 175

Gly Ser Pro Pro Gln Tyr Leu Leu Arg Tyr Lys Ser Asp Ser Asp Lys
            180                 185                 190

Gln Gln Gly Ser Gly Val Ser Ser Arg Phe Ser Ala Ser Lys Asp Ala
        195                 200                 205

Ser Ala Asn Ala Gly Ile Leu Leu Ile Ser Gly Leu Gln Ser Glu Asp
210                 215                 220

Glu Ala Asp Tyr Tyr Cys Met Ile Trp His Ser Gly Ala Ser Ala Val
225                 230                 235                 240

Phe Gly Gly Gly Thr Lys Leu Thr Val Leu Ser Gly Gly Gly Gly Ser
            245                 250                 255

Asp Val Gln Leu Val Gln Ser Gly Ala Glu Val Lys Lys Pro Gly Ala
        260                 265                 270

Ser Val Lys Val Ser Cys Lys Ala Ser Gly Tyr Thr Phe Thr Arg Tyr
    275                 280                 285

Thr Met His Trp Val Arg Gln Ala Pro Gly Gln Gly Leu Glu Trp Ile
    290                 295                 300

Gly Tyr Ile Asn Pro Ser Arg Gly Tyr Thr Asn Tyr Ala Asp Ser Val
305                 310                 315                 320

Lys Gly Arg Phe Thr Ile Thr Thr Asp Lys Ser Thr Ser Thr Ala Tyr
            325                 330                 335

Met Glu Leu Ser Ser Leu Arg Ser Glu Asp Thr Ala Thr Tyr Tyr Cys
        340                 345                 350

Ala Arg Tyr Tyr Asp Asp His Tyr Cys Leu Asp Tyr Trp Gly Gln Gly
    355                 360                 365

Thr Thr Val Thr Val Ser Ser Gly Glu Gly Thr Ser Thr Gly Ser Gly
        370                 375                 380

Gly Ser Gly Gly Ser Gly Ala Asp Asp Ile Val Leu Thr Gln Ser
385                 390                 395                 400

Pro Ala Thr Leu Ser Leu Ser Pro Gly Glu Arg Ala Thr Leu Ser Cys
            405                 410                 415

Arg Ala Ser Gln Ser Val Ser Tyr Met Asn Trp Tyr Gln Gln Lys Pro
            420                 425                 430

Gly Lys Ala Pro Lys Arg Trp Ile Tyr Asp Thr Ser Lys Val Ala Ser
```

```
                435                 440                 445
Gly Val Pro Ala Arg Phe Ser Gly Ser Gly Ser Gly Thr Asp Tyr Ser
        450                 455                 460

Leu Thr Ile Asn Ser Leu Glu Ala Glu Asp Ala Ala Thr Tyr Tyr Cys
465                 470                 475                 480

Gln Gln Trp Ser Ser Asn Pro Leu Thr Phe Gly Gly Gly Thr Lys Val
                485                 490                 495

Glu Ile Lys

<210> SEQ ID NO 41
<211> LENGTH: 1497
<212> TYPE: DNA
<213> ORGANISM: artificial sequence
<220> FEATURE:
<223> OTHER INFORMATION: A240 VL - D8 VH x SEQ ID NO: 77 VHVL ;
      Bispecific single chain antibody

<400> SEQUENCE: 41
caggccgtgc tgactcagcc ggcttccctc tctgcatctc ctggagcatc agccagtctc      60
acctgcacct tgcgcagggg catcaatgtt ggtgcctaca gtatatactg gtaccagcag     120
aagccaggga gtcctcccca gtatctcctg aggtacaaat cagactcaga taagcagcag    180
ggctctggag tctccagccg cttctctgca tccaaagatg cttcggccaa tgcagggatt    240
ttactcatct ctgggctcca gtctgaggat gaggctgact attactgtat gatttggcac    300
agcggcgctt ctgcggtgtt cggcggaggg accaagttga ccgtcctagg tggtggtggt    360
tctggcggcg cggctccgg tggtggtggt tctgaggtgc agctggtcga gtctggggga    420
ggcgtggtcc agcctgggag gtccctgaga ctctcctgtg cagcctctgg attcacctc    480 agtacctatg ccatgcactg gtccgccag gctccaggca aggggctgga gtgggtggca    540
cttatatcaa atgatggaag caataaatac tatgcagact ccgtgaaggg ccgattcacc    600
atctccagag acaattccaa gaacacgctg tatctgcaaa tgaacagcct gagagctgag    660
gacacggctg tgtattactg tactagagat agggggctac ggttctactt tgactactgg    720
ggccaaggga ccacggtcac cgtctcctcc ggaggtggtg gatccgacgt ccaactggtg    780
cagtcagggg ctgaagtgaa aaaacctggg gcctcagtga aggtgtcctg caaggcttct    840
ggctacacct ttactaggta cacgatgcac tgggtaaggc aggcacctgg acagggtctg    900
gaatggattg gatacattaa tcctagccgt ggttatacta attacgcaga cagcgtcaag    960
ggccgcttca atcactacag acaaatcc accagcacag cctacatgga actgagcagc   1020
ctgcgttctg aggacactgc aacctattac tgtgcaagat attatgatga tcattactgc   1080
cttgactact ggggccaagg caccacggtc accgtctcct caggcgaagg tactagtact   1140
ggttctggtg aagtggagg ttcaggtgga gcagacgaca ttgtactgac ccagtctcca   1200
gcaactctgt ctctgtctcc aggggagcgt gccaccctga ctgcagagc cagtcaaagt   1260 gtaagttaca tgaactggta ccagcagaag ccgggcaagg cacccaaaag atggatttat   1320
gacacatcca agtggcttc tggagtccct gctcgcttca gtggcagtgg gtctgggacc   1380
gactactctc tcacaatcaa cagcttggag gctgaagatg ctgccactta ttactgccaa   1440
cagtggagta gtaacccgct cacgttcggt ggcgggacca aggtggagat caaatag      1497

<210> SEQ ID NO 42
<211> LENGTH: 498
<212> TYPE: PRT
<213> ORGANISM: artificial sequence
```

-continued

```
<220> FEATURE:
<223> OTHER INFORMATION: A240 VL - D8 VH x SEQ ID NO: 77 VHVL ;
      Bispecific single chain antibody

<400> SEQUENCE: 42
```

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Gly Gly Gly Gly Ser Gly Gly Gly Ser Gly Gly
        115                 120                 125

Gly Gly Ser Glu Val Gln Leu Val Glu Ser Gly Gly Val Val Gln
    130                 135                 140

Pro Gly Arg Ser Leu Arg Leu Ser Cys Ala Ala Ser Gly Phe Thr Leu
145                 150                 155                 160

Ser Thr Tyr Ala Met His Trp Val Arg Gln Ala Pro Gly Lys Gly Leu
                165                 170                 175

Glu Trp Val Ala Leu Ile Ser Asn Asp Gly Ser Asn Lys Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Thr Arg Asp Arg Gly Leu Arg Phe Tyr Phe Asp Tyr Trp
225                 230                 235                 240

Gly Gln Gly Thr Thr Val Thr Val Ser Ser Gly Gly Gly Gly Ser Asp
                245                 250                 255

Val Gln Leu Val Gln Ser Gly Ala Glu Val Lys Lys Pro Gly Ala Ser
            260                 265                 270

Val Lys Val Ser Cys Lys Ala Ser Gly Tyr Thr Phe Thr Arg Tyr Thr
        275                 280                 285

Met His Trp Val Arg Gln Ala Pro Gly Gln Gly Leu Glu Trp Ile Gly
    290                 295                 300

Tyr Ile Asn Pro Ser Arg Gly Tyr Thr Asn Tyr Ala Asp Ser Val Lys
305                 310                 315                 320

Gly Arg Phe Thr Ile Thr Thr Asp Lys Ser Thr Ser Thr Ala Tyr Met
                325                 330                 335

Glu Leu Ser Ser Leu Arg Ser Glu Asp Thr Ala Thr Tyr Tyr Cys Ala
            340                 345                 350

Arg Tyr Tyr Asp Asp His Tyr Cys Leu Asp Tyr Trp Gly Gln Gly Thr
        355                 360                 365

Thr Val Thr Val Ser Ser Gly Glu Gly Thr Ser Thr Gly Ser Gly Gly
    370                 375                 380

Ser Gly Gly Ser Gly Gly Ala Asp Asp Ile Val Leu Thr Gln Ser Pro

```
                385                 390                 395                 400
Ala Thr Leu Ser Leu Ser Pro Gly Glu Arg Ala Thr Leu Ser Cys Arg
                    405                 410                 415

Ala Ser Gln Ser Val Ser Tyr Met Asn Trp Tyr Gln Gln Lys Pro Gly
                420                 425                 430

Lys Ala Pro Lys Arg Trp Ile Tyr Asp Thr Ser Lys Val Ala Ser Gly
                435                 440                 445

Val Pro Ala Arg Phe Ser Gly Ser Gly Ser Gly Thr Asp Tyr Ser Leu
450                 455                 460

Thr Ile Asn Ser Leu Glu Ala Glu Asp Ala Ala Thr Tyr Tyr Cys Gln
465                 470                 475                 480

Gln Trp Ser Ser Asn Pro Leu Thr Phe Gly Gly Gly Thr Lys Val Glu
                485                 490                 495

Ile Lys

<210> SEQ ID NO 43
<211> LENGTH: 1500
<212> TYPE: DNA
<213> ORGANISM: artificial sequence
<220> FEATURE:
<223> OTHER INFORMATION: SEQ ID NO: 77 VHVL x D8 VH - A240 VL ;
      Bispecific single chain antibody

<400> SEQUENCE: 43
gacgtccaac tggtgcagtc aggggctgaa gtgaaaaaac tggggcctc agtgaaggtg     60 tcctgcaagg cttctggcta cacctttact aggtacacga tgcactgggt aaggcaggca    120
cctggacagg gtctggaatg gattggatac attaatccta gccgtggtta ctactaattac   180 gcagacagcg tcaagggccg cttcacaatc actacagaca atccaccag cacagcctac    240 atggaactga gcagcctgcg ttctgaggac actgcaacct attactgtgc aagatattat    300
gatgatcatt actgccttga ctactgggc caaggcacca cggtcaccgt ctcctcaggc     360
gaaggtacta gtactggttc tggtggaagt ggaggttcag gtggagcaga cgacattgta    420
ctgacccagt ctccagcaac tctgtctctg tctccagggg agcgtgccac cctgagctgc    480
agagccagtc aaagtgtaag ttacatgaac tggtaccagc agaagccggg caaggcaccc    540
aaaagatgga tttatgacac atccaaagtg gcttctggag tccctgctcg cttcagtggc    600
agtgggtctg gaccgactac tctctctcaca atcaacagct tggaggctga agatgctgcc   660
acttattact gccaacagtg gagtagtaac ccgctcacgt tcggtggcgg gaccaaggtg    720
gagatcaaat ccggaggtgg tggatccgag gtgcagctgg tcgagtctgg ggaggcgtg     780 gtccagcctg ggaggtccct gagactctcc tgtgcagcct ctggattcac cctcagtacc    840
tatgccatgc actgggtccg ccaggctcca ggcaaggggc tggagtgggt ggcacttata    900
tcaaatgatg gaagcaataa atactatgca gactccgtga agggccgatt caccatctcc    960
agagacaatt ccaagaacac gctgtatctg caaatgaaca gcctgagagc tgaggacacg   1020
gctgtgtatt actgtactag agatagggg ctacggttct actttgacta ctggggccaa    1080
gggaccacgg tcaccgtctc tcaggtggt ggtggttctg gcggcggcgg ctccggtggt    1140
ggtggttctg agctcgtgct gactcagccg gcttccctct ctgcatctcc tggagcatca   1200
gccagtctca cctgcacctt ggcagggc atcaatgttg gtgcctacag tatatactgg     1260
taccagcaga agccagggag tcctcccag tatctcctga ggtacaaatc agactcagat    1320
aagcagcagg gctctggagt ctccagccgc ttctctgcat ccaaagatgc ttcggccaat   1380
```

-continued

```
gcagggattt tactcatctc tgggctccag tctgaggatg aggctgacta ttactgtatg    1440
atttggcaca gcggcgcttc tgcggtgttc ggcggaggga ccaagttgac cgtcctatag    1500
```

<210> SEQ ID NO 44
<211> LENGTH: 499
<212> TYPE: PRT
<213> ORGANISM: artificial sequence
<220> FEATURE:
<223> OTHER INFORMATION: SEQ ID NO: 77 VHVL x D8 VH - A240 VL ;
      Bispecific single chain antibody

<400> SEQUENCE: 44

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Ser Gly Gly Gly Gly Ser Glu Val Gln Leu Val Glu Ser
                245                 250                 255

Gly Gly Gly Val Val Gln Pro Gly Arg Ser Leu Arg Leu Ser Cys Ala
            260                 265                 270

Ala Ser Gly Phe Thr Leu Ser Thr Tyr Ala Met His Trp Val Arg Gln
        275                 280                 285

Ala Pro Gly Lys Gly Leu Glu Trp Val Ala Leu Ile Ser Asn Asp Gly
    290                 295                 300

Ser Asn Lys Tyr Tyr Ala Asp Ser Val Lys Gly Arg Phe Thr Ile Ser
305                 310                 315                 320

Arg Asp Asn Ser Lys Asn Thr Leu Tyr Leu Gln Met Asn Ser Leu Arg
                325                 330                 335

Ala Glu Asp Thr Ala Val Tyr Tyr Cys Thr Arg Asp Arg Gly Leu Arg

```
                340               345               350
Phe Tyr Phe Asp Tyr Trp Gly Gln Gly Thr Thr Val Thr Val Ser Ser
            355                   360               365

Gly Gly Gly Gly Ser Gly Gly Gly Ser Gly Gly Gly Ser Glu
370                 375                 380

Leu Val Leu Thr Gln Pro Ala Ser Leu Ser Ala Ser Pro Gly Ala Ser
385                 390                 395                 400

Ala Ser Leu Thr Cys Thr Leu Arg Arg Gly Ile Asn Val Gly Ala Tyr
                405                 410                 415

Ser Ile Tyr Trp Tyr Gln Gln Lys Pro Gly Ser Pro Pro Gln Tyr Leu
            420                 425                 430

Leu Arg Tyr Lys Ser Asp Ser Asp Lys Gln Gln Gly Ser Gly Val Ser
        435                 440                 445

Ser Arg Phe Ser Ala Ser Lys Asp Ala Ser Ala Asn Ala Gly Ile Leu
    450                 455                 460

Leu Ile Ser Gly Leu Gln Ser Glu Asp Glu Ala Asp Tyr Tyr Cys Met
465                 470                 475                 480

Ile Trp His Ser Gly Ala Ser Ala Val Phe Gly Gly Gly Thr Lys Leu
                485                 490                 495

Thr Val Leu
```

<210> SEQ ID NO 45
<211> LENGTH: 1500
<212> TYPE: DNA
<213> ORGANISM: artificial sequence
<220> FEATURE:
<223> OTHER INFORMATION: SEQ ID NO: 77 VHVL x A240 VL - D8 VH ;
      Bispecific single chain antibody

<400> SEQUENCE: 45

```
gacgtccaac tggtgcagtc aggggctgaa gtgaaaaaac ctggggcctc agtgaaggtg      60
tcctgcaagg cttctggcta cacctttact aggtacacga tgcactgggt aaggcaggca     120
cctggacagg gtctggaatg gattggatac attaatccta gccgtggtta ctaattac      180
gcagacagcg tcaagggccg cttcacaatc actacagaca atccaccag cacagcctac     240
atggaactga gcagcctgcg ttctgaggac actgcaacct attactgtgc aagatattat     300
gatgatcatt actgccttga ctactggggc caaggcacca cggtcaccgt ctcctcaggc     360
gaaggtacta gtactggttc tggtggaagt ggaggttcag gtggagcaga cgacattgta     420
ctgacccagt ctccagcaac tctgtctctg tctccagggg agcgtgccac cctgagctgc     480
agagccagtc aaagtgtaag ttacatgaac tggtaccagc agaagccggg caaggcaccc     540
aaaagatgga tttatgacac atccaaagtg gcttctggag tccctgctcg cttcagtggc     600
agtgggtctg ggaccgacta ctctctcaca atcaacagct ggaggctga agatgctgcc     660
acttattact gccaacagtg gagtagtaac ccgctcacgt tcggtggcgg gaccaaggtg     720
gagatcaaat ccggaggtgg tggatcccag gccgtgctga ctcagccggc ttccctctct     780
gcatctcctg gagcatcagc cagtctcacc tgcaccttgc gcaggggcat caatgttggt     840
gcctacagta tactggta ccagcagaag ccagggagtc ctccccagta tctcctgagg     900
tacaaatcag actcagataa gcagcagggc tctggagtct ccagccgctt ctctgcatcc     960
aaagatgctt cggccaatgc agggattta ctcatctctg gctccagtc tgaggatgag    1020
gctgactatt actgtatgat ttggcacagc ggcgcttctg cggtgttcgg cggagggacc    1080
aagttgaccg tcctaggtgg tggtggttct ggcggcggcg gctccggtgg tggtggttct    1140
```

```
gaggtgcagc tggtcgagtc tgggggaggc gtggtccagc ctggggaggtc cctgagactc    1200 tcctgtgcag cctctggatt caccctcagt acctatgcca tgcactgggt ccgccaggct    1260
ccaggcaagg ggctggagtg gtggcactt atatcaaatg atggaagcaa taaatactat    1320
gcagactccg tgaagggccg attcaccatc tccagagaca attccaagaa cacgctgtat    1380
ctgcaaatga acagcctgag agctgaggac acggctgtgt attactgtac tagagatagg    1440
gggctacggt tctactttga ctactggggc caagggacca cggtcaccgt ctcctcctag    1500
```

<210> SEQ ID NO 46
<211> LENGTH: 499
<212> TYPE: PRT
<213> ORGANISM: artificial sequence
<220> FEATURE:
<223> OTHER INFORMATION: SEQ ID NO: 77 VHVL x A240 VL - D8 VH ;
      Bispecific single chain antibody

<400> SEQUENCE: 46

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Ser Gly Gly Gly Gly Ser Gln Ala Val Leu Thr Gln Pro
                245                 250                 255

Ala Ser Leu Ser Ala Ser Pro Gly Ala Ser Ala Ser Leu Thr Cys Thr
            260                 265                 270

Leu Arg Arg Gly Ile Asn Val Gly Ala Tyr Ser Ile Tyr Trp Tyr Gln
        275                 280                 285

Gln Lys Pro Gly Ser Pro Pro Gln Tyr Leu Leu Arg Tyr Lys Ser Asp

Ser Asp Lys Gln Gln Gly Ser Gly Val Ser Ser Arg Phe Ser Ala Ser
305                 310                 315                 320

Lys Asp Ala Ser Ala Asn Ala Gly Ile Leu Leu Ile Ser Gly Leu Gln
            325                 330                 335

Ser Glu Asp Glu Ala Asp Tyr Tyr Cys Met Ile Trp His Ser Gly Ala
            340                 345                 350

Ser Ala Val Phe Gly Gly Gly Thr Lys Leu Thr Val Leu Gly Gly Gly
            355                 360                 365

Gly Ser Gly Gly Gly Gly Ser Gly Gly Gly Gly Ser Glu Val Gln Leu
    370                 375                 380

Val Glu Ser Gly Gly Gly Val Val Gln Pro Gly Arg Ser Leu Arg Leu
385                 390                 395                 400

Ser Cys Ala Ala Ser Gly Phe Thr Leu Ser Thr Tyr Ala Met His Trp
            405                 410                 415

Val Arg Gln Ala Pro Gly Lys Gly Leu Glu Trp Val Ala Leu Ile Ser
            420                 425                 430

Asn Asp Gly Ser Asn Lys Tyr Tyr Ala Asp Ser Val Lys Gly Arg Phe
            435                 440                 445

Thr Ile Ser Arg Asp Asn Ser Lys Asn Thr Leu Tyr Leu Gln Met Asn
    450                 455                 460

Ser Leu Arg Ala Glu Asp Thr Ala Val Tyr Tyr Cys Thr Arg Asp Arg
465                 470                 475                 480

Gly Leu Arg Phe Tyr Phe Asp Tyr Trp Gly Gln Gly Thr Thr Val Thr
            485                 490                 495

Val Ser Ser

<210> SEQ ID NO 47
<211> LENGTH: 756
<212> TYPE: DNA
<213> ORGANISM: artificial sequence
<220> FEATURE:
<223> OTHER INFORMATION: A5B7 VH - A240 VL ; Single chain Fv

<400> SEQUENCE: 47
gaggtgcagc tggtcgagtc aggaggaggc ttggtacagc ctggggttc tctgagactc      60
tcctgtgcaa cttctggtt caccttcact gattactaca tgaactggt ccgccagcct     120
ccaggaaagg cacttgagtg gttgggtttt attggaaaca aagctaatgg ttacacaaca     180
gagtacagtg catctgtgaa gggtcggttc accatctcca gagataaatc ccaaagcatc     240
ctctatcttc aaatgaacac cctgagagct gaggacagtg ccacttatta ctgtaccaga     300
gataggggc tacggttcta ctttgactac tggggccaag gaccacggt caccgtctcc     360
tcaggtggtg gtggttctgg cggcggcggc tccggtggtg gtggttctca ggccgtgctg     420
actcagccgg cttccctctc tgcatctcct ggagcatcag ccagtctcac ctgcaccttg     480
cgcagggca tcaatgttgg tgcctacagt atatactggt accagcagaa gccagggagt     540
cctcccagt atctcctgag gtacaaatca gactcagata gcagcaggg ctctggagtc     600
tccagccgct ctctgcatc caaagatgct cggccaatg cagggatttt actcatctct     660
gggctccagt ctgaggatga ggctgactat tactgtatga tttggcacag cggcgcttct     720
gcggtgttcg gcggagggac caagttgacc gtccta                              756

<210> SEQ ID NO 48
<211> LENGTH: 252

<212> TYPE: PRT
<213> ORGANISM: artificial sequence
<220> FEATURE:
<223> OTHER INFORMATION: A5B7 VH - A240 VL ; Single chain Fv

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
                85                  90                  95

Tyr Cys Thr Arg Asp Arg Gly Leu Arg Phe Tyr Phe Asp Tyr Trp Gly
            100                 105                 110

Gln Gly Thr Thr Val Thr Val Ser Ser Gly Gly Gly Ser Gly Gly
            115                 120                 125

Gly Gly Ser Gly Gly Gly Ser Gln Ala Val Leu Thr Gln Pro Ala
    130                 135                 140

Ser Leu Ser Ala Ser Pro Gly Ala Ser Ala Ser Leu Thr Cys Thr Leu
145                 150                 155                 160

Arg Arg Gly Ile Asn Val Gly Ala Tyr Ser Ile Tyr Trp Tyr Gln Gln
                165                 170                 175

Lys Pro Gly Ser Pro Pro Gln Tyr Leu Leu Arg Tyr Lys Ser Asp Ser
            180                 185                 190

Asp Lys Gln Gln Gly Ser Gly Val Ser Ser Arg Phe Ser Ala Ser Lys
        195                 200                 205

Asp Ala Ser Ala Asn Ala Gly Ile Leu Leu Ile Ser Gly Leu Gln Ser
    210                 215                 220

Glu Asp Glu Ala Asp Tyr Tyr Cys Met Ile Trp His Ser Gly Ala Ser
225                 230                 235                 240

Ala Val Phe Gly Gly Gly Thr Lys Leu Thr Val Leu
                245                 250

<210> SEQ ID NO 49
<211> LENGTH: 753
<212> TYPE: DNA
<213> ORGANISM: Homo sapiens
<220> FEATURE:
<221> NAME/KEY: misc_feature
<223> OTHER INFORMATION: A5 VH - A240 VL ; Single chain Fv

<400> SEQUENCE: 49
gaggtgcagc tggtcgagtc tgggggaggc gtggtccagc ctggggaggtc cctgagactc        60 tcctgtgcag cctctggatt caccctcagt acctatgcca tgcactgggt ccgccaggct       120
ccaggcaagg ggctggagtg gtggcactt atatcaaatg atggaagcaa taaatactat       180
gcagactccg tgaagggccg attcaccatc tccagagaca attccaagaa cacgctgtat       240
ctgcaaatga acagcctgag agctgaggac acggccgtgt attactgtgc gagagatagg       300
gggctacggt tctactttga ctactggggc caagggacca cggtcaccgt ctcctcaggt       360
ggtggtggtt ctggcggcgg cggctccggt ggtggtggtt ctcaggccgt gctgactcag       420

```
ccggcttccc tctctgcatc tcctggagca tcagccagtc tcacctgcac cttgcgcagg    480
ggcatcaatg ttggtgccta cagtatatac tggtaccagc agaagccagg gagtcctccc    540
cagtatctcc tgaggtacaa atcagactca gataagcagc agggctctgg agtctccagc    600
cgcttctctg catccaaaga tgcttcggcc aatgcaggga ttttactcat ctctgggctc    660
cagtctgagg atgaggctga ctattactgt atgatttggc acagcggcgc ttctgcggtg    720
ttcggcggag ggaccaagtt gaccgtccta tag                                 753
```

<210> SEQ ID NO 50
<211> LENGTH: 250
<212> TYPE: PRT
<213> ORGANISM: Homo sapiens
<220> FEATURE:
<221> NAME/KEY: MISC_FEATURE
<223> OTHER INFORMATION: A5 VH - A240 VL ; Single chain Fv

<400> SEQUENCE: 50

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Arg Phe Tyr Phe Asp Tyr Trp Gly Gln Gly
            100                 105                 110

Thr Thr Val Thr Val Ser Ser Gly Gly Gly Gly Ser Gly Gly Gly Gly
        115                 120                 125

Ser Gly Gly Gly Gly Ser Gln Ala Val Leu Thr Gln Pro Ala Ser Leu
    130                 135                 140

Ser Ala Ser Pro Gly Ala Ser Ala Ser Leu Thr Cys Thr Leu Arg Arg
145                 150                 155                 160

Gly Ile Asn Val Gly Ala Tyr Ser Ile Tyr Trp Tyr Gln Gln Lys Pro
                165                 170                 175

Gly Ser Pro Pro Gln Tyr Leu Arg Tyr Lys Ser Asp Ser Asp Lys
            180                 185                 190

Gln Gln Gly Ser Gly Val Ser Ser Arg Phe Ser Ala Ser Lys Asp Ala
        195                 200                 205

Ser Ala Asn Ala Gly Ile Leu Leu Ile Ser Gly Leu Gln Ser Glu Asp
    210                 215                 220

Glu Ala Asp Tyr Tyr Cys Met Ile Trp His Ser Gly Ala Ser Ala Val
225                 230                 235                 240

Phe Gly Gly Gly Thr Lys Leu Thr Val Leu
                245                 250

<210> SEQ ID NO 51
<211> LENGTH: 759
<212> TYPE: DNA
<213> ORGANISM: Homo sapiens
<220> FEATURE:
<221> NAME/KEY: misc_feature
<223> OTHER INFORMATION: B9 VH - A240 VL ; Single chain Fv

<400> SEQUENCE: 51

```
gaggtgcagc tggtcgagtc tgggggaggc ttggtccagc ctggagggtc cctgagactc      60
tcctgtgcag cgtctggatt caccgtcagt agctactgga tgcactgggt ccgccaagct     120
ccagggaagg ggctggaatg ggtaggtttc attagaaaca agctaatgg tgggacaaca      180
gaatacgccg cgtctgtgaa aggcagattc accatctcaa gagatgattc caagaacacg     240
ctgtatcttc aaatgaacag cctgagagcc gaggacacgg ccgtgtatta ctgtgcaaga     300
gataggggc tacggttcta ctttgactac tggggccaag ggaccacggt caccgtctcc      360
tcaggtggtg gtggttctgg cggcggcggc tccggtggtg gtggttctca ggccgtgctg     420
actcagccgg cttccctctc tgcatctcct ggagcatcag ccagtctcac ctgcaccttg     480
cgcaggggca tcaatgttgg tgcctacagt atatactggt accagcagaa gccagggagt     540
cctccccagt atctcctgag gtacaaatca gactcagata gcagcaggg ctctggagtc      600
tccagccgct tctctgcatc caagatgct tcggccaatg cagggatttt actcatctct      660
gggctccagt ctgaggatga ggctgactat tactgtatga tttggcacag cggcgcttct     720
gcggtgttcg gcggagggac caagttgacc gtcctatag                            759
```

<210> SEQ ID NO 52
<211> LENGTH: 252
<212> TYPE: PRT
<213> ORGANISM: Homo sapiens
<220> FEATURE:
<221> NAME/KEY: MISC_FEATURE
<223> OTHER INFORMATION: B9 VH - A240VL ; Single chain Fv

<400> SEQUENCE: 52

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Gln Ala Val Leu Thr Gln Pro Ala
    130                 135                 140

Ser Leu Ser Ala Ser Pro Gly Ala Ser Ala Ser Leu Thr Cys Thr Leu
145                 150                 155                 160

Arg Arg Gly Ile Asn Val Gly Ala Tyr Ser Ile Tyr Trp Tyr Gln Gln
                165                 170                 175

Lys Pro Gly Ser Pro Pro Gln Tyr Leu Leu Arg Tyr Lys Ser Asp Ser
            180                 185                 190

Asp Lys Gln Gln Gly Ser Gly Val Ser Ser Arg Phe Ser Ala Ser Lys
        195                 200                 205
```

Asp Ala Ser Ala Asn Ala Gly Ile Leu Leu Ile Ser Gly Leu Gln Ser
                210                 215                 220

Glu Asp Glu Ala Asp Tyr Tyr Cys Met Ile Trp His Ser Gly Ala Ser
225                 230                 235                 240

Ala Val Phe Gly Gly Gly Thr Lys Leu Thr Val Leu
                245                 250

<210> SEQ ID NO 53
<211> LENGTH: 753
<212> TYPE: DNA
<213> ORGANISM: Homo sapiens
<220> FEATURE:
<221> NAME/KEY: misc_feature
<223> OTHER INFORMATION: D8 VH - A240VL ; Single chain Fv

<400> SEQUENCE: 53
gaggtgcagc tggtcgagtc tgggggaggc gtggtccagc ctggcggagtc cctgagactc        60 tcctgtgcag cctctggatt caccctcagt acctatgcca tgcactgggt ccgccaggct       120
ccaggcaagg ggctggagtg ggtggcactt atatcaaatg atggaagcaa taaatactat       180
gcagactccg tgaagggccg attcaccatc tccagagaca attccaagaa cacgctgtat       240
ctgcaaatga acagcctgag agctgaggac acggctgtgt attactgtac tagagatagg       300
gggctacggt tctactttga ctactggggc caagggacca cggtcaccgt ctcctcaggt       360
ggtggtggtt ctggcggcgg cggctccggt ggtggtggtt ctcaggccgt gctgactcag       420
ccggcttccc tctctgcatc tcctggagca tcagccagtc tcacctgcac cttgcgcagg       480
ggcatcaatg ttggtgccta cagtatatac tggtaccagc agaagccagg gagtcctccc       540
cagtatctcc tgaggtacaa atcagactca gataagcagc agggctctgg agtctccagc       600
cgcttctctg catccaaaga tgcttcggcc aatgcaggga ttttactcat ctctgggctc       660
cagtctgagg atgaggctga ctattactgt atgatttggc acagcggcgc ttctgcggtg       720
ttcggcggag ggaccaagtt gaccgtccta tag                                    753

<210> SEQ ID NO 54
<211> LENGTH: 250
<212> TYPE: PRT
<213> ORGANISM: Homo sapiens
<220> FEATURE:
<221> NAME/KEY: MISC_FEATURE
<223> OTHER INFORMATION: D8 VH - A240VL ; Single chain Fv

<400> SEQUENCE: 54

Glu Val Gln Leu Val Glu Ser Gly Gly Gly Val Val Gln Pro Gly Arg
1               5                   10                  15

Ser Leu Arg Leu Ser Cys Ala Ser Gly Phe Thr Leu Ser Thr Tyr
            20                  25                  30

Ala Met His Trp Val Arg Gln Ala Pro Gly Lys Gly Leu Glu Trp Val
            35                  40                  45

Ala Leu Ile Ser Asn Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Arg Gly Leu Arg Phe Tyr Phe Asp Tyr Trp Gly Gln Gly
            100                 105                 110

```
Thr Thr Val Thr Val Ser Ser Gly Gly Gly Ser Gly Gly Gly
            115                 120                 125

Ser Gly Gly Gly Ser Gln Ala Val Leu Thr Gln Pro Ala Ser Leu
    130                 135                 140

Ser Ala Ser Pro Gly Ala Ser Ala Ser Leu Thr Cys Thr Leu Arg Arg
145                 150                 155                 160

Gly Ile Asn Val Gly Ala Tyr Ser Ile Tyr Trp Tyr Gln Gln Lys Pro
                165                 170                 175

Gly Ser Pro Pro Gln Tyr Leu Leu Arg Tyr Lys Ser Asp Ser Asp Lys
            180                 185                 190

Gln Gln Gly Ser Gly Val Ser Ser Arg Phe Ser Ala Ser Lys Asp Ala
        195                 200                 205

Ser Ala Asn Ala Gly Ile Leu Leu Ile Ser Gly Leu Gln Ser Glu Asp
210                 215                 220

Glu Ala Asp Tyr Tyr Cys Met Ile Trp His Ser Gly Ala Ser Ala Val
225                 230                 235                 240

Phe Gly Gly Gly Thr Lys Leu Thr Val Leu
                245                 250

<210> SEQ ID NO 55
<211> LENGTH: 363
<212> TYPE: DNA
<213> ORGANISM: Mus musculus
<220> FEATURE:
<221> NAME/KEY: misc_feature
<223> OTHER INFORMATION: A5B7 VH ; VH region

<400> SEQUENCE: 55
gaggtgcagc tggtcgagtc aggaggaggc ttggtacagc ctgggggttc tctgagactc      60
tcctgtgcaa cttctgggtt caccttcact gattactaca tgaactgggt ccgccagcct     120
ccaggaaagg cacttgagtg gttgggtttt attggaaaca agctaatgg ttacacaaca      180 gagtacagtg catctgtgaa gggtcggttc accatctcca gagataaatc ccaaagcatc     240
ctctatcttc aaatgaacac cctgagagct gaggacagtg ccacttatta ctgtaccaga     300 gataggggc tacggttcta ctttgactac tggggccaag ggaccacggt caccgtctcc      360
tca                                                                  363

<210> SEQ ID NO 56
<211> LENGTH: 121
<212> TYPE: PRT
<213> ORGANISM: Mus musculus
<220> FEATURE:
<221> NAME/KEY: MISC_FEATURE
<223> OTHER INFORMATION: A5B7 VH ; VH region

<400> SEQUENCE: 56

Glu Val Gln Leu Val Glu Ser Gly Gly Gly Leu Val Gln Pro Gly Gly
1               5                   10                  15

Ser Leu Arg Leu Ser Cys Ala Thr Ser Gly Phe Thr Phe Thr Asp Tyr
            20                  25                  30

Tyr Met Asn Trp Val Arg Gln Pro Pro Gly Lys Ala Leu Glu Trp Leu
        35                  40                  45

Gly Phe Ile Gly Asn Lys Ala Asn Gly Tyr Thr Thr Glu Tyr Ser Ala
    50                  55                  60

Ser Val Lys Gly Arg Phe Thr Ile Ser Arg Asp Lys Ser Gln Ser Ile
65                  70                  75                  80

Leu Tyr Leu Gln Met Asn Thr Leu Arg Ala Glu Asp Ser Ala Thr Tyr
```

```
                      85                  90                  95
Tyr Cys Thr Arg Asp Arg Gly Leu Arg Phe Tyr Phe Asp Tyr Trp Gly
                     100                 105                 110

Gln Gly Thr Thr Val Thr Val Ser Ser
            115                 120
```

<210> SEQ ID NO 57
<211> LENGTH: 357
<212> TYPE: DNA
<213> ORGANISM: Homo sapiens
<220> FEATURE:
<221> NAME/KEY: misc_feature
<223> OTHER INFORMATION: A5 VH ; VH region

<400> SEQUENCE: 57

```
gaggtgcagc tggtcgagtc tggggggaggc gtggtccagc ctggggaggtc cctgagactc      60 tcctgtgcag cctctggatt caccctcagt acctatgcca tgcactgggt ccgccaggct     120
ccaggcaagg ggctggagtg ggtggcactt atatcaaatg atggaagcaa taaatactat     180
gcagactccg tgaagggccg attcaccatc tccagagaca attccaagaa cacgctgtat     240
ctgcaaatga acagcctgag agctgaggac acggccgtgt attactgtgc gagagatagg     300
gggctacggt tctactttga ctactggggc caagggacca cggtcaccgt ctcctca       357
```

<210> SEQ ID NO 58
<211> LENGTH: 119
<212> TYPE: PRT
<213> ORGANISM: Homo sapiens
<220> FEATURE:
<221> NAME/KEY: MISC_FEATURE
<223> OTHER INFORMATION: A5 VH ; VH region

<400> SEQUENCE: 58

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Arg Phe Tyr Phe Asp Tyr Trp Gly Gln Gly
            100                 105                 110

Thr Thr Val Thr Val Ser Ser
        115
```

<210> SEQ ID NO 59
<211> LENGTH: 363
<212> TYPE: DNA
<213> ORGANISM: Homo sapiens
<220> FEATURE:
<221> NAME/KEY: misc_feature
<223> OTHER INFORMATION: B9 VH ; VH region

<400> SEQUENCE: 59

```
gaggtgcagc tggtcgagtc tggggggaggc ttggtccagc ctggggaggtc cctgagactc      60
```

```
tcctgtgcag cgtctggatt caccgtcagt agctactgga tgcactgggt ccgccaagct    120
ccagggaagg ggctggaatg ggtaggtttc attagaaaca aagctaatgg tgggacaaca    180
gaatacgccg cgtctgtgaa aggcagattc accatctcaa gagatgattc aagaacacg     240 ctgtatcttc aaatgaacag cctgagagcc gaggacacgg ccgtgtatta ctgtgcaaga    300 gataggggc tacggttcta ctttgactac tggggccaag gaccacggt caccgtctcc      360 tca                                                                   363
```

<210> SEQ ID NO 60
<211> LENGTH: 121
<212> TYPE: PRT
<213> ORGANISM: Homo sapiens
<220> FEATURE:
<221> NAME/KEY: MISC_FEATURE
<223> OTHER INFORMATION: B9 VH ; VH region

<400> SEQUENCE: 60

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser
        115                 120
```

<210> SEQ ID NO 61
<211> LENGTH: 357
<212> TYPE: DNA
<213> ORGANISM: Homo sapiens
<220> FEATURE:
<221> NAME/KEY: misc_feature
<223> OTHER INFORMATION: D8 VH ; VH region

<400> SEQUENCE: 61

```
gaggtgcagc tggtcgagtc tgggggaggc gtggtccagc ctgggaggtc cctgagactc     60
tcctgtgcag cctctggatt caccctcagt acctatgcca tgcactgggt ccgccaggct    120
ccaggcaagg ggctggagtg ggtggcactt atatcaaatg atggaagcaa taaatactat    180
gcagactccg tgaagggccg attcaccatc tccagagaca attccaagaa cacgctgtat    240
ctgcaaatga acagcctgag agctgaggac acggctgtgt attactgtac tagagatagg    300
gggctacggt tctactttga ctactggggc caagggacca cggtcaccgt ctcctca       357
```

<210> SEQ ID NO 62
<211> LENGTH: 119
<212> TYPE: PRT
<213> ORGANISM: Homo sapiens
<220> FEATURE:
<221> NAME/KEY: MISC_FEATURE
<223> OTHER INFORMATION: D8 VH ; VH region

<400> SEQUENCE: 62

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Asp Arg Gly Leu Arg Phe Tyr Phe Asp Tyr Trp Gly Gln Gly
            100                 105                 110

Thr Thr Val Thr Val Ser Ser
        115

<210> SEQ ID NO 63
<211> LENGTH: 348
<212> TYPE: DNA
<213> ORGANISM: Homo sapiens
<220> FEATURE:
<221> NAME/KEY: misc_feature
<223> OTHER INFORMATION: A240 VL ; VL region

<400> SEQUENCE: 63
caggccgtgc tgactcagcc ggcttccctc tctgcatctc ctggagcatc agccagtctc     60
acctgcacct tgcgcagggg catcaatgtt ggtgcctaca gtatatactg gtaccagcag    120
aagccaggga gtcctcccca gtatctcctg aggtacaaat cagactcaga taagcagcag    180
ggctctggag tctccagccg cttctctgca tccaaagatg cttcggccaa tgcagggatt    240
ttactcatct ctgggctcca gtctgaggat gaggctgact attactgtat gatttggcac    300
agcggcgctt ctgcggtgtt cggcggaggg accaagttga ccgtccta                 348

<210> SEQ ID NO 64
<211> LENGTH: 116
<212> TYPE: PRT
<213> ORGANISM: Homo sapiens
<220> FEATURE:
<221> NAME/KEY: MISC_FEATURE
<223> OTHER INFORMATION: A240VL ; VL region

<400> SEQUENCE: 64

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys

```
                100                 105                 110
Leu Thr Val Leu
        115

<210> SEQ ID NO 65
<211> LENGTH: 10
<212> TYPE: PRT
<213> ORGANISM: Mus musculus
<220> FEATURE:
<221> NAME/KEY: MISC_FEATURE
<223> OTHER INFORMATION: CDR-H3* A5B7 Shorter CDR-3 of VH of A5B7 with D
      corresponding to Kabat position 95; Kabat positions 100, 100a,
      100b, 101, 102 correspond to FYFDY, respectively
<220> FEATURE:
<221> NAME/KEY: MISC_FEATURE
<223> OTHER INFORMATION: with "X1", "X2", "X3" and "X4" corresponding to
      Kabat positions 96 ("X1"), 97 ("X2"), 98 ("X3") and 99 ("X4"),
      respectively, of CDR-H3 of murine monoclonal antibody A5B7 and
      wherein "X" represents any amino acid residue. "X1" is preferably
      "R"
<220> FEATURE:
<221> NAME/KEY: misc_feature
<222> LOCATION: (2)..(5)
<223> OTHER INFORMATION: Xaa can be any naturally occurring amino acid

<400> SEQUENCE: 65

Asp Xaa1 Xaa2 Xaa3 Xaa4 Phe Tyr Phe Asp Tyr
1               5                   10

<210> SEQ ID NO 66
<211> LENGTH: 10
<212> TYPE: PRT
<213> ORGANISM: Mus musculus
<220> FEATURE:
<221> NAME/KEY: MISC_FEATURE
<223> OTHER INFORMATION: CDR-H3 A5B7 CDR-3 of VH of A5B7 corresponding
      to Kabat positions 95, 96, 97, 98, 99, 100, 100a, 100b, 101, 102

<400> SEQUENCE: 66

Asp Arg Gly Leu Arg Phe Tyr Phe Asp Tyr
1               5                   10

<210> SEQ ID NO 67
<211> LENGTH: 19
<212> TYPE: PRT
<213> ORGANISM: Homo sapiens
<220> FEATURE:
<221> NAME/KEY: MISC_FEATURE
<223> OTHER INFORMATION: CDR-H2 B9 ; CDR-2 of VH B9

<400> SEQUENCE: 67

Phe Ile Arg Asn Lys Ala Asn Gly Gly Thr Thr Glu Tyr Ala Ala Ser
1               5                   10                  15

Val Lys Gly

<210> SEQ ID NO 68
<211> LENGTH: 5
<212> TYPE: PRT
<213> ORGANISM: Homo sapiens
<220> FEATURE:
<221> NAME/KEY: MISC_FEATURE
<223> OTHER INFORMATION: CDR-H1 B9 ; CDR1 of VH B9

<400> SEQUENCE: 68

Ser Tyr Trp Met His
1               5

<210> SEQ ID NO 69
```

```
<211> LENGTH: 17
<212> TYPE: PRT
<213> ORGANISM: Homo sapiens
<220> FEATURE:
<221> NAME/KEY: MISC_FEATURE
<223> OTHER INFORMATION: CDR-H2 A5/D8 ; CDR-2 of VH A5/D8

<400> SEQUENCE: 69

Leu Ile Ser Asn Asp Gly Ser Asn Lys Tyr Tyr Ala Asp Ser Val Lys
1               5                   10                  15
Gly

<210> SEQ ID NO 70
<211> LENGTH: 5
<212> TYPE: PRT
<213> ORGANISM: Homo sapiens
<220> FEATURE:
<221> NAME/KEY: MISC_FEATURE
<223> OTHER INFORMATION: CDR-H1 A5/D8 ; CDR-1 of VH A5/D8

<400> SEQUENCE: 70

Thr Tyr Ala Met His
1               5

<210> SEQ ID NO 71
<211> LENGTH: 10
<212> TYPE: PRT
<213> ORGANISM: Homo sapiens
<220> FEATURE:
<221> NAME/KEY: MISC_FEATURE
<223> OTHER INFORMATION: CDR-L3 A240 ; CDR-3 of VL A240

<400> SEQUENCE: 71

Met Ile Trp His Ser Gly Ala Ser Ala Val
1               5                   10

<210> SEQ ID NO 72
<211> LENGTH: 11
<212> TYPE: PRT
<213> ORGANISM: Homo sapiens
<220> FEATURE:
<221> NAME/KEY: MISC_FEATURE
<223> OTHER INFORMATION: CDR-L2 A240 ; CDR-2 of VL A240

<400> SEQUENCE: 72

Tyr Lys Ser Asp Ser Asp Lys Gln Gln Gly Ser
1               5                   10

<210> SEQ ID NO 73
<211> LENGTH: 14
<212> TYPE: PRT
<213> ORGANISM: Homo sapiens
<220> FEATURE:
<221> NAME/KEY: MISC_FEATURE
<223> OTHER INFORMATION: CDR-L1 A240 ; CDR-1 of VL A240

<400> SEQUENCE: 73

Thr Leu Arg Arg Gly Ile Asn Val Gly Ala Tyr Ser Ile Tyr
1               5                   10

<210> SEQ ID NO 74
<211> LENGTH: 32
<212> TYPE: DNA
<213> ORGANISM: artificial sequence
<220> FEATURE:
<223> OTHER INFORMATION: 5' CEACAM5 EcoRI ; oligonucleotide

<400> SEQUENCE: 74
```

-continued gaattcgcca ccatggagtc tccctcggcc cc                                                                32

<210> SEQ ID NO 75
<211> LENGTH: 24
<212> TYPE: DNA
<213> ORGANISM: artificial sequence
<220> FEATURE:
<223> OTHER INFORMATION: 3' CEACAM5 SaII ; oligonucleotide

<400> SEQUENCE: 75
gtcgacctat atcagagcaa cccc                                                                         24

<210> SEQ ID NO 76
<211> LENGTH: 702
<212> TYPE: PRT
<213> ORGANISM: Homo sapiens
<220> FEATURE:
<221> NAME/KEY: MISC_FEATURE
<223> OTHER INFORMATION: CEACAM5 (NM_004363) ; protein

<400> SEQUENCE: 76

```
Met Glu Ser Pro Ser Ala Pro Pro His Arg Trp Cys Ile Pro Trp Gln
1               5                   10                  15

Arg Leu Leu Leu Thr Ala Ser Leu Leu Thr Phe Trp Asn Pro Pro Thr
            20                  25                  30

Thr Ala Lys Leu Thr Ile Glu Ser Thr Pro Phe Asn Val Ala Glu Gly
        35                  40                  45

Lys Glu Val Leu Leu Leu Val His Asn Leu Pro Gln His Leu Phe Gly
    50                  55                  60

Tyr Ser Trp Tyr Lys Gly Glu Arg Val Asp Gly Asn Arg Gln Ile Ile
65                  70                  75                  80

Gly Tyr Val Ile Gly Thr Gln Gln Ala Thr Pro Gly Pro Ala Tyr Ser
                85                  90                  95

Gly Arg Glu Ile Ile Tyr Pro Asn Ala Ser Leu Leu Ile Gln Asn Ile
            100                 105                 110

Ile Gln Asn Asp Thr Gly Phe Tyr Thr Leu His Val Ile Lys Ser Asp
        115                 120                 125

Leu Val Asn Glu Glu Ala Thr Gly Gln Phe Arg Val Tyr Pro Glu Leu
    130                 135                 140

Pro Lys Pro Ser Ile Ser Ser Asn Asn Ser Lys Pro Val Glu Asp Lys
145                 150                 155                 160

Asp Ala Val Ala Phe Thr Cys Glu Pro Glu Thr Gln Asp Ala Thr Tyr
                165                 170                 175

Leu Trp Trp Val Asn Asn Gln Ser Leu Pro Val Ser Pro Arg Leu Gln
            180                 185                 190

Leu Ser Asn Gly Asn Arg Thr Leu Thr Leu Phe Asn Val Thr Arg Asn
        195                 200                 205

Asp Thr Ala Ser Tyr Lys Cys Glu Thr Gln Asn Pro Val Ser Ala Arg
    210                 215                 220

Arg Ser Asp Ser Val Ile Leu Asn Val Leu Tyr Gly Pro Asp Ala Pro
225                 230                 235                 240

Thr Ile Ser Pro Leu Asn Thr Ser Tyr Arg Ser Gly Glu Asn Leu Asn
                245                 250                 255

Leu Ser Cys His Ala Ala Ser Asn Pro Pro Ala Gln Tyr Ser Trp Phe
            260                 265                 270

Val Asn Gly Thr Phe Gln Gln Ser Thr Gln Glu Leu Phe Ile Pro Asn
        275                 280                 285
```

-continued

```
Ile Thr Val Asn Asn Ser Gly Ser Tyr Thr Cys Gln Ala His Asn Ser
    290                 295                 300
Asp Thr Gly Leu Asn Arg Thr Thr Val Thr Thr Ile Thr Val Tyr Ala
305                 310                 315                 320
Glu Pro Pro Lys Pro Phe Ile Thr Ser Asn Asn Ser Asn Pro Val Glu
                325                 330                 335
Asp Glu Asp Ala Val Ala Leu Thr Cys Glu Pro Glu Ile Gln Asn Thr
            340                 345                 350
Thr Tyr Leu Trp Trp Val Asn Asn Gln Ser Leu Pro Val Ser Pro Arg
        355                 360                 365
Leu Gln Leu Ser Asn Asp Asn Arg Thr Leu Thr Leu Leu Ser Val Thr
370                 375                 380
Arg Asn Asp Val Gly Pro Tyr Glu Cys Gly Ile Gln Asn Glu Leu Ser
385                 390                 395                 400
Val Asp His Ser Asp Pro Val Ile Leu Asn Val Leu Tyr Gly Pro Asp
            405                 410                 415
Asp Pro Thr Ile Ser Pro Ser Tyr Thr Tyr Tyr Arg Pro Gly Val Asn
                420                 425                 430
Leu Ser Leu Ser Cys His Ala Ala Ser Asn Pro Pro Ala Gln Tyr Ser
            435                 440                 445
Trp Leu Ile Asp Gly Asn Ile Gln Gln His Thr Gln Glu Leu Phe Ile
        450                 455                 460
Ser Asn Ile Thr Glu Lys Asn Ser Gly Leu Tyr Thr Cys Gln Ala Asn
465                 470                 475                 480
Asn Ser Ala Ser Gly His Ser Arg Thr Thr Val Lys Thr Ile Thr Val
                485                 490                 495
Ser Ala Glu Leu Pro Lys Pro Ser Ile Ser Ser Asn Asn Ser Lys Pro
            500                 505                 510
Val Glu Asp Lys Asp Ala Val Ala Phe Thr Cys Glu Pro Glu Ala Gln
                515                 520                 525
Asn Thr Thr Tyr Leu Trp Trp Val Asn Gly Gln Ser Leu Pro Val Ser
        530                 535                 540
Pro Arg Leu Gln Leu Ser Asn Gly Asn Arg Thr Leu Thr Leu Phe Asn
545                 550                 555                 560
Val Thr Arg Asn Asp Ala Arg Ala Tyr Val Cys Gly Ile Gln Asn Ser
            565                 570                 575
Val Ser Ala Asn Arg Ser Asp Pro Val Thr Leu Asp Val Leu Tyr Gly
                580                 585                 590
Pro Asp Thr Pro Ile Ile Ser Pro Pro Asp Ser Ser Tyr Leu Ser Gly
        595                 600                 605
Ala Asn Leu Asn Leu Ser Cys His Ser Ala Ser Asn Pro Ser Pro Gln
610                 615                 620
Tyr Ser Trp Arg Ile Asn Gly Ile Pro Gln Gln His Thr Gln Val Leu
625                 630                 635                 640
Phe Ile Ala Lys Ile Thr Pro Asn Asn Asn Gly Thr Tyr Ala Cys Phe
                645                 650                 655
Val Ser Asn Leu Ala Thr Gly Arg Asn Asn Ser Ile Val Lys Ser Ile
            660                 665                 670
Thr Val Ser Ala Ser Gly Thr Ser Pro Gly Leu Ser Ala Gly Ala Thr
                675                 680                 685
Val Gly Ile Met Ile Gly Val Leu Val Gly Val Ala Leu Ile
        690                 695                 700
```

<210> SEQ ID NO 77
<211> LENGTH: 243
<212> TYPE: PRT
<213> ORGANISM: artificial sequence
<220> FEATURE:
<223> OTHER INFORMATION: De-immunized anti-CD3 VHVL single chain Fv as
      described in WO2005/040220

<400> SEQUENCE: 77

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
                100                 105                 110

Thr Thr Val Thr Val Ser Ser Gly Glu Gly Thr Ser Thr Gly Ser Gly
            115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys

<210> SEQ ID NO 78
<211> LENGTH: 38
<212> TYPE: DNA
<213> ORGANISM: artificial sequence
<220> FEATURE:
<223> OTHER INFORMATION: 5'-huVK1-SacI-2001 ; oligonucleotide

<400> SEQUENCE: 78
gagccgcacg agcccgagct ccagatgacc cagtctcc                          38

<210> SEQ ID NO 79
<211> LENGTH: 38
<212> TYPE: DNA
<213> ORGANISM: artificial sequence
<220> FEATURE:
<223> OTHER INFORMATION: 5'-huVK2/4-SacI-2001 ; oligonucleotide

<400> SEQUENCE: 79
gagccgcacg agcccgagct cgtgatgacy cagtctcc                          38

<210> SEQ ID NO 80
<211> LENGTH: 38
<212> TYPE: DNA
<213> ORGANISM: artificial sequence
<220> FEATURE:
<223> OTHER INFORMATION: 5'-huVK3-SacI-2001 ; oligonucleotide

<400> SEQUENCE: 80
gagccgcacg agcccgagct cgtgwtgacr cagtctcc                          38

<210> SEQ ID NO 81
<211> LENGTH: 38
<212> TYPE: DNA
<213> ORGANISM: artificial sequence
<220> FEATURE:
<223> OTHER INFORMATION: 5'-huVK5-SacI-2001 ; oligonucleotide

<400> SEQUENCE: 81
gagccgcacg agcccgagct cacactcacg cagtctcc                          38

<210> SEQ ID NO 82
<211> LENGTH: 38
<212> TYPE: DNA
<213> ORGANISM: ARTIFICIAL SEQUENCE
<220> FEATURE:
<223> OTHER INFORMATION: 5'-huVK6-SacI-2001 ; oligonucleotide

<400> SEQUENCE: 82
gagccgcacg agcccgagct cgtgctgact cagtctcc                          38

<210> SEQ ID NO 83
<211> LENGTH: 47
<212> TYPE: DNA
<213> ORGANISM: artificial sequence
<220> FEATURE:
<223> OTHER INFORMATION: 3'-hu-Vk-J1-SpeI-BsiWI ; oligonucleotide

<400> SEQUENCE: 83
gacgacacta gttgcagcca ccgtacgttt gatttccacc ttggtcc                47

<210> SEQ ID NO 84
<211> LENGTH: 47
<212> TYPE: DNA
<213> ORGANISM: artificial sequence
<220> FEATURE:
<223> OTHER INFORMATION: 3'-hu-Vk-J2/4-SpeI-Bsi/WI ; oligonucleotide

<400> SEQUENCE: 84
gacgacacta gttgcagcca ccgtacgttt gatctccasc ttggtcc                47

<210> SEQ ID NO 85
<211> LENGTH: 47
<212> TYPE: DNA
<213> ORGANISM: artificial sequence
<220> FEATURE:
<223> OTHER INFORMATION: 3'-hu-Vk-J3-SpeI-BsiWI ; oligonucleotide

<400> SEQUENCE: 85
gacgacacta gttgcagcca ccgtacgttt gatatccact ttggtcc                47

<210> SEQ ID NO 86
<211> LENGTH: 47
<212> TYPE: DNA

<213> ORGANISM: artificial sequence
<220> FEATURE:
<223> OTHER INFORMATION: 3'-hu-Vk-J5-SpeI-BsiWI ; oligonucleotide

<400> SEQUENCE: 86
gacgacacta gttgcagcca ccgtacgttt aatctccagt cgtgtcc                47

<210> SEQ ID NO 87
<211> LENGTH: 41
<212> TYPE: DNA
<213> ORGANISM: artificial sequence
<220> FEATURE:
<223> OTHER INFORMATION: 5'-huVL1a-SacI-2001 ; oligonucleotide

<400> SEQUENCE: 87
gagccgcacg agcccgagct cgtgttgacg cagccgccct c                      41

<210> SEQ ID NO 88
<211> LENGTH: 41
<212> TYPE: DNA
<213> ORGANISM: artificial sequence
<220> FEATURE:
<223> OTHER INFORMATION: 5'-huVL1b-SacI-2001 ; oligonucleotide

<400> SEQUENCE: 88
gagccgcacg agcccgagct cgtgctgact cagccaccct c                      41

<210> SEQ ID NO 89
<211> LENGTH: 44
<212> TYPE: DNA
<213> ORGANISM: artificial sequence
<220> FEATURE:
<223> OTHER INFORMATION: 5'-huVL2-SacI-2001 ; oligonucleotide

<400> SEQUENCE: 89
gagccgcagg agcccgagct cgccctgact cagcctscct ccgt                   44

<210> SEQ ID NO 90
<211> LENGTH: 35
<212> TYPE: DNA
<213> ORGANISM: artificial sequence
<220> FEATURE:
<223> OTHER INFORMATION: 5'-huVL4-SacI-2001 ; oligonucleotide

<400> SEQUENCE: 90
acctgcgagc tcgtgctgac tcarycmycc tctgc                             35

<210> SEQ ID NO 91
<211> LENGTH: 33
<212> TYPE: DNA
<213> ORGANISM: artificial sequence
<220> FEATURE:
<223> OTHER INFORMATION: 5'-huVL5-SacI-2001 ; oligonucleotide

<400> SEQUENCE: 91
acctgcgagc tcgtgctgac tcagccrsct tcc                               33

<210> SEQ ID NO 92
<211> LENGTH: 32
<212> TYPE: DNA
<213> ORGANISM: artificial sequence
<220> FEATURE:
<223> OTHER INFORMATION: 5'-huVL6-SacI-2001 ; oligonucleotide

<400> SEQUENCE: 92
acctgcgagc tcatgctgac tcagccccac tc                                32

<210> SEQ ID NO 93
<211> LENGTH: 41
<212> TYPE: DNA
<213> ORGANISM: artificial sequence
<220> FEATURE:
<223> OTHER INFORMATION: 5'-huVL3/9-SacI-2001 ; oligonucleotide

<400> SEQUENCE: 93
gagccgcacg agcccgagct cgwgctgact cagccaccyt c             41

<210> SEQ ID NO 94
<211> LENGTH: 41
<212> TYPE: DNA
<213> ORGANISM: artificial sequence
<220> FEATURE:
<223> OTHER INFORMATION: 5'-huVL7/8-SacI-2001 ; oligonucleotide

<400> SEQUENCE: 94
gagccgcacg agcccgagct cgtggtgacy caggagccmt c             41

<210> SEQ ID NO 95
<211> LENGTH: 33
<212> TYPE: DNA
<213> ORGANISM: artificial sequence
<220> FEATURE:
<223> OTHER INFORMATION: 3'-hu-VIam-BInI-SpeI-2001 ; oligonucleotide

<400> SEQUENCE: 95
cgtgggacta gtcttgggct gacctaggac ggt                      33

<210> SEQ ID NO 96
<211> LENGTH: 33
<212> TYPE: DNA
<213> ORGANISM: artificial sequence
<220> FEATURE:
<223> OTHER INFORMATION: 3'-hu-VIam2-BInI-SpeI-2002 ; oligonucleotide

<400> SEQUENCE: 96
cgtgggacta gtcttgggct gaccgaggac ggt                      33

<210> SEQ ID NO 97
<211> LENGTH: 31
<212> TYPE: DNA
<213> ORGANISM: artificial sequence
<220> FEATURE:
<223> OTHER INFORMATION: 5'-primer 5'-AVH-XhoI ; oligonucleotide

<400> SEQUENCE: 97
gtcacactcg agtcaggagg aggcttggta c                        31

<210> SEQ ID NO 98
<211> LENGTH: 31
<212> TYPE: DNA
<213> ORGANISM: artificial sequence
<220> FEATURE:
<223> OTHER INFORMATION: 3'-primer 3'-AVH-BstEII ; oligonucleotide

<400> SEQUENCE: 98
gtcacaggtg accgtggtcc cttggcccca g                        31

<210> SEQ ID NO 99
<211> LENGTH: 10
<212> TYPE: PRT
<213> ORGANISM: artificial sequence
<220> FEATURE:

<223> OTHER INFORMATION: Flag tag

<400> SEQUENCE: 99

Thr Gly Asp Tyr Lys Asp Asp Asp Asp Lys
1               5                   10

<210> SEQ ID NO 100
<211> LENGTH: 22
<212> TYPE: DNA
<213> ORGANISM: artificial sequence
<220> FEATURE:
<223> OTHER INFORMATION: 5'-huVH1,3,5-XhoI-2001 ; oligonucleotide

<400> SEQUENCE: 100
aggtgcagct gctcgagtct gg                                          22

<210> SEQ ID NO 101
<211> LENGTH: 23
<212> TYPE: DNA
<213> ORGANISM: artificial sequence
<220> FEATURE:
<223> OTHER INFORMATION: 5'-huVH4-XhoI-2001 ; oligonucleotide

<400> SEQUENCE: 101
caggtgcagc tgctcgagtc ggg                                         23

<210> SEQ ID NO 102
<211> LENGTH: 23
<212> TYPE: DNA
<213> ORGANISM: artificial sequence
<220> FEATURE:
<223> OTHER INFORMATION: 5'-huVH4B-XhoI-2001 ; oligonucleotide

<400> SEQUENCE: 102
caggtgcagc tactcgagtg ggg                                         23

<210> SEQ ID NO 103
<211> LENGTH: 17
<212> TYPE: DNA
<213> ORGANISM: artificial sequence
<220> FEATURE:
<223> OTHER INFORMATION: 3'-hu-VH-BstEII-2001 ; oligonucleotide

<400> SEQUENCE: 103
ctgaggagac ggtgacc                                                17

<210> SEQ ID NO 104
<211> LENGTH: 17
<212> TYPE: DNA
<213> ORGANISM: artificial sequence
<220> FEATURE:
<223> OTHER INFORMATION: 3'-hu-VH-J3-BstEII-2001 ; oligonucleotide

<400> SEQUENCE: 104
ctgaagagac ggtgacc                                                17

<210> SEQ ID NO 105
<211> LENGTH: 51
<212> TYPE: DNA
<213> ORGANISM: artificial sequence
<220> FEATURE:
<223> OTHER INFORMATION: 3'-A134-VH1A ; oligonucleotide

<400> SEQUENCE: 105
gtagtcaaag tagaaccgta gcccccctatc tctygcacag taatacacgg c         51

```
<210> SEQ ID NO 106
<211> LENGTH: 51
<212> TYPE: DNA
<213> ORGANISM: artificial sequence
<220> FEATURE:
<223> OTHER INFORMATION: 3'-A134-VH1B ; oligonucleotide

<400> SEQUENCE: 106
gtagtcaaag tagaaccgta gccccctatc tctygcacag taatacayrg c                51

<210> SEQ ID NO 107
<211> LENGTH: 51
<212> TYPE: DNA
<213> ORGANISM: artificial sequence
<220> FEATURE:
<223> OTHER INFORMATION: 3'-A134-VH3A ; oligonucleotide
<220> FEATURE:
<221> NAME/KEY: variation
<222> LOCATION: (34)..(34)
<223> OTHER INFORMATION: /replace= "a"
      /replace = "c"
      /replace = "g"

<400> SEQUENCE: 107
gtagtcaaag tagaaccgta gccccctatc tcttgyacag taatacacrg c                51

<210> SEQ ID NO 108
<211> LENGTH: 51
<212> TYPE: DNA
<213> ORGANISM: artificial sequence
<220> FEATURE:
<223> OTHER INFORMATION: 3'-A134-VH3B ; oligonucleotide
<220> FEATURE:
<221> NAME/KEY: variation
<222> LOCATION: (34)..(34)
<223> OTHER INFORMATION: /replace= "a"
      /replace = "c"
      /replace = "g"

<400> SEQUENCE: 108
gtagtcaaag tagaaccgta gccccctatc tcttgcacag taatacaarg c                51

<210> SEQ ID NO 109
<211> LENGTH: 51
<212> TYPE: DNA
<213> ORGANISM: artificial sequence
<220> FEATURE:
<223> OTHER INFORMATION: 3'-A134-VH4 ; oligonucleotide

<400> SEQUENCE: 109
gtagtcaaag tagaaccgta gccccctatc tctsgcacag taatacacrg c                51

<210> SEQ ID NO 110
<211> LENGTH: 53
<212> TYPE: DNA
<213> ORGANISM: artificial sequence
<220> FEATURE:
<223> OTHER INFORMATION: 3' A134-JH6-BstEII ; oligonucleotide

<400> SEQUENCE: 110
cgagacggtg accgtggtcc cttggcccca gtagtcaaag tagaaccgta gcc             53

<210> SEQ ID NO 111
<211> LENGTH: 207
<212> TYPE: PRT
<213> ORGANISM: Homo sapiens
<220> FEATURE:
<221> NAME/KEY: MISC_FEATURE
```

<223> OTHER INFORMATION: CD3 epsilon (NM_000733) ; protein

<400> SEQUENCE: 111

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205

<210> SEQ ID NO 112
<211> LENGTH: 5
<212> TYPE: PRT
<213> ORGANISM: Mus musculus
<220> FEATURE:
<221> NAME/KEY: MISC_FEATURE
<223> OTHER INFORMATION: CDR-H3 A5B7 Shorter CDR-3 of VH of A5B7
      corresponding to Kabat positions 100, 100a, 100b, 101, 102

<400> SEQUENCE: 112

Phe Tyr Phe Asp Tyr
1               5

<210> SEQ ID NO 113
<211> LENGTH: 6
<212> TYPE: PRT
<213> ORGANISM: Mus musculus
<220> FEATURE:
<221> NAME/KEY: MISC_FEATURE
<223> OTHER INFORMATION: CDR-H3 A5B7 Shorter CDR-3 of VH of A5B7
      corresponding to Kabat positions 99, 100, 100a, 100b, 101, 102

<400> SEQUENCE: 113

Arg Phe Tyr Phe Asp Tyr
1               5

<210> SEQ ID NO 114
<211> LENGTH: 7
<212> TYPE: PRT
<213> ORGANISM: Mus musculus
<220> FEATURE:

```
<221> NAME/KEY: MISC_FEATURE
<223> OTHER INFORMATION: CDR-H3 A5B7 Shorter CDR-3 of VH of A5B7
      corresponding to Kabat positions 98, 99, 100, 100a, 100b, 101, 102

<400> SEQUENCE: 114

Leu Arg Phe Tyr Phe Asp Tyr
1               5

<210> SEQ ID NO 115
<211> LENGTH: 8
<212> TYPE: PRT
<213> ORGANISM: Mus musculus
<220> FEATURE:
<221> NAME/KEY: MISC_FEATURE
<223> OTHER INFORMATION: CDR-H3 A5B7 Shorter CDR-3 of VH of A5B7
      corresponding to Kabat positions 97, 98, 99, 100, 100a, 100b, 101,
      102

<400> SEQUENCE: 115

Gly Leu Arg Phe Tyr Phe Asp Tyr
1               5

<210> SEQ ID NO 116
<211> LENGTH: 9
<212> TYPE: PRT
<213> ORGANISM: Mus musculus
<220> FEATURE:
<221> NAME/KEY: MISC_FEATURE
<223> OTHER INFORMATION: DR-H3 A5B7 Shorter CDR-3 of VH of A5B7
      corresponding to Kabat positions 96, 97, 98, 99, 100, 100a, 100b,
      101, 102

<400> SEQUENCE: 116

Arg Gly Leu Arg Phe Tyr Phe Asp Tyr
1               5

<210> SEQ ID NO 117
<211> LENGTH: 759
<212> TYPE: DNA
<213> ORGANISM: artificial sequence
<220> FEATURE:
<223> OTHER INFORMATION: A240 VL - A5B7 VH ; single chain Fv

<400> SEQUENCE: 117
caggccgtgc tgactcagcc ggcttccctc tctgcatctc ctggagcatc agccagtctc      60
acctgcacct tgcgcagggg catcaatgtt ggtgcctaca gtatatactg gtaccagcag     120
aagccaggga gtcctcccca gtatctcctg aggtacaaat cagactcaga taagcagcag     180
ggctctggag tctccagccg cttctctgca tccaaagatg cttcggccaa tgcagggatt     240
ttactcatct ctgggctcca gtctgaggat gaggctgact attactgtat gatttggcac     300
agcgcgcgct tctgcggtgt tcggcgaggg accaagttga ccgtcctagg tggtggtggt     360
tctggcggcg gcggctccgg tggtggtggt tctgaggtgc agctggtcga gtcaggagga     420
ggcttggtac agcctggggg ttctctgaga ctctcctgtg caacttctgg gttcaccttc     480
actgattact acatgaactg ggtccgccag cctccaggaa aggcacttga gtggttgggt     540
tttattggaa acaaagctaa tggttacaca acagagtaca gtgcatctgt gaagggtcgg     600
ttcaccatct ccagagataa atcccaaagc atcctctatc ttcaaatgaa caccctgaga     660
gctgaggaca gtgccactta ttactgtacc agagataggg gctacggttc tactttgac      720 tactggggcc aagggaccac ggtcaccgtc tcctcctga                           759

<210> SEQ ID NO 118
```

<211> LENGTH: 252
<212> TYPE: PRT
<213> ORGANISM: artificial sequence
<220> FEATURE:
<223> OTHER INFORMATION: A240 VL - A5B7 VH ; single chain Fv

<400> SEQUENCE: 118

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Ala Thr Ser Gly Phe Thr Phe
145                 150                 155                 160

Thr Asp Tyr Tyr Met Asn Trp Val Arg Gln Pro Pro Gly Lys Ala Leu
                165                 170                 175

Glu Trp Leu Gly Phe Ile Gly Asn Lys Ala Asn Gly Tyr Thr Thr Glu
            180                 185                 190

Tyr Ser Ala Ser Val Lys Gly Arg Phe Thr Ile Ser Arg Asp Lys Ser
        195                 200                 205

Gln Ser Ile Leu Tyr Leu Gln Met Asn Thr Leu Arg Ala Glu Asp Ser
    210                 215                 220

Ala Thr Tyr Tyr Cys Thr Arg Asp Arg Gly Leu Arg Phe Tyr Phe Asp
225                 230                 235                 240

Tyr Trp Gly Gln Gly Thr Thr Val Thr Val Ser Ser
                245                 250

<210> SEQ ID NO 119
<211> LENGTH: 753
<212> TYPE: DNA
<213> ORGANISM: Homo sapiens
<220> FEATURE:
<221> NAME/KEY: misc_feature
<223> OTHER INFORMATION: A240VL - A5 VH ; single chain Fv

<400> SEQUENCE: 119
caggccgtgc tgactcagcc ggcttccctc tctgcatctc ctggagcatc agccagtctc        60
acctgcacct tgcgcagggg catcaatgtt ggtgcctaca gtatatactg gtaccagcag       120
aagccaggga gtcctcccca gtatctcctg aggtacaaat cagactcaga taagcagcag       180
ggctctggag tctccagccg cttctctgca tccaaagatg cttcggccaa tgcagggatt       240
ttactcatct ctgggctcca gtctgaggat gaggctgact attactgtat gatttggcac       300
agcggcgctt ctgcggtgtt cggcggaggg accaagttga ccgtcctagg tggtggtggt       360

```
tctggcggcg gcggctccgg tggtggtggt tctgaggtgc agctggtcga gtctggggga    420
ggcgtggtcc agcctgggag gtccctgaga ctctcctgtg cagcctctgg attcacccte    480 agtacctatg ccatgcactg ggtccgccag gctccaggca aggggctgga gtgggtggca    540
cttatatcaa atgatggaag caataaatac tatgcagact ccgtgaaggg ccgattcacc    600
atctccagag acaattccaa gaacacgctg tatctgcaaa tgaacagcct gagagctgag    660
gacacggccg tgtattactg tgcgagagat aggggggctac ggttctactt tgactactgg    720
ggccaaggga ccacggtcac cgtctcctcc tga                                 753
```

<210> SEQ ID NO 120
<211> LENGTH: 250
<212> TYPE: PRT
<213> ORGANISM: Homo sapiens
<220> FEATURE:
<221> NAME/KEY: MISC_FEATURE
<223> OTHER INFORMATION: A240VL - A5 VH ; single chain Fv

<400> SEQUENCE: 120

```
Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Val Val Gln
    130                 135                 140

Pro Gly Arg Ser Leu Arg Leu Ser Cys Ala Ala Ser Gly Phe Thr Leu
145                 150                 155                 160

Ser Thr Tyr Ala Met His Trp Val Arg Gln Ala Pro Gly Lys Gly Leu
                165                 170                 175

Glu Trp Val Ala Leu Ile Ser Asn Asp Gly Ser Asn Lys Tyr Tyr Ala
            180                 185                 190

Asp Ser Val Lys Gly Arg Phe Thr Ile Ser Arg Asp Asn Ser Lys Asn
        195                 200                 205

Thr Leu Tyr Leu Gln Met Asn Ser Leu Arg Ala Glu Asp Thr Ala Val
    210                 215                 220

Tyr Tyr Cys Ala Arg Asp Arg Gly Leu Arg Phe Tyr Phe Asp Tyr Trp
225                 230                 235                 240

Gly Gln Gly Thr Thr Val Thr Val Ser Ser
                245                 250
```

<210> SEQ ID NO 121
<211> LENGTH: 759
<212> TYPE: DNA
<213> ORGANISM: Homo sapiens
<220> FEATURE:

<221> NAME/KEY: misc_feature
<223> OTHER INFORMATION: A240VL - B9 VH ; single chain Fv

<400> SEQUENCE: 121

| | |
|---|---|
| caggccgtgc tgactcagcc ggcttccctc tctgcatctc ctggagcatc agccagtctc | 60 |
| acctgcacct tgcgcagggg catcaatgtt ggtgcctaca gtatatactg gtaccagcag | 120 |
| aagccaggga gtcctcccca gtatctcctg aggtacaaat cagactcaga taagcagcag | 180 |
| ggctctggag tctccagccg cttctctgca tccaaagatg cttcggccaa tgcagggatt | 240 |
| ttactcatct ctgggctcca gtctgaggat gaggctgact attactgtat gatttggcac | 300 |
| agcggcgctt ctgcggtgtt cggcggaggg accaagttga ccgtcctagg tggtggtggt | 360 |
| tctggcggcg gcggctccgg tggtggtggt tctgaggtgc agctggtcga gtctggggga | 420 |
| ggcttggtcc agcctgggag gtccctgaga ctctcctgtg cagcgtctgg attcaccgtc | 480 |
| agtagctact ggatgcactg ggtccgccaa gctccaggga aggggctgga atgggtaggt | 540 |
| ttcattagaa acaaagctaa tggtgggaca acagaatacg ccgcgtctgt gaaaggcaga | 600 |
| ttcaccatct caagagatga ttccaagaac acgctgtatc ttcaaatgaa cagcctgaga | 660 |
| gccgaggaca cggccgtgta ttactgtgca agagataggg ggctacggtt ctactttgac | 720 |
| tactggggcc aagggaccac ggtcaccgtc tcctcctga | 759 |

<210> SEQ ID NO 122
<211> LENGTH: 252
<212> TYPE: PRT
<213> ORGANISM: Homo sapiens
<220> FEATURE:
<221> NAME/KEY: MISC_FEATURE
<223> OTHER INFORMATION: A240VL - B9 VH ; single chain Fv

<400> SEQUENCE: 122

Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110

Leu Thr Val Leu Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Arg Ser Leu Arg Leu Ser Cys Ala Ala Ser Gly Phe Thr Val
145                 150                 155                 160

Ser Ser Tyr Trp Met His Trp Val Arg Gln Ala Pro Gly Lys Gly Leu
                165                 170                 175

Glu Trp Val Gly Phe Ile Arg Asn Lys Ala Asn Gly Gly Thr Thr Glu
            180                 185                 190

Tyr Ala Ala Ser Val Lys Gly Arg Phe Thr Ile Ser Arg Asp Asp Ser

```
            195                 200                 205
Lys Asn Thr Leu Tyr Leu Gln Met Asn Ser Leu Arg Ala Glu Asp Thr
    210                 215                 220

Ala Val Tyr Tyr Cys Ala Arg Asp Arg Gly Leu Arg Phe Tyr Phe Asp
225                 230                 235                 240

Tyr Trp Gly Gln Gly Thr Thr Val Thr Val Ser Ser
                245                 250
```

<210> SEQ ID NO 123
<211> LENGTH: 753
<212> TYPE: DNA
<213> ORGANISM: Homo sapiens
<220> FEATURE:
<221> NAME/KEY: misc_feature
<223> OTHER INFORMATION: A240VL - D8 VH ; single chain Fv

<400> SEQUENCE: 123

```
caggccgtgc tgactcagcc ggcttccctc tctgcatctc ctggagcatc agccagtctc    60
acctgcacct tgcgcagggg catcaatgtt ggtgcctaca gtatatactg gtaccagcag   120
aagccaggga gtcctcccca gtatctcctg aggtacaaat cagactcaga taagcagcag   180
ggctctggag tctccagccg cttctctgca tccaaagatg cttcggccaa tgcagggatt   240
ttactcatct ctgggctcca gtctgaggat gaggctgact attactgtat gatttggcac   300
agcggcgctt ctgcggtgtt cggcggaggg accaagttga ccgtcctagg tggtggtggt   360
tctggcggcg gcggctccgg tggtggtggt tctgaggtgc agctggtcga gtctggggga   420
ggcgtggtcc agcctgggag gtccctgaga ctctcctgtg cagcctctgg attcaccctc   480
agtacctatg ccatgcactg ggtccgccag gctccaggca aggggctgga gtgggtggca   540
cttatatcaa atgatggaag caataaatac tatgcagact ccgtgaaggg ccgattcacc   600
atctccagag acaattccaa gaacacgctg tatctgcaaa tgaacagcct gagagctgag   660
gacacggctg tgtattactg tactagagat agggggctac ggttctactt tgactactgg   720
ggccaaggga ccacggtcac cgtctcctcc tga                                753
```

<210> SEQ ID NO 124
<211> LENGTH: 250
<212> TYPE: PRT
<213> ORGANISM: Homo sapiens
<220> FEATURE:
<221> NAME/KEY: MISC_FEATURE
<223> OTHER INFORMATION: A240VL - D8 VH ; single chain Fv

<400> SEQUENCE: 124

```
Gln Ala Val Leu Thr Gln Pro Ala Ser Leu Ser Ala Ser Pro Gly Ala
1               5                   10                  15

Ser Ala Ser Leu Thr Cys Thr Leu Arg Arg Gly Ile Asn Val Gly Ala
            20                  25                  30

Tyr Ser Ile Tyr Trp Tyr Gln Gln Lys Pro Gly Ser Pro Pro Gln Tyr
        35                  40                  45

Leu Leu Arg Tyr Lys Ser Asp Ser Asp Lys Gln Gln Gly Ser Gly Val
    50                  55                  60

Ser Ser Arg Phe Ser Ala Ser Lys Asp Ala Ser Ala Asn Ala Gly Ile
65                  70                  75                  80

Leu Leu Ile Ser Gly Leu Gln Ser Glu Asp Glu Ala Asp Tyr Tyr Cys
                85                  90                  95

Met Ile Trp His Ser Gly Ala Ser Ala Val Phe Gly Gly Gly Thr Lys
            100                 105                 110
```

```
Leu Thr Val Leu Gly Gly Gly Ser Gly Gly Gly Ser Gly Gly
        115                 120                 125

Gly Gly Ser Glu Val Gln Leu Val Glu Ser Gly Gly Val Val Gln
        130                 135                 140

Pro Gly Arg Ser Leu Arg Leu Ser Cys Ala Ala Ser Gly Phe Thr Leu
145                 150                 155                 160

Ser Thr Tyr Ala Met His Trp Val Arg Gln Ala Pro Gly Lys Gly Leu
                165                 170                 175

Glu Trp Val Ala Leu Ile Ser Asn Asp Gly Ser Asn Lys Tyr Tyr Ala
                180                 185                 190

Asp Ser Val Lys Gly Arg Phe Thr Ile Ser Arg Asp Asn Ser Lys Asn
                195                 200                 205

Thr Leu Tyr Leu Gln Met Asn Ser Leu Arg Ala Glu Asp Thr Ala Val
                210                 215                 220

Tyr Tyr Cys Thr Arg Asp Arg Gly Leu Arg Phe Tyr Phe Asp Tyr Trp
225                 230                 235                 240

Gly Gln Gly Thr Thr Val Thr Val Ser Ser
                245                 250
```

<210> SEQ ID NO 125
<211> LENGTH: 1500
<212> TYPE: DNA
<213> ORGANISM: artificial sequence
<220> FEATURE:
<223> OTHER INFORMATION: A5 VH - A240 VL# x SEQ ID NO: 77 VHVL ;
      Bispecific single chain antibody

<400> SEQUENCE: 125

```
gaggtgcagc tggtcgagtc tgggggaggc gtggtccagc ctgggaggtc cctgagactc      60
tcctgtgcag cctctggatt caccctcagt acctatgcca tgcactgggt ccgccaggct     120
ccaggcaagg gctgagtg gtggcactt atatcaaatg atggaagcaa taaatactat        180
gcagactccg tgaagggccg attcaccatc tccagagaca attccaagaa cacgctgtat     240
ctgcaaatga acagcctgag agctgaggac acggccgtgt attactgtgc gagagatagg     300
gggctacggt tctactttga ctactggggc caagggacca cggtcaccgt ctcctcaggt     360
ggtggtggtt ctggcggcgg cggctccggt ggtggtggtt ctcaggccgt gctgactcag     420
ccggcttccc tctctgcatc tcctggagca tcagccagtc tcacctgcac cttgcgcagg     480
ggcatcaatg ttggtgccta cagtatatac tggtaccagc agaagccagg gagtcctccc     540
cagtatctcc tgaggtacaa atcagactca gataagcagc agggctctgg agtctccagc     600
cgcttctctg catccaaaga tgcttcggcc aatgcaggga ttttactcat ctctgggctc     660
cagtctgagg atgaggctga ctattactgt atgatttggc acagcggcgc ttctgcggtg     720
ttcggcggag ggaccaagtt gaccgtccta tccggaggtg gtggatccga cgtccaactg     780
gtgcagtcag ggctgaagt gaaaaaacct ggggcctcag tgaaggtgtc ctgcaaggct     840
tctggctaca cctttactag gtacacgatg cactgggtaa ggcaggcacc tggacagggt     900
ctggaatgga ttggatacat taatcctagc cgtggttata ctaattacgc agacagcgtc     960
aagggccgct tcacaatcac tacagacaaa tccaccagca cagcctacat ggaactgagc    1020
agcctgcgtt ctgaggacac tgcaacctat tactgtgcaa gatattatga tgatcattac    1080
tgccttgact actggggcca aggcaccacg gtcaccgtct cctcaggcga aggtactagt    1140
actggttctg gtggaagtgg aggttcaggt ggagcagacg acattgtact gacccagtct    1200
```

-continued

```
ccagcaactc tgtctctgtc tccaggggag cgtgccaccc tgagctgcag agccagtcaa    1260
agtgtaagtt acatgaactg gtaccagcag aagccgggca aggcacccaa aagatggatt    1320
tatgacacat ccaaagtggc ttctggagtc cctgctcgct tcagtggcag tgggtctggg    1380
accgactact ctctcacaat caacagcttg gaggctgaag atgctgccac ttattactgc    1440
caacagtgga gtagtaaccc gctcacgttc ggtggcggga ccaaggtgga gatcaaatag    1500
```

<210> SEQ ID NO 126
<211> LENGTH: 499
<212> TYPE: PRT
<213> ORGANISM: artificial sequence
<220> FEATURE:
<223> OTHER INFORMATION: A5 VH - A240 VL# x SEQ ID NO: 77 VHVL ;
      Bispecific single chain antibody

<400> SEQUENCE: 126

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Leu Arg Phe Tyr Phe Asp Tyr Trp Gly Gln Gly
            100                 105                 110

Thr Thr Val Thr Val Ser Ser Gly Gly Gly Ser Gly Gly Gly Gly
        115                 120                 125

Ser Gly Gly Gly Gly Ser Gln Ala Val Leu Thr Gln Pro Ala Ser Leu
    130                 135                 140

Ser Ala Ser Pro Gly Ala Ser Ala Ser Leu Thr Cys Thr Leu Arg Arg
145                 150                 155                 160

Gly Ile Asn Val Gly Ala Tyr Ser Ile Tyr Trp Tyr Gln Gln Lys Pro
                165                 170                 175

Gly Ser Pro Pro Gln Tyr Leu Leu Arg Tyr Lys Ser Asp Ser Asp Lys
            180                 185                 190

Gln Gln Gly Ser Gly Val Ser Ser Arg Phe Ser Ala Ser Lys Asp Ala
        195                 200                 205

Ser Ala Asn Ala Gly Ile Leu Leu Ile Ser Gly Leu Gln Ser Glu Asp
    210                 215                 220

Glu Ala Asp Tyr Tyr Cys Met Ile Trp His Ser Gly Ala Ser Ala Val
225                 230                 235                 240

Phe Gly Gly Gly Thr Lys Leu Thr Val Leu Ser Gly Gly Gly Gly Ser
                245                 250                 255

Asp Val Gln Leu Val Gln Ser Gly Ala Glu Val Lys Lys Pro Gly Ala
            260                 265                 270

Ser Val Lys Val Ser Cys Lys Ala Ser Gly Tyr Thr Phe Thr Arg Tyr
        275                 280                 285

Thr Met His Trp Val Arg Gln Ala Pro Gly Gln Gly Leu Glu Trp Ile
    290                 295                 300

Gly Tyr Ile Asn Pro Ser Arg Gly Tyr Thr Asn Tyr Ala Asp Ser Val

```
                305                 310                 315                 320
Lys Gly Arg Phe Thr Ile Thr Thr Asp Lys Ser Thr Ser Thr Ala Tyr
                325                 330                 335

Met Glu Leu Ser Ser Leu Arg Ser Glu Asp Thr Ala Thr Tyr Tyr Cys
                340                 345                 350

Ala Arg Tyr Tyr Asp Asp His Tyr Cys Leu Asp Tyr Trp Gly Gln Gly
                355                 360                 365

Thr Thr Val Thr Val Ser Ser Gly Glu Gly Thr Ser Thr Gly Ser Gly
                370                 375                 380

Gly Ser Gly Gly Ser Gly Gly Ala Asp Asp Ile Val Leu Thr Gln Ser
385                 390                 395                 400

Pro Ala Thr Leu Ser Leu Ser Pro Gly Glu Arg Ala Thr Leu Ser Cys
                405                 410                 415

Arg Ala Ser Gln Ser Val Ser Tyr Met Asn Trp Tyr Gln Gln Lys Pro
                420                 425                 430

Gly Lys Ala Pro Lys Arg Trp Ile Tyr Asp Thr Ser Lys Val Ala Ser
                435                 440                 445

Gly Val Pro Ala Arg Phe Ser Gly Ser Gly Ser Gly Thr Asp Tyr Ser
                450                 455                 460

Leu Thr Ile Asn Ser Leu Glu Ala Glu Asp Ala Ala Thr Tyr Tyr Cys
465                 470                 475                 480

Gln Gln Trp Ser Ser Asn Pro Leu Thr Phe Gly Gly Gly Thr Lys Val
                485                 490                 495

Glu Ile Lys

<210> SEQ ID NO 127
<211> LENGTH: 1500
<212> TYPE: DNA
<213> ORGANISM: artificial sequence
<220> FEATURE:
<223> OTHER INFORMATION: SEQ ID NO: 77 VHVL x A5 VH - A240 VL# ;
      Bispecific single chain antibody

<400> SEQUENCE: 127
gacgtccaac tggtgcagtc aggggctgaa gtgaaaaaac tggggcctc  agtgaaggtg      60 tcctgcaagg cttctggcta cacctttact aggtacacga tgcactgggt aaggcaggca    120
cctggacagg gtctggaatg gattggatac attaatccta gccgtggtta tactaattac    180
gcagacagcg tcaagggccg cttcacaatc actacagaca atccaccag cacagcctac     240 atggaactga gcagcctgcg ttctgaggac actgcaacct attactgtgc aagatattat    300
gatgatcatt actgccttga ctactggggc caaggcacca cggtcaccgt ctcctcaggc    360
gaaggtacta gtactggttc tggtggaagt ggaggttcag gtggagcaga cgacattgta    420
ctgacccagt ctccagcaac tctgtctctg tctccagggg agcgtgccac cctgagctgc    480
agagccagtc aaagtgtaag ttacatgaac tggtaccagc agaagccggg caaggcaccc    540
aaaagatgga tttatgacac atccaaagtg gcttctggag tccctgctcg cttcagtggc    600
agtgggtctg ggaccgacta ctctctcaca atcaacagct ggaggctga  agatgctgcc    660 acttattact gccaacagtg gagtagtaac ccgctcacgt tcggtggcgg gaccaaggtg    720
gagatcaaat ccggaggtgg tggatccgag gtgcagctgg tcgagtctgg ggaggcgtg    780 gtccagcctg gaggtccct  gagactctcc tgtgcagcct ctggattcac cctcagtacc    840
tatgccatgc actgggtccg ccaggctcca ggcaaggggc tggagtgggt ggcacttata    900
tcaaatgatg gaagcaataa atactatgca gactccgtga agggccgatt caccatctcc    960
```

-continued

```
agagacaatt ccaagaacac gctgtatctg caaatgaaca gcctgagagc tgaggacacg    1020
gccgtgtatt actgtgcgag agataggggg ctacggttct actttgacta ctggggccaa    1080
gggaccacgg tcaccgtctc ctcaggtggt ggtggttctg gcggcggcgg ctccggtggt    1140
ggtggttctc aggccgtgct gactcagccg gcttccctct ctgcatctcc tggagcatca    1200
gccagtctca cctgcacctt gcgcaggggc atcaatgttg gtgcctacag tatatactgg    1260
taccagcaga agccagggag tcctccccag tatctcctga ggtacaaatc agactcagat    1320
aagcagcagg gctctggagt ctccagccgc ttctctgcat ccaaagatgc ttcggccaat    1380
gcagggattt actcatctc tgggctccag tctgaggatg aggctgacta ttactgtatg    1440
atttggcaca gcggcgcttc tgcggtgttc ggcggaggga ccaagttgac cgtcctatag    1500
```

<210> SEQ ID NO 128
<211> LENGTH: 499
<212> TYPE: PRT
<213> ORGANISM: artificial sequence
<220> FEATURE:
<223> OTHER INFORMATION: SEQ ID NO: 77 VHVL x A5 VH - A240 VL# ;
      Bispecific single chain antibody

<400> SEQUENCE: 128

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
                20                  25                  30

Thr Met His Trp Val Arg Gln Ala Pro Gly Gln Gly Leu Glu Trp Ile
            35                  40                  45

Gly Tyr Ile Asn Pro Ser Arg Gly Tyr Thr Asn Tyr Ala Asp Ser Val
        50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Ser Gly Gly Gly Ser Glu Val Gln Leu Val Glu Ser
                245                 250                 255

Gly Gly Gly Val Val Gln Pro Gly Arg Ser Leu Arg Leu Ser Cys Ala

|  | 260 |  |  |  | 265 |  |  |  | 270 |  |  |
|---|---|---|---|---|---|---|---|---|---|---|---|

Ala Ser Gly Phe Thr Leu Ser Thr Tyr Ala Met His Trp Val Arg Gln
       275            280          285

Ala Pro Gly Lys Gly Leu Glu Trp Val Ala Leu Ile Ser Asn Asp Gly
  290             295          300

Ser Asn Lys Tyr Tyr Ala Asp Ser Val Lys Gly Arg Phe Thr Ile Ser
305           310          315          320

Arg Asp Asn Ser Lys Asn Thr Leu Tyr Leu Gln Met Asn Ser Leu Arg
       325            330         335

Ala Glu Asp Thr Ala Val Tyr Tyr Cys Ala Arg Asp Arg Gly Leu Arg
          340         345         350

Phe Tyr Phe Asp Tyr Trp Gly Gln Gly Thr Thr Val Thr Val Ser Ser
       355            360         365

Gly Gly Gly Gly Ser Gly Gly Gly Ser Gly Gly Gly Ser Gln
  370             375         380

Ala Val Leu Thr Gln Pro Ala Ser Leu Ser Ala Ser Pro Gly Ala Ser
385           390          395         400

Ala Ser Leu Thr Cys Thr Leu Arg Arg Gly Ile Asn Val Gly Ala Tyr
          405         410         415

Ser Ile Tyr Trp Tyr Gln Gln Lys Pro Gly Ser Pro Pro Gln Tyr Leu
       420            425         430

Leu Arg Tyr Lys Ser Asp Ser Asp Lys Gln Gln Gly Ser Gly Val Ser
       435            440         445

Ser Arg Phe Ser Ala Ser Lys Asp Ala Ser Ala Asn Ala Gly Ile Leu
  450             455         460

Leu Ile Ser Gly Leu Gln Ser Glu Asp Glu Ala Asp Tyr Tyr Cys Met
465           470          475         480

Ile Trp His Ser Gly Ala Ser Ala Val Phe Gly Gly Gly Thr Lys Leu
          485         490         495

Thr Val Leu

<210> SEQ ID NO 129
<211> LENGTH: 1506
<212> TYPE: DNA
<213> ORGANISM: artificial sequence
<220> FEATURE:
<223> OTHER INFORMATION: B9 VH - A240 VL# x SEQ ID NO: 77 VHVL ;
     Bispecific single chain antibody

<400> SEQUENCE: 129

| | | | | | |
|---|---|---|---|---|---|
| gaggtgcagc | tggtcgagtc | tgggggaggc | ttggtccagc | ctggggaggtc | cctgagactc | 60 |
| tcctgtgcag | cgtctggatt | caccgtcagt | agctactgga | tgcactgggt | ccgccaagct | 120 |
| ccagggaagg | ggctggaatg | ggtaggtttc | attagaaaca | agctaatgg | tgggacaaca | 180 |
| gaatacgccg | cgtctgtgaa | aggcagattc | accatctcaa | gagatgattc | aagaacacg | 240 |
| ctgtatcttc | aaatgaacag | cctgagagcc | gaggacacgg | ccgtgtatta | ctgtgcaaga | 300 |
| gataggggc | tacggttcta | ctttgactac | tggggccaag | ggaccacggt | caccgtctcc | 360 |
| tcaggtggtg | gtggttctgg | cggcggcggc | tccggtggtg | gtggttctca | ggccgtgctg | 420 |
| actcagccgg | cttccctctc | tgcatctcct | ggagcatcag | ccagtctcac | ctgcaccttg | 480 |
| cgcaggggca | tcaatgttgg | tgcctacagt | atatactggt | accagcagaa | gccagggagt | 540 |
| cctccccagt | atctcctgag | gtacaaatca | gactcagata | agcagcaggg | ctctggagtc | 600 |
| tccagccgct | tctctgcatc | caaagatgct | tcggccaatg | cagggatttt | actcatctct | 660 |

```
gggctccagt ctgaggatga ggctgactat tactgtatga tttggcacag cggcgcttct    720
gcggtgttcg gcggagggac caagttgacc gtcctatccg aggtggtgg atccgacgtc     780
caactggtgc agtcaggggc tgaagtgaaa aaacctgggg cctcagtgaa ggtgtcctgc    840
aaggcttctg gctacacctt tactaggtac acgatgcact gggtaaggca ggcacctgga    900
cagggtctgg aatggattgg atacattaat cctagccgtg gttatactaa ttacgcagac    960
agcgtcaagg gccgcttcac aatcactaca gacaaatcca ccagcacagc ctacatggaa   1020
ctgagcagcc tgcgttctga ggacactgca acctattact gtgcaagata ttatgatgat   1080
cattactgcc ttgactactg gggccaaggc accacggtca ccgtctcctc aggcgaaggt   1140
actagtactg gttctggtgg aagtggaggt tcaggtggag cagacgacat tgtactgacc   1200
cagtctccag caactctgtc tctgtctcca ggggagcgtg ccaccctgag ctgcagagcc   1260
agtcaaagtg taagttacat gaactggtac cagcagaagc cgggcaaggc acccaaaaga   1320
tggatttatg acacatccaa agtggcttct ggagtccctg ctcgcttcag tggcagtggg   1380
tctgggaccg actactctct cacaatcaac agcttggagg ctgaagatgc tgccacttat   1440
tactgccaac agtggagtag taacccgctc acgttcggtg cgggaccaa ggtggagatc    1500
aaatag                                                              1506
```

<210> SEQ ID NO 130
<211> LENGTH: 501
<212> TYPE: PRT
<213> ORGANISM: artificial sequence
<220> FEATURE:
<223> OTHER INFORMATION: B9 VH - A240 VL# x SEQ ID NO: 77 VHVL ;
    Bispecific single chain antibody

<400> SEQUENCE: 130

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Arg Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Gln Ala Val Leu Thr Gln Pro Ala
    130                 135                 140

Ser Leu Ser Ala Ser Pro Gly Ala Ser Ala Ser Leu Thr Cys Thr Leu
145                 150                 155                 160

Arg Arg Gly Ile Asn Val Gly Ala Tyr Ser Ile Tyr Trp Tyr Gln Gln
                165                 170                 175

Lys Pro Gly Ser Pro Gln Tyr Leu Leu Arg Tyr Lys Ser Asp Ser
            180                 185                 190

Asp Lys Gln Gln Gly Ser Gly Val Ser Ser Arg Phe Ser Ala Ser Lys
        195                 200                 205
```

Asp Ala Ser Ala Asn Ala Gly Ile Leu Leu Ile Ser Gly Leu Gln Ser
210                 215                 220

Glu Asp Glu Ala Asp Tyr Tyr Cys Met Ile Trp His Ser Gly Ala Ser
225                 230                 235                 240

Ala Val Phe Gly Gly Gly Thr Lys Leu Thr Val Leu Ser Gly Gly Gly
            245                 250                 255

Gly Ser Asp Val Gln Leu Val Gln Ser Gly Ala Glu Val Lys Lys Pro
        260                 265                 270

Gly Ala Ser Val Lys Val Ser Cys Lys Ala Ser Gly Tyr Thr Phe Thr
    275                 280                 285

Arg Tyr Thr Met His Trp Val Arg Gln Ala Pro Gly Gln Gly Leu Glu
290                 295                 300

Trp Ile Gly Tyr Ile Asn Pro Ser Arg Gly Tyr Thr Asn Tyr Ala Asp
305                 310                 315                 320

Ser Val Lys Gly Arg Phe Thr Ile Thr Thr Asp Lys Ser Thr Ser Thr
            325                 330                 335

Ala Tyr Met Glu Leu Ser Ser Leu Arg Ser Glu Asp Thr Ala Thr Tyr
        340                 345                 350

Tyr Cys Ala Arg Tyr Tyr Asp Asp His Tyr Cys Leu Asp Tyr Trp Gly
    355                 360                 365

Gln Gly Thr Thr Val Thr Val Ser Ser Gly Glu Gly Thr Ser Thr Gly
370                 375                 380

Ser Gly Gly Ser Gly Gly Ser Gly Gly Ala Asp Asp Ile Val Leu Thr
385                 390                 395                 400

Gln Ser Pro Ala Thr Leu Ser Leu Ser Pro Gly Glu Arg Ala Thr Leu
            405                 410                 415

Ser Cys Arg Ala Ser Gln Ser Val Ser Tyr Met Asn Trp Tyr Gln Gln
        420                 425                 430

Lys Pro Gly Lys Ala Pro Lys Arg Trp Ile Tyr Asp Thr Ser Lys Val
    435                 440                 445

Ala Ser Gly Val Pro Ala Arg Phe Ser Gly Ser Gly Ser Gly Thr Asp
450                 455                 460

Tyr Ser Leu Thr Ile Asn Ser Leu Glu Ala Glu Asp Ala Ala Thr Tyr
465                 470                 475                 480

Tyr Cys Gln Gln Trp Ser Ser Asn Pro Leu Thr Phe Gly Gly Gly Thr
            485                 490                 495

Lys Val Glu Ile Lys
        500

<210> SEQ ID NO 131
<211> LENGTH: 1506
<212> TYPE: DNA
<213> ORGANISM: artificial sequence
<220> FEATURE:
<223> OTHER INFORMATION: SEQ ID NO: 77 VHVL x B9 VH - A240 VL# ;
      Bispecific single chain antibody

<400> SEQUENCE: 131
gacgtccaac tggtgcagtc aggggctgaa gtgaaaaaac ctggggcctc agtgaaggtg    60
tcctgcaagg cttctggcta cacctttact aggtacacga tgcactgggt aaggcaggca   120
cctggacagg gtctggaatg gattggatac attaatccta gccgtggtta tactaattac   180
gcagacagcg tcaagggccg cttcacaatc actacagaca aatccaccag cacagcctac   240
atggaactga gcagcctgcg ttctgaggac actgcaacct attactgtgc aagatattat   300

```
gatgatcatt actgccttga ctactggggc caaggcacca cggtcaccgt ctcctcaggc    360
gaaggtacta gtactggttc tggtggaagt ggaggttcag gtggagcaga cgacattgta    420
ctgacccagt ctccagcaac tctgtctctg tctccagggg agcgtgccac cctgagctgc    480
agagccagtc aaagtgtaag ttacatgaac tggtaccagc agaagccggg caaggcaccc    540
aaaagatgga tttatgacac atccaaagtg gcttctggag tccctgctcg cttcagtggc    600
agtgggtctg ggaccgacta ctctctcaca atcaacagct ggaggctga agatgctgcc     660
acttattact gccaacagtg gagtagtaac ccgctcacgt tcggtggcgg gaccaaggtg    720
gagatcaaat ccggaggtgg tggatccgag gtgcagctgg tcgagtctgg gggaggcttg    780
gtccagcctg ggaggtccct gagactctcc tgtgcagcgt ctggattcac cgtcagtagc    840
tactggatgc actgggtccg ccaagctcca gggaaggggc tggaatgggt aggtttcatt    900
agaaacaaag ctaatggtgg gacaacagaa tacgccgcgt ctgtgaaagg cagattcacc    960
atctcaagag atgattccaa gaacacgctg tatcttcaaa tgaacagcct gagagccgag   1020
gacacggccg tgtattactg tgcaagagat aggggggctac ggttctactt tgactactgg   1080
ggccaaggga ccacggtcac cgtctcctca ggtggtggtg gttctggcgg cggcggctcc   1140
ggtggtggtg gttctcaggc cgtgctgact cagccggctt ccctctctgc atctcctgga   1200
gcatcagcca gtctcacctg caccttgcgc aggggcatca atgttggtgc ctacagtata   1260
tactggtacc agcagaagcc agggagtcct ccccagtatc tcctgaggta caaatcagac   1320
tcagataagc agcagggctc tggagtctcc agccgcttct ctgcatccaa agatgcttcg   1380
gccaatgcag ggattttact catctctggg ctccagtctg aggatgaggc tgactattac   1440
tgtatgattt ggcacagcgg cgcttctgcg gtgttcggcg gagggaccaa gttgaccgtc   1500
ctatag                                                              1506
```

<210> SEQ ID NO 132
<211> LENGTH: 501
<212> TYPE: PRT
<213> ORGANISM: artificial sequence
<220> FEATURE:
<223> OTHER INFORMATION: SEQ ID NO: 77 VHVL x B9 VH - A240 VL# ;
      Bispecific single chain antibody

<400> SEQUENCE: 132

```
Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140
```

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Ser Gly Gly Gly Ser Glu Val Gln Leu Val Glu Ser
                245                 250                 255

Gly Gly Gly Leu Val Gln Pro Gly Arg Ser Leu Arg Leu Ser Cys Ala
            260                 265                 270

Ala Ser Gly Phe Thr Val Ser Ser Tyr Trp Met His Trp Val Arg Gln
        275                 280                 285

Ala Pro Gly Lys Gly Leu Glu Trp Val Gly Phe Ile Arg Asn Lys Ala
    290                 295                 300

Asn Gly Gly Thr Thr Glu Tyr Ala Ala Ser Val Lys Gly Arg Phe Thr
305                 310                 315                 320

Ile Ser Arg Asp Asp Ser Lys Asn Thr Leu Tyr Leu Gln Met Asn Ser
                325                 330                 335

Leu Arg Ala Glu Asp Thr Ala Val Tyr Tyr Cys Ala Arg Asp Arg Gly
            340                 345                 350

Leu Arg Phe Tyr Phe Asp Tyr Trp Gly Gln Gly Thr Thr Val Thr Val
        355                 360                 365

Ser Ser Gly Gly Gly Gly Ser Gly Gly Gly Ser Gly Gly Gly Gly
    370                 375                 380

Ser Gln Ala Val Leu Thr Gln Pro Ala Ser Leu Ser Ala Ser Pro Gly
385                 390                 395                 400

Ala Ser Ala Ser Leu Thr Cys Thr Leu Arg Arg Gly Ile Asn Val Gly
            405                 410                 415

Ala Tyr Ser Ile Tyr Trp Tyr Gln Gln Lys Pro Gly Ser Pro Pro Gln
        420                 425                 430

Tyr Leu Leu Arg Tyr Lys Ser Asp Ser Asp Lys Gln Gln Gly Ser Gly
    435                 440                 445

Val Ser Ser Arg Phe Ser Ala Ser Lys Asp Ala Ser Ala Asn Ala Gly
    450                 455                 460

Ile Leu Leu Ile Ser Gly Leu Gln Ser Glu Asp Glu Ala Asp Tyr Tyr
465                 470                 475                 480

Cys Met Ile Trp His Ser Gly Ala Ser Ala Val Phe Gly Gly Gly Thr
            485                 490                 495

Lys Leu Thr Val Leu
            500

<210> SEQ ID NO 133
<211> LENGTH: 1500
<212> TYPE: DNA
<213> ORGANISM: artificial sequence
<220> FEATURE:
<223> OTHER INFORMATION: D8 VH - A240 VL# x SEQ ID NO: 77 VHVL ;
      Bispecific single chain antibody

<400> SEQUENCE: 133

```
gaggtgcagc tggtcgagtc tgggggaggc gtggtccagc ctgggaggtc cctgagactc      60
tcctgtgcag cctctggatt caccctcagt acctatgcca tgcactgggt ccgccaggct     120
ccaggcaagg gctggagtg gtggcactt atatcaaatg atggaagcaa taaatactat      180
gcagactccg tgaagggccg attcaccatc tccagagaca attccaagaa cacgctgtat     240
ctgcaaatga acagcctgag agctgaggac acggctgtgt attactgtac tagagatagg     300
gggctacggt tctactttga ctactgggc caagggacca cggtcaccgt ctcctcaggt      360
ggtggtggtt ctggcggcgg cggctccggt ggtggtggtt ctcaggccgt gctgactcag     420
ccggcttccc tctctgcatc tcctggagca tcagccagtc tcacctgcac cttgcgcagg     480
ggcatcaatg ttggtgccta cagtatatac tggtaccagc agaagccagg agtcctccc      540
cagtatctcc tgaggtacaa atcagactca gataagcagc agggctctgg agtctccagc     600
cgcttctctg catccaaaga tgcttcggcc aatgcaggga ttttactcat ctctgggctc     660
cagtctgagg atgaggctga ctattactgt atgatttggc acagcggcgc ttctgcggtg     720
ttcggcggag ggaccaagtt gaccgtccta tccggaggtg gtggatccga cgtccaactg     780
gtgcagtcag gggctgaagt gaaaaaacct ggggcctcag tgaaggtgtc ctgcaaggct     840
tctggctaca cctttactag gtacacgatg cactgggtaa ggcaggcacc tggacagggt     900
ctggaatgga ttggatacat taatcctagc cgtggttata ctaattacgc agacagcgtc     960
aagggccgct tcacaatcac tacagacaaa tccaccagca cagcctacat ggaactgagc    1020
agcctgcgtt ctgaggacac tgcaacctat tactgtgcaa gatattatga tgatcattac    1080
tgccttgact actggggcca aggcaccacg gtcaccgtct cctcaggcga aggtactagt    1140
actggttctg gtgaagtgg aggttcaggt ggagcagacg acattgtact gacccagtct    1200
ccagcaactc tgtctctgtc tccaggggag cgtgccaccc tgagctgcag agccagtcaa    1260
agtgtaagtt acatgaactg gtaccagcag aagccgggca aggcacccaa agatgggatt    1320
tatgacacat ccaaagtggc ttctggagtc cctgctcgct tcagtggcag tgggtctggg    1380
accgactact ctctcacaat caacagcttg gaggctgaag atgctgccac ttattactgc    1440
caacagtgga gtagtaaccc gctcacgttc ggtggcggga ccaaggtgga gatcaaatag    1500
```

<210> SEQ ID NO 134
<211> LENGTH: 499
<212> TYPE: PRT
<213> ORGANISM: artificial sequence
<220> FEATURE:
<223> OTHER INFORMATION: D8 VH - A240 VL# x SEQ ID NO: 77 VHVL ;
      Bispecific single chain antibody

<400> SEQUENCE: 134

```
Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Ala Met His Trp Val Arg Gln Ala Pro Gly Lys Gly Leu Glu Trp Val
        35                  40                  45

Ala Leu Ile Ser Asn Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Thr Arg Asp Arg Gly Leu Arg Phe Tyr Phe Asp Tyr Trp Gly Gln Gly
                100                 105                 110

Thr Thr Val Thr Val Ser Ser Gly Gly Gly Ser Gly Gly Gly Gly
                115                 120                 125

Ser Gly Gly Gly Ser Gln Ala Val Leu Thr Gln Pro Ala Ser Leu
130                 135                 140

Ser Ala Ser Pro Gly Ala Ser Ala Ser Leu Thr Cys Thr Leu Arg Arg
145                 150                 155                 160

Gly Ile Asn Val Gly Ala Tyr Ser Ile Tyr Trp Tyr Gln Gln Lys Pro
                165                 170                 175

Gly Ser Pro Pro Gln Tyr Leu Leu Arg Tyr Lys Ser Asp Ser Asp Lys
                180                 185                 190

Gln Gln Gly Ser Gly Val Ser Ser Arg Phe Ser Ala Ser Lys Asp Ala
                195                 200                 205

Ser Ala Asn Ala Gly Ile Leu Leu Ile Ser Gly Leu Gln Ser Glu Asp
210                 215                 220

Glu Ala Asp Tyr Tyr Cys Met Ile Trp His Ser Gly Ala Ser Ala Val
225                 230                 235                 240

Phe Gly Gly Gly Thr Lys Leu Thr Val Leu Ser Gly Gly Gly Gly Ser
                245                 250                 255

Asp Val Gln Leu Val Gln Ser Gly Ala Glu Val Lys Lys Pro Gly Ala
                260                 265                 270

Ser Val Lys Val Ser Cys Lys Ala Ser Gly Tyr Thr Phe Thr Arg Tyr
                275                 280                 285

Thr Met His Trp Val Arg Gln Ala Pro Gly Gln Gly Leu Glu Trp Ile
                290                 295                 300

Gly Tyr Ile Asn Pro Ser Arg Gly Tyr Thr Asn Tyr Ala Asp Ser Val
305                 310                 315                 320

Lys Gly Arg Phe Thr Ile Thr Thr Asp Lys Ser Thr Ser Thr Ala Tyr
                325                 330                 335

Met Glu Leu Ser Ser Leu Arg Ser Glu Asp Thr Ala Thr Tyr Tyr Cys
                340                 345                 350

Ala Arg Tyr Tyr Asp Asp His Tyr Cys Leu Asp Tyr Trp Gly Gln Gly
                355                 360                 365

Thr Thr Val Thr Val Ser Ser Gly Glu Gly Thr Ser Thr Gly Ser Gly
                370                 375                 380

Gly Ser Gly Gly Ser Gly Gly Ala Asp Asp Ile Val Leu Thr Gln Ser
385                 390                 395                 400

Pro Ala Thr Leu Ser Leu Ser Pro Gly Glu Arg Ala Thr Leu Ser Cys
                405                 410                 415

Arg Ala Ser Gln Ser Val Ser Tyr Met Asn Trp Tyr Gln Gln Lys Pro
                420                 425                 430

Gly Lys Ala Pro Lys Arg Trp Ile Tyr Asp Thr Ser Lys Val Ala Ser
                435                 440                 445

Gly Val Pro Ala Arg Phe Ser Gly Ser Gly Ser Gly Thr Asp Tyr Ser
                450                 455                 460

Leu Thr Ile Asn Ser Leu Glu Ala Glu Asp Ala Ala Thr Tyr Tyr Cys
465                 470                 475                 480

Gln Gln Trp Ser Ser Asn Pro Leu Thr Phe Gly Gly Gly Thr Lys Val
                485                 490                 495

Glu Ile Lys
```

<210> SEQ ID NO 135
<211> LENGTH: 1500
<212> TYPE: DNA
<213> ORGANISM: artificial sequence
<220> FEATURE:
<223> OTHER INFORMATION: SEQ ID NO: 77 VHVL x D8 VH - A240 VL# ;
      Bispecific single chain antibody

<400> SEQUENCE: 135

```
gacgtccaac tggtgcagtc aggggctgaa gtgaaaaaac ctggggcctc agtgaaggtg     60
tcctgcaagg cttctggcta cacctttact aggtacacga tgcactgggt aaggcaggca    120
cctggacagg gtctggaatg gattggatac attaatccta gccgtggtta tactaattac    180
gcagacagcg tcaagggccg cttcacaatc actacagaca atccaccag cacagcctac     240
atggaactga gcagcctgcg ttctgaggac actgcaacct attactgtgc aagatattat    300
gatgatcatt actgccttga ctactggggc caaggcacca cggtcaccgt ctcctcaggc    360
gaaggtacta gtactggttc tgtggaagt ggaggttcag gtggagcaga cgacattgta     420
ctgacccagt ctccagcaac tctgtctctg tctccagggg agcgtgccac cctgagctgc    480
agagccagtc aaagtgtaag ttacatgaac tggtaccagc agaagccggg caaggcaccc    540
aaaagatgga tttatgacac atccaaagtg gcttctggag tccctgctcg cttcagtggc    600
agtgggtctg ggaccgacta ctctctcaca atcaacagct ggaggctga agatgctgcc     660
acttattact gccaacagtg gagtagtaac ccgctcacgt tcggtggcgg gaccaaggtg    720
gagatcaaat ccggaggtgg tggatccgag gtgcagctgg tcgagtctgg gggaggcgtg    780
gtccagcctg ggaggtccct gagactctcc tgtgcagcct ctggattcac cctcagtacc    840
tatgccatgc actgggtccg ccaggctcca ggcaaggggc tggagtgggt ggcacttata    900
tcaaatgatg gaagcaataa atactatgca gactccgtga agggccgatt caccatctcc    960
agagacaatt ccaagaacac gctgtatctg caaatgaaca gcctgagagc tgaggacacg   1020
gctgtgtatt actgtactag ataggggg ctacggttct actttgacta ctggggccaa    1080
gggaccacgg tcaccgtctc ctcaggtggt ggtggttctg gcggcggcgg ctccggtggt   1140
ggtggttctc aggccgtgct gactcagccg gcttccctct ctgcatctcc tggagcatca   1200
gccagtctca cctgcacctt gcgcaggggc atcaatgttg gtgcctacag tatatactgg   1260
taccagcaga agccagggag tcctccccag tatctcctga ggtacaaatc agactcagat   1320
aagcagcagg gctctggagt ctccagccgc ttctctgcat ccaaagatgc ttcggccaat   1380
gcagggattt tactcatctc tgggctccag tctgaggatg aggctgacta ttactgtatg   1440
atttggcaca gcggcgcttc tgcggtgttc ggcggaggga ccaagttgac cgtcctatag   1500
```

<210> SEQ ID NO 136
<211> LENGTH: 499
<212> TYPE: PRT
<213> ORGANISM: artificial sequence
<220> FEATURE:
<223> OTHER INFORMATION: SEQ ID NO: 77 VHVL x D8 VH - A240 VL# ;
      Bispecific single chain antibody

<400> SEQUENCE: 136

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile

```
                35                  40                  45
Gly Tyr Ile Asn Pro Ser Arg Gly Tyr Thr Asn Tyr Ala Asp Ser Val
 50                  55                  60

Lys Gly Arg Phe Thr Ile Thr Thr Asp Lys Ser Thr Ser Thr Ala Tyr
 65                  70                  75                  80

Met Glu Leu Ser Ser Leu Arg Ser Glu Asp Thr Ala Thr Tyr Tyr Cys
                 85                  90                  95

Ala Arg Tyr Tyr Asp Asp His Tyr Cys Leu Asp Tyr Trp Gly Gln Gly
                100                 105                 110

Thr Thr Val Thr Val Ser Ser Gly Glu Gly Thr Ser Thr Gly Ser Gly
                115                 120                 125

Gly Ser Gly Gly Ser Gly Gly Ala Asp Asp Ile Val Leu Thr Gln Ser
130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
                180                 185                 190

Gly Val Pro Ala Arg Phe Ser Gly Ser Gly Ser Gly Thr Asp Tyr Ser
                195                 200                 205

Leu Thr Ile Asn Ser Leu Glu Ala Glu Asp Ala Ala Thr Tyr Tyr Cys
210                 215                 220

Gln Gln Trp Ser Ser Asn Pro Leu Thr Phe Gly Gly Gly Thr Lys Val
225                 230                 235                 240

Glu Ile Lys Ser Gly Gly Gly Gly Ser Glu Val Gln Leu Val Glu Ser
                245                 250                 255

Gly Gly Gly Val Val Gln Pro Gly Arg Ser Leu Arg Leu Ser Cys Ala
                260                 265                 270

Ala Ser Gly Phe Thr Leu Ser Thr Tyr Ala Met His Trp Val Arg Gln
                275                 280                 285

Ala Pro Gly Lys Gly Leu Glu Trp Val Ala Leu Ile Ser Asn Asp Gly
                290                 295                 300

Ser Asn Lys Tyr Tyr Ala Asp Ser Val Lys Gly Arg Phe Thr Ile Ser
305                 310                 315                 320

Arg Asp Asn Ser Lys Asn Thr Leu Tyr Leu Gln Met Asn Ser Leu Arg
                325                 330                 335

Ala Glu Asp Thr Ala Val Tyr Tyr Cys Thr Arg Asp Arg Gly Leu Arg
                340                 345                 350

Phe Tyr Phe Asp Tyr Trp Gly Gln Gly Thr Thr Val Thr Val Ser Ser
                355                 360                 365

Gly Gly Gly Gly Ser Gly Gly Gly Ser Gly Gly Gly Gly Ser Gln
                370                 375                 380

Ala Val Leu Thr Gln Pro Ala Ser Leu Ser Ala Ser Pro Gly Ala Ser
385                 390                 395                 400

Ala Ser Leu Thr Cys Thr Leu Arg Arg Gly Ile Asn Val Gly Ala Tyr
                405                 410                 415

Ser Ile Tyr Trp Tyr Gln Gln Lys Pro Gly Ser Pro Gln Tyr Leu
                420                 425                 430

Leu Arg Tyr Lys Ser Asp Ser Asp Lys Gln Gln Gly Ser Gly Val Ser
                435                 440                 445

Ser Arg Phe Ser Ala Ser Lys Asp Ala Ser Ala Asn Ala Gly Ile Leu
450                 455                 460
```

```
Leu Ile Ser Gly Leu Gln Ser Glu Asp Glu Ala Asp Tyr Tyr Cys Met
465                 470                 475                 480

Ile Trp His Ser Gly Ala Ser Ala Val Phe Gly Gly Gly Thr Lys Leu
                485                 490                 495

Thr Val Leu

<210> SEQ ID NO 137
<211> LENGTH: 31
<212> TYPE: DNA
<213> ORGANISM: artificial sequence
<220> FEATURE:
<223> OTHER INFORMATION: 5'CEAI LH ; oligonucleotide

<400> SEQUENCE: 137
aggtgtacac tccgacattg agctcaccca g                               31

<210> SEQ ID NO 138
<211> LENGTH: 47
<212> TYPE: DNA
<213> ORGANISM: artificial sequence
<220> FEATURE:
<223> OTHER INFORMATION: 3'CEAI VL Linker ; oligonucleotide

<400> SEQUENCE: 138
ggagccgccg ccgccagaac caccaccacc tttgatctcg agcttgg              47

<210> SEQ ID NO 139
<211> LENGTH: 48
<212> TYPE: DNA
<213> ORGANISM: artificial sequence
<220> FEATURE:
<223> OTHER INFORMATION: 5'CEAI VH Linker ; oligonucleotide

<400> SEQUENCE: 139
ggcggcggcg gctccggtgg tggtggttct caggtccaac tgcaggag             48

<210> SEQ ID NO 140
<211> LENGTH: 22
<212> TYPE: DNA
<213> ORGANISM: ARTIFICIAL SEQUENCE
<220> FEATURE:
<223> OTHER INFORMATION: 3'CEAI LH ; oligonucleotide

<400> SEQUENCE: 140
aatccggagg agacggtgac cg                                         22

<210> SEQ ID NO 141
<211> LENGTH: 14
<212> TYPE: PRT
<213> ORGANISM: artificial sequence
<220> FEATURE:
<223> OTHER INFORMATION: De-immunized polypeptide linker

<400> SEQUENCE: 141

Gly Glu Gly Thr Ser Thr Gly Ser Gly Ser Gly Gly Ala Asp
1               5                   10

<210> SEQ ID NO 142
<211> LENGTH: 1524
<212> TYPE: DNA
<213> ORGANISM: artificial sequence
<220> FEATURE:
<223> OTHER INFORMATION: SEQ ID NO:77 VHVL x E12 VH - A240 VL ;
      Bispecific single chain antibody
```

<400> SEQUENCE: 142

```
gacgtccaac tggtgcagtc aggggctgaa gtgaaaaaac ctggggcctc agtgaaggtg      60
tcctgcaagg cttctggcta cacctttact aggtacacga tgcactgggt aaggcaggca     120
cctggacagg gtctggaatg gattggatac attaatccta gccgtggtta tactaattac     180
gcagacagcg tcaagggccg cttcacaatc actacagaca atccaccag cacagcctac      240
atggaactga gcagcctgcg ttctgaggac actgcaacct attactgtgc aagatattat     300
gatgatcatt actgccttga ctactggggc caaggcacca cggtcaccgt ctcctcaggc     360
gaaggtacta gtactggttc tggtggaagt ggaggttcag gtggagcaga cgacattgta     420
ctgacccagt ctccagcaac tctgtctctg tctccagggg agcgtgccac cctgagctgc     480
agagccagtc aaagtgtaag ttacatgaac tggtaccagc agaagccggg caaggcaccc     540
aaaagatgga tttatgacac atccaaagtg gcttctggag tccctgctcg cttcagtggc     600
agtgggtctg ggaccgacta ctctctcaca atcaacagct ggaggctga agatgctgcc      660
acttattact gccaacagtg gagtagtaac ccgctcacgt tcggtggcgg gaccaaggtg     720
gagatcaaat ccggaggtgg tggatccgag gtgcagctgg tcgagtctgg gggaggcttg     780
gtccagcctg gaggtccct gagactctcc tgtgcagcgc tggattcac cgtcagtagc       840
tactggatgt actgggtccg ccaagctcca gggaagggc tggaatgggt aggtttcatt       900
ctcaacaaag ctaatggtgg aacaacagaa tacgccgcgc tgtgaaagg cagattcacc      960
atctcaagag atgattccaa gaacacgctg tatcttcaaa tgaacagcct gagagccgag    1020
gacacggccg tgtattactg tgcaagagat aggggggctac ggttctactt tgactactgg    1080
ggccaaggga ccacggtcac cgtctcctca ggtggtggtg gttctggcgg cggcggctcc    1140
ggtggtggtg gttctgagct cgtgctgact cagccggctt ccctctctgc atctcctgga    1200
gcatcagcca gtctcaccctg caccttgcgc aggggcatca atgttggtgc ctacagtata   1260
tactggtacc agcagaagcc agggagtcct ccccagtatc tcctgaggta caaatcagac    1320
tcagataagc agcagggctc tggagtctcc agccgcttct ctgcatccaa agatgcttcg    1380
gccaatgcag ggatttact catctctggg ctccagtctg aggatgaggc tgactattac    1440
tgtatgattt ggcacagcgg cgcttctgcg gtgttcggcg agggaccaa gttgaccgtc    1500
ctacatcatc accatcatca ttag                                                  1524
```

<210> SEQ ID NO 143
<211> LENGTH: 507
<212> TYPE: PRT
<213> ORGANISM: ARTIFICIAL SEQUENCE
<220> FEATURE:
<223> OTHER INFORMATION: SEQ ID NO: 77 VHVL x E12 VH - A240 VL ; Bispecific single chain antibody

<400> SEQUENCE: 143

```
Asp Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80
```

```
Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys Ser Gly Gly Gly Gly Ser Glu Val Gln Leu Val Glu Ser
                245                 250                 255

Gly Gly Gly Leu Val Gln Pro Gly Arg Ser Leu Arg Leu Ser Cys Ala
            260                 265                 270

Ala Ser Gly Phe Thr Val Ser Ser Tyr Trp Met His Trp Val Arg Gln
        275                 280                 285

Ala Pro Gly Lys Gly Leu Glu Trp Val Gly Phe Ile Leu Asn Lys Ala
    290                 295                 300

Asn Gly Gly Thr Thr Glu Tyr Ala Ala Ser Val Lys Gly Arg Phe Thr
305                 310                 315                 320

Ile Ser Arg Asp Asp Ser Lys Asn Thr Leu Tyr Leu Gln Met Asn Ser
                325                 330                 335

Leu Arg Ala Glu Asp Thr Ala Val Tyr Tyr Cys Ala Arg Asp Arg Gly
            340                 345                 350

Leu Arg Phe Tyr Phe Asp Tyr Trp Gly Gln Gly Thr Thr Val Thr Val
        355                 360                 365

Ser Ser Gly Gly Gly Gly Ser Gly Gly Gly Gly Ser Gly Gly Gly Gly
    370                 375                 380

Ser Glu Leu Val Leu Thr Gln Pro Ala Ser Leu Ser Ala Ser Pro Gly
385                 390                 395                 400

Ala Ser Ala Ser Leu Thr Cys Thr Leu Arg Arg Gly Ile Asn Val Gly
                405                 410                 415

Ala Tyr Ser Ile Tyr Trp Tyr Gln Gln Lys Pro Gly Ser Pro Pro Gln
            420                 425                 430

Tyr Leu Leu Arg Tyr Lys Ser Asp Ser Asp Lys Gln Gln Gly Ser Gly
        435                 440                 445

Val Ser Ser Arg Phe Ser Ala Ser Lys Asp Ala Ser Ala Asn Ala Gly
    450                 455                 460

Ile Leu Leu Ile Ser Gly Leu Gln Ser Glu Asp Glu Ala Asp Tyr Tyr
465                 470                 475                 480

Cys Met Ile Trp His Ser Gly Ala Ser Ala Val Phe Gly Gly Gly Thr
                485                 490                 495
```

-continued

Lys Leu Thr Val Leu His His His His His
                500                 505

<210> SEQ ID NO 144
<211> LENGTH: 5
<212> TYPE: PRT
<213> ORGANISM: HOMO SAPIENS
<220> FEATURE:
<221> NAME/KEY: MISC_FEATURE
<223> OTHER INFORMATION: CDR-H1 E12 ; CDR1 of VH E12

<400> SEQUENCE: 144

Ser Tyr Trp Met His
1               5

<210> SEQ ID NO 145
<211> LENGTH: 19
<212> TYPE: PRT
<213> ORGANISM: Homo sapiens
<220> FEATURE:
<221> NAME/KEY: MISC_FEATURE
<223> OTHER INFORMATION: CDR-H2 E12 ; CDR-2 of VH E12

<400> SEQUENCE: 145

Phe Ile Leu Asn Lys Ala Asn Gly Gly Thr Thr Glu Tyr Ala Ala Ser
1               5                   10                  15

Val Lys Gly

<210> SEQ ID NO 146
<211> LENGTH: 121
<212> TYPE: PRT
<213> ORGANISM: Homo sapiens
<220> FEATURE:
<221> NAME/KEY: MISC_FEATURE
<223> OTHER INFORMATION: E12 VH ; VH region

<400> SEQUENCE: 146

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
                20                  25                  30

Trp Met His Trp Val Arg Gln Ala Pro Gly Lys Gly Leu Glu Trp Val
            35                  40                  45

Gly Phe Ile Leu Asn Lys Ala Asn Gly Gly Thr Thr Glu Tyr Ala Ala
        50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
            100                 105                 110

Gln Gly Thr Thr Val Thr Val Ser Ser
        115                 120

<210> SEQ ID NO 147
<211> LENGTH: 252
<212> TYPE: PRT
<213> ORGANISM: HOMO SAPIENS
<220> FEATURE:
<221> NAME/KEY: MISC_FEATURE
<223> OTHER INFORMATION: E12 VH - A240 VL ; Single chain Fv

<400> SEQUENCE: 147

-continued

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Val Ser Ser Tyr
            20                  25                  30

Trp Met His Trp Val Arg Gln Ala Pro Gly Lys Gly Leu Glu Trp Val
        35                  40                  45

Gly Phe Ile Leu Asn Lys Ala Asn Gly Gly Thr Thr Glu Tyr Ala Ala
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Asp Arg Gly Leu Arg Phe Tyr Phe Asp Tyr Trp Gly
                100                 105                 110

Gln Gly Thr Thr Val Thr Val Ser Ser Gly Gly Gly Gly Ser Gly Gly
            115                 120                 125

Gly Gly Ser Gly Gly Gly Gly Ser Glu Leu Val Leu Thr Gln Pro Ala
        130                 135                 140

Ser Leu Ser Ala Ser Pro Gly Ala Ser Ala Ser Leu Thr Cys Thr Leu
145                 150                 155                 160

Arg Arg Gly Ile Asn Val Gly Ala Tyr Ser Ile Tyr Trp Tyr Gln Gln
                165                 170                 175

Lys Pro Gly Ser Pro Pro Gln Tyr Leu Leu Arg Tyr Lys Ser Asp Ser
            180                 185                 190

Asp Lys Gln Gln Gly Ser Gly Val Ser Ser Arg Phe Ser Ala Ser Lys
        195                 200                 205

Asp Ala Ser Ala Asn Ala Gly Ile Leu Leu Ile Ser Gly Leu Gln Ser
    210                 215                 220

Glu Asp Glu Ala Asp Tyr Tyr Cys Met Ile Trp His Ser Gly Ala Ser
225                 230                 235                 240

Ala Val Phe Gly Gly Gly Thr Lys Leu Thr Val Leu
                245                 250
```